US007407792B2

(12) United States Patent
Liu et al.

(10) Patent No.: US 7,407,792 B2
(45) Date of Patent: Aug. 5, 2008

(54) COMPOSITIONS, ORGANISMS AND METHODOLOGIES EMPLOYING A NOVEL HUMAN KINASE

(75) Inventors: Wei Liu, Sudbury, MA (US); Leeying Wu, Lexington, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/505,718

(22) Filed: Aug. 17, 2006

(65) Prior Publication Data
US 2006/0294601 A1 Dec. 28, 2006

Related U.S. Application Data

(62) Division of application No. 10/684,190, filed on Oct. 10, 2003, now Pat. No. 7,122,361.

(60) Provisional application No. 60/417,209, filed on Oct. 10, 2002.

(51) Int. Cl.
C12N 1/20 (2006.01)
C07H 21/04 (2006.01)
(52) U.S. Cl. .................... 435/252.3; 435/194; 536/23.2
(58) Field of Classification Search .................. 435/194, 435/252.3; 536/23.2
See application file for complete search history.

(56) References Cited

U.S. PATENT DOCUMENTS

| 4,489,710 | A | 12/1984 | Spitler |
| 4,522,811 | A | 6/1985 | Eppstein et al. |
| 4,569,789 | A | 2/1986 | Blattler et al. |
| 4,625,014 | A | 11/1986 | Senter et al. |
| 4,638,045 | A | 1/1987 | Kohn et al. |
| 4,671,958 | A | 6/1987 | Rodwell et al. |
| 4,751,180 | A | 6/1988 | Cousens et al. |
| 4,935,233 | A | 6/1990 | Bell et al. |
| 5,459,039 | A | 10/1995 | Modrich et al. |
| 5,498,531 | A | 3/1996 | Jarrell |
| 5,919,619 | A | 7/1999 | Tullis |
| 6,506,559 | B1 | 1/2003 | Fire et al. |
| 6,759,222 | B2 | 7/2004 | Meyers |
| 2004/0038881 | A1 | 2/2004 | Bandman et al. |
| 2004/0197792 | A1* | 10/2004 | Whyte et al. .................. 435/6 |

FOREIGN PATENT DOCUMENTS

| WO | 89/10134 | 11/1989 |
| WO | 97/07668 | 3/1997 |
| WO | 97/07669 | 3/1997 |
| WO | 99/14346 | 3/1999 |
| WO | 99/27132 | 6/1999 |
| WO | 00/44895 | 8/2000 |
| WO | 00/63364 | 10/2000 |
| WO | 00/73469 A2 | 12/2000 |
| WO | 01/29058 | 4/2001 |
| WO | 01/36646 | 5/2001 |
| WO | 01/66594 A2 | 9/2001 |
| WO | 01/68836 | 9/2001 |
| WO | 01/70949 | 9/2001 |
| WO | 01/75067 A2 | 10/2001 |
| WO | 01/75164 | 10/2001 |
| WO | 01/92513 | 12/2001 |
| WO | 02/08399 | 1/2002 |
| WO | 02/18557 A2 | 3/2002 |
| WO | 02/24924 A2 | 3/2002 |
| WO | 02/46384 A2 | 6/2002 |
| WO | 02/081731 A2 | 10/2002 |
| WO | 03/050084 A2 | 6/2003 |
| WO | 2004/032877 | 4/2004 |

OTHER PUBLICATIONS

20040197792 [Applicants' SEQ ID No. 1 Vs SEQ ID No. 27 from Published Application 20040197792].*
Altschul et al., "Gapped Blast and Psi-Blast: A New Generation of Protein Database Search Programs," *Nucleic Acids Research*, 1997, pp. 3389-3402, vol. 25, No. 17, Oxford University Press.
Berger P. et al., "Loss of Phosphatase Activity in Myotubularin-Related Protein 2 is Associated with Charcot-Marie Tooth Disease Type 4B1," *Human Molecular Genetics*, 2002, pp. 1569-1579, vol. 11, No. 13, Oxford University Press.
Boe R. et al., "The Protein Phosphatase Inhibitor Okadaic Acid Induces Morphological Changes Typical of Apoptosis in Mammalian Cells," *Experimental Cell Research*, 195, 1991, pp. 237-246, Academic Press, Inc.
Bottim N, et al., "Low-Molecular-Weight Protein Tyrosine Phosphatase and Human Disease: In Search of Biochemical Mechanisms," *Archivum Immunologiae Et Therapiae Experimentalis*, 2002 pp. 95-104, vol. 50.
Brown-Shimer, et al., "Effect Of Protein Tyrosine Phosphatase 1B Expression on Transformation by the Human Neu Oncogene," *Cancer Research*, 52, 1992, pp. 478-548.
Chen et al., "The Myotonic Dystrophy Kinase-Related Cdc42—Binding Kinase is Involved in the Regulation of Neurite Outgrowth in PCl2 Cells," *The Journal of Biological Chemistry*,1999, pp. 19901-19905, vol. 274, No. 28, The American Society For Biochemistry And Molecular Biology, Inc.
Delagrave et al., "Recursive Ensemble Mutagenesis," *Protein Engineering*, 1993, pp. 327-331, vol. 6, No. 3, Oxford University Press.
Dong et al., "Cdc42 Antagonizes Inductive Action of cAMP on Cell Shape, via Effects of the Myotonic Dystrophy Kinase-Related Cdc42-Binding Kinase (MRCK) on Myosin Light Chain Phosphorylation," *European Journal of Cell Biology*, Apr. 2002, pp. 231-242, vol. 81.

(Continued)

*Primary Examiner*—Tekchand Saidha
(74) *Attorney, Agent, or Firm*—Maria Restrepo-Hartwig

(57) ABSTRACT

This invention provides compositions, organisms and methodologies employing a novel human protein kinase, HPK3P23. The novel human kinase has sequence homology to the catalytic domains of several protein kinases. The gene encoding this novel protein kinase is localized in or near the 3p23 locus of the human chromosome 3. The sequence similarity between the novel human protein and the catalytic domain of protein kinases indicates that the novel human protein may function as a protein kinase.

4 Claims, 3 Drawing Sheets

OTHER PUBLICATIONS

Engelman et al., "Identifying Nonpolar Transbilayer Helices in Amino Acid Sequences of Membrane Proteins," *Ann. Rev. Biophys. Chem.*, 1986, pp. 321-353, vol. 15, Annual Reviews Inc.

Florea et al., "A Computer Program for Aligning a cDNA Sequence with a Genomic DNA Sequence," *Genome Research*, 1998, pp. 967-974, vol. 8, Cold Spring Harbor Laboratory Press.

Gossen et al., "Transcriptional Activation by Tetracyclines in Mammalian Cells," *Science*, Jun. 23, 1995, pp. 1766-1769, vol. 268.

Guatelli et al., "Isothermal, in Vitro Amplification of Nucleic Acids by a Multienzyme Reaction Modeled After Retroviral Replication," *Proc. Natl. Acad. Sci. USA*, Mar. 1990, pp. 1874-1878, vol. 87.

Haseloff et al., "Simple RNA Enzymes with New and Highly Specific Endoribonuclease Activities," *Nature*, Aug. 18, 1988, pp. 585-591, vol. 334.

Hyrup et al., "Peptide Nucleic Acids (PNA): Synthesis, Properties and Potential Applications," *Bioorganic & Medicinal Chemistry*, 1996, pp. 5-23, vol. 4, No. 1, Elsevier Science Ltd., Great Britain.

Ishida et al., "Treatment of Myeloid Leukemic Cells with the Phosphatase Inhibitor Okadaic Acid Induces Cell Cycle Arrest at Either G1/S or G2/M Depending on Dose," *Journal of Cellular Physiology*, 1992, pp. 484-492.

Janssens et al., "Protein Phosphatase 2A: A Highly Regulated Family of Serine/Threonine Phosphatases Implicated in Cell Growth and Signaling," *J. Biochem*, 353, 2001, pp. 417-443.

Kedra et al., "The Germinal Center Kinase Gene and a Novel Cdc25-Like Gene are Located in the Vicinity of the Pygm Gene on 11q13," *Hum. Genet.*, 1997, pp. 611-619, vol. 100.

Keen et al., "Rapid Detection of Single Base Mismatches as Heteroduplexes on Hydrolink Gels," *Trends in Genetics*, 1997, p. 5, vol. 7.

Kwoh et al., "Transcription-Based Amplification System and Detection of Amplified Human Immunodeficiency Virus Type 1 with a Bead-Based Sandwich Hybridization Format," *Proc. Natl. Acad. Sci. USA*, Feb. 1989, pp. 1173-1177, vol. 86.

Lam et al., "Characterization of a Monoclonal Antibody Panel Shows that the Myotonic Dystrophy Protein Kinase, DMPK, is Expressed Almost Exclusively in Muscle and Heart," *Human Molecular Genetics*, 2000, pp. 2167-2173, vol. 9, No. 4, Oxford University Press.

Lee et al., "Expression of Small Interfering RNAs Targeted Against HIV-1 Rev Transcripts in Human Cells," *Nature Biotechnology*, May 2002, pp. 500-505, vol. 19.

Leung et al., "Myotonic Dystrophy Kinase-Related Cdc42-Binding Kinase Acts as a Cdc42 Effector in Promoting Cytoskeletal Reorganization," *Molecular and Cellular Biology*, Jan. 1998, pp. 130-140, vol. 18, No. 1, American Society For Microbiology.

Lizardi et al., "Exponential Amplification of Recombinant-RNA Hybridization Probes," *Biotechnology*, Oct. 1988, pp. 1197-1202, vol. 6.

Maratea et al., "Deletion and Fusion Analysis of the Phage Øx174 Lysis Gene E," *Gene*, 1985, pp. 39-46, vol. 40, Elsevier Science Publishers.

Meyers et al., "Optimal Alignments in Linear Space," *Cabios*, 1988, pp. 11-17, vol. 4, No. 1, Press Limited, Oxford England.

Murphy et al., "Genetic Construction, Expression, and Melanoma-Selective Cytotoxicity of a Diphtheria Toxin-Related α-Melanoma-Stimulating Hormone Fusion Protein," *Proc. Natl. Aca. Sci. USA*, Nov. 1986, pp. 8258-8262, vol. 83.

Needleman et al., "A General Method Applicable to the Search for Similarities in the Amino Acid Sequence of Tow Proteins," *J. Mol. Bio.*, 1970, pp. 443-453, vol. 48.

No et al., "Ecdysone-Inducible Gene Expression in Mammalian Cells and Transgenic Mice," *Proc. Natl. Acad. Sci. USA*, Apr. 1996, pp. 3346-3351, vol. 93.

Nomura et al., "Enhancement by Cyclosporin a of Taxol-Induced Apoptosis of Human Urinary Bladder Cancer Cells," *Urol Res*, 2002, pp. 102-111, vol. 30.

O'gorman et al., "Recombinase-Mediated Gene Activation and Site-Specific Integration in Mammalian Cells," *Science*, Mar. 1991, pp. 1351-1355, vol. 251.

Rosenbaum et al., "Temperature-Gradient Gel Electrophoresis," *Biophysical Chemistry*, 1987, pp. 12753, vol. 265.

Saiki et al., "Genetic Analysis of Amplified DNA with Immobilized Sequence-Specific Oligonucleotide Probes," *Proc. Natl. Acad. Sci. USA*, Aug. 1989, pp. 6230-6234, vol. 86.

Straub et al., "Genome-Wide Scans of Three Independent Sets of 90 Irish Multiplex Schizophrenia Families and Follow-Up of Selected Regions in All Families Provides Evidence for Multiple Susceptibility Genes," *Mol. Psychiatry*, 2002, pp. 542-559, vol. 7, No. 6.

Sui et al., "A DNA Vector-Based RNAi Technology to Suppress Gene Expression in Mammalian Cells," *Proc. Natl. Acad. Sci.*, Apr. 16, 2002, pp. 5515-5520, vol. 99, No. 8.

Tan et al., "Phosphorylation of a Novel Myosin Binding Subunit of Protein Phosphatase 1 Reveals a Conserved Mechanism in the Regulation Ofactin Cytoskeleton," *The Journal of Biological Chemistry*, 2001, pp. 21209-21216, vol. 276, No. 24.

Tan et al., "Intermolecular and Intramolecular Interactions Regulate Catalytic Activity of Myotonic Dystrophy Kinase-Related Cdc42-Binding Kinase A," *Molecular and Cellular Biology*, Apr. 2001, pp. 2767-2778, vol. 21, No. 8.

Wang et al., "Ligand-Inducible and Liver-Specific Target Gene Expression in Transgenic Mice," *Nature Biotechnology*, Mar. 1997, pp. 239-243, vol. 15.

Wary et al., "A Homozygous Deletion within the Carbonic Anhydrase-Like Domain of the Ptprg Gene in Murine L-Cells," *Cancer Research*, Apr. 1, 1993, pp. 478-482, vol. 53.

Wilmut et al., "Viable Offspring Derived from Fetal and Adult Mammalian Cells," *Letters to Nature*, Feb. 1997, pp. 810-813, vol. 385.

Ye et al., "Regulated Delivery of Therapeutic Proteins After in Vivo Somatic Cell Gene Transfer," *Science*, Jan. 1999, pp. 88-91, vol. 283.

Zhao et al., "Reversible Modification of Tissue-Type Plasminogen Activator by Methylphosphonate Esters," *Bioorganic & Medicinal Chemistry*, 1996, pp. 523-529, vol. 4.

Zy, "Protein Tyrosine Phosphatases: Structure and Function, Substrate Specificity, and Inhibitor Development," *Annu Rev Pharmacol Toxicol*, 2002, pp. 209-234, vol. 42.

Hayashi, K. et al., "Activity and substrate specificity of the murine STK2 Serine/Threonine kinase that is structurally related to the mitotic regulator protein NIMA of *Aspergillus nidulans*," *Biochem. Biopys. Res. Commun.*, 264(2):449-56 (1999).

Aravind, L. and Koonin, E.V., "Phosphoesterase domains associated with DNA polymerases of diverse origins," *Nucleic Acids Res.*, 26(16):3746-52 (1998).

Myers, R.M. et al., "Detection of single base substitutions by ribonuclease cleavage at mismatches in RNA:DNA duplexes," *Science*, vol. 230 (4731):1242-1246 (1985).

Databse GenEmbl, on STN, AN AF021935, Leung, T. et al., "Myotonic Dystrophy Kinase-Related Cdc42-Binding Kinase Acts as a Cdc42 Effector in Promoting Cytoskeletal Reorganization," Sequence Comparison, pp. 18-21.

Collins, F.S., "Generation and initial analysis of more than 15,000 full-length human and mouse cDNA sequences," *Proc. Natl. Acad. Sci. USA*, 99(26):16899-16903 (2002).

Databse GenCore on STN, AN AAD34299, Bandman, O. et al., Database N_Geneseq_29Jan04(WO 02/18557-A2), Mar. 7, 2002, Sequence Comparison, pp. 1-4.

International Search Report mailed on Jun. 23, 2005, for WO 2004/032877, and associated sequence search alignments.

* cited by examiner

```
Query:  369  LGSGAFGCVYK---VRKHSGQNLLAMKEVNLHNPAFGKDKKDRDSSVRNIVSELTIIKEQ    425
Sbjct:    7  LGEGAFGEVYKGTLKGKGKEVEVAVKT--LKEDASEQQIEE------FLREAKIMR-K      56

Query:  426  LYHPNIVRYYKTFLENDRLYIVMELIEGAPLGEHFSSLKEKHHHFTEERLWKIFIQLCLA    485
Sbjct:   57  LDHPNIVKLLGVCTEEEPLMIVMEYMEGGDLLDYLR--KNRPKELSLSDLLSFALQIARG   114

Query:  486  LRYLHKEKRIVHRDLTPNNIMLGDKDKVTVTDFGLAKQKQENSKLTSVVG--TILYSCPE    543
Sbjct:  115  MEYLE-SKNFVHRDLAARNCLVGENKTVKIADFGLSRDLYSDDYYKVKGGKLPIRWMAPE   173

Query:  544  VLKSEPYGEKADVWAVGCILYQMATL-SPPFYSTNMLSLATKIVEAVYEPVPEGIYSEKV    602
Sbjct:  174  SLKEGKFTSKSDVWSFGVLLWEIFTLGESPYPGMSNEEVLEYLKKGYRLPQPPNC-PDEI   232

Query:  603  TDTISRCLTPDAEARPDIVEVSSMI    627
Sbjct:  233  YDLMLQCWAEDPEDRPSFSELVERL    257

FIG. 1

Query:  363  YAILDHLGSGAFGCVYKVRKHSGQNLLAMKEVNLHNPAFGKDKKDRDSSVRNIVSELTII    422
Sbjct:    1  YELGEKLGSGSFGKVYKGKHKNTGEIVAIKKL---------KKESIKEKKRFLREIRIL     50

Query:  423  KEQLYHPNIVRYYKTFLENDRLYIVMELIEGAPLGEHFSSLKEKHHHFTEERLWKIFIQL    482
Sbjct:   51  R--RLSHPNIVRLIGVFEEDDHLYLVMEYMEGGDL--FDYLRRNGLLLSEKEAKKIALQI   106

Query:  483  CLALRYLHKEKRIVHRDLTPNNIMLGDKDKVTVTDFGLAKQ-KQENSKLTSVVGTILYSC    541
Sbjct:  107  LRGLEYLH-SRGIVHRDLKPENILLDENGTVKIADFGLARLLKSSYSKLTTFVGTPEYMA   165

Query:  542  PEVLKSEPYGEKADVWAVGCILYQMATLSPPFYSTNMLSLATKIVEAVYEPVPEGIYSEK    601
Sbjct:  166  PEVLEGRGYSSKVDVWSLGVVLYELLTGKPPFSGIDPLEELFRIIKRGLRLPLPPNCSEE   225

Query:  602  VTDTISRCLTPDAEARPDIVEV    623
Sbjct:  226  LKDLIKKCLNKDPEKRPTAKEI   247

FIG. 2
```

```
Query:  363  YAILDHLGSGAFGCVYKVRKHSGQNLLAMKEVNLHNPAFGKDKDRDSSVRNIVSELTII        422
Sbjct:    1  YELLEVLGKGAFGKVYLARDKKTGKLVAIKVIK------EKLKKKKRERILREIKIL          52

Query:  423  KEQLYHPNIVRYYKTFLENDRLYIVMELIEGAPLGEHFSSLKEKHHFTEERLWKIFIQL        482
Sbjct:   53  K-KLDHPNIVKLYDVFEDKDKLYLVMEYCEGGDLFDLL----KKRGRLSEDEARFYARQI      107

Query:  483  CLALRYLHKEKRIVHRDLTPNNIMLGDKDKVTVTDFGLAKQKQENS-KLTSVVGTILYSC     541
Sbjct:  108  LSALEYLHS-NGIIHRDLKPENILLDSDGHVKLADFGLAKQLDSGGTLLTTFVGTPEYMA     166

Query:  542  PEVLKSEPYGEKADVWAVGCILYQMATLSPPFYSTNMLSLATKIVEAVYEPVP--EGIYS   599
Sbjct:  167  PEVLLGKGYGKAVDINSLGVILYELLTGKPFPFPGDDQLDALFKKIGKPPPFPPPEWKIS    226

Query:  600  EKVTDTISRCLTPDAEARPDIVEV        623
Sbjct:  227  PEAKDLIKKLLVKDPEKRLTAEEA        250
```

FIG. 3

```
Query:  369  LGSGAFGCVYKVRKHSGQNLLAMKEVNLHNPAFGKDKDRDSSVRNIVSELTIIKEQLYH     428
Sbjct:   48  LDGSGNERAVKIYKTGTLEFKRRDRYVDGDFRFKYRKINP-----RKLVRLWAEKE---F      99

Query:  429  PNIVRYYKTFL-----ENDRLYIVMELIEGAPLGEHFSSLKEKHHFTEERLWKIFIQL     482
Sbjct:  100  RNLQRLYEAGVPVPKPIAWRRNVLVMEFIGG----DGLPAPRLKDVEPEEEEDELYDDI     155

Query:  483  CLALRYLHKEKRIVHRDLTPNNIMLGDKDKVTVTDFGLAKQKQE                   526
Sbjct:  156  LEEMRKLYKEGELVHGDLSEYNILVHD-GKVVIIDVSQSVELDH                   198
```

FIG. 4

| GES | | |
|---|---|---|
| Peak Range | Peak Type | Peak Height |
| 25 - 37 | Certain | 2.126 |
| 112 - 112 | Putative | 0.535 |
| 242 - 242 | Putative | 0.515 |
| 562 - 577 | Putative | 1.205 |
| 855 - 858 | Putative | 0.886 |

SEQUENCE LISTING

<160> NUMBER OF SEQ ID NOS: 90

<210> SEQ ID NO 1
<211> LENGTH: 3644
<212> TYPE: DNA
<213> ORGANISM: Homo sapiens

<400> SEQUENCE: 1

| | | | | | |
|---|---|---|---|---|---|
| atgagagtat | tatttgatga | atctgttttg | ccacctacag | tttattttaa | gaactgcagc | 60 |
| atcttgttcc | ttgcttcctt | gggtgctttt | ggtgtcctga | ctggcttgtt | ggtttggtcc | 120 |
| ttcatgcagt | atatggagat | tgtagccaat | gagtacctcg | gctatggaga | agagcagcac | 180 |
| actgtggaca | agctggtcaa | catgacatat | atttttcaaa | aacttgctgc | agtcaaagat | 240 |
| caaagagaat | gggtcaccac | aagtggagcc | cacaagacat | tagtaaattt | acttggtgcc | 300 |
| cgagatacta | atgttctatt | gggttccctt | ctggctctgg | ctagtttagc | agaaagacta | 360 |
| acagcggagt | tgctgcgcct | actttgtgca | gagccccagg | tgaaagagca | ggtgaagctc | 420 |
| tatgagggga | taccggtcct | cctcagtctg | ctccactctg | accacttgaa | gctcctctgg | 480 |
| agcattgtct | ggattctggt | acaggtttgt | gaggaccctg | agaccagcgt | ggaaattcgc | 540 |
| atttggggag | gcatcaaaca | gcttcttcat | attttacaag | agacagaaa | ttttgtttct | 600 |
| gatcactcct | ccattggaag | cctgtccagt | gcaaatgctg | caggccgaat | ccagcagctt | 660 |
| catttatcag | aagacttgag | ccctagggaa | atacaagaaa | atactttctc | acttcaagca | 720 |
| gcctgctgtg | ctgccctcac | tgagctggtg | ctcaatgaca | ccaatgccca | ccaggtggtt | 780 |
| caggaaaatg | gtgtatatac | aatagcaaaa | ttaattttac | caaataagca | aaagaatgca | 840 |
| gcaaaaagta | atctattaca | ggtaataaac | atgtctcttg | tccttcagta | tcaagttatt | 900 |
| gaaatcttgg | gtaactatga | cttgtttgag | atcttcattg | acatagggca | ttatgtacgt | 960 |
| gatatcagtg | cttatgaaga | attggtatcc | aagctgaatt | tattagtgga | ggatgaactg | 1020 |
| aagcaaattg | ctgaaaatat | tgaaagcatt | aatcagaaca | aagctccttt | gaaatatata | 1080 |
| ggcaactatg | caattttgga | tcatcttgga | agtggagctt | ttggctgtgt | ttacaaggtt | 1140 |
| agaaagcata | gtggtcaaaa | tcttttagca | atgaaagagg | tcaatttaca | taacccagca | 1200 |
| tttgaaaagg | ataagaaaga | tcgagacagc | agcgtaagga | atattgtttc | tgaattaaca | 1260 |
| ataattaaag | agcagcttta | tcatcccaac | attgtacgtt | attacaaaac | atttctggaa | 1320 |
| aatgataggt | tgtacatagt | tatggagctg | atagaaggag | ccccgcttgg | agagcatttc | 1380 |
| agttctttga | aggaaaaaca | tcaccatttt | actgaagaaa | gactatggaa | aatatttata | 1440 |
| cagctgtgct | tagctcttcg | atacttacac | aaggagaaga | ggattgtcca | tagagatctg | 1500 |
| acaccaaaca | acattatgtt | gggggataag | gacaaagtaa | ccgttactga | ctttggcctg | 1560 |
| gcaaagcaaa | aacaagaaaa | cagtaaactc | acgtctgtgg | ttggaacaat | cctgtattct | 1620 |
| tgccccgagg | tactgaagag | tgagccgtat | ggggagaagg | ctgatgtctg | ggcagtaggc | 1680 |
| tgcatccttt | atcagatggc | gactttgagt | cccccttct | acagcactaa | catgctgtcc | 1740 |
| ttggctacaa | aaatagtgga | ggcggtatat | gaaccagtcc | agaaggtat | ctactctgaa | 1800 |
| aaagtaacag | acaccatcag | caggtgcctc | actcctgatg | cggaagctcg | tccagatatt | 1860 |
| gtagaagtca | gttcgatgat | atcagatgtc | atgatgaaat | atttagacaa | cttatctaca | 1920 |
| tcccagttgt | cctggaaaa | gaagctagaa | cgggaacgaa | gacgcacaca | aaggtatttt | 1980 |
| atggaagcca | accggaacac | cgtcacatgt | caccatgagc | tggctgttct | atctcacgag | 2040 |

-continued

```
accttttgaga aggcaagttt gagtagcagc agcagtggag cagccagcct gaaaagtgaa    2100
ctttcagaaa gcgcagacct gccccctgaa ggcttccagg cctcctatgg taaagacgaa    2160
gacagggcct gtgacgaaat cctgtcagat gataacttca acctggaaaa tgctgagaaa    2220
gatacatatt cagaggtaga tgatgaattg gacatttcgg ataactccag cagctccagt    2280
tcaagccctc tgaaagaatc tacattcaac atttttaaaga aagttttag tgcttcagga    2340
ggagaaagac aatcccaaac aagggacttc actggaggaa caggatcaag accaagacca    2400
gctttgctgc ctcttgacct gcttctgaaa gtgccacccc acatgctcag ggcccacatt    2460
aaggaaatag aggctgagtt agtgacaggg tggcagtccc atagccttcc tgctgtgatt    2520
cttcgaaatc tcaaagatca tgggccacag atgggcacat tcttgtggca agcatcagca    2580
ggaattgctg tgtcccagag gaaagtgcgt cagatcagtg atcctattca gcagatatta    2640
attcagctgc acaaaataat ctatatcaca cagcttcctc cagctttgca ccacaatttg    2700
aaaagaaggg ttatagagag attcaagaaa tccctcttca gccagcagag taacccttgt    2760
aatttgaaat ctgaaattaa aaagttatct cagggatctc cagaaccgat tgagcccaac    2820
ttttcacag cagattacca tttattacat cgttcatccg gtggaaacag cctgtcccca    2880
aatgacccta caggtttacc aaccagcatt gaattggagg aaggaataac atatgaacag    2940
atgcagactg tgattgaaga agtccttgag gaaagtggct attacaattt tacatctaac    3000
aggtatcatt cctatccatg ggggaccaag aatcacccaa ccaaaagatg aaaatgctgc    3060
attttgagtg gacttgattt tctcagtgaa gttcaagttc tggacttcag ccgctattgc    3120
aagatgccca aggattgggt gctgctagag ggtgtggaaa agaccaagat gccatggggc    3180
ctgcaggact tctttctggg ggtcctgtgc tggagtatat gacagctgcg gtacttgagg    3240
gcttcattgc cagaacacat tatatacagg atgtcagagc taccagtgtg ctgctgggag    3300
aaaatgctgc aaaattcatc ttttggagga ttgagcatcg aatggtatct tcattctaca    3360
ttcgctacga tgcggcatca acaaggcggg tgggagttcg catcacacca gatcaaggtg    3420
gggtcagaat tccaaaaaaa gatgtcacag gaactgggga gacccctaaa acagttgaga    3480
gacacccagg tgaagagtcc aagttttgga ctggatacga agattttgga attgctagtg    3540
cattggtgag agtagactct aacaatgtgc atgaaagtgg aaagaaagag aagactccag    3600
aaataagggc ctatcctgaa gaacacccat gcggaatcca ctag                     3644
```

<210> SEQ ID NO 2
<211> LENGTH: 1016
<212> TYPE: PRT
<213> ORGANISM: Homo sapiens

<400> SEQUENCE: 2

```
Met Arg Val Leu Phe Asp Glu Ser Val Leu Pro Pro Thr Val Tyr Phe
1               5                   10                  15

Lys Asn Cys Ser Ile Leu Phe Leu Ala Ser Leu Gly Ala Phe Gly Val
                20                  25                  30

Leu Thr Gly Leu Leu Val Trp Ser Phe Met Gln Tyr Met Glu Ile Val
            35                  40                  45

Ala Asn Glu Tyr Leu Gly Tyr Gly Glu Glu His Thr Val Asp Lys
        50                  55                  60

Leu Val Asn Met Thr Tyr Ile Phe Gln Lys Leu Ala Ala Val Lys Asp
65                  70                  75                  80

Gln Arg Glu Trp Val Thr Thr Ser Gly Ala His Lys Thr Leu Val Asn
```

-continued

```
                85                  90                  95
Leu Leu Gly Ala Arg Asp Thr Asn Val Leu Leu Gly Ser Leu Leu Ala
            100                 105                 110
Leu Ala Ser Leu Ala Glu Arg Leu Thr Ala Glu Leu Leu Arg Leu Leu
            115                 120                 125
Cys Ala Glu Pro Gln Val Lys Glu Gln Val Lys Leu Tyr Glu Gly Ile
            130                 135             140
Pro Val Leu Leu Ser Leu Leu His Ser Asp His Leu Lys Leu Leu Trp
145                 150                 155                 160
Ser Ile Val Trp Ile Leu Val Gln Val Cys Glu Asp Pro Glu Thr Ser
                165                 170                 175
Val Glu Ile Arg Ile Trp Gly Gly Ile Lys Gln Leu Leu His Ile Leu
            180                 185                 190
Gln Gly Asp Arg Asn Phe Val Ser Asp His Ser Ser Ile Gly Ser Leu
            195                 200                 205
Ser Ser Ala Asn Ala Ala Gly Arg Ile Gln Gln Leu His Leu Ser Glu
210                 215                 220
Asp Leu Ser Pro Arg Glu Ile Gln Glu Asn Thr Phe Ser Leu Gln Ala
225                 230                 235                 240
Ala Cys Cys Ala Ala Leu Thr Glu Leu Val Leu Asn Asp Thr Asn Ala
                245                 250                 255
His Gln Val Val Gln Glu Asn Gly Val Tyr Thr Ile Ala Lys Leu Ile
            260                 265                 270
Leu Pro Asn Lys Gln Lys Asn Ala Ala Lys Ser Asn Leu Leu Gln Val
            275                 280                 285
Ile Asn Met Ser Leu Val Leu Gln Tyr Gln Val Ile Glu Ile Leu Gly
            290                 295                 300
Asn Tyr Asp Leu Phe Glu Ile Phe Ile Asp Ile Gly His Tyr Val Arg
305                 310                 315                 320
Asp Ile Ser Ala Tyr Glu Glu Leu Val Ser Lys Leu Asn Leu Leu Val
                325                 330                 335
Glu Asp Glu Leu Lys Gln Ile Ala Glu Asn Ile Glu Ser Ile Asn Gln
            340                 345                 350
Asn Lys Ala Pro Leu Lys Tyr Ile Gly Asn Tyr Ala Ile Leu Asp His
            355                 360                 365
Leu Gly Ser Gly Ala Phe Gly Cys Val Tyr Lys Val Arg Lys His Ser
            370                 375                 380
Gly Gln Asn Leu Leu Ala Met Lys Glu Val Asn Leu His Asn Pro Ala
385                 390                 395                 400
Phe Gly Lys Asp Lys Lys Asp Arg Asp Ser Ser Val Arg Asn Ile Val
                405                 410                 415
Ser Glu Leu Thr Ile Ile Lys Glu Gln Leu Tyr His Pro Asn Ile Val
            420                 425                 430
Arg Tyr Tyr Lys Thr Phe Leu Glu Asn Asp Arg Leu Tyr Ile Val Met
            435                 440                 445
Glu Leu Ile Glu Gly Ala Pro Leu Gly Glu His Phe Ser Ser Leu Lys
            450                 455                 460
Glu Lys His His His Phe Thr Glu Glu Arg Leu Trp Lys Ile Phe Ile
465                 470                 475                 480
Gln Leu Cys Leu Ala Leu Arg Tyr Leu His Lys Glu Lys Arg Ile Val
                485                 490                 495
His Arg Asp Leu Thr Pro Asn Asn Ile Met Leu Gly Asp Lys Asp Lys
            500                 505                 510
```

```
Val Thr Val Thr Asp Phe Gly Leu Ala Lys Gln Lys Gln Glu Asn Ser
        515                 520                 525
Lys Leu Thr Ser Val Val Gly Thr Ile Leu Tyr Ser Cys Pro Glu Val
530                 535                 540
Leu Lys Ser Glu Pro Tyr Gly Glu Lys Ala Asp Val Trp Ala Val Gly
545                 550                 555                 560
Cys Ile Leu Tyr Gln Met Ala Thr Leu Ser Pro Pro Phe Tyr Ser Thr
                565                 570                 575
Asn Met Leu Ser Leu Ala Thr Lys Ile Val Glu Ala Val Tyr Glu Pro
                580                 585                 590
Val Pro Glu Gly Ile Tyr Ser Glu Lys Val Thr Asp Thr Ile Ser Arg
            595                 600                 605
Cys Leu Thr Pro Asp Ala Glu Ala Arg Pro Asp Ile Val Glu Val Ser
            610                 615                 620
Ser Met Ile Ser Asp Val Met Met Lys Tyr Leu Asp Asn Leu Ser Thr
625                 630                 635                 640
Ser Gln Leu Ser Leu Glu Lys Lys Leu Glu Arg Glu Arg Arg Arg Thr
                645                 650                 655
Gln Arg Tyr Phe Met Glu Ala Asn Arg Asn Thr Val Thr Cys His His
                660                 665                 670
Glu Leu Ala Val Leu Ser His Glu Thr Phe Glu Lys Ala Ser Leu Ser
                675                 680                 685
Ser Ser Ser Ser Gly Ala Ala Ser Leu Lys Ser Glu Leu Ser Glu Ser
690                 695                 700
Ala Asp Leu Pro Pro Glu Gly Phe Gln Ala Ser Tyr Gly Lys Asp Glu
705                 710                 715                 720
Asp Arg Ala Cys Asp Glu Ile Leu Ser Asp Asp Phe Asn Leu Glu
                725                 730                 735
Asn Ala Glu Lys Asp Thr Tyr Ser Glu Val Asp Asp Glu Leu Asp Ile
                740                 745                 750
Ser Asp Asn Ser Ser Ser Ser Ser Ser Pro Leu Lys Glu Ser Thr
                755                 760                 765
Phe Asn Ile Leu Lys Arg Ser Phe Ala Ser Gly Gly Glu Arg Gln
770                 775                 780
Ser Gln Thr Arg Asp Phe Thr Gly Gly Thr Gly Ser Arg Pro Arg Pro
785                 790                 795                 800
Ala Leu Leu Pro Leu Asp Leu Leu Lys Val Pro Pro His Met Leu
                805                 810                 815
Arg Ala His Ile Lys Glu Ile Glu Ala Glu Leu Val Thr Gly Trp Gln
                820                 825                 830
Ser His Ser Leu Pro Ala Val Ile Leu Arg Asn Leu Lys Asp His Gly
        835                 840                 845
Pro Gln Met Gly Thr Phe Leu Trp Gln Ala Ser Ala Gly Ile Ala Val
        850                 855                 860
Ser Gln Arg Lys Val Arg Gln Ile Ser Asp Pro Ile Gln Gln Ile Leu
865                 870                 875                 880
Ile Gln Leu His Lys Ile Ile Tyr Ile Thr Gln Leu Pro Pro Ala Leu
                885                 890                 895
His His Asn Leu Lys Arg Arg Val Ile Glu Arg Phe Lys Lys Ser Leu
                900                 905                 910
Phe Ser Gln Gln Ser Asn Pro Cys Asn Leu Lys Ser Glu Ile Lys Lys
        915                 920                 925
```

```
Leu Ser Gln Gly Ser Pro Glu Pro Ile Glu Pro Asn Phe Phe Thr Ala
    930                 935                 940

Asp Tyr His Leu Leu His Arg Ser Ser Gly Gly Asn Ser Leu Ser Pro
945                 950                 955                 960

Asn Asp Pro Thr Gly Leu Pro Thr Ser Ile Glu Leu Glu Glu Gly Ile
                965                 970                 975

Thr Tyr Glu Gln Met Gln Thr Val Ile Glu Glu Val Leu Glu Glu Ser
            980                 985                 990

Gly Tyr Tyr Asn Phe Thr Ser Asn  Arg Tyr His Ser  Tyr Pro Trp Gly
        995                 1000                1005

Thr Lys  Asn His Pro Thr Lys  Arg
    1010                1015

<210> SEQ ID NO 3
<211> LENGTH: 220860
<212> TYPE: DNA
<213> ORGANISM: Homo sapiens
<220> FEATURE:
<221> NAME/KEY: misc_feature
<222> LOCATION: (44415)..(44535)
<223> OTHER INFORMATION: Can be any one of A, T, C and G.
<220> FEATURE:
<221> NAME/KEY: misc_feature
<222> LOCATION: (106884)..(107279)
<223> OTHER INFORMATION: Can be any one of A, T, C and G.
<220> FEATURE:
<221> NAME/KEY: misc_feature
<222> LOCATION: (217784)..(218607)
<223> OTHER INFORMATION: Can be any one of A, T, C and G.

<400> SEQUENCE: 3
atgagagtat tatttgatga atctgttttg ccacctacag tttatttaa gaactgcagc        60 atcttgttcc ttgcttcctt gtgtgctttt ggtgtcctga ctggcttgtt ggtttggtcc      120
ttcatgcagt atatggagat tgtagccaat gagtacctcg ctatggaga agagcagcac      180 actgtggaca agctggtcaa catgacatgt aagtgttatt gcagggacac agccattttt      240
gtggacttgc tagaaaaagc agtatggtgt ttgcagcagg aaacaaggat actttaaata      300
tttattaatg ttcgcacaca cagctcaggt gttgagcatc caggccaatt gttatattca      360
gtggcaacat acagccagaa gaaagatgtt tagattacaa cctttacctt gaaaagcaca      420
atttatttaa tgcaagagag gcttccataa aagcaaattt tggtaaaatc tattttttgcg      480 tcttttttatt tctgttaaaa tgtcagagac tatccagttt tttttctata aagttgggtt      540
aatcatgatt gcctacctca tagaatctga acatccaga gcatgaaaaa gaaaaataac       600
aacaaacctt atctgatgct gcgaatgtga aacattgga ctgtgagtgt gaggtattcc      660
ttagtcactc aatcttctcc cgttggaggc tcttcccagc cctgctgtcc tgcactccag      720
ctttgatgag tcacagacgt cctgccgtgt gggatgcctg tccgttttct ttgtgtgact      780
ggactggctc ttcatatctg cttgtggagc agcacagta ttctcagatc cagggagaga       840
agagtttatg gcaagccctg ggcactagga agtctctttg aggatgacta ttttcctcag      900
ctgaggaaac gtgcaggttc ctctcatttg ctggccttcc ctctcttctt tataagttga      960
aatcttcaca gagaggatct ttgaagaata ggcctcactt tgaactggta atgatgttaa     1020
ggaacttcaa gtgaaagag aggtttgcct tttttggtat tttatatttt cattattaca     1080
ataatattag aaaataaata ccagtggagc ttgaggagta attcttgggg taaaaaagta     1140
gccatgctgc tcctgcatct gttgttcctt ttgtgctgtg ttcccttttga cctttctctg     1200 cctgcccata tgcactgcag atctgtgctc ctggaagtac tccccctttta atctctggat    1260
```

```
gcctctttgc gctctttctt tcctttatag atattttca aaaacttgct gcagtcaaag    1320
atcaaagaga atgggtcacc acaagtggag cccacaaggt gagtggcccc tgaaagagtt    1380
aatgcttcag ctccctatgg caatagttca cattagggaa gttcagagcc tttgcggtta    1440
agtcatgtgt aattagaatc cacaaaccta ccagcctggc ctgagattgt ggatctttgt    1500
caaccctttt atattcttta ccagcattac aagttaatag agatataata aatacaagtt    1560
ttctggaact ctcttctttt ttttcctatg ccatttaata ccaactaggt ttattactta    1620
aatattattt gaaaagcccc agctatgtat aaattcaccc taggtgtgca tttataaata    1680
agtcaacaga aataaacaaa atgtacatat gtatacatat aaattccata tggcatgtgg    1740
ggctatatta gtttgaacca tatatgattg ccattgtagg tcaaaacaga ctatatttat    1800
agcaaaactg tttagactgt agccatgtgg agccaagttt cagaaacctg ttgagtttca    1860
tatcccggga agccactttc tagtgtatat gggagcaaga ttgcctaaaa tgtgttaaca    1920
catgctgctc atggtctaga ggatgattct aggtgataca caggtcaaca ttttttgttt    1980
cagtagccag ctatttcaca ggtattattg cttacaattg gaaaaatttt ttttgagtta    2040
acattaaaga tgttagttga atatggcaaa aaatgtgaaa atgatatgta atggattgaa    2100
gtttgggaaa cattagaaga cagagaagaa agagagaaga aaaagaggaa aggatcagac    2160
aaataaagat aatgataact tcattaagat aaaatgaaat cataaaggca aaaaatccat    2220
atactgaaaa cataaaaatt accttagccg ttgttgcgca ggttgcagct ctgacctgag    2280
acattttggg aggcactttt caggggcact ccgcattctg aaaatgtaga gaattttcca    2340
aataagaaaa tttgccttaa cgagaattca gggaaagcca ctgacaagct acagacttcc    2400
agctaagtca tgttagttag gatgatgctt gggagcatca gtgatgcact ttcaacatca    2460
attagaaatc tgggaggcaa atggaatgct cgatagtatt catatcttgt ttagtttggc    2520
aaaagaatga aagtttcaat attttgttga aaaatcgttt cataatttgg aaagtgccta    2580
gcacaatgcc tggctcaaag tgagttctca atggctgatc actaccacta ttgtaattta    2640
tgtcattaat cttcctggtt cttcccagcg tgggatcaga agggggagag aatacttggg    2700
cacatggaaa tagaaggatg tatgagaacc aggctggtca tgtagcttga tgccttttct    2760
tcctgtcctg ggcaaggaat ggctacaaga ggttactgtc aagagttcca agtaaggag    2820 agatggactc ctgccatctg taaagaactg gatattttga atgtttaata aaactctttt    2880
taagataaac tttatattg actgcaaaaa ataaaaagga agctgcataa ggcttgatag    2940
ggcataattt ttttcactat tctatgggta aagccataat aaaataaaca acttgattat    3000
attgacaaaa agtgttttata aagatatatt taatgccatg aaaaaatttc agtagataac    3060
attaagaaaa aaacataaga gagagcagct ttaacattat atatagtttg tgcttaattg    3120
tatatgcaca tacattataa actactaagc aaaaaaaaaa aaacagttaa gcctatatga    3180
tcttaagagg gaagcatttt gtcattcaag cagctggtaa tggaaaataa attaatgtta    3240
atgttgaaaa aagaagcttg tagtacttat ataattaaac tttatttttac ttcattttc    3300 agacattagt aaatttactt ggtgcccgag atactaatgt tctattgggt tcccttctgg    3360
ctctggctag tttagcagaa aggtaagtag tgtattctaa tatactttcc agttctgcta    3420
ctatagcaat ttaggtggta aggatgcaaa ataatcagtt actttgtcaa ctacttaata    3480
caatttcttg ataaataagt gtgaaataac atgttgaaga gaatcctgga tagaaggcat    3540
tatttaaaaa tttaaactgg aaaggcaaat tgcagtttaa aattttcttt ttatttcctg    3600
```

```
actggaaata tttagtctttt tcatctaacc ctcagttact tctaatttca aaattaccat  3660
aatatttctt tggcagttga atctttctga ccatcttaat tcattcttac ctgtgaattt  3720
taacatacag aacgttttca aacatctgtg ggctttgaaa aattttcaag aagatctttc  3780
ctcttataaa tgtcatgatt attttaaatg tttttatgac aataagtgga ccattgcttt  3840
tctgtgaata acatatgatt cctttgtttt tttgatctct tctcccaaga taatattgga  3900
gctaggatat taaataaata aatttatatg gttaggcttt gtgtccccac ccaaatctca  3960
tcttgaattg taatccctgt aatccccata attccctcat gtcaagggag agaccaggtg  4020
gaggtcattg aatcatgggg ccatttcctc catgctgttc tcatgatagt gagtgagttc  4080
tcatgagagc tgatggtttt ataagggggct cttccccctt ggctcggcac ttatccttcc  4140
tgctgccttg tgaagaaggt gccttgcttc tcctttatct tccaccatga ctgtaagttt  4200
cctgaggcct ccctagccat gctgaactgt gagtcaagta aacctctttc ctttataaat  4260
cacccagtct caggcagttc tttataccag tttgaaaaag gactaataca tggatctagc  4320
aaaatatgct tttagtaatt gctaatattt ttcaatttat agtcaagaat gtagggagaa  4380
gataagtgaa ctcaacattg tagaaaatct gttgatgatt ttacatgaat atgacttgct  4440
ttctaaaagg taggattgct aacagtagaa aaagacaatg cagtgccttt atttgacaga  4500
tacacttgtt attattttta ttacgtcatg ttatttacat tgtaactgaa tatgatgagt  4560
cagcttggca tttattttct gtttaagttt atataaagaa aatagagcaa agaagtatat  4620
ccatttatgt ttagtcctgc attacttcta gatctgggca tagaagctga tgaaataaat  4680
ttttgtgata tcatttttaa tgttttgttt attgcattta tttatatcct gccttttag  4740
ggaaagaaac tctgaggtgg ctctagtttt agtaatttca aattgtatat tacaataagt  4800
gattaggttg ctaaaatcca tttgcatgaa ggcaagtaaa ataagatagc aactgacttg  4860
ttttgtgatc acctgctacg ataactcaaa atctagagta aaatggattc attttttactt  4920
gaactgcata ttgttctaat aactatccag atagttatta gattgtactt aaatagagtt  4980
gcaatctata tcatttgata tttagttgag taattttcta aagaggcaaa atagataaaa  5040
agaaatctcc agcaatggag ccctgacact taactcatag taaatccttt tggattcttc  5100
ttcaaaactc tcataaaaga gcattaaata tagataatac ttatagactt ggttatctga  5160
acaaacaagg ttccaagctt ggtaccaggt gttgaaaacc aaagatgaat aagttataaa  5220
tatgtagtgt agaagagggt caaacagtgc tataactgat acggtagaca gatgcacagg  5280
gtactctggg aacatggagc agagacttcc caattagaat gtggagtcat gcaaagtttc  5340
ctggaggaaa gagaagatat ctaggcagag agagagagac aacataaaaa cagtatgtgc  5400
ttggacatgg aggcatgaaa ttgggtgtgt tagaggaatg tgatggttgg gcacagcagg  5460
accataagaa caaagtgcc agagaactag aacagatagt taatgataaa tttaaaatgt  5520
agctaacttt gatcagtgtt ttctatatgc caagacctgc tctaagcact ttgcttatta  5580
actcatgtga tctgcacatt aaccctattt ttcccgtatt ttatagataa ggcaacaaga  5640
caccttttatc caggtcatga tggtctctga taaataacga tgtgaatttt atcatgaaca  5700
ttatggggac tcatgggaac attttaagca tgatcaaatt tgttttttga aagatcactt  5760
tgatagcagt gtatgtggga gtgaggtggg ggtgtttgtt tatatccaca cattgagatc  5820
cacttacaac aaagagaggc tgggaaagtt cgtgaaggta agaatacta tttatcaagg  5880
aacatttatt attaatgtca gagcacaaaa tttgggaggg agaggagcca taggtaatca  5940
gctcagggga aaggaatgag aaagccgtat gagaatgaga atattggaga ggtagatgaa  6000
```

```
agagggattt atatcttgag catgacaaag gattacaagg atgggaggag cagtggggtt    6060
acctagctgc ctggtgttca aaagaatccc aacgttgccc aggaaataga aaacactaag    6120
agctcttgat tgacagtgga ggagtgtgaa aagaggagta tgtgtcttga tgactcccag    6180
tcttgtggct tggaagactg aaaatattgt ggtgccatga gacaagatcg gggatataag    6240
gtgaagaata gacctgggga ggaggctaat gactttgagt ttaggggtag tatgagagt     6300
acttgtggaa tatccatgtg gctaaaactt ctggaagtta ggagcaatgc ctgggctgag    6360
atcatgatga cagggttgaa agagtgtttg aaatcatggg aatggatgac accatccagg    6420
aggggagtgt ttagagtatg aaactggagg actaaggatg attctataaa acgtttatca    6480
tcataatatt tcatggcaca gctgaacctt gtgtctttac catcaattta atgcactttg    6540
cactgagtat atagtaactg agtgctttgc ccttaactta cctgcattgt agtgtttttg    6600
acattttcta agaatgtctt attttgcaat tacatagtaa gtttctgaag actagaataa    6660
ggcttttatt attattatta ttatttttt tttttagtct ttagcacaat gcagatgtca     6720
ttgtttgtcc ttgataccta tttgctggtc agtaggtttg tttttttgttt ttgtttttgt   6780
tttttaaaca gagtctcgct ctgtcaccca ggctggagtg cagtggcaag tgacctcggc    6840
tcactgcaac ctctgcctcc tgggttcaag caattcttct gcctcagcct cccaagtggc    6900
tgggattaca ggcacacacc accacgccct gccaatgctg gtcagtaggt ttttaatcag    6960
accaacgatg atgcaacgag cctataattt agaacagtgg tctgcaaact atgacctaca    7020
gtctaagttt attccactgc ttattttgt aaataaagat ttatttttaac ataggatgc     7080
gaatttattt ttatatgttg tctatggctg ctttcatgct atctcagcat agctgagtag    7140
ttgtgacaca gattgtacag ttagtaaagc taaaagtgtt tggctttgat cgggctcctt    7200
acagaaaatg gcacattgac ccatgactta caaaatgtta gggttatatt tcatgcactg    7260
atgatagctt tagtcttaat gtaaagtaat caactcatga tgctgtgatt ctcaccccac    7320
cctctgtacc cctttcagac taacagcgga gttgctgcgc ctactttgtg cagagcccca    7380
ggtgaaagag caggtgaagc tctatgaggg gataccggtc ctcctcagtc tgctccactc    7440
tgaccacttg aagctcctct ggagcattgt ctggattctg tacaggtttt gtgaggaccc    7500
tgagaccagc gtgaaattc gcatttgggg aggcatcaaa cagcttcttc atattttaca    7560
agggtgagta aaagtgggct ttggcctact ttgccctgtt tgttgaagtc tggggactct    7620
gtgacaagat ggcagattgg tgtgtgtcac ctcattccct cctgctttgg gatttctttg    7680
gtaattcatg ctttccaaag tcatctagac ttgtcacaag catgttctaa atcaatgtca    7740
ggggcattca tcttttaaat tccttgggga cccagatata tttatctttg catcaccaac    7800
ctccagtaca gtgctgggaa tgtagaaggc catcaatctg caaatataat gaaggctgaa    7860
tggaaatcca gtaacctaaa aaaacccttt gtcttgccac cttttccttg aattagtata    7920
tgcattttgt cattccaagt ataatgatta ctaatatttt cctaaaatgt tgtgtgtgc     7980
acatatgtta ttatctataa agagaaaaca aagcctatat gaaaggagca ggtgtacaat    8040
ccttgttttt gaaagatgat atcattaatc aagtggttgc catgttacta actctagtcc    8100
agttctctac ttttctctct aatcttcatt acgtcctct aaggtgggca ttatctctct     8160
tttaaaagta gaattccagt gacattctaa gtcaggagca cggagaatgg atagttttgt    8220
tcccaattga aattctctag aagtacgttg caaactaact tctgtatttt ctgaattaaa    8280
tagattgaag tatttaataa taatatcttg tggtaccatc catgggaaga ttctattacc    8340
```

```
taatattgtt ataaagtata attcagttct atgggtgctg aaccaaagtt aaaaatgagt    8400
atgtctcctt gaactggatc gtctttatga tctgcagtac ataaataaag ctcattctaa    8460
taaaagcaga gggacttatc aattttcata taactagata ttatcaaatc aatgttgtta    8520
tgactttgta tttgttatgc ttccagcgat attgcagaac tgtgtgttac caacttcatt    8580
ttctcttaag gaacattcag aagcataaga atagactgta cagacatgaa cagtagcttt    8640
gttaacaata tttgtcatta cctaaacaaa ggaaaaattt atagactgtt gacaacctac    8700
ttgcttcatg aatgtgacat aaaaatatca attactttat agtataaatt ataagtcatt    8760
cattagtgct gtgacataat aagccagccc cttggtcaaa ataattacaa ttgccaaagg    8820 tttttttattt aggtttgcag gatgacgatg gtaatgatga tcatggtggt ggttattctt    8880
tattattgga caatcatacc tattataata ggtatgggtt gccctcttgg agaacagcta    8940
ttttcataag gataaaatga aattctgtaa tagttaagca gaatttcaaa gacaaaacct    9000 gccttttttct catatagaat tgaatctagc tttcttcttt tgctgaagtc ataactatcc    9060
ttggtaaaaa agaggtcttt cacatctaaa gtatcatttt ccagtccatt ttgatggtgc    9120
aatgttagca aacttttccc caggacaatg acatatttta actcttattc tatgttaaat    9180
atgtactggt gctttgggag aatttattac cccagctgga taaacagtttt cttttcagag    9240 cttgtgcctg accctgggct gactgcagct ggcattaggg gtagacgttt ccaggctgtc    9300
ttgtggctgg agtatgaaga acactgtttt cagggcagtt tctgggacac tttctcatgc    9360
ctgttcacct gccatctcaa actcaaaggc agctcccaaa gggctctctt gatcaggtga    9420
agagatccct acaatttgag ttttaagaga atcatgttga cagataagat caccacctgt    9480
gactgtccct aggcctagct ccattacctt ccccatgctc attgcaggga ggacactagt    9540
ggacccagat gacatgagag ggaagtcaag gaaactccat ccatgttaca tttaggcaca    9600
gagaaatcca ggtagagttg ctgctataaa aaataaatac atggaaaaaa atggtaacta    9660
tgtaaaacaa aagggaacaa agcaggtgaa agacagatga agaactatta tggaagaaag    9720
tgtactgagt aaacagaaaa gccaatgctt tatttcatca aagacattaa gcagagcatg    9780
aatttatgaa atgagattaa agatgaaaca aattttttgga cacaaaaaag ggagaagact    9840
gcagagctag gaaagaaaac aaggactgaa taacacctac agaaccgata aattgctaga    9900
tcaccagaaa aaaatggaaa tagtaaaatg tagggtaagc ttgaaaaaaa ttacatataa    9960
tgcagaagaa aaagaccaat gaataaaaga aattagaaaa tgaaagatac gcccaataga   10020
agaagacagg ttttcaacat gtggacaatt gagatccctg aagtacagag taaaatgaaa   10080
agggccaaac atttccaaga tatgataggg gagaactttc ttaaaataaa ggaagattga   10140
aagttcatgg aaaaagaaaa ctgagaataa tcaagactga gatgtattca ggtgaatcaa   10200
ctccaggaaa atagaaaatt caaaaacaaa ggtggccatg tagagcagtg gggagaggac   10260
acttttcaat aaatagtgag aaatcagtaa ccataaaaaa atggttctta ccacacacca   10320
tacacaaaaa tcaattccag gtggattgga aagtgaaaca ataatgatgc cttcatgacc   10380
tgagggaggc aaagatttct taaatgtgac acagaaagga ctgacggtga agggaaattg   10440
ataaatggtc tatgcattaa cttttctttt tcagagacag aaattttgtt tctgatcact   10500
cctccattgg aagcctgtcc agtgcaaatg ctgcaggccg aatccagcag cttcatttat   10560
cagaagactt gagccctagg gaaatacaag aaaatacttt ctcacttcaa gcaggtattt   10620
atgttttatt atttgatatg ctataattta ttgtgttgta ttattattca ctatcataga   10680
ttagtgtagt agtgttaagt aggcaaaatt tagaagttta caaaaatgta aagtgaaatc   10740
```

```
cacatggatg ccagaaactt cttggtccca gtgttggact tgcagatgaa tgatacaaca    10800
aatgtttctt tgtcttctgt gttctgaacc tagcaagaga taaacacaga agtcagagat    10860
aaggatacaa aacgttagct ttattatgag gaaagctgga ttaggggatg cagcttgatc    10920
tgtggccaga atcatgcttt ctagaatttt ctagatccca gggcaccta cataagggg     10980 aatctacagt gcacacactt gtctcaccag gtgcaagaga gtaccttccc catgcttctt    11040
gagctccaaa gagaagactg aaagatgctg ccctgtctag gattttcaca tgcaagcagg    11100
agcagcaatg catcaatgct ttttggcagg gccaccttga gcagtcatgc agtttgtgcc    11160
ctgcctgggg gcacctggcc tttgggacaa ctggagctac agtgccgtct gagtgctatt    11220
ggccaatttg ggtgccctag agcggcccac agaaagggag cagagaggtg tggtatgggc    11280
cagcaggaga cagggagact ctgaggggaa agagcagact gcaggagagg gaatgaggga    11340
gtggggaagt gggagagggc aggctttcct tgctgtctac tattttctcc tgaagaatac    11400
agaagatatt tcttcataga tggtgtgaaa acaaggacat aggagctcct cctcaaagtg    11460
ccatttctgc ttactctgaa aggccccctgt ctcagtacaa ggtcttgtgc tgggggttta   11520
ctgtttgaag actccccaga agtctaatcc agtggaatct cagagctctg agtgtttcta    11580
gcaatcattc aaagagtgga tgagattgac ggtgatagaa ttcagaagaa cagttactta    11640
gatgtggaat tataggagag tgagtgcctg agaaggggca caaggagcct ttgagaactg    11700
gaaatatagc ctacacattc ctctgggtgg aggatggtta cagggcacat agatatgtag    11760
tatctcattg agccttacac ttaagatgtg tttacgttac atagcttatt ctatacccgt    11820
attagtccat tttcacgctg ctgctaaaga catacccaag acagggcaat ttacaaaaga    11880
aagaggttta atggacttac agttccacat ggttggggaa gcctcacaat catggtggaa    11940
ggcaaggaga agcaagtcac atcttacatg gatgatggca ggcaagagag ggcttgtgca    12000
gggaaactcc acgcactttc aatggttttta caaaaaaaac attttaaaaa caatcagatc    12060
tcaagtgaga ctcattcact atcatgagaa cagcacagga aagacccacc cccataattc    12120
aatcccctct cactgggttc ctcccatgac acatgaaaat tgtgggagtt acaattcaag    12180
attgagattt gggtggggac acagtcaaac catatcattt tgctcccggc ccctcccaaa    12240
tcgtatgtcc tcacatttca aaaccagtca tgccttccca acagtccccc aaagtcttaa    12300
ctcatttcag cattaactca gaagtccaca gtccaacatc tcatctgaga caaggcaagt    12360 ccctttgcc tgtgagcctg taaaatcaaa agcaagtcag ttacttccta gatacaatgg      12420
ggtacagaca ttggataaat acagctgttc caaatgggag aaattggcca aaacaaaggg    12480
gggctacagg ccccaagcaa gtccagaatc cagcagggca gtcaaatctt aaagctccaa    12540
aatgatctcc tttgactcca tgtcttgcat ctgggtcacg ctgatgctat aagtgggttc    12600
ccatgatctt gggcagctcc gccctgtgg ctatgtgagg tacagcttcc ctctcggctg      12660
ctttcatggg ttgatgttga gtttctttgg cttttccagg tacactgtgc acacttgtca    12720
gtggatctgc cattctactg gaggacagtg gcctgcttct tacagctcca ctaggcagta    12780
ccccagcagg gactctgtgt gggggctctg accccacatt tccttctga actgccctag     12840 cagatgttct ccatgagagc cccgcccctg cagcaaactt ctgcctgggc atccaggcat    12900
ttccatacat cctctgaaat ctaggcagag gttcccaaac cctaattctt gacttttgtg    12960
tacaagcaga ctcaacacca catggaagct gccaaggctt ggggcttcca ccctctgaag    13020
caacagccta agctgtacct tggccccttt tagtcatgac tgaagtggct gggatgcagg    13080
```

```
gcaccaagtc cctagactgc gcacagcaga gggaccctgg gtccagtcca tgaaaccgtt    13140
tttccctctg aaacctccag gcctgtgatg ggagggactg ccacaaaggt ctctgacaca    13200
ccctggagaa attttctcca ttgttttggg ggttaacatt tggctcctca ttacttatgc    13260
aaatttctgc agcaggcttg aatttctttt cagaaaatta gattttcttt tctattgcat    13320
tgtcagatgg caaattttcc aaactttat gctgtgttcc tcttttaaaa ctcaatgcct     13380
ttaatagcat tcaagtcacc ccttgaatgc tttgctgctt agaaatttct tctgccaggt    13440
accctaaatc atttctctca agttcaaagt tccacagatc tctagggcag gggcaaaatg    13500
ccaccaatct ctttgctaaa acatagcaag agtcaccttg gctccagtta ccaacaattt    13560
cctcatctcc atctgagacc acctcggcct ggatttcatt gtccatatca ttatcagcat    13620
ttggtcaaag ccattcaaca agcctctagg gagttccaaa ctttcccaca ttttcctgtc    13680
ttcttgtgag ccctccaaat tgttccaagc tctgcttgtt acccagttcc aaagtcactt    13740
tcacaatttc tgttatcttt tcagcaaagc ccgactctac tggtaccaat ttactctatt    13800
agtccatttt catgctgctg ataaagacat acctgagact gggcaatttc caaagaaag     13860
gggtttaatg gacttacagt tccacatggc tggggaggcc tcacaatcat ggcggaaggc    13920
aaggaggagc aagtcatatc ttaagtggat ggcagcaggc aaagagaggg cttgtgcaag    13980
gaaactccca tttttaaaac catcagatct tgtgagactc attcactatc acaagaacag    14040
tgcaggaaag acccaccccc ataattcaat cacttcacac cgggttcctc ctatgacatg    14100
tgggaattgt ggggattaca attcatgatg agatttgggt ggggacacag ccaaaccatg    14160
ttaataccta ataaaaatg gaaaataaa aattaaaaac ataaacggtt aagagtaggg      14220
tctgagtttt ggctccaccc tcattgatgg ctatatggcc ttgggaaagt tccttaattt    14280
ctccaagctc cagttttgct tatgtaaaat ggtgatgata atcatggtat caatgataga    14340
agatcattgt gagaattatg tgggaatata tgtaaaatct tcagcacagt aaaatggaat    14400
tatcctttat aggagctctg tgctatagag tctggcatac ttctgagagc acaagtatct    14460
cagtgcaaaa taccaccaaa ggctgccaca gtggctgtca ggaggcaaga gtggctgctgc   14520
ttagggctgg ggatttaacg tctggcagac tggggctgca ctcctggtca tttccactta    14580
ctggttgtgt ggcctagtct agtaactctt tgaaactgtt ttctcaccag taacagtggt    14640
aatcacagtg catactctta ttataaggat tgagttgaat aatatattta aagcattctt    14700
ttatttatca accattatag atatatttgt tgagcacctg ctaagtgcca ggcatgtttt    14760
gggcactggg gattacaatg aaatggacag atgcaatact tgcctcctgg tacgaagaaa    14820
gtgctcaata aatggttgca gtggaataga cacgcacatg aattcatgg ggaggagaat     14880
tagaagccat tacaagtcaa cttctttct tccagagctg tgccaaaagg aaaattagtg     14940
tttcttgaga agttactttg ctaataaaaa tagcaaaata ataaaaatac cctgtggagt    15000
aagagtattt atgtgatagt atatttattg taatgatgca cactatgcat ttgattgttg    15060
tcattccagc ctgctgtgct gccctcactg agctggtgct caatgacacc aatgcccacc    15120
aggtggttca ggtgagagca ctccttctca aggtcaggtc tccataacca ttcataatca    15180
actcaccttg tggtgcagtc tgtatcccag aacataggtt ttgggattcc catcatgtga    15240
ttttaaaact attttaacat ttctcgttta actaataaag ttccacttta tattcttctc    15300
cttcctcctt taactcattt gacttaaaaa ggactgacat gtggttaatt gatgtttctt    15360
cattatgtta tgtgcggtcc cttttatttt ttctttctaa aagggatact ctgaattgca    15420
ttaattctgg gtgtatagaa taccataagg taaggacagc aatcattttg attaagacta    15480
```

```
tgcatcagat tattaagtta aaaatgatga ttgagacaca gcaaacaaaa tatttattgc   15540
caagaaactg attttgcaaa gtataatcca ctaattaatc tactatatgt acagctatat   15600
atacatgttt gtgtgtgtat gtatatatac acataaatat aaattaatag atctatatta   15660
ataaacatac acatgtatat gtacaaccct tgtatgggtt tctatcacaa aagttacctc   15720
ctacttagtg aattttacag agaaaacatt tttggttgtg tcattacaat atccaacttc   15780
aagatccgta catgttagta agggatcagc tcatcaatga ttaaattagg acataagaga   15840
aactcagcag atcaggggt agttgataga acagggcatc tgaagttggc cagattgagg   15900
ttcaattcct ggaattatta cttcttggct tggcttctaa aaaataatg tatccactct   15960 aagtattggt tttctcatgt ataaaacaag gaaattatag actaatttca cagagttgtt   16020
acagagatta gatgcaataa ggcaaataaa gctctttgca gttataatat gaatgcctgc   16080
acacagtaaa gatcagtaca ttatatattt actagataat agaaaagtgg ctgtaaggta   16140
ttattatttg ttcattcctt catgtgtata tttcaattaa aaaatctaga aagatgtcaa   16200
gattataata aagacataaa ttaataactg gaatataatt tctcccttta tggttgtggt   16260
aattaaggat ataaataaat atcaaagata taaatctaag atattgggac acctttactc   16320 tgtcccttt taatctctca ttgtttttaa ggtatttgaa tcactttacg tttatgtact   16380
ttattataat cttgattctc cacagacagt tgaaatttta agattgtagt tgtactcttt   16440
ggtgtttaaa agtgttatgt tgacatttta aatattgtcc tgtaatgttt acttcaaggt   16500
ccatagttat actaatattt cttctttgat attaatgttt gagattgttt atttgcctct   16560
ttttgcttgt gtatcactac agtgttgtca ctcatagtat gaccccttta ttctttcagg   16620
aaaatggtgt atatacaata gcaaaattaa ttttaccaaa taagcaaaag aatgcagcaa   16680
aaagtaatct attacaggta ataaacatgt ctcttgtcct tcagtatcaa gttattgaaa   16740
tcttgggtaa ctatggtaaa atgatctatg attttttagaa tgtttaggtt agtactggtc   16800
cctgtactga ctatgaggga aaaatatctg gcaaggaaga ctggcatgga atcaaataat   16860
attaaaacaa tacagaaggc ttaacagtgg tttctctgtg tgggagaatt aggtgattta   16920
tttaggtgtt tctttgctta tcaataagtt ctattttttt aaaaaaatat gcattcctta   16980
tgtatcagaa tataacaaca gggggaaaat tatttgccat catggatctt gatgatgag   17040 aagggacttg ccaagtggat aaggggatat tgggtggggc accaatggca tctgctgcag   17100
ggtggaaggg cattccatgc agagggaaca gcatgcacca agtgtgaaag ctgtgagctt   17160
agagtgtgct gagggaagtg tgagctgctc agtggggttg gggtgtgtgg ttgtgggggc   17220
cagtgctcca gcagatgagg cctcacatgt aagaaagggg aacagttagg caggttctac   17280
attcattttt gaggagtggg tgttgggaga gctgagtaaa gggtgagctg ctcagtggaa   17340
ctggggtgtg tggtttgggg aggcagtgct ccaggagttg agggctcaca tgtaagaaag   17400
gggaacagtt acgcagggtt ctatgttcgt ttttgaggag tgggtattgg cagagtgggg   17460
gcggggggca gtggcgctaa tgtcaaaatc tgatttaaag ttagtctttg caatagttgt   17520
agctcatctt tttttttccc ccaagtcatt ttgaaaagga agaaagaaac aacctttgtc   17580
tccaatctga tttaagagtt atcatccaaa atgatggcca aacccagcag actctttcgg   17640
ggtgtctctg tgctggcagg caggggtttt tggagcgcta ccaacgggaa ggtgcaggca   17700
tgggacttga tttcttcagt gcatcacaga tatatgacac tgtgctgtta aacagataaa   17760
gacaaaccca tcctgcagag acatttcgtt aagccagtag agggttttt agaattccag   17820
```

```
atggagggct tttgaggaat atgcatgctc tcccttctct acagtctcca ctgctctcac    17880
ctggctcctt catgtcattt tgttaccggc ctcacctctc tgggcaattt tgtatgggac    17940
ccttctgtgt tcagatcact gattttagga aatgatccca gatttgattc accaaaccct    18000
gatcactcca atggtggcct attgtgcagg cacagctgca ggctgggcac actctttttt    18060
ctcagtactg caaaatgtca gatgtttatt tttcctaggt aaaggctcac aggcctcttt    18120
ctgagcgttc tagggagtta gtgtagattg ttctatttgg ggaatgctta agactcttta    18180
ctcaagagac caatttgtca agtttgaatc cagtgtgcct gcggctattt ttatatgtca    18240
tcatttctag tgtttatttt ctcacagaaa ccatataaat attgaggtat gcatagcagg    18300
ctagaaacaa aataaacctt gagctcctgg aaatctttag acatttggtt ttctcagcat    18360
cggaatttta tttcttgtct ctgtactcat tttgtacttt ctagaaagaa attaatgacg    18420
agtaccaagt gaagcaaggc caatattccc agcattctac aacataaaca ctttttaaat    18480
acaggaatga ccccaggtgt tggtgttttt tgttttcagt tagaagcttt ggctccaact    18540
tggaccagcc acttacaata aagtcacgtt aatgtttact tcctgttaat tctttcctga    18600
aaatgtttta atttgttgag ctaccatttg agaatcacat atcctttgt tttcagtgt    18660
tatgctttca gagccttgag atttctcttc agtatggaaa gaaacagacc actctttaaa    18720
aggtatgagg ttagagaaat ataagtgatc attaggttta ggagatcatt agattgaact    18780
gttttcacat acttggctta gatgcaacag aaggaaaata atgcgtcagt atgcaaacca    18840
tgtgtcttca gatttcttat ttcacagata gaagtgagct actgtagtga ttcagtatcc    18900
agccacactg aatattaaca gaatgatgat gaaagagcat aaattgctat atcaatacaa    18960
ctccccttaa ttacatgtga ctgctgtgat tttagctttc tttttgataa ttaaagatat    19020
taacattttt aaaagatggc attaaaatat gagcttcttt ttttccagct agaaatttga    19080
aagtcaatcg ggtaatttca ctttaatcaa agggaattta atcaaaggga aaacaaactg    19140
ttttttttgtg tgtctttgat ggtgtaggag ctcatttgaa ggggaggctg atgttctgg    19200
ggtcaagata ctgtgttggt gagcctgacc aaaaggtcac catttcggga agcaaacact    19260
ggttccctca gtggtgttct gcacaccatt tagttaggtg ggttagccaa aatcataggc    19320
ccaagttttt attaaaattt tgttaataag gcagaataga cataaagtat tgagttaata    19380
tagtattttt tgttcagaaa gcatggagcg tcacttttcg gccttttggc tgagatcaag    19440
tgcagaaagc atgagcattt tatgttgtt actttattc tatactgttt ggatttagag    19500
gaaaataaag taaaattagt tctcttttt tttttttttt ttgacaaagg ctcatcctgt    19560
tgcttctcct gcctcagcct cctgagtagc tgggactaca ggcatgcacc accacacctg    19620
gctaattttt gtattttcag tagagatggg ttttcaccac gttggccagg ctggtcttga    19680
actcctgacc tcaggttatc cacccgccgt ggcctcccaa agtgttggga ttacaggcgt    19740
gagccaccac acccagctac ttattcttta taatcttttca tttcagagct ctaaatcatc    19800
cctttttagtg aactcaaaga tttaaaacc ccttgaaacc agtgtcttgg gaatgatgaa    19860
tgaatctctt tatttgtttt atttttcatg taccagtatt tttattttca tgaaactttt    19920
atttaaaagt tgggttagta tttacttctt actaaaatct gagttaaatg acatttgtga    19980
aagtgctcca cacccaaaaa aacacccaat aaatgtttcc ttctaatgta ttcaatgcct    20040
ataccccaa atatcttaca agtaagattt ttgtataatc tgtatcatat ctaatttaa    20100
attatggtaa aaatattaac atgccatcta ccttcttaaa attttaagtg tacagtgtta    20160
ttaactgtaa gcacaaggtt gtacagcaga tctctagaac tttcttctcc atttgttttt    20220
```

```
ttcttacctc tcaaaaactg taaatagtgt attttttcga gataagttgg ggaatattat   20280
ttccccaact tgttgataa ccaaaagaag ttaaatttgt ttcatgtaat taatcagtga    20340
gtgagctgca ttcaaaaggg aagtaatggg ccgggtgcgg tggctcacac ctgtaatccc   20400
agcactttgg gaggccaaga caggcggatc acgaggtcag gagatcgaga ccatcctggc   20460
taacatggtg aaaccccgtc tctactaaaa atacaaaaaa ttagccgggc atggtggcag   20520
gcacctgtag tcccagctac ttgggaggct gaggcaggag aatggcgtga acgtgggagg   20580
cagagcttgc agtgagctga gatcatgcca ctgcactcca gcctgggtga cacagtgaga   20640
ctctgtctca aaaaataaa aaagggaagt aatgatcaac tgtgtccaag ttctacttta    20700
agtgtgtgta atattctctg tagacttttc cccacagact tgtttgagat cttcattgac   20760
atagggcatt atgtacgtga tatcagtgct tatgaagaat tggtatccaa gctgaattta   20820
ttagtggtaa gtcctgagtt ttcaatattt tggcaggctg ctatgtagtc aggatgtaat   20880
ttatcacaga aacccatttc ctttttatat tttgattagg aggatgaact gaagcaaatt   20940
gctgaaaata ttgaaagcat taatcagaac aaagctcctt tgaaatatat aggcaactat   21000
gcaattttgg atcatcttgg aagtggagct tttggctgtg tttacaaggt gacttccccc   21060
ttggggaaca tttctgatac tcccaaccaa accggatgtc acacttgcac accgatattc   21120
aattgagtta gaactcttgt cattgaaaaa tagcaaacag atatgaaaat tagaatgatt   21180
gttttttgtcc aacagagata gccacactaa tattgtttta gctgtaagct ctagaaattg   21240
gccactgact ttttaagaca aaaggcatta ttaatctctc acaaaggtat tcaaaatagt   21300
ttctcccaat gcatgatgca atctctaaat taaaaaatgc tactaagtat tgcagactga   21360
cccaggggat accagtgttt tgagctgagc ttaatgtaaa tacagctgga actttaaatg   21420
ctctgtgact tatttatatg acttagttac tcatgtgact tgttagtct atctctttct    21480
tcctcttctct atcttctcct tctttaccct gttccttttg ttgttgttgt gttttttcttt   21540
atttttaggtt agaaagcata gtggtcaaaa tcttttagca atgaaagagg tcaatttaca   21600
taacccagca tttgggaagg ataagaaaga tcgagacagc agcgtaagga atattgtttc   21660
tgaattaaca ataattaaag agcaggtaaa tgttttcctt gtttctgaag atgtttttct   21720
taaatacatg tcattgcaag aaagtagagt tgtggtgctc ttgtccatgc tgcttatgaa   21780
ctagttccat gtgaaataat tgacactgaa gcagtgatat ttttgccagc ttttttccta   21840
aggcttgaca ttgaagcata aaacactgtc tggagtttat atcagggtca tggatgcaaa   21900
acaatcggat ttacagtaca gaatgcatca tatatgagga atcctttct tttcattgtg    21960
agcatatcta ttctttctc cttatatttt aggatatttg gttacttagt tacatacata    22020
gaaatatgac taagagtttc ttgactttg ccaaatggaa ccaagctgtt aacattcctc    22080
aaatatgact ttattagatc taaaatgtag attttcaagt tgggttatta tgtattggca   22140
tgagcagaat actctgatat aatgtaacag ctcaattaac tctcattatg aaagtttgtt   22200
tgaggaggaa gaataaacat ttcaaagaga aatggaattt ctttgtgtga tccaagaaca   22260
cattggtttc tttttcagcc ttccttattt gcacattcat cacgaatact gttcattat    22320
aattcctgtg gtgcactatc agctttgctg cttttgtcct ccactggtca catttgcata   22380
gcatctgtgt tgggatgtaa caaattccat aaacaaggag acctttgttc ataaaaatcg   22440
atagttctac tccagtgtgt acattatagt aaatattatc attaattgtt tattttatag   22500
ttgattttat atactaatag actagacttt aaaaagtttg ttcatgtgta gtttgttcat   22560
```

```
gtgtttgtat ggtcatctag ccttccacag tgtgctcttt cattgtagca caaggctaga    22620
acagggcttt tgacctaagc cagtccagtg ttttcatctg gacccaaatt tggttttagt    22680
ccttgtgggt gagccaggtc cagaatatgg ttctggttgg ttacctggtc acatattgct    22740
tacgatctgc tggccacttg ctagttgatg aagtagatta tttgttttag cacatttcct    22800
aagaaaagaa actgtcaaac cagggtcaga taggaagcat atgcttgggc tttgaggtaa    22860
ctcaaaattg ccctctcact agaggatcaa actgatggaa aggatgataa cattgagtcc    22920
ttaaaggagg aggtagtggc aggcagaagc aaaacaaatg gggctagaat ggagagtaca    22980
ttaagattaa cctgcattaa caaagaggat cccaaatgca ggtgcttaga aagaggactc    23040
acagtacagt gggttatttc tcttcacgg aacaatccca aagtgagtaa accaggttga     23100
aggtgttctc tgctccatgc gatcatttgg ggatgcaggc ttttttctct cttcttgtgc    23160
tgttaccttc tagtgcattg tcttcatctg tgtggttgaa actgccatag ccatgctcac    23220
atccaaggtg agatgaggag gatcatggag ggctattccc aaggtttaga gttcacacag    23280
gaagcacaca tgcttcctct catattccac aggtcagaac tgagtggtag cctcaccccc    23340
agcttcaagg gaggctgaga atcttctct aactgggaag ccatgtccag cttcaactgt     23400
attgcaatgg gacagcaggt ttttggtgga cagctagcaa tctcccttca aaaagacttg    23460
cagaaagacc aaaaagagat gcaagcaagc catttgttga tgtgatggtg actgttctaa    23520
gacaaatttt atctagaaac tcaaattata agcaaaaact acaaaattat tagcattctt    23580
ctagaaaatg atcttttta attaaaaaat tagaaattcc actaacattc ttaacttata     23640
tcaaagagaa attgcaccat tttttaaaaa cggtgaggaa gactttattc aatactattg    23700
caatagaagt caaactattg taatagagga gagagattga acccaactct gaattcgagg    23760
actggacagc tggggactca gagccaatgg tcagggtgag ggagggtcag tggatggaag    23820
tttactaaga ggaacttggt tagatatcaa gggtgagtgg atgagaaact taattggatg    23880
tcaagggtgg gaaattttc cataaactga cttagcagga tataagttgc taaaactgac     23940
agaccaagga tgaggcctag tcacgaagag gactcagagg agcctgacta aagcttggtt    24000
aagtaggaag tccttgtcaa ctgttattat gacttaaact gagtcgactc ttagattatg    24060
ttattttcta ctaatcattt tggagagcat agaaagacag aaatagtgta aataggcaca    24120
aactttccat aaatatttag atggtagaga gaggtaaaga acaatgaata tttgtagtca    24180
acagaagtta ccgcatttca ctttctcct ttatacagtc tgtgtgtcgg gttgtgacaa     24240
ggtgtgctaa agaaattctt aaggttcctt ctacctctat agttctcttg gttaagttcg    24300
atagtaaagt taggtgatag aacgttttta atttattta ataaagctat agaggattgc     24360
tattttcaga tcagtttata agcaacaagt ttttaaaaat cacaacaatc tcagttcgat    24420
gatatcttga aatgcttagt tttgtaaata aatataattt ctttgtagtt ttcaaatatg    24480
aagtccaact aagtagtcag tgaaaaaact tgtattttga agcagtgcaa tacatgtttg    24540
ttatttattt tcttatagct ttatcatccc aacattgtac gttattacaa aactttctg     24600 gaaagtaagt atgagttttc atgatatttc taaataagga aacattttg tcacatatat     24660 ttttgtatca gaatgtcaca aaagaaacct aatcaactat tttattgacc ttttttgtt     24720 aatatgacag tagatggtct taagcatcac tttcttgact agtgaaacag tgacctagtc    24780
agtcacctga agatagttat aaaatactta gctgcctgtg tgaaaaacgc atgaacaaac    24840
caaaatagtt attgctattc tcatatacaa aaaaatcact taataggatc aaggaaaaag    24900
aaaactaatg gatggtggtt tccttaagaa aagaaagttg ttttttgttga ctcaggtgtc    24960
```

```
attttccatc cccaaaataa gttggagaga gctaggtctt tgagatttct tttacctgaa    25020
gttcaggtaa atgccacaaa ggtggcgatg gagcccagac tgattctggc agccaggctt    25080
gctttctgca ggtatgatgg aatgctgaac tagaaccaaa acagataaag ctaaactcag    25140
ccactctttt ttttttttt ttttaagtag ggcctatgac agaaataata caagtattgc     25200
taagctttaa tgatatgtgt cacatatgaa atgtcgaaat aaatctccac ttgaagaatg    25260
atttaaagag acataaggca atgactgggg cttccggact acctcttttt cagtgctatt    25320
gttatttaag aaaaccttt tgtgtgtgtat tttgccattt gttacaattt tacccatctc     25380
ccttccccta gatgactcag aaaaactcag tgctaaaact catgcagtaa atcctgtccc    25440
cttagccatt tgttcttgat attaaaataa ttttctataa tttagtgtat atcccttcaa    25500
aaaaatcaag gttggcttca gacttgtact gaaatgatat aaattgtctt aatataaaaa    25560
acaaaaacgt tttttactac ctgacagctt ccaaaaagaa ctggaaatgg cggccgggca    25620
cggtggctca cgcctatgat cctagcattt gggaggccg aggctggcga atcacttgag     25680
gtcaggggct cgaaaccagc ctggccaaca tggtgaaacc ctgtctctac taaaaaaaaa    25740 aaaaaaaaa aaaaaagct gggcgtggtg gcaggcgcct gtaatcccac ctacttggga     25800
agctgaggca ggagaattgc ttgaacccgg gaggcagagg ttgcactgag ccaagatcgc    25860
gccactgcac ttcagctttg ccacagagca agactctgcc tcagaaagaa aaaaaaggc     25920 tgggcgcggt ggctcacact tgtaatccca ccactttggg aggctgagat gggccgatca    25980
cgaggtcagg aaatcgagac catcctggct aacacggtga aaccccgtct ttactaaaaa    26040
tacaaaaaaa ttagccgggc gtcgtggcgg gcgcctgtag tcccagctac tcgggagact    26100
gaggcaggag aatggcgtga acccagagg cagagcgtgc agtgagccaa gatcgcgcca     26160
ctgcagtcca gcctgggcaa cagagtgaga ctccatctca aaaaaaaaa aaaaaaaaa     26220 aaagaattgg aaatggctta aaatacata aaatatgata aaatagatta ggaaattgca     26280
ataaagagga atgaaggatg agaaaattaa aaataaagct agaggtagta ttggtacata    26340
aatgaatatt tcttgaaatt atgaaaaatt ggaaacaata taaatgtcta tctgtaggaa    26400
aatgattaaa taaattatgg tatcccata ttgtgcaata ccatacaacc agcagaaaga     26460
atggtatgga tctgtgtgta ctgaaatata aggctgctta atgaaaaaaa gcataaatta    26520
cagaacatga ttccattttt gtcaacattt tctacacaca tattttgtat acatcccaaa    26580
gtttcaaaag acacatatca catcccattg ttaataaacc ctattggttt tagaggagga    26640
agtagaattt actcctttgt tttttggcat ccaaagcaaa aagacaaaca caatcagtca    26700
tgaagttctc tgtatctgta agataaaacc tggagaagtc cagttttgtt ttttttttgtt    26760 tgtttgtttg tttgtttgtt ttgcttttga aaggcataac agaaatttct atcatgtgtg    26820
ttattttcaa ctgtgtcatt gcaagaccat ggcattattc cagtgtaaaa ttctgtaagg    26880
taaatctatc agactatgaa acaatacagt tgaaaatgca attttctgaa tgtctgactt     26940
gatttgagcg taaattttag actactggga ggaaggatgg gcttacggtt tcttcaggga    27000
atcctccatg actggagatc atttacttgt tctctgtggc acctttcaat cattccacat    27060
cctggcatac atagaaaatg atacatttgc cagtgtaaac ttatgctaag gggttgtctg    27120
tagccagaag ataactgtgg ctgggcccca gtttccctaa gacccctca cctccacctc     27180 ttccagggct gagtggatcc atattttagc acatcatccc taattcttta gtgttagtgt    27240
cccgcacaga cactgggaag cttgaactct cattcgtaaa gttttcaag atgcctgtat     27300
```

```
tgagtttaaa tttctgtgac cttttgtgat atttatatag atgataggtt gtacatagtt    27360
atggagctga tagaaggagc cccgcttgga gagcatttca gttctttgaa ggaaaaacat    27420
caccatttta ctgaagaaag actatggaaa atatttatac aggtatgctt ttatcttcat    27480 taaattttc ttaaaacagt aatgttctga gctggcttct taaagacgtg cagtagtcat    27540
ctttggctat atgtatgttg ggggaaataa aatttgtttt ctattcattg tttcaagctg    27600
tgcttagctc ttcgatactt acacaaggag aagaggattg tccatagaga tctgacacca    27660
aacaacatta tgttggggga taaggacaaa gtaaccgtta gtaagtataa agattttaa    27720 acttttaact gaagaattcc tgaatactat cctagagtag tagtgtccag tagaactttt    27780
ggcactcatg ggaatgttct ttgtctatgc tgtccaatac agtagccact agccacatgt    27840
ggctattgag cacttgaaat gtgattagtg tgactgagga aatacatctt aaattttaat    27900 taatttttt ttcttcgaga cagagtcttg ctctgtcacc caggctggag tgcagtggta    27960
cgatctcagc tcactgcaac ctccacctcc cgggtttcaa gtgattcttg cacctcagca    28020
tcctgaatag ctgggattat gggcacccgc caccatgccc acctaatttt gtattttag    28080 tagagacagg gtttcaccat gttggccagg ctggtctcaa actcctggcc ttgtgtgatc    28140
caccctcctc gtcctcccaa agtgctggga ttgcaggtgt gagccccaat gcccggccaa    28200
attttactaa atttaatttt agacatccct atgtgataag tggctaccat gttgacagt    28260 gactagtata gttctaaatg actgagctat attttgccca tatgagagaa tgaagtactc    28320
ttagaatact taagtattta attccaaaat caatggtttt caggttttt cttactgtag    28380 aacactgcct catcaacaaa agcttttatg accaacacat gagcacattg ttttgaacca    28440
ttttaccata gtctgtgcct tatgagtgac aaatgtacat atggagggct ataaatcctc    28500
tagccatttg tatatttcaa catagagttt ttatcacaat ttacttcatc tgtagcaggt    28560
aggcctgatg ttggataaaa tttcgcaaat gagaaggctt actttctcct cccagttgtt    28620
gaattcttac tcataactta aaattaagtt tttagcttag gatgacatat tagctttctc    28680
ctgcctgcct catgaacact tgtgttaccc tcatggactt taatggttca ctaactacaa    28740
ttagggagac accttcctaa accagcagtc tccaaatgtt tttcaccgta acatcccagc    28800
aataaaaatt ttttgagaat acactgccaa tatacatagg cttatgtata aattctatac    28860
atatatatta ctgaacaaag attctgtagt aaataacaaa atctacagaa ataaaacata    28920
aaggaataca tttaaaaata aaaatagagg tcttaatatt tttgctgccc ctactcccat    28980
tgggttgcct tagaaactca gtgctggaga ctactgccat caatgttatt gatgtggaga    29040
catcattgat gtcatatgac aacatatgac agcatctaaa gctgagtccc ttggttttag    29100
aatttcagta cccatgaagg caattccaaa tgtacacatt tgctataaca acatgtgttc    29160
aggaatgatg ataagattta ctgtccaaat tttcgtaagt agaacatcat attaatatat    29220
ttgttgaaaa ataaaaaaca acctacaaca gaaactctag ataaccttca atacaaagct    29280
acttggaaat atttcgaagc caatgcattg tgaaataaaa aaagagaaaa taactgtgaa    29340
tctttatctt ggacacacat ttgcttaatc atttgaaatt aattataact ttgtttacct    29400
taggcttttt atgttttctc tttttataaa ttgaacttat atttcctgaa aattttttat    29460
aatttattta tttgctggaa tgtcaattta taagttaata aggattatta taaattgtgt    29520
gttttaattt tataacaaat agtatatata tataacacag ttatgtatat atataacaca    29580
gttatgtata tatataacac agttatgtat atatataaca cagttatgta tatatataac    29640
acagttatgt atatatataa cacagttatg tatatatata taacacagtt atgtatatat    29700
```

```
atatatatat ataatacaca tttatgtata tatacaacag aacaaatatg tttaatcctc   29760
cttaaatggc tgttcaggcc atattttctg agtaatagcc aactctgcat tttattttcc   29820
tatgaagatt agctgtaatc atttcctttc attacattta aatgtactaa gcttaatctt   29880
ttattgcagt agcctggttt atttttttct aaacttatat ttactttctt taatcattat   29940
cacgcatcaa aatagtttat aaaataaaaa gcttatagag aaaaacagtt ttatgcccca   30000 tcccttgaa actttagttc tgttcccaca aaatggccac gtctccactt tttattcttt    30060
ttcttatggt atttgatttt ctattgtaat gggtgagaat ttagttttct tcttcttct    30120 tccccatcta ctatcctgcc agtacagtta cagcagaatt ttatgttaag tcaatattca   30180
atgtttacat tattgctgct gtgtaattat tgttcgatgt tgattaccta tcctttctca   30240
taggtagttt tgttttctc agagttaatg attgccttct tttttgtttg tgttcccagt    30300
tttctttgta cctattattt acttttctcc aaatcttcca gaagaattat aaaaccctct   30360
cagtactatt ttccacatgg tcaaacatga taagtactcc cactttttgtt ttcctggact   30420 cctcattcct gcagctgctt gttgcagtgt actctgggtt tcactttagg cctgctgcac   30480
agccattatc atggaactat tgtttgttgg tcttccgatt gtagactcca tttcttatgt   30540
tctgtgtctt tttctttgta aacttcccctg ctctgctgaa gtaagtcttc tggtactttt   30600
ctaataaaga gtgctttggg cgttatgttt tttggatgtt cgcttgctac aaatattttt   30660
atgggaccct cttattggac tggtatttgg cttggtgtat gtattctcag atgaaagttc   30720
ttattctctc aagtttaaa ggcatttctc tagtcttctg gtatctagtt ttgctgtcag    30780
gaaatccagt gttcttctga ggcctatttc ttgatacatg aggtatttta tcactctgga   30840
aaatttcaga atgttccctt tatccactgc tttggatggg tctttaaaat tcaatgtgtc   30900
tgtagccacg tgtgctcttc aatctggaga cttaaaattt aagtcctggg aagttttcct   30960
gcattatttc ttcactactt ttctcccctc tgctctctct gttttcattt ttagaatctt   31020
tttagtctta gataccatat gtacaaaatg atctcctaat ttaaaaagta attatcttag   31080
tttttaatgt ttgtctcttt gttataatta tttcttcaac tttcttttcc attccattga   31140
atattaaatt tatattatca tattttaatt tcaaaaattt ttgtcttatt ttgtgtttta   31200
tttttatgga accctgtttt tattctttct cagggtaata tagactttt tttcttagc    31260 atcctgaatt gtttctgcat cttctgaagg tatatatata tatgcatata catatacaca   31320
cacacacaca cacacacaca caccatatgt acatatacac acacatatac acacacacat   31380
ataaaacata tataactaaa cagtagcata tatacatgtt ttattcctgc ttagtattat   31440
ctgtctttct ggctgggggc ttttctcaac tgtcttgtga ccctgggctg gtctctaata   31500
attttgagga aggcatgaaa aaggctgtca gaagcactgc gagttccagt tgaggctgtc   31560
atctggtgcc cttcattata ataaaatgga aattttcctt tgaagactcc aaaatcagta   31620
tctaaacttt gttttttcta gagaatactc ttcaagtatc ttgcctgggg gtatgtgcgc   31680
ctgtttgctg tcattctgag cagcgtcaac aaacgggggct caaggaacca cattcagttt   31740
ataaattttc gtcgaattct accgtgcttg gttccttgct ggtttatttc tttgaaaaat   31800
gaatattttc tgttagtggc agagggtgct tgatttactg gctgtgtgta tgtgggaggg   31860
cacctgggaa cttgatctca attctatgta ttgagctttc tgcttctctt ctcccttgga   31920
tggcaccctg ggctctgcag ggttaaatgg gctcccttaa gccttcctcc tcagatgcat   31980
gggtagcatt tttgctctgc tgagtctgac accatcttct acctgctttc catctgccac   32040
```

```
acatttattg gaatatctca tcctctgttg ttgccaagcc cattctcatt gttcctgtgg   32100
gttagtaaca ttccaaagaa tatccctct cccagctttt tttttttttt tttttttttt   32160
ccattttagg gggtttgaga tttagaggag ataaaaacat atggtcaatt cacctttaa   32220 cccacaacac ccagccaatt tttgtatttt aggagagacg gggtttcacc atgttggcca   32280
ggatggtctc gatctgttga cctcatgatc cgcccgcctc ggcctcccaa agtgctggga   32340
ttacaggcgt gagccaccgc gctcggccta cttccagatt ttaaggccgt ttagctttaa   32400
gtgaagcagt attttcctag tgtcaaataa agaagcagca caggttggtg catactggt   32460 gaggctagca gccttcagac acagaagcta gtgagctcag aatgggatcc tagcctagtc   32520
tagtttctct tcactaaagc aattgtgtgg ttagggcatt catgtactcc cattattttc   32580
agtgactata aaatgatttt atgactgaaa agataatcca cagagatttg atgtcattct   32640
ttaaaaaata ctttaaatat aatagtgctg aaatatttt cagtgtctat ctctattgat   32700
ataatgtaaa tatgtccatt agtctcttat ctttaagagg gattatggtt aaattaaaac   32760
cctgcagcat taatttaaaa gtaagtgtat aaaatttcca tattttagga agtggaatgc   32820
agctgcaatt agtagagcct gtgagaatgg gctggctgct gtgggtgtga aagcatgtca   32880
ccacagaggg gcagccttgt tatgttttat ttttctcttt gcttgcgcta aaggtttat   32940 ttacttccag aaaagaaaca cagaattgcc aaatgatgtt taagatgcat gagacaaagt   33000
gtactgaaaa tgtgatcaga aaaaaagct ttcagaaaac taaaattttc atcttctcat   33060
ttttctcaat ataggtgaat taaatgtttt aagattgagg ttggtttgca cttatttata   33120
gtaagcatgc tggcaggagt ttgctttgat gaggaagcag aatagaaagt actcacatat   33180
tctgctatgc ttggttttgc aaatgctata tatttttaag tctaaatata tttccatttg   33240
aaagactatc ttttgatggc atgtgccatg acacatgttc aggtcttgtt ctccatttat   33300
ttgcagcctt tgaaaccatc caaggaaaca gaccccgatt cagtggtaca tggggtgaga   33360
cacagtcaac atttgcccta aatactgtca cttgccaaat aaggtccata ttgtgccatc   33420
acattacaaa atgactcttg agggaatttg gtaaaactga acttacccct gaacccacca   33480
ttccagattt cttgaccttt tcaaaaaccc ttattttaat gtaaaccttc catgtccgct   33540
tgcctcctct gctttcaaat aaaaaaggaa aagaaaaaac aaaactcatt taattatagt   33600
taatagattt caggcatgga ctttagtaca tgacacagaa ggtcacatgt tcatcttgca   33660
aacaaacagg ctatgtgaat ttctgtttct caagtgatat ttggcacctg ctctgatgat   33720
aacaacaaga aaaacctga ttcagtgtaa agtttatcaa aggctccaag gctcttcaaa   33780
tgttatcaca ggtcaggcat tgctgggata gatataagat gaaagccat ggtttctgct   33840 ccctgagctc acagtcctat ggggaaaacg tctgttattc actcagcaat taccttccta   33900
gctgacacat cctacaagtg agcacagcaa gcatgaagga cataaccct gtcttaatga   33960 agcttataat tctgttacag agtgatgaag gctagaatgt atatgcaaaa tactgtaaca   34020
tgtaataagt aacctgaaat tctcaacagc ttaaaacagt ggcaaaatac agcctaaaac   34080
agtggcaaaa tacagcctgt gggacaaatc aagttgtgac ctattattat atgtcctgtg   34140
agttaagact ggttttttata tttttaaatg cttgttgaaa aaggaagaat acatgacaaa   34200
gaccatatat gttccattta ggcaaagcct aaaatgttta ctatctggtc tttacagaaa   34260 atttttgtctg cctctgactt aacaagactc ctatcctgct aatgctacat gtccattatg   34320
tgtcaataag ggagcttcct ctgtacttgc ttctacatcc cagaggcagg aaagacagaa   34380
catgggaaac catgccgtgg ctcttaaaac ttctgtccca aagtaacaca tgttacttct   34440
```

```
actcagattt cattggtcaa agaaagtcag gtgtagcagg atgtggatgc attcctcctc    34500
cgagagaata tgagtgaata gttatatagt ctatcacagc tatataagca ctggggaaaa    34560
tgtgactaac tgtgccttag ggatcttttg gtgcagagtt aagcaggaag ggtaagagca    34620
gttaatgcag aggcatagca catgcagagg atagagacat gaaggagtat agtgtgtcta    34680
ggaactatca aggtgtttga tgtggcaaga gatgaaggag ccttggtggg tggggagctt    34740
ggtcaaagac ttatcctcag agattttcca gactagaaat tatatgatca gatctgggag    34800
gtagaaggat tattaaaatg gcaggtgagg gagcatgctg gggaaagact ggacccagat    34860
actcagttta ggacatgtat cagttaggat atgttcaggt gcaaaaagcc agactaacga    34920
tggcttaaac catgaggata tttagttatc tcacaacaag gggtctgaga gtgagtagtt    34980
ccagggtggg ttcagcagct tagggtgatc taggcctttc tgtcctttct ttccagtatc    35040
cccagcagat tgacttctcc atatgtttgt catctcatag tcacaggatg gttgccagag    35100
ctccagacat tattaccaaa ttcaaagatg ggaggcaagg tggctgcttg ggtaaaatct    35160
agaaaaaaaa attgtcttct ccaaatgctg tctcatctgc ttttactgtt aaagaaaatc    35220
ttccaaagaa ggtctccatt agccttctta tattgtgttg actgaaacca agtcatgtga    35280
ctactcctca ttgtaagaga gactgttgag gtgagcttcc agcctctata gttggagatg    35340
agaaagggag aggatttggt tgatggtttt tggagagctg gcccacaatg tttgccactg    35400
aaggctcttg cacttttgtc caggaaagtc atgatgtggg ttttttccaat gacagaagga    35460
gaagagaatg tgaaaaaggg gctcaattca gcagttattt gggacctaga attaaaaaga    35520
tttgtcggcc agttaatgag atgtgaggta tgagaacagt tgagaaagag gctgagtttg    35580
tgaagattgc tctgccattg gcagagattt aggtgtaagg ttttggacat gcttagttaa    35640
aatctaatta tgctcttctt ctggttaaaa tccttcaagt aattgcctat aatatttaag    35700
ataaagttta gtttccttat ggcacccaaa gcccctttctt cgtaatctcc tccttgctcc    35760
ttgctctgac ctcctgggac agattgcact ttcctgaaca ggatgtggct gtatgcctct    35820
gggacttcta acatgccatc cctctgcctg gaatgctctt cctcccttct gccactcagg    35880
tcaaatgccc ttcctccagg tggcatcttt gacatccaca tctgatatgt ccagtttctg    35940
ggacccctta gtacactggg cttgcctgtc tcatagcaca tggcacaaag tattgaaaac    36000
actggcttat tgccatcttc tccttgaggt gagagaaatg aactttcttg accttctttc    36060
tctgatagca cttaatattt ttattcacca aatgaataga agaatgaatg aattaatgag    36120
caaatgaaca aaaacacatc caggtggaaa tattcagaag ccatttaca aatagggagc     36180
agagattgag gtgatacctg ggtttgagat ctccttctga tagccaagat tgtctagaaa    36240
gagtgcttaa aacaagagga gttgaatatt aatgtagaaa ttgcatgcgc acatgggcaa    36300
aggtccaagc agttcccact gtcatcttag caaacagtaa ctcaaagaaa aaattttact    36360
ttcttgaatg ccaccaaagt ttcagacatt gaattggacc taccctgtat tgccagaatc    36420
ttcagtattt taaattttttc agaggattag aggacttttta attgttattg gttggctaaa    36480
ctgtggctga gaaatttgtg tcattatata aaaaaaagag ttagtattgc atttctgata    36540
gggaactcaa agtccttatg tgcacattac tcatatactt acaaaacctc ctggtcaaat    36600
acatatatga tggactctat tcatggtttt tgtaggtctg tcgacatgcc ttgctttgaa    36660
cttgttctgt ggtttacttc ccgttaaccg gatatagtgt ctatagagtt tgagctgaca    36720
cgacttgagt actcttaaaa gactacagaa tattgagcca cttgtgttaa ataccctcat    36780
```

```
agcaactgtt gtaagaagga tcaccatgga attttctca gtcaacagat tggcctcatg   36840
ttagtaagaa agtaagaata tttttgtcaa gttatcacag ttgccttgta ttgccattgg   36900
gtctcataac ataaaaagga aatgtcaaag gaaattcagt caaatccaat ttctgaagta   36960
ctttaaagat tcttacacct ttggtgggtc attctgcatt tctcagattc tatatttta   37020
agttggctac aagaaaaaga taagaatggg aattcgacaa agttagagcc agatggggtt   37080
agtttccaac cctgacaatt gttatccttt tctgatgaga cagtgaactg ggtgagcaca   37140
gaaggagaca ccaaatttt atgacccttag gtgaaagttg gaaatagtaa cctcataatt   37200
gaggtttata aggccaaata aaaacaccga agactaaggt taatacagta gagttcattt   37260
tagtgtgtat ttgggatatg atttggttct ctgagagctt taactgaag ggggtggaat   37320
ctgatgtgtg atgtcgtctg gatgagttgt tttcactctg tgagttttcc caaagtgtgt   37380
tttctgaaga aacatagtga gtaggcagta gtacctattt tgtagagac taattcagtg   37440
gtacagagta ctatgcttct gattatgtca tcagcattc cagccagcta agtctactaa   37500
agccattgga gcttcagagg tactgccctg atctccatcc taggccttt aagaactagt   37560
atcatgccac acacagtatg tgtgtgtgtg catgtgtgtg tgtgtatgcc tgcatgtgtg   37620
cgcatatgtg aaaaaaagag agtgcacccc tgacttccca tccttatagg agtctggccc   37680
ttggcacttt tatgtaatgt tagagctata tgtacagagc tccattattc caactgaata   37740
accagaaaca accccattc tgaagaatga ttttagaaga gccctctgtg gtttacttcc   37800
cattaaccc agatacagtg tctatttgag tctgagctaa ggacattagt tttcccaagg   37860
atccagtctg ttgatacaca tcttagagct aggtaatgtt tatgtaccac agatatggag   37920
ttacctagaa ttcagaaagc attcttttat caagtgttga attttcatc atgaagctct   37980
gtgtcatcat aactccatca ataaaatcaa gcaaataatg atgctgttga gaaacagaag   38040
ttccttccct ctccctcatc cctggtggag tctgcactgg agaaggaagc tttggagaag   38100
tggaaagtgg catggtacag gggtccctgg cacaccaaca ccaaacacct gccgcctact   38160
ctttgtttag gaatatctac tttagactta attagcatgc catttgttga attagaaata   38220
attttaatat taatagtagt tggacttcat ttagctgaag gtcaggaagc agtttgaggg   38280
gcagagatta gaatctgaat gaccttcaga ggaggaagtg tcagtgagac aggggttcgt   38340
tgagggaaaa ctctgagcat tatcctggga aactccttcc cgtccctcac tgactcctgc   38400
actgagagga tgttactgat ggtcctgttg ctgtggacat tgtaggttag ccattccatt   38460
tactgaggca gcaggaaaga gtagagtggt aaatgagctg gagatctta ttctggcctg   38520
tttcacagtt gtgctcaagt agactcctct gtcattgcct agtattatag aggttttcaaa   38580
taatcatttc ccgaaattgt caggtcatta attattttca ttttactcag ggaagacatc   38640
tttaagatga taaaaatttt tagctatgct ttgaagaaaa ggaacaacca cccatagcta   38700
catcccttga gcatttacta tgtgataaaa ggatagatat gcatttctc attcaatact   38760
ctgatgcctt ttaaagatag tgaaaaggt ttagagagtt tagaaaactt gcttaaattc   38820
cctgtttgta gattgacagt gtcagcaatg aaccatgtct acttctagag gtcatctctt   38880
aaccaagtct ctctctacta ttctctcaga ggaagccatt tcaggtaacg aaaaagacat   38940
gtttgaaagg caccaagatg cttatggtca agtgctgtac aaggatgagt agtttgttgg   39000
aggggacatt ttaatttggg caattatgag agaggtcagt cacctgaaca tggctgcagg   39060
gtcttgcata gcctgtcaat aaccccccatt tggccacgca gttcctcagt agaccatttt   39120
cccttgacca tagggccttt gagcatgcca tttcctctgc ctggaagtct cttcttcact   39180
```

```
ttctcctctt acctagataa tgtctgcctt ccttcagatg ttaacccagt caccatttgt    39240
cacagaggct tttcccaatc agctgttttc cttataatac cctctcttaa ccccatatat    39300
gggggaaggt taggaagcag ttgggggggca gagattagaa tctgagtgac cttcagagaa    39360
ggaagtgtca gtgggacagg gatttgttga aggtcagtct tctttaatga tcttatcaca    39420
actgtaagtt tacatttata tgtgtgattc tttatttaat gtgtatctac accactggtc    39480
cctaaagtct gtgtcatcat ggatggtttt tgacctggtt atcatcttat cttgagtacc    39540
tggttcagca cctagaacat atgctcttag tgttggacaa atgagtaaat ggacaatcat    39600
gaagtccaga taaggcagct ggaaactttg taaaaaatag caatcggaag accttctggt    39660
acataagtgg gggcctgatg tgatgaaggc aggtgttggt agattgtttc gttgtcaaat    39720
accctgtagg atggattaaa aggaaaagct ttctaaagaa gtgcatcccc tttttttgcag   39780 gaagagtgag agcctaagct cctggcacat ttaaactata atcagacaaa tcaaaagaaa    39840
gatgcagata caagagctgg tgaggggttg aatatagcag caagtgagaa aaggcaaaga    39900
tttcaagccc aggaaatggg gaagatgaga tgccatctgg ttgactggga tatccctgat    39960
gactgaatga tgagcccagt cttgggtggg aagtggcagg tgctttatag ggctggaggt    40020
gaaaccccag acaaaggctg ggactttaca gctgaatttg gaagtcactg acacatatgt    40080
gatgggtgaa aggttgtgaa cagctgggtt ccctgtggat agggttggga ataccttgca    40140
tctatacagt atttcaaact gcttttcacc tattgtcatg ctgttgttga acaatccttt    40200
tgcaaacagt aaggtaagtt ttataggcca ttttttgaaaa ccagagagca agaatctagg    40260
gactcagcca aagcacacac aactttttcca tctgaaggct ggtaattgta gggctatagt   40320
gtaaacatgc tatagaattt aacatttttct gtatcatttg tcctgtcaaa ggggagaatt   40380
tctttggatc ctatttttttt ttcataatgt gctgtatgca aaatgttttc tattgtcatt   40440
ttgaatacct gtaatggcac atgaatgctt ttatgagtac aatttctgaa ataaaacatt    40500
ttcttcttct ccaaatatga tcacaaatga ggaaagagta atagaaacat ttctgttacc    40560
acccaggtct cccaaatgtc caaacaatat tagttttttgc tcattttaag aatacctctc    40620
aactctctgt gtttttatgg atatctgtcc aagtgtctgc tattatctaa attaactgga    40680
gtgaataaaa tcattgtaat gctcctcagt ttttgccttt caaataaat ggcatttag     40740 taagaataag atgactctta catagcatta gaaagaaaag ccaaagcatt attttttggtt   40800 ataagttggt caagaattgt atgctaaaat tatagtgggc tccctaaaaa tattgaagtt    40860
gtgaatattg aatacttttt ttttttctgta tagtgattgc ttaattttaa ctaattttct   40920
ccagtacata aaagggggaaa gatagcaagc catctagttt gtgaatagtt gttaacacca   40980
ccttatacga tttagtcttc taatatgtcc tatatgtgaa tagtactatt aggtggagag    41040
gttagacaga tagataggta gatagataga tagatagata gatagataga tagatagata    41100
gaagatagat agatggatgg aaagatagat ggatatacat atagttatgc ctatatatgt    41160
acatatacat gtattaaaag atatgtatcc atcagtctac agggataagc aatacaaagt    41220
cctctcatgg atctttcata ctagttagaa atgacagacc ctaaatgaat gaaaaaatac    41280
taaataaata cataaagtaa tttcagataa tgaaatatgt taagaattaa ataaatgtaa    41340
tagaagaata ttgaaggaga ggacttttttt tttatagtgt gtactagaaa agtcattctg   41400
aacgcccaga tcatgtatgg tcgtgtagac cttgtagtag tttggctttt attcttagta    41460
tttatcaaac gtctttgtag agttttaacc ttgtaagtag tgacaaatga gtaaatggac    41520
```

```
actcgtgatg gcaactttag atatttaaaa gatccttttg gacctgaagt ggagaattat   41580
atttcatgag gagagatgga gggagggagt ctgttcggga ggaatagctc agtagcctca   41640
gtgagacgtc acagtagcat ggacggatga tggcagttgt attcattatc cattgctggg   41700
taacacattc cccagaaatt tggagggtta aaataacaaa tatttatttt cttatcattt   41760
ctgagggtca ggagtccagg agcagtttat ctgggtgatt ctgacttagg gtttctcatg   41820
aggctgtagt caaactgtca gccagggatg catcatctga agcctggact ggggctggag   41880
ggtcagcttc caagaaggct caataccatg gctggcaatg ggttctgggt tttgactgga   41940
gtgagtgcct catttctctt ccatttggcc ttttatcctt gagggctgct cttctctata   42000
taacctcttc agcagaataa cctttactat tctacatggt tgctgggttc tgagagagag   42060
tcagtgagca agagagagca caacacaatt ggaagctgta gtttctttat aaccgaacct   42120
tggaagtaac atctcatccg ttctgctata ttcagttcat tagccatgag ttaccaagtc   42180
tcatccacac ataagagaag gacaattaag attcacctcc tgaagggagg aatgttaaag   42240
aactggtgaa cattttttcaa aactacaact tcagtggagg tgatgagagg tggcctaatt   42300
cactatatat ataaacttttt tgtagaaaca ataggatttt gctgtggtaa aggaaagtga   42360
ggaactatat cagtcaggac tcattcatga gacaggaaca accgagtaat tttaacagga   42420
caagtttcat gtattaaaat gattttttaac tagtactaag attaactaca aagagttaaa   42480
gataacccaa taagaacac aggaatagca tatacaggta taccttggag atactgtgga   42540 cttttgttcca gaacaccaca atacagcaaa tattgcaata aagcaagtca tataaacttt   42600
ttggtttttc agtttgtaca cgttgtgttc acattatgtt atagtctatt tgtgtgcaat   42660
agtctatttg tgtgtattat gtctaaaaag caatttaggc atacctcca attaaaacat   42720 aattcgttgc taaaaagtgc taacaatcat ctgagccttc agcaagtcat aatctttttg   42780
ctggtggagg gtcatgactt gatgctgctt actgatcagg gtggtggttg ctcaagtttg   42840
gtgtggctgt ggcaatttaa taaaatgaga caacagtgaa gtttgctgca gagattgtct   42900
cttcttttca caaataaat gtctgtagca tgaaatgctg tttgatagca tttttacccac   42960 agtaaagctt cttttcaaaat tggagtcaat cctctcaaac cctgctgcct ccatgtcaat   43020
taaatttatg gaatattcta aatcttttct tgtcatttta acaacgttca cagcatcttt   43080
cccaggagtg gattccattc caagaaacct gtttctttgc tcatccagaa gaagcaactc   43140
ttcatccatt caagttttat tgtgagattg caatgattca gtcacatctt caggctccca   43200
ttctaattct agttctcttg ttatttccac cacatctgca gtgagtttct tcactgaaat   43260
cttgaaccct tcaaagtcat ccataagggt tgtaatcaac ttcttccaaa ctcctgttaa   43320
tgttgatatt ttgacctctt cccatgaatc atgaatgtac ttaatgatat ctagaatggt   43380
gaatcttttc caggaggtaa acgttgccca gatccattag aggagtcact atctatggca   43440
gctatagcct tatgaaatgt atctctgaat tagtaaaagt agaaatgact ccttgatcta   43500
tggactacag aatggatatt gtgttagcag acatgaaaat aacattaatc ttttttttaca   43560 tatccaccag agctcttgag tgatgaggtg tattgtcaac aaacactaat attttgaaag   43620 gaattttttta ctaagcagta gttcttaaca atgggcttaa aatattcagt aaaccatgct   43680
gcaaatagaa ggactgtcat tcagactttg ttgttccact tatagacaac aagcagagta   43740
tatgtagcaa cattcttaag ggccctagga ttttcagaat ggtcaataag cattggcttc   43800
aacttaatta ccagctgcat tagtccttaa taagagagcc agcctgttct ttgaagcttt   43860
gaagccaggc attgacttct cctccctaac tatgaaagtc ctagatggca tcttcttca   43920
```

```
gtagaaggga attttgtcta cattggatat ctattcctta gtgtagctac cttcatcaac    43980
tgtcttagcc agatctggat aacttgccat agcttctata tcagaattgg ctacttcacc    44040
ttgcactttt atgttatgga aatgtcttct tccttaaacc tcgtgaacca acctctgcta    44100
gcttccagac tttcttctgc agctttctca cctctctcag tcttcacaga attgaagaga    44160
gttagggcct tgctccagat tgggcattgg cttaagggaa tgtgttggtt tgaccttctg    44220
tctcagatca cttaaacttt ctctttatca gcaataaggc tgttttactt tcttatcatt    44280
tgtgtgttca gaagtgccac tccactgagt agcactttta atttccttcc agagcttttc    44340
cattacaaca tggctgtttg atgccagagg cctaactttc agcctgtctc agctttggac    44400
atgcctttct cactnnnnnn nnnnnnnnnn nnnnnnnnnn nnnnnnnnnn nnnnnnnnnn    44460
nnnnnnnnnn nnnnnnnnnn nnnnnnnnnn nnnnnnnnnn nnnnnnnnnn nnnnnnnnnn    44520
nnnnnnnnnn nnnnncaatg tatggttatt aactggccta atttcaatat tattgtgtct    44580 aggggataa ggaggctcat agagtagtga aagctgggg gaacagccag tcaatgtagc    44640
agtcaggatg cacacaatgt ttagcaatta agtttgccgt cttatatgcg catggtttgt    44700
agtgtcccaa aacaatgaca atagtaacat caaagtatca ctaatcacag ataaccata    44760 acagatataa taataataaa gtttgaaata ttatgagaat taccaaaatg tgagagacat    44820
ataaagtgag cagatgctgt tgaaaaaatg gtgctcatag gcttgctgga tacagggttg    44880
ccacaaacct tcaatttgta aaaagaatg caatatttgc aaagtacaat aaagtgaagc    44940
acaataaaat gaggtataca tatataagca gctactacct ctagggctga ggcaaactat    45000 acaagaagg agcaaatttt aagacagccc ctctcctcaa gggctgagat ccagactttg    45060
ttggagaggg tatgactata gcccacagat ggcagaaatt gcattgaaat gctgcaggat    45120
aaagctgtca aacagaaagc tgccctgga atgatgacca tgttttttcag gaagccattt    45180 tctggggtat gagtagaact cagtaggaag ctgttggctt gggtgctcct gagactaact    45240
agactgagcc tggctagaat gccggtagaa gttactggga atctacctgt ggaggtgttg    45300
tgaaaacagc tgagatgcca gcagaatttc atggtatgtt gtctgctggg gtgcttgcaa    45360
aacttgccag gaagctggat atagtgccag tggaactgtc tacgaagctg cctctagggg    45420
aagtgagcac cactaagcat cctgcacact gcacaagtgc tacaggagca aggaaagaga    45480
ggaagcatgt cagaacctgg aaaagaagag aagcctctcc tgtagtttct cttcagcaca    45540
ccctctactg acaaagcttt acatcaagcc agctggcgaa ggagagacat tatcaaggtc    45600
cagctccatt aacaaagcag ggcaatgatg aagggtggat ttgatgctga aagggaataa    45660
gttgacagct agcacaagaa ctaaggaaag taccctaggtc aatgatggtg ccacttactg    45720
agatgggaaa ccaaggagga gttgtttggg ttaagattga gaattctctt tgagtgtgtt    45780
aattttgaga tgcctaggag acacttaagt gaaagttttg attatccaga tgaatatgta    45840
aatctggtgc tcggagagag aagggacta tttccaacaa atggtgcagg aacagttgca    45900
aatccccata aaaaaatcag aacctcaacc tacatattgt atcttatata aaattagct    45960 cagcttggat catagcacta tatgaaactt aaattatgaa acttctggaa gaaaaaaatg    46020
gatatagtct ttgcagtatt gggctaggca aatatttctt agacagcatc aaagccataa    46080
catgtaaaat aaactaataa atttgactta gtcaaagttt aaaacttcta ttcctttgaaa    46140 aacgttaaga gaatgaaaag ataagctgca gactagtaga aaatatttgc aaattgtagg    46200
ccgggcgcag tggctcacgc ctgtaatccc agcactttgg gaggccgagg caggtggatc    46260
```

```
acgaggtcag gatcgagacc atcctggcta acactgtgaa accccgtctt tactaaaaat    46320
acaaaaaaac tagccgggcg tggtggcgga cacctgtagt cccagctact cgggaggctg    46380
aggcaggaga atggcatgaa cccaggaggc ggagcttgca gtaagccgag attgcgccac    46440
tgcactccag cctggatgac agagtgagac tctgtctcaa aaaaaaaaaa aaaaggaaat    46500
atttgcaaat tgtatatctg acaataatt tgtatccaaa acttaaaaat aagaaaataa    46560
ataacctaat gaaaaatgca aaatttgag cagccacttc actaaggaag atacccaggt    46620
gctcactgtg ccagcatata tactaaaatt ggagtgatac agagattagc atggcccgtg    46680
cacaaggatg acatgcaaat gcatgaagtg gtccatttct ttaaatgaag atgcccagat    46740
ggcaaataaa tacatgaaaa gtgttcaaca caaataagct ctaaggaaat gcaaatcaaa    46800
actatactga gatatcacta tgtacctatt agaatggctg attaaacaaa aactgacaac    46860
attaaatgct gatggggatg cagaagcaac tggaacgctc aaatttctgg tgagagaaaa    46920
aactggaaaa cattttgact tggcagtttt tataaaatca aattaaacac atgcttataa    46980
tatgatccag taatcccact ccaaggcatt tttcaaaggg aaatttaaaa ttatgttccc    47040
acaaaaattc atatgcacat attgtactta cctgaatctt caatagaatg ttgactagga    47100
atgctgagaa tggtggacat gttttgtttt tgaacttaaa agggaaacac tcagttttc    47160 agggttaagt agattattag ctacagcttt ttttggtaga tgctctttat caggttaaga    47220
aaatacccaa ctattcttat tttgctgaaa ggaatagatg ttgaattttg ctgacgcttt    47280
ttgcacatct gttgagatga tcatggtttt ccttctttaa tgtactgatc tggtgaacta    47340
cactgatgat ttttttaaaat tattatttat ttatttattt atttatttat ttatttattt    47400
atttagactg attttcgctc atgttgccca ggctggagtg cagtgatgtg atcttggctt    47460
actgcaagct ctgcccgccg ggttccagtg attccctgt ctcagcctcc tgagtaactg    47520
ggattacagg cacctgccac cacacccaga taatttttt gcattttag tagagatggg    47580 atatccccat gttggccagg gtggtctcaa acttctgacc tcagttgttc cacctgcctc    47640
ggcctcccaa agcgctggga ttacaggtgt gagccaccag gcttggccaa ttaattttta    47700
tttgaaaatt attttggatt caggggctat atgtgcatgt ttgttacatg gatatattgc    47760
atactgctgg tgttcaggct tctattgaac tcacactgat ggatttttaa aagtcaaatt    47820
agccttgtat tcctggcata aaccccactt gatcattatg tattatgctt tttatatgtc    47880
actggatttg atttacttac attttgtcaa taattttgt gtctgtgttc atgaggctct    47940
tgttctgtag ttttctttc ttgtcatgcc tttgactggt tttagaatga tgtaatgttg    48000
gctttatgaa gtgatttggg aaatattccc tcttctattt tctggtagag tttgtgtaga    48060
attggtatat atttcttaaa agtttggttg agtttatcat tgaattgatc tggtccttat    48120
ttttctatat tggcagtgtc ttggtgagat ttggggcttt agaatcaagc aaccccagat    48180
taatatctca ctttgttaat ttctccctgt gagacattgg gcaagtcaca cattctcttt    48240
gagcctattt cctcatctat caaatgggta attgtgataa ttaaataata atatacatca    48300
tttattcaat actctactac atgtatttat atataatcaa tacatggggg tggagccaag    48360
atggccgaat aggaacagct cccagcatga gcgacgcaga agacgggtga cttctgcatt    48420
tccaactgag gtactgggtt catctcactg aggagtgtcg gaaagtgggt gcaggacagt    48480
gggtgcagtg caccgagcat gagccaaagc agggcgaggc attgcctcac ccgggaagtg    48540
taaggggtca gggaattccc tttcctagtc aaagaaacgg gtgacagatg gcacctgaaa    48600
aatcaggtca ctcccaccct aatactgcgc ttttccaacg gtcttagcaa acgccacacc    48660
```

-continued

```
aggagattat atcccgtgcc tggctcggag ggtcctatac ccacggagcc tcgctcattg   48720
ctagcacagc agtctgagtt caaactgcaa ggcagcagcg aggctggggg aggggtgcct   48780
gccattgccg aggcttgagt aggtaaacaa agcagccggg aagctcaaac tgggtggagc   48840
ccaccgcagc tcaaggaggc ctgcctgcct ctgtagactc cacctctggg ggcagagcat   48900
tgccaaacaa aaggcagcag aaaactctgc agacttaaat gtccctgtct gacagctttg   48960
aagagagtag tggttctctc agcacgcagc tggagatctg agaacggaca gactgtctcc   49020
tcaagtgggt ccctgacccc cgattagact aactgggagg cacccccctag taggggcaga   49080 ctgacacctc acatggccgt gtactcctct gagacaaaac ttccagagga ataatcaggc   49140
agcaacattt gctgttcacc aatatccgct gttctgcagc ctccgctgct gatacccagg   49200
caaacagggt ctggagtaga cctccagcaa actccaacag acctgcagct gagggtcctg   49260
actgttagaa ggaaaactaa caaacaggac atccacacca aaaccccatc tgtacgtcac   49320
catcatcaaa gaccaaaggt agacaaaacc acaaagatgg ggcaggaaaa ctggaaactc   49380
taaaaatcag agtgcctctc ctcctccaaa ggaatgcagc tcctcaccag caatggaaca   49440
aagctggatg gagaatgact ttgacgagtt gagagaagaa ggcttcagac gatcaaacta   49500
ctctgagcta aaggaggaag ttcgaagcca cggcaaagaa gttaaaaacc ttgaaaaaaa   49560
attagatgaa tggctaacta gaataatcaa tgcagagaag tccttaaagg acatgatgga   49620
gctgaaaacc aaggcacgag aactacatga tgaatgcaca agcctcagta gccgattcga   49680
tcaactggaa gaaaaggtat cagtgatgga agatcaaatg aatgaaatga agcgagaaga   49740
gaagtttaga gaaaaagag taaaagaaa caaacaaagc ctccaagaaa tatgggacta   49800
tatgaaaaga ccaaatctac gtctgattgg tgtatctgaa agtgacgggg agaatggaac   49860
caagttggaa aacactctgt gggatattat ccaggggtac ttccccaatc tagcaaggca   49920
ggccaacatt taaattcagg aaatacagag aacgccacaa agatactcct tgagaagagc   49980
aactccaaga cacataattg tcagattcac cgaagttgaa atgaaggaaa aatgttaag   50040 ggcagccaca gagaaaggtc aggttaccca caaagggaaa cccatcagac taacatctga   50100
tctctctgca gaaactctac aagccagaag agagttgggg ccaatattca acattcttaa   50160
agaaaagaat tttcaaccca gaatttcata ggctcaaaat aaagggatgg aggaagatct   50220
cccaagcaaa tggaaaacaa aaaaagggag gggttgcaat cctagtctct gataaaacag   50280
actttaaacc aacaagaaac aaaagagaca aagaaggcca ttacataatg gtaaagggat   50340
caattcaaca agaagagcta gctatcctaa atatatatgc acccaataca ggggtacccc   50400
gattgataaa gcaagtcatt agagacctag aaggagactt agactcccac acaataatag   50460
tgggagacgt taacaccca ctgtcaacat tagacagatc aacaagacag aaagttaaca   50520
aggatatcca ggaattgaac tcagctctgc accaagcaga cctaatagac atctacagaa   50580
ctctccaccc caaatcaaca gaatatccat tcttttcagc accaccac acttattcca   50640 aaattgacca catagttgga agtaaagcac tcctcagcaa atgtaaaaga acagaaatta   50700
taacaaactg tctctcagac cacagtgcaa tcaaactaga actcaggatt aagaatctca   50760
ctcaaaacct ctcaactaca tggaaactga acaaccttct cctgaatgac tcctgggtac   50820
ataacgaaat gaaggcagaa ataaagatgt tctttgaaac caatgagaac aaagacacaa   50880
cataccagaa tctctgggac acattcaaag cagtgtgtag agggaaattt atagcactaa   50940
atgccaacaa gagaaagcag gaaagatcta aaattgacat cctaacatca cattaaaag   51000
```

```
aactagagaa gtaagagcaa acacatttta aagctagcag aaggcaagaa ataactaaga    51060
tcagagcaga actgaaggaa atagagacac aaaaaaaccc ttcaaaaaat caatgaatcc    51120
aggagctggt attttgaaaa catcaacaaa attgatggac tgctagcaag actaataaag    51180
aagaaaagag agaagaatca aatagacgca ataaaaaatg ataaagggga tatcaccacc    51240
gatcccacag aaatacaaac taccatcaga gaatactata acacctcta cgcaaataaa    51300 ctagaaaatc tagaagaaat ggataaattc ctggacacat acaccctccc aagactaaac    51360
caggaagaag tagaatctct gaatagacca ataacaggct ctgaaattga ggcaataatc    51420
aatagtttac caaccaaaaa aagtctagga ccagatggat tcacagccga attctaccag    51480
aggtacaagg aagagctggt accattcctt ctgaaactat tccaatcaat aaaaaaaga    51540 gggaatcctt cctaactcat tttatgaggc cagcatcatc ctgataccaa agcctggcag    51600
agacacaacc aaaaaagaga attttagacc aatatccctg atgaacattg atgcaaaaat    51660
tctcaataaa atactggcaa accaaatcca gcagcacatc aaaagcttta tccaccatga    51720
tcaagtgggc ttcatccctg ggatgcaagg ctggttcaac atacgcaaat caataaacgt    51780
aatcctgcat ataaacagaa ccaaaaacaa aaaccacatg attatctcaa cagatgcaga    51840
aaaggccttt gacaaaattc aacaacgctt catgctaaaa actctcaata aattaggtat    51900
tgatgggacc tatctcaaaa taataagagc tatctatgac aaacccacag gcaatatcat    51960
actgaatggg caaaaactgg aagcattccc tttgaaaact ggcacaagac agggacgccc    52020
tctctcacca ctcctattca acatagtgtt ggaatttctg gccagggcaa tcaggcagga    52080
gaaggaaata aagggtattc aattaggaaa caaggaagtc aaattgtccc cgtttgcaga    52140
tgattgtata tttagaaaac cccatcgtct cagcccaaaa tctccttaag ctgatagaca    52200
acttcagcaa agtctcagga tacaaaatta atgtacaaaa atcacaagca ttcttataca    52260
ccaataacag aaaaacatag agccaaatca tgagtgaact cgcattcaca attgcttcaa    52320
agagaataaa atacctagga atccaactta caagggatgt gaaggacctc ttcaaggaga    52380
actacaaacc actgctcaat gaaataaaag aggatacaaa caatggaag aacattccat    52440 gctcatgggt aggaagaatc aatattgtga aaatggccat actgcccaag gtaatttata    52500
ggttcaatgc catccccatc aagctaccaa tgattttctt cacacaattg gaaaaaact    52560 actttaaagt tcatatggaa ccaaaaaaga gcccacattg ctaagtcaat cctaagccaa    52620
aagaacaaag ctggaggcat cactctacct gacttcaaac tatactacaa ggctacggta    52680
gccaaaacag catggtactg gtaccaaaac agagatacag accaatggaa cagaacagag    52740
ccctcagaaa taatgccgca tatctacaac catctgaagt ttgacaaacc tgacaaaaac    52800
aagcaatggg gaaaggattc cctatttaat aaacggtgct gggaaaactc gctagccata    52860
tgtagaaagc tgaaactgga tcccttcctt acaccttata caaaattaa ttcaaggtgg    52920 attaaagacg taaatgttag acctaaaacc ataaaaaccc tagaagaata cctaggcaat    52980
accattcagg acataggcat gggcgaggac ttcatgtcta aaacaccaaa agcaatggca    53040 acaaagcca aaattgacaa gtgaaatcta attaagctaa agagcttctg cacagcaaaa    53100
gaaactacca tcagagtcaa caggcaacct acagaatggg agaaaatttt tgcaatctac    53160
tcatctgaca aagggctaat atccagaatc tacagtgaac tccctcaaat ttacaataaa    53220
aaaaaaacag ctgcatcaac aagtgggtga aggatataaa cagacacttc tcaaaagaag    53280
acatttatga agccaaagga cagatgaaaa aatgctcatc atcagtggcc atcagagaaa    53340
tgcaaatcaa aaccacaatg agataccatc tcacaccagt tagaatgacg atcattaaaa    53400
```

```
agtcaggaaa caacaggtgc tggagaggat gtggagaaat aggaacactt ttacactgtt    53460
ggtgggactg taaactagtt caaccattgt ggaagtcagt gtggcgattc ctcagggatc    53520
tagaactaga aatagcattt gacccagcca tcccattact gggtatgtac ccaaagaatt    53580
ataaatcatg ctgatataaa gacacatgca cacgtaagtt tattgcggca ctattcacaa    53640
tagcaaagac ttggaaccaa cccaaatgtc caacaatgat agactggatt aaggaaatgt    53700
ggcacatata caccatggaa tattatgcag ccataaaaaa tgatgaattc atgtctttgg    53760
aggacatgga tgaagctgga aaccatcatt ctcagcaaac tatcgcaaga acaaaaaacc    53820
aaacaccgca tgttctcact cataggtggg aattgaacaa tgagaacaca tggactcagg    53880
aaggggaaca tcacacacca gggcctgttg tggggtaggg ggaggggga gggatagcat    53940 ttggagatat acctaatgtt aaatgacgag ttactgggtg cagcacacca acatggcaca    54000
tgtatacata tgtaacaaac ttgcacgttg tgcacatgta ccctaaaatt taaagtataa    54060
taaaaaatat atataataca tacatgacat ttgcatatat taaattattt aaattttact    54120
ttcatactat tctgtttaca atatatatca gcagtatatt attataatcc ttattttata    54180
gataagaaag ctattggagg ccgggcacgg aggctcacgc ctgtaatccc agcactttgg    54240
gaggctgagg tgggcggatc atgaggtcag gagatcgaga ccatcctggc taacactgtg    54300
aaacccagtc tctactaaaa atacaaaaaa taaaaaaatt agctggacgt gctggcgggc    54360
gcctgtagtc ccagcgactt gggaggctga ggcaggagaa tggcgtgaac ccggcaggca    54420
gagcttgcag taagccgaga ttgcgccact gcactccaga ctaggtgaca gagtgagact    54480
ccgtctcaaa aaaaaaaaa aaaagaaaa agaaagcta ttggaaaaca agataaaata    54540
acttgcccag ggttactcaa gttgctcata atagagtcag tattcagatt gaggctgtcc    54600
agttcctgag tcctgtcttt taagcactaa gctatactaa tgataatacc tgtctttcag    54660
agtgctatga gtgttaaatg aggcaattca tgtaagtggc tgaatttatg ctagtataaa    54720
cttgttgttt agtaaacgtg tattattatt aataatgcga attttttatta ttttgaaatg    54780 aaatgacttt ggaatatttt tgacctgaaa ggtattttag tatatataat caaatactgc    54840
attgaagttt gttccagtga aattccatga gcatttgctg tgctttacaa catgatattg    54900
agaatatcaa agcttatttg gaaaaacaac ttgaattctt gcactggttc tgcattgtct    54960
tttttgtgca atcctggtaa ttaaatttct tgaaatatct gtgaatctgt agcaaacgga    55020
taggaaaaat atctgttttt atcattttga cctaagttgt tgagtggttt ataaaagaca    55080
ggctgggcct ggtggctcac gcctgtaatc ccagcacttt gagaggccaa ggcaggtgga    55140
tcacaaggtc aggagttcaa gaccagcctg gccaacgtgg taaaaccacg tctctactaa    55200
aactacaaaa attagccggg catggtggca cgtgcctgta atcccagcta cttgggaggc    55260
tgaggcacga gaattgcttg aacctgggag gcagaggttt cagtgagccg agatcgcacc    55320
actgcactcc aacctgggtg acagagtgag attctgtctc aaaaaaaaaa aaaaaaaaa    55380 agagagaaaa aagagaagta cctgaagata ttttgaaaag tacaagattg tgctaatatt    55440
acatatagat atttggtgtt ctgtgataaa aatcagaata tgttgttgat atataaatat    55500
tttgagatta ttttgaacat acttgtactg tgattagtac acgttgatgc cagttaattt    55560
taggttttca ggccttcatg gtatttattt gggtgtacct tacttttctt ttagcctgac    55620
aaggtcatga ctgccctatg ccaaatgtta gattcattct gtttacttaa aaattataaa    55680
ggataaccta aaaaatggaa tcacagtttc aataagtact ttgtcctatg tttcagtcag    55740
```

```
caagacttat tttatgtttt tttaaaatga taaacctcat tatatcaaaa tatatagcat    55800
taagaaaaga aaagcctttg gttatgaagt gtagtagtta ttgtgtagat tgtcaaatgc    55860
taaggaacaa tgataactct gggaaaatat agtaacatat tgcgttgttt tgtgaattgt    55920
agctgacttt ggcctggcaa agcaaaaaca agaaaacagt aaactcacgt ctgtggttgg    55980
aacaatcctg tattcttggt aaggacaatt cttttatggc tctcaaacat catacttaac    56040
tgatttaggc tttcatttat attattgact tgcaaaggaa agagaatttc aggaaagaaa    56100
gcttatttta taagttttt caattatcta ggtaatacac attactagaa ttgtggatca    56160
ttatgtatgc ttaaaacaac caccacaaaa ataatctttc ttctaaggta tcatgcccct    56220
catggggatt acttatatca attgtaaatt gcaatgatcc ttggcatata gtaggtgtgc    56280
aatagttgtt taatgaatct gagaatgaag taatagatat gctacccaac atgatacttg    56340
gaacatttta ttgtaccctc ttgtatgtat gactcttttt ctcttttcta cctataaaca    56400
ttcaagtgca gggcaaggat ttttgtacac taatacctat cctagtatct ggcaaataat    56460
aggcactgaa taaactttat tgtgtgaatg aataaataat gatatgtata cttagacata    56520
tgtttacaaa gtaaattgct tcttagataa atgagtgttt atattttgat aaatcgagac    56580
acttaaattc tttggcatac tttgggggtt cctttgcaag ccattaatta ttatgaagta    56640
agaatcttct tttgctgatc acatgtcatt tgtctgaatc tgctgaaatt agcaaacagt    56700
tatggtaaag agtagaaaag cagatttcag ggaaatattc tgaaatctga ttcaacaggt    56760
caagcaatca agacactttt attttttttt aaatctagcc tatagttgta caattgagtc    56820
ctggggatag aattaaacac gactcttctt gaggaagagt agaaattgtc taaaaatagc    56880
agcctaattt tacaaagtcc tttcatgcag aagtgttcag aataatgttt taagagggtg    56940
acttttcatt tatcttactg gatatgtttt acatctttat tcttgaaagt ggtttcatga    57000
gaagatgcaa agaaactgtg gcaggctaac atgtaccttg taagctgcaa gcttatatga    57060
tgtctactta tcctcttaac agtaaggctg acctactcgt tactttctga gagaagaata    57120 atttctttt gtttcactgt gtactgtttt tataaaataa acaataaaat ttgatcataa    57180
aagtgtcaag taatcatata tctctgaaca gatttgattg tcaaattgca gaacaattaa    57240
aacacaaact taaatttctg ctggtcatac ttggtgaaag catattttta ttcctgagac    57300
tttgaattaa gtttagaatt gctccatatga tagtatcaac tgtgtgtgtg tgtgtgtgtg    57360
tgtgtgtgtg tgtgtaagag aaagagacag aatccataga atacgtagga agaaatccaa    57420
aacatgccaa cttttttgcc gtattagcgc aaacacggct tcacattttc atttaatttt    57480
taaattaact gaagggtttg taagctgaac ctactcatat agataagcta ttatttcatg    57540
tatgtgtact atgattgttt taatagcatg tacagtatat cttactacca tttatctttc    57600
tgtcaacttc ttattctttt aaattgcttt aaaaatttct ttctactccc ttctctcatc    57660
tctccgagtt attagaaatg cctcttgtct gataggtttt actatgaatt tgggctcaca    57720
aaccgtcttt cttgctagtt tttgatgtcc ttaactgagt atggagttaa agaactcag    57780 tcctacatca tattgtgttt ctttcttaat ttgggattct ccaaaagcag aatctgggac    57840
aagaatttga gtgaaattgt ttatttagga ggaggtccca ggaaacacta ttaggagagt    57900
ggtgaagtga gattgggagg gaaagcagcc agtacagtga acattaataa ttaggttcat    57960
agagtattat ctgggatata gtgtaaagca ggggtgtcca atcttttggc ttctctgggc    58020
tacattggaa gaggaaaaat tgtcttggac cacacacaaa atacactgac actaaagata    58080
gctgatgggc ttttaaaaat tgaaaaaaac caaaatctca taatgtttta aaaagatttt    58140
```

```
ttgagtttat gttgggctac atgcggtccg tgggccgggg gttggactag cttggtgtac   58200
aggatgtctt tgagttgccc tgcgcaccgg atgagaggtt ggagtatttt ttttccaatc   58260
acaaggggga gccctcagca tctgactgag ggctgctctg gggagcttat gcccaggtgc   58320
ttatggcatg ccagggcgtg ggctggggca ttccaggcag agagctggag ggccattgct   58380
tgaggtatga tgccatagac ttgtactgga aatgtgagta ggagtctggc tagggtcccg   58440
acattctaga atttttttgt aattctataa ttcttatttt cattaatttt tctaagcttg   58500
tctgagccta taaatgtgga cctgggatgt ggacatttgg atgccataga gatgcctagg   58560
caccccttcc ccttccctgc agggtcccca gagtttgatg tccccatgtc attttgccct   58620
ttccatttgc ttttgcttcc tcagatatta acttactgaa tggaagaaag gtctctttgt   58680
caactcttgt aggaagtgcc tcagagcatt tattctgtat tcagctgcta gataaagggt   58740
ttgtgggcac attgctggac cgattgtact agaacagaag gtcagtaaag gttcttttca   58800
ttcatctgat gtgatttatt attaggcagg tatttgttat ccttctcaag ggaaaaaaat   58860
atccaaatat ggtacttgtt tccatttttt atctctatgt cttcctccaa ttccagagaa   58920
gaaaattaga caccatcttc aacttcattt tttgggaaga gtatagagtt tgaggctctg   58980
ggaagcattt tcagctagtt cttcacagaa catatatggg attttatgaag ctagtatgat   59040 gtataaaata caataaaagt tttccaataa aaatggaaaa cttcaactat tcctggaatg   59100
ggaattatta gtctatggct tagtataatc ccattcatat tatgacacta gataattaga   59160
agagaagctc atgaacttta aattggatgg atcaaaataa acctgtaggt aaaactgatt   59220
aagtagagac aaagtgaagc atgcctatta actgcacttc ttaaattttt aaaaaaatta   59280
tttttttgat acataaagtt gatagaattc ttaagaaagc tataatacac tcaaaatttt   59340 gagaattttta agtggcttaa aacacttaag tgacttccag ctgctcatgc aaagaccaag   59400
ccctcagtat ggccacaagc agacaacctt gcattctctg gcctctgcca agttcttcag   59460
ctttaccaca aaccaaactt taacaattcc tagctgtttc atctgggctc cctctgacca   59520
cagggccttt gcacatgcag ctcccttgc ctggaatact ctttttctatt tgtcatctgg   59580 ttaattctta cctgccttca gctgaacccc cttagacaag gtctatttcc tctgatctac   59640
acactctatg tactttttcct tcacacaatt gaacttttg ttgattttgt gataagcaat   59700
tatgattttg ttcatcacaa tccccagcag tcctaagtct ggtactttaa aactcacaag   59760
taatatttgc tacatgaatg atcaagtact tgcatgatta taaacattag tggaaataac   59820
atattagaaa gaaaattatt tctttttgtt gtaacaaatt tttaattccc tgtcctttcc   59880
cttcttgctg ttccttcaga tctccaaaat actcctcctt ggaatactct tccttcagag   59940
atagctgcag agtttacttc tttacttcat tctgctcttt gcttaaatgc cacttatgta   60000
gagaggattt ccctgatcac ttgccccaaa tagcaacctc ccttcagact gctttatttt   60060
ttcatagtct tgcctctacc tgaccttatg ttgtacttga attggcttat agtgtgtctc   60120
tccactacac acaagctcca taagcatagg acttgcgtct cctttgttca ccactgtttc   60180
cccaggacct agaggagttg actagcagaa tcttaagaaa tactttgaat aattgaagtg   60240
aaaacaagtc attttttaat attaatatga taaaaattag tgtatatttt tattgagttc   60300
tagtatatct ttgaactttt ctgatttta ccctaataaa gcctgaagaa aatgcttttc   60360
atttgagata gtaagtacct tgatggtagg gtctatttta ttttgttttc tctttgctta   60420
ttttatcttt atatattaca tagttactac aacagtgagt aaatgagatc aagtaggatg   60480
```

```
ttaaacattt taacaaaata aaatgtgtaa agattatata ttacagaaat atgtattctt    60540
cagtgaccaa taaagtggcc ctgagggaaa tttcaaaaaa gagatgtgtt agatcgttct    60600
tggattgcta taaagaaata cctgagactg gataatttat aaagaaaaga gtttaactg     60660 gttcatggtt ctgcaggctg cacaggaagc atgacgctgg tatcttcttg gcttctgggg    60720
aggccccagg aaacttacat tcatggtgga aggtgaaggg ggagcaggca tatcacatgg    60780
ccagagcagg agcaggagag ggaaagtgag gaagtgccac acactttaaa aacaaccaga    60840
actcatgaga acacactcac tgtcagaaca acagcactaa agggatggta ctaacccatt    60900
catgagaaat ccaccccat gatccagtca ttttccacta ggcccacct tcaacactgg      60960 gaataacaat tcaatatgag atttgggcag ggattttcaa aaataagcat aattggaaaa    61020
agaccatggt attgacagag acagggcatt atcaagagca caaactctag aatcagatgg    61080
cctgggttta aattctagat cggctattga gagttttaaa tgattgaatt tttctgtgcc    61140
tcagtttcct catctgcaac ctggggatga taataatagt gcccatgtcc taggattatt    61200
gtgagattaa atgaggtgat acatgtcaca tgctgggaac agtgcctggc tggcatatgg    61260
taagcactca ctagataata gtgattgtta tttcctgtta gtctaaagtt tgaaaggata    61320
gtactcattt aaatgtatat attatattct gcatatatag gaggttatag aacactaggc    61380
ggatttaacc taaagaagac tacctcaagg tatttaataa tcaaactcac aaatatcagg    61440
gataaagaaa ggatctcaaa agcagcaaga gaaagaaac aaataacatg caatggacct      61500
caatacatct ggcagcagac ttttcagtgg aagccttacg ggccagaaga gagtggcatg    61560
acatattgaa agtgctgaag gaaaaaaaaa atttacccca gaatagtata tctggtgaaa    61620
atatccttca aacatgaagg agaaataaag actttcccag acaaacaaaa gctaagggat    61680
ttcatcaaca tctgacctgt cctatgagaa atgctaaagg gggttcttca atcagaaatg    61740
aaagggcatt aatgaggaat aagaaaccat ctgaacatac aaaactcact ggtaatagta    61800
aatacacagg ctgggcacag tggctgacac ctgtaatccc agcactttgg gagaccaagg    61860
caggtggatc acgaggtcag gagatcgaga ccatcctgac taaacagtg aaaccccgtc      61920 tctactaaaa atacaaaaaa ttagccgggc atggtggtgg gcgcctgtag tcccagctac    61980
ttgggaggct gaggcaggag aatggcgtga acctgggagg cggtgcttgc agtgagtgga    62040
gatcgtgcta ctgcactcca gcctgggtga cagagagaga ctccatctca aaaaaaaaaa    62100
aatagtaaat acacagaaaa acaaagaata ttataaatact gtaattgtgg tatataaact    62160
actgttagct taagtaagac taaaatgtga atcaataaaa ataactacaa caacttttca    62220
agacatagca caataacata taaagagaaa caataagtta aaaagtgggg ggacaaaatt    62280
aaagtataca gttttatgt tttcttttg cttgtttgtt tatgcaatca gtatcatcag       62340
tttaaaataa tgggttacaa catagtattt gcaagtttca tggtaacctc aaatcaaaaa    62400
acatacaaca gatacacaaa aagtaaaaag taataaatta aatcatacca taaagaaaa     62460 tcaccttcac taacaggaag acaggaaaga agaatgaaag agaataccc aaaacaacca      62520 gaaaacataa atgacaaaat ggcaggaata agttcttact tatcaataat aacattgaat    62580
gtaaatggat gaaactctcc aatcaaaaga cagagtggcc cagtggacaa aaaactaaga    62640
cgcaatgatc tgttgcctat taaaaatgca tttcacctct aaagacacat agactgaaaa    62700
taaagagaag gaaaaagata ttccatgcca atggaagcca aaaaagagca gaagtagcta    62760
tacttatatc agaaaaaata tatttcaaga caaaaactgt aagaagagac aaagaaagtc    62820
attatataat gataaaggag tcacttcagc aagaagatat aacaattgta aatatatatg    62880
```

```
cacccaatac tggagcaccc agatatataa aagaaatatt attagagtga aagaaagaga   62940
gatggacaaa aatataattg tattagtctg ttttcaaact gctataaaga actacctgag   63000
actgggtaac ttataaagga aagaggttta attgatttgc agttcagcgt ggctggggag   63060
acctcaggaa acttacaaac atggtggaag acaggggaag caaggctcct tctttacaag   63120
gcagcaggaa ggagaatgaa tgcaggagga actaccaaac acaaaaccga tcacatgaga   63180
attcactatc atgagaacag cttgggggat atcgccccca tgattcaatt acctccacct   63240
ggtctctccc ttgacatgtg gggattatag ggattacaat tcaagatgag attttgggtg   63300
gggtgtagcc aaaccattat caacaataat agctggagac ttcaataccc catagcattg   63360
gacagacctc ccagatagaa aatcagtaaa ggatcattgg acttaatctg cactgtagac   63420
caaatggacc taatggatag ttacagaata tctcatccaa tggctacaga atatacattc   63480
ttctcagcac atgaattatt ctcaaggata aaccatatgt taggtcacaa aacaagtctt   63540
aaaacattta aaaaaagtt gaaataatat caaacatctt ctctgactgt aatagaataa   63600
aactagaaat cagtgacaag aggaatattg gatactctac aaacacatgg aaattaaaca   63660
gtatgctcct gaatgaccag tgggtcaatg aataaataag taaattgaaa aaattttga   63720 aacaaataat aatggaaaca caacatacca aaacctatgg gatacagtga aagtagtacc   63780
aagagagaag tttgtagcta taaatgccta aaccaaaaag aagaaaaact tcaaataaat   63840
aacctaatga tgcatctgag agaactagag aagccaaagc aaatgaaacc caaaattagt   63900
agaagaaaag taataataaa gagcagatat aaaagcaatg gaaatgaaga aaacaataca   63960
aaagatcaac aaaatggaaa gttgtttttt ggaaaagtta aacaaaatta acaaaccttt   64020
agacagacta aaaaaaggg agaagaccca aataaataca atcagggatg aaaaaggaga   64080
cattacaatt gatactgcag aaattcaaag aataattagt ggctaccacg aacaactatg   64140
tgccaataaa ctggaaaaatt tagaagtaag taaattacta gacacataca acctaccaag   64200
atggaaccat gaagaaactc aaaacccaaa cagaccaata acaagtagtg agatggaagc   64260
cataatgaaa agtctcccag taaagaaaac ctgagaccca atggcttcac tgttgaatgc   64320
taccagatgt ttaaagaata actaatacca atcctacaca aactattgca aaaaatggag   64380
gaagagggta tacttccaaa cttacaccgt gaggccagta ttaccctgat acaaaaacca   64440
gacaaagacg cctccagaaa aaaaaaaaaa aaagaaaaga aagaaaga aaattaaaag    64500 aaaactgcag gccaatattg cttgagtgca ggagtttaag accagcctgg gcaacatggc   64560
gaaaccctgt ctctactaac aatgcaaaat attagccagg catggtggtg tgcatgtgta   64620
gtcccagcta cttggaaggc tgaggcggga ggaatgattt agtccaggag gtggaggttg   64680
cagtgagctg agatcgcacc actgcactgc agtttgggtg acagagactc tgtctcaaaa   64740
aaataaaata aaataaaata aaataaacaa aattctagca aatcaaatcc aacaatacat   64800
taaaatgatt attcctcatg atcaagtggg atttatccca gagatgcaag gatatgtaaa   64860
tcaatcaatg tgatacattg tatcaacaga ctggaggaca acaactatat gatcatttca   64920
attgatgctg acaaaacatt tgataaaaatt caacatccct tcatgatgaa aagccctaaa   64980
aaacctgggt acaaaagaa catacctcaa cataaaaaa gccatttaca acagacccac    65040
agctaatatc atactgaatg gggaaaaatt gaaaacctct tcttgaagac ctagaacatg   65100
acagggatgt taactttcat cattgttatt caaaatagta ctggaagccc tagccagagc   65160
agccagataa gagaaataaa taaaaggcat ccaaattggg aaggaagaag tcaagttatc   65220
```

```
cttgtttgca gatgatatga tcttatattt ggaaaaacct gatcttatat ttggaaaaac   65280
ctgacgactc caccaaaaaa ctattagaac tgatcaacaa atttagtaaa gctgcaggat   65340
acaaaatcaa catacaaaaa gcagtagcat ttctatacac caacagcgca caatgtgaaa   65400
aagaaatcaa gaaagtaata tcatttatga gagctacaaa taaagtaaaa tacctaggaa   65460
ttaacttaac cgaagaagtg aaatatggga ctaaaaattg tgtgggaata aaaatttgtg   65520
gtgctaaaaa ttaaataatt gaactcatgg agaaagaaca tagaaggatg gtcaccgggg   65580
ctaggaaggg tagtgggcag gggttggggg gattggggtg attaatgggt ataaaaaata   65640
gaattagtga ataagagcta atatttgata gcacaacagg gtgactatag ttaaaaaaat   65700
ttaattatac attttacaat aactgaaaga gtataattag attgtttttaa cacaatgctt   65760 gaagtgatgg atatcctatt tactgtgatg tgattattat tcattgcatg cctgtgtcaa   65820
aatatctcat aaaccccata aacatataca cctactatat atttacaagt aaagttaaaa   65880
ataaaaaatt taaaaaatct aaatttactt gaggatgaaa ggttggagga gagagaggat   65940
cagaaaaaat acctattgag tattatgctt actggtgggt gacaaaataa tctgcaacaa   66000 accccccatga catgcagttt acctatataa caaacctgca gatgtacccc tgaacctaaa   66060
agtcataata aaaaagggtg aatgtaggta cataatgcca ttgtacatta tgcattttttc   66120 agtctgatttt gttctgaact cctcagaatc acaaaacgca agaaagaaag ctctctgatg   66180
attgattctg tcagtggaag tccttgcttc ttttatcaat tggaaattca gaatcattta   66240
tcttcagtct ctatattctt tttctcttgc cctttttatag tctttacttt tacaagtaaa   66300
agtgaatcat aagcactaga tttccttctc catgtttatt tatctacttt gtcattttga   66360
acatttaata cctagtggtt atgtatagta tttctcattt cctattggaa caagattcaa   66420
gaggaaatac atagtgataa gatgtgttac tttaacatgt ttttctgagg gtgggagggg   66480
tgtggtcaaa agaagtttcc tcatgtattt accacaaatt aatttattga ataattaaga   66540
aattagaatc atttgatgat ggagagatgt atatttcaga tatgtattgg atgcataaca   66600
atccatccca aaatttagtt gcttaaaacc acgatggttt atataggttt gcttgatcat   66660
tcctctgttg gttcccctga actcatgtgg atgcatttgg ctgaattatt ggcttggctg   66720
ggcagtccaa gatggcttca ttaataaggc agttcgtgtt gatgcttggc tagagtccct   66780
tggatctttt tcaggtggcc tttcgtttac atgacagtag tggagtaaca ttccaagaaa   66840
gtaaaagctg agctgcaagg cccgattggg gctagccttg gatgtcacta aacatcccttt   66900 ctgccatatt ctgttggtca aagcacataa gagccagccc aaatgtgtga aatacattta   66960
tctctagatg gaaggaggtg catggtactt gtggccatat tcaacaaatc ataatgcagc   67020
accgtatttc tttaaaaaag aagaagaatc ccccaaatgg cttcaggaat caagacatgt   67080
gaaacaaaga aatagtctat tttaaacact aacggttggc acgttagccc cacatctcct   67140
tagaatgaag tatagcagcc tggatccaac taggagatag aaatgatgca gtgggctaaa   67200
taggggaagt ttaatatgaa gaacaattat gatgaaagag taactataag atgtaagaaa   67260
actacatggt actttagggt tgagtgacag taccaaggaa ggataaactt ggaaggggtt   67320
cagatttcat tggaaaaagt gtggtagccc aatagacagc agaaaagttg gctagatggt   67380
ccaggctgaa gctgttctgg agctgctagg caagctggga gcaaccctct gaagtgcagg   67440
tgagggagca aggcatcagc atctgcggtg tgggcacata gtgggagtcc agctgccaca   67500
ggtgcccttc agagttttaaa ggccacaggg aaggagaaa aggggggcgag tccaggaact   67560 gcacaagcag gaggccttca gagggtgcag gctacacagg ggctctggtt tctgttttga   67620
```

```
gaaggttgaa gaaaaatgat caccaggctg aggctgcagg gttgcagagg gagaatgggc   67680
tatggttggg ataggctcta ctggttagtc ctatacctat actgcctact cgtggcccat   67740
gtcagaaatt gcaggaaacc tcttcctcct gcagtgtccc tccaatccat gtatagagaa   67800
agcttaatat tgtgctcact ttaaaggaga aatatttaaa gggattccat tgtttattga   67860
ataatacatt aagagacaac aggcaataag ttaataacag acacaataag aaacttcagg   67920
gcttggccca gcataacagt ggactgggca actagtagaa tagggccaca tccctgctag   67980
gggatgttca atgcctttaa ttcttctgta aaataggtgt tttatttctc tgtgcctcca   68040
aacttttggt gtatctccag agtgtctttt tgaattgtga aaattaaatc tttcagttca   68100
attctgaata ggctcagcgt atttggtgaa aagcaggagc tatagtttgg ctgggttgag   68160
tttgtgctgt gacactggaa gacctagaat tttcctcttg gcattgtaaa gccacagggt   68220
atctctcagc ctgacagtta cttgatgaaa atgcggtttt tttgggggaa tatctgtgga   68280
atgaaactgg gaaagggaa ggagagatgt gtattcatca ttttatctgt ccctcaagtg   68340
gatattccaa tatttacttc acaggagcag atgacttagt tctttaccac tagaagaatt   68400
caatttaatt tggggacacg gacacacaga cacacacaca cacacacaca cacacccca   68460 tggtgtcagt caagtgtaga agattaaagg gttagaaaac cctatgatgc ttgtaatgag   68520
tctccaggat aatatagaaa gtagggtaga acagggacct cccagcacag agctgcagaa   68580
ctcgagggaa aggccattgg ggctggggtg gatgctctgt tttctatata ataaatgtgc   68640
catattctat gcactaacta agaatttat aaacagatat attttcctcg aattcagaca   68700
ttatgacagt atatgtatag aagggagtct ggttgacgga taaatggtc acaagaaatc   68760 aaaaggaaag aagagaaaag atagcaaggt gatgagggta aacatataat ggaaagagtg   68820
gagaagtcag aggattcaaa caatggggaa atatgaaagt gaaattacca tattagggc   68880 aaaagaatta aataaacatt ttcattattt tgcagggcta catttaattt gtcttattct   68940
tgtgaatgag ttactccaag tgaccttacc agtcatatat cccttacat caatttattt   69000 cttaactcat ttagctatta gtactttatt aattttata tttaatttta attattaact   69060
tttttatctt ggcatttcag actgttcata acaaccctag aagtaatgac acgatgctaa   69120
cacaagaaaa ccttcctttg aagtgccaga aattgttttc tctaaaatag tagaatatta   69180
gttagaaggc caatattttg aaattcaagc gtctctttgg agaaggattt taaaaaaatc   69240 cttaaaaca ttttaaaaca agacaataaa ctgttaaact gtgacaattt tatggcctat   69300
cataaaatgt caaaataaag attttaaaat gttaacttta tgtaaccttg atacattggc   69360
aatactcaac cattttaaaa ccttcatttt cactgaaagg catacttcta ggatcctcac   69420
atttggcagt taagttttga agattttaca tatattggtc aatttcattt tagtactcta   69480
gggttccagg aaggccacat ctattcctca gtaaagcatt tgcctctcag tctgttcagc   69540
tcctcctcac cttaattctt ctgagttcat ctgtaatttt cataacaaag tgtactttct   69600
tcataaattt agtaaataat gctcagaact tcagcagtga gagaagtaag atgccagtgg   69660
acatgggtgc atctgtgcac agtgggcaac tgtgatgtgt ggctgtccct tcccctagga   69720
gccaacagga catagtgcag actctagacc tggattgcct gggcccaatc ctggatctac   69780
accttcctgt ttgactttgg gcaagctact taatttttct gggcctaaat ttcctcacct   69840 gaaatgggg cagagggcag taatgataat ttctacaaca tagggttgtt atgaggattg   69900
agaagatagt tggatggatg gatggaagga tggatggatg gcaatagatt gatcaatcga   69960
```

```
ttgataagta gatagtatta tctgtagcat agcagggatt taataaacat tacctattgt    70020
caggctggaa gcaacagcct cattctttag gaaaatattt cttccctgcc tttacttcaa    70080
gcacatggtt taaatggctt atacattggg aatactcaaa aaagtatcaa tgccaaaagt    70140
cccattgctt tagagatcct gcctccttgg ccttacatgg tggaacaatt ctagtatgca    70200
tgtccctata gcccaaaatg ttaaaagtag aagtgttttc ttgattcaag tttaaccatt    70260
cagaattctt tcttgagaac gtgttgagct gaggctcagt taaaagttga agctgggagg    70320
caaaaggccc agcagtgttt tggtggccat ggttgtagcc agggaggaag tcagtctgac    70380
agcatgaggt caatacttag aataagagat ggcaatgtcc aggctcaaga ttccattttc    70440
ttaagtccca gctgcaactt tgctcttcct gcacttacag gagcctatca ataaagtccc    70500
ctatttgcct aaccttgctg ggtttctttc tcttgtctct tagtttgggt tgccctgaag    70560
gcagaccctg agaaaagaat tgaagtgcaa gtggtttatt ctggaggtga tcctaggaaa    70620
catgaataaa agagtagggg aagtgagaca gggtagggaa gtaagcagat aaaggatttc    70680
ttgggcaagt taccactgtg ggcaattaga actcaaatct gttgaggtac ttgggagcca    70740
tttatttgaa tacccaaaag gagaaagagc agtatttata cacttgctct tgaagtcact    70800
gggtaaggtc tgtttctggg gtacagtaat tcatcagcac ttcaggctca tcatgttgca    70860
gacacagaaa gtcatgagat taaagaaaat cctcagacaa acctgcaaat ggttggaatt    70920
cagtccagtg tgctcgcaag aagtaagggt caggggatgt taataggaca cctacaacat    70980
ctgcttcaag ttaacaatga aaacaacttt gactgtcaca acagagatat ggttgtaggg    71040
tggcctcaaa gtctgtacat gccagattgt ctgaaaaaat cttattttc cccccatgct     71100 ctctgaacaa attcttctat gctgaatatt tggaagtctt taaagatgtc cctgaagtct    71160 gttttagat tttcctcaca gttacattga gttgagaatt ttttccccca gtcatgccca     71220
gagagactgt ctgcctccct gtagttctgg ggtgctactc cctgtaccaa ctttgcaaac    71280
aaaatagcaa taccaggctg atgaggtaat gatcatttta aaatagatgt gataggccag    71340
gcatggtggc tcatgcctgt aattccagca ctttaggagg ccaaggcagg cagatcacct    71400
gaggtcagga gttcgagacc agcctggcca acatggtgta accctgtctc tactaaaaaa    71460
atacaaaaat tagccaggcg tggtggtgca cacctttaat ctcatctact cgggaggctg    71520
aggcaggaga attgcttgag cctgggagac agaggttgca gtgagccaag attatgccat    71580
tgcactccag tctggccaac acagtgagac tctgtctcaa aaaaaaaaa aaaagatgag    71640 atagtaataa aagtaaatca gaatgaggta agaatattct cctgtgaggg tctctgctac    71700
cttgaataaa gactatcaaa tgtttacatg gaagttgctc aactgtctct ttttatttct    71760
tagtctgtta aggagcagga atacacattt ttatgtgact ttatatttag agaaaggcat    71820
ttgtataatt atgtattatt gggagattgt attatctttt ttgtgaaatc accataatta    71880
tttagttatg tacttgaatt ttaaaagcta gtgctatttg gcttgaatac aaatacaaaa    71940
tatgtgatgt caacctataa tgccagcttt ttttttcta caaaaaatca ttagagacaa    72000
gcaaatggca gttgatgtat aatgagaaat ttcaaggctg ttggatctga atttaatttg    72060
tatttgtgac tcagagtagg caatgctgga aaatcatttg atgactggag tgtaatcact    72120
gggtgaacat aatccatttg tttaattgcc cagactcctc actgtattta cagttaattg    72180
gttcccatta aggtcctctt aatagagacc ataaaacagt aggattagag aaacctgaaa    72240
aggaacattt agtttgagtc ctttcttgaa gccaagttgt aacatgtgct catctatttc    72300
attttttacc atcttcataa cagactgagg gagaaaaaga ctctcaggca ggtgctttat    72360
```

```
aaattatttt tactgttttg gcctatgaac atttctatag ccagaaaata aaaaaaaatc   72420
tagtgttcct acatataatt gaagttttc tcttatgact tgaaattctt tttgggttta    72480
gtggccaggc aaagcaaatg gtcactaccc aacatttaat gactcttcat gtactgaaag   72540
gttattttaa gccttttttc cctaaatttc gttgctcatt catagttttt gtaacctttt   72600
gattcagact tctagatatt acatacaaag atcggataga aaacctttca atatcttagg   72660
aaagtcatgt gaacccatct gatgaggagg gatacaagtc tcttataaaa tgtgattta    72720 gtgctgcatt tttaacttac agattttctt tattctccaa agacgggttt atttacttca   72780
ggactgatga agcaaattaa aattataaat tctcctcccc cttccacaga gattttcgag   72840
tctgccttct tctcccttc tcctacccac aattaccctc actacaaatg ctggagcttc    72900
ccttccattg ggctccagcc aatttgggaa aattttgaaa gtaaattagt ttcagtgaca   72960
atataatcaa aatacaaaat tactacattt gaatatttct catcactgat tttaaaatc    73020 tattgataat attcaggaag ttttacattc tttctgggca cttaacattc ttagttattt   73080
taattttttt tgtgaacttg acattttatt tcttaattca ttttagccaa ttgtgagaat   73140
tatgcattaa aatgggagat tggccccttt ccactgcatc acagatgaaa aatggaaagt   73200
acctttgatt ggtcccctcc cacaagcaat cactggttgt gggccaagtc ttcatgtgta   73260
actttgttaa cttcactta gcctctgatt ggttgactct tgcaaccaat cagactagtt    73320
gtgggccaaa tcttcattta tagagggtat aaccaagtaa ccaatgggaa acctctagag   73380
ggtatttaaa ccccagaaaa ttctgtaacc agtgcccttg agctgcttgc ttcagcctgc   73440
ccctgctctg tggagtgtac tttcatttcc ataaatctgt gctttcgttg cttcacatac   73500
acacacacac acacacacac acacacacac acacacacac gaaaggggag gttggttaga   73560
taaataacac taagctggta atacagtaat gtatttgttg acccagaagc atatttacaa   73620
tattaaataa aaaaataggt taccaatggc atatatttta tgatcctatc acagatagaa   73680
atatctgaaa atattgtcaa gtcaagcaga catcacagac aaaagtgaat tagaaattaa   73740
aggaatatga atacatataa caaaataaaa acaacaaaac ttcaaatctg aaaaaagttt   73800
ataatttgtt gattaaagtt tcttatattg ttttcttatt agaaaatcag tatattctct   73860
gcagaaaatg aagaaaaaat cccattaaga atattcgtaa tcctactaac ccagaaatgg   73920
aaaaaactca cagaaaatag cttattgtcc agattccaaa ttcctttcta tgtgaacaca   73980
caaacacaca tacacaaata ctgatattaa tgagtgcttt tctatagctt cagttttaat   74040
atctggatcg aatcccaata cttggttaaa atcatgattc attcagccaa tctccttttt   74100
ttagatatgc aaattatttc catcttttcc ctaactcata ttacacaggg cacgtattct   74160
tggctaaaac taaattagaa ataagaaaac aaaagttatc tgtggcaaag ttagcctcta   74220
gcacaccatc ccttcttaa tccccaaata aaaaaccctg actacacttg ttggtgaata    74280
ttttgttatt ggctatagta tttacaacct ttctgctgta tgcagctcac taatcttctc   74340
tactcttgag ggtgcggaaa gcatggtgta ttattggtga cacagccctt tttatacaat   74400
ttcacatatc agagctggtt ttgcaaggat gacttgatga tttgatgccc accatttct    74460 ttactgttaa aaaatttcaa tagttttgg ggtacaggtg gttttgggat gcatggatag    74520
gttcttaagt ggtgatttct gagactttag tgtacccatc acctgagcaa tgtacactct   74580
atccaatata tagtctcacc ccactcccac ccttcctcac cccactccca cccttcctcc   74640
tgagttccca aaatccatta tatcattctt atgcctttgc atactcacag tttagctccc   74700
```

```
actaataatt gagaacatat gatgttgtgg gaagtcaggg acccccgaacg gagggaccgg    74760 ctggagccac ggcagaggaa cataaattgt gaagatttca tggacattta tcagttccca    74820
aaattaatac ttttataatt tcttacacct gtctttactg caatctctga acataaattg    74880
tgaagatttc atggacattt atcagttccc aaataatact cttataattt cttatgcctg    74940
tctttaatct cttaatcctg ttatcttcgt aagctgagaa tgtacgtcac ctcaggacca    75000
ctattgtaca aactgattgt aaaacatgca tgtttgaaca atatgaaatc agtgcacctt    75060
ggaaatgaat acaataacag caattttagg gaacaaggga agacaaccaa aggtctgact    75120
gcctgcgggg tcaggcagaa tagagccata ttttcttct tgcagagagc ctataaacag    75180
acatgcaagt aggagagata tcgctgaatt cttttcccgg caaggaatat taataattaa    75240
tacccagggg aaggaatgca ttcctggggg gaggtctata aacggccact ttgggagtgt    75300
ctgtcttatg cggttgagat aaggacagaa atatgccctg gtctcctgca gtaccctgag    75360
gcttattaga gtggggaaaa gatcccaccc tagtaaattt gagatcagac tggttctgtg    75420
ctcttgaacc ctgttttctg ttgtttaaga tgtttatcaa dacaatatgt gcacagctga    75480
acatagaacc tcatcagtaa ctctaatttt gcctttgcc ttgtgatctt tgctttgccc    75540
tttgccttgt catctttatt gcctttaag gcatgtgatc tttgtgacct attccctgtt    75600
catacaccct ctccctttt aaagtcctta ataaaaacct gctggttttg cggctcaggt    75660
gggacatcac ggacttaccg atatgtgatg tcacccctg gaggcccagc tgtaaaattc    75720
ctctctttgt attctttctc tttatttctc agactggccg acacttaggg aaaatagaac    75780
ctacattgaa atattgggag ctggttcccc cgataatatg atatttggtt ttccattcct    75840
gagttacttc agttagaata atggcctcca gctccaccca agttgctgca aaagacatta    75900
ttttgttcct ttttatagct gagtagtatt ccatagtgta tatatacatt tgttcttaa    75960 aaatatttca tttatttatt tacttatttt ttaacttta agttcaggtg tacatgtgca    76020
ggatgtgcag gtttgttaca ttgttagtta tatagattat ttcatcaccc aggtattaaa    76080
cttagcatcc attagttatt tttcctgatc ctctctctcc ttccatcctc caccctccag    76140
tagaccccag tgtgccttgt tccccctcta tgagtccatg tgttctcatc atttagctcc    76200
cacttataag taagaatgtg cagtatttgt ttttctgttt ctgcattagt ttgctaatga    76260
taatggcctc cagctctatc catgttcctg caaaggacat gatcttattc tttttatgg    76320 ttgcatagta ttccatggtg tatatgtatc acatttctt tatatgtatc acttttttt    76380 acccagtcta tcattttga gcatttacgt tgattccatg tcttggctat tgtgaatagt    76440
gcagcaatga acatgtgcat gaacaagtga atagtgcatg catgtttctt tataatagaa    76500
caatttctat tcctttgggt atatacccag taatggaatt gctgggtcga atggaatttc    76560
tgtctttagg tctttgagga attgccacac tgtcttccac aatggttgaa ctaatttaca    76620
ctcccatcaa caatgtaaaa gcatttcttt ttctccacaa cctcatcagc atctgttatt    76680
ttttgacttc ttagtgatag ccattgtgat gggcgtgaga tgacatctca ttggggtttt    76740
gatttgcatt tctctaataa tcagtaatgt tgagcttttc atatgcttgt tggctgaatg    76800
tataccttct tctgaaaagt gtttgttcat gtcctttgcc cacttttaa tggcgttgtt    76860 tgtttgtttt gtaaatttgt ttaagctcct tatagatgct ggatattaga ccttcgtcag    76920
atgcatagtt tgcaaaaatt atctcccatt ctgtaggctg tcttttgct gtgttgatag    76980 tttcttttgc tgtacagaag ctctttagtt taattagatt tgatttgtca attttttgctt    77040 ttgttgcaat tacttttggc atcttcatca tgaaatcttt gtcagtgcct atgtcctaaa    77100
```

```
tggtattgcc taggttttct tctagggttt ttatagtttt gggttttaga tttaagtctt   77160
taatccatct tgagttgatt tttgtgtgtg gtataagaaa ggggttcagt ttcaattttc   77220
tgcttgtggc tagccagtga tcccagcacc atttattaaa tagggaatcc tttccccatt   77280
gcttgttttt gtcaggtttc ttaaacatca gatggttgta ggtgtgcaat cttatttctg   77340
aattatctat tgtgttccat tggtctatgt gtctgttctt gtaccaatac catgctgttt   77400
tggttactat agccctgtag tatagcttgg agtcaggtaa catgataccT gcagctttgt   77460
tcttttTgct taggatctcc ttggctagtt gggcactttt ttggttccat atgaatttta   77520
aaatagcttt ttctagttct gtgaaggacg tcaaattata gtttcatggg aatagcattg   77580
aatgtatgaa ttgctttggg cagtatggcc attttcacag tattgattct tcctatccat   77640
gaacatggaa tgttttttcca tttgtttgtg tcctttctga tttctttgag cagtggtttg   77700
tagttctcct tatagagatc cttcacttcc cttgttagct gtattcctag gtattttatt   77760
cttttTgtgg cagttgtgaa tgggagttca tttgtgattt ggatattggc ctgattgttg   77820
ttggtgtata ggaatgctag tgattTttgc acattgaatt gtatcctgag actTtgctga   77880
agttgatcac cagcttaaga aattTttggg atgagacaat ggggttTtct tgatatagga   77940
tcatgtcatc tgaaaacagg gatagtttga tttcctctct tcctatctga acatccttta   78000
ttactTtctc ttgcttgatt gtcctggcca gaatTtccaa tattatgttg aataggagtt   78060
gtaagagagc attcttgtgc tggttTtcaa ggaaaatgct tccaggtTtt gcccatttag   78120
tataatattg gaagtgggtt tgtcatatat ggctcTtact attTtgaggt gtgtttcttc   78180
aataccagtt tattgagaga ttTtagcatg aagggatgtt gaatTttatt gaaagccTtt   78240
tctgaatcta ttgagaataa tcatgttgtt tttttTctTt agttctcttt atgtaatgaa   78300
tcacatTtat tgatttgcgt atgttgaacc aaccttgcat tccaggaatg aagcctactt   78360
cactgtggtg gttaagctTt ttgatgtggt gctggattca gtttgccagt atTttgttga   78420
ggattTttgc attgatgttc atcaaggata ttggcctgaa gtTttcctTt tTtgttgtat   78480
ctctgccagg ttTtagtatc aggatgttgc tggcctcata gaatgggtta gggaagagtt   78540
cctccttTaa aatTttttgg aatagTttca gtaggaatgg taccagctct tctTtgtaca   78600
tcTtatacca catTttcTtt atccacttgt tggttgatgg gcactTaggt tggtTtcata   78660
tctTtgcaat tgtgaattgt gctgctacaa acatgcatTt tcataaaaca acTtctTttc   78720
cttTtggtag gtacccagta gtgggaTtgc tagatcaaat ggtagttcta cttTtggTtc   78780
tttatgtaat cttcTtacag ttTttccatag tgattgtact agtTtacatt cccatcagca   78840
gtgtaaaaat gtTcctTttt caccacatcc acaccaacat ctattgtTtt ggatTttTta   78900
aaaaaacgtt ttaattatgg ccattcTtgc aggagtaagg tggtatctca tTatggTttt   78960
aatTtgtgtt tccctgatga ttagtgatgt tgagcatTtt tcatatgTtt gctggTtgtt   79020
tctatgtctt cttTtaagaa ctgtctatTc atgtgcTttg cccactTttt gatgggatTa   79080
tTtgtTtTtt tcTtgttgac ttgtTttgag ttccttgtag attgtggata ctagtccTtt   79140
gttggatgta tagtTtgtga atatTtctc ccactctgtg ggttgtctgt tgtttactct   79200
gctgattatt tatattgctg tgcagaaggt tTtagtTtta attaggtccc atTtatTtat   79260
tTttgtTttc gttgcatTtg gtTttgggt cTtagtcatg aatTgtTtgc ctaagccaat   79320
gtccagtaga gttTttctga ttcaggtgTt agatttaagt ctTtgatcca tcTtgatttg   79380
atTtTttgtTt aaggtgagag atggggatcc agtTttatTc ttctacatgt ggcTtgccag   79440
```

```
ttatctcaga accgtttatt gaatagtgta tcctttcccc caatttatgt ttttgtttgt    79500
tttgttgaag atcagttggc tgtaagtctt tggcttatt tcttggttct ctattctgtt    79560
ccattgtctc catgcctatt tttataccag taacatgctg tttgctaact atagccttgt    79620
agtataattt gaagtctggt aatgtgatgc ctccagattt acacttttg cttagccttg    79680 ctttggctat gtgggctctt ttttgttcc atatgaattt taggattttt tttctaattc      79740
tgtgaagaat gatgatgata ttttgatgga aattccattg aatctgtata ttgctttgga    79800
tagtatggtc atttcttaa tattgattct tcctatccat gagcatggga tatgttccca     79860
tttgtgcatg tcatctctga tttctttcag cagtgtttgg tagttttcct tgcagagatc    79920
attcacttcc ttggttaagt atattcctaa gtattttatt tgttttgcag tctttgtaaa    79980
aagagttgca ttcttgattt gattctcagc ttggtcattc ttggtgtgta gcagtgctac    80040
tggtttgtgt acattgatta tgtattctga gactttattg aatccattta ttggatctag    80100 gagcttttg gatgagtttt taggttttct gcgtatatga tcatatcacg atgtgttatc     80160
tttttgatat gctgttggat ttggttagct agtattttat tgagaagttt tccatctata    80220
ttcatcaggg ttattaatct gtagttttct ttttttgtta tgtcctttcc tggttttgt     80280 attagggtga cagtggtttc ctagaatgaa ttagggatga ttccctctct ctctatcttt    80340
gggatagttt cagtagaatc aataccaatt cttcttagaa tgcctagtag aattcagctg    80400
agaatctgtc ttgtcctggc tttttgttgg cagtgttttt attactgatt gagtcttact    80460
gcttgttatt ggtctgttca gagttttctat ttcttatttg atctcggaga gttgtatgtt   80520
tccaagattt tgtccatttc ctctatattt cctgatttgt gcatgtaaag gtgttcatag    80580
tagccctgaa tgatcttttt tatttctgtg gtattggttg taatgtctcc agtttcattg    80640
ctaattgagc ttatttggat cttctctctt cttttcatgg ttagtctcac taatggccta   80700
tcaattttgt ttatctttc aaagaatcag attttttgttt catttatctt ttgtactttt    80760
ttgtttcact ttcatttagt tatactctga tgtgtgttat ttcttttctt ctgctgggtt   80820
tgggtttaat ttgctcctgt ttgtgtagtt ttttgaggtg tgacattaga ttatcaattt    80880
gtgctctttc agacttttg atataggcat ttaatgctat gaactttcct tttagcacca    80940
cttttgctgt attccagagg ttttgataag ttgtgtcact gttatcattc atttcaaata    81000 attttaaat tttcatattg attaatcatt caagagcaca ttatttaatt ttcaagtatt    81060
tgtttgattt ggagggttcc ttttagagtt gatttccagg tttattccac tgtggtttga    81120
gaagatactt catatgattt tgactttctt aaattaattg agagttgttt tgtggcctat    81180
catatggtcc atcttggaga atatttcatg tactgaagag aagaatgtat attctgcagt    81240
tgttgggaag agtgttctgt aaatacctgt taagtccatt tgttctagga tatagtttaa    81300
gtccaccatt tctttgttga cattctgtct tgatgatctg tctattggga gtattgaagt    81360
cccccactac cattgagttg ctatctatct catttttga gtctggtagt aattgtttta    81420
taaatctggg agctccagtg ttaggtgcgt atgtatttag gattgtaatg tcttctcatt    81480
ggactaatcc tttcatcaat atataatgtc cttctttgcc ttttcttact attgttgctt    81540
taaagtctgt tttgtctcat ataagaattg ctattcctgc ttgcttttca tttctttttg    81600 catgattat cttttttcac ccctgtcctt taagttatt tgaatcctta tgtgttaggt      81660
gagtctcttg aggacagcag atatttggtt ggttgttttc tatccattct gctattccgt    81720 atttttaag tggagcatct aggccattta cgttcattgt taatactgag atgtgaggta     81780
ctattctatt catcatgtta cttgttacct agatactttt tttacattgt attattgttt    81840
```

```
tataggccct ctgagatgta tgctttaagg tggttctatt ttggtgcaca ttgaacttttt    81900 gtttcaagat ttagaagttc ttttagcatt tcttgtagtg ctagtttcgt agtggcaaat    81960
tccctcagca tttgtttgtc tgaaaaagac tttctctctc ctttatttat gaagcttagt    82020
tctactggct atacaaatct tggctgaaaa ttaatttgtt caaggaggct aaagatagga    82080
tcccaatccc ttctggcttg taaggtttct cctgagaaat cttctgttag tctgatcggt    82140
ttctctttat aggtcacctg atgcttttgt cttacttctg ttaaaattct tttcttcatg    82200
ctgatttggg tttgcctgat aactatgtgc ttttgtgatg atcttttgt aattaattc     82260 ccaggagttc ttcgagcttc ttgtatttgg atatctagat ctctagtaag gccagggaag    82320
ttttcctcaa ttattcccta aaataagttt tccaaactta tttgttcttt tccctcagga    82380
acaccaatta ttcttgagtt tgactgtttt atataatctc atatttcttg gagactttgt    82440
tcatgtcttt tgagtctttt ttctttatct ttgactgatt gggttaattt gaaagccttt    82500
tctttgggct ctgaaattct ttcttctaca tgttctagtc tattgttgaa actatccatt    82560 gcatttgta tttccttaag tgtgtctttc atttccagaa gttctgattg gttttttcctt    82620 atgatatcta tctctccgga aaattttta ttcatttcct agattaaaaa aatttcttta    82680
tgttggtttt aaccttcctc tgttatctcc ttgagtaact taataatcaa ccttctgaat    82740
tctttatcta gcatttcaga gatttccctt tagtttggat tcattaatgt ggaactcgtg    82800 tgatctttg ggggtgttat agaaccctgt tttgtcatat tgccagaatt acttttctgg    82860
ttccttctca tttgggtaga ctgttcttc agattgttct tgaattatt tttgatttaa    82920 ctctgttttt caatgagttc ctatttttcc ttttaaggat cagactttaa tgtttatagt    82980
ttattatagc ctaatttgat tctttgtact gttaggggta aagactctgt atgagttcct    83040
aagttgtaga ctttgtgcac tggctttcct agatgctggt tgtagtaatt atgtgtttgg    83100
tgtgtgggca aattcactgt cttctattgg gttggaatgg cagggatatc ttgaagctta    83160
tctcattctc ttgaggtgca aacttttattt atttatttaa ttttccccta gtattttatt    83220
tactgagttg atgattcacg cttcaggcca gtaggggggg tatccctgag taggaaccag    83280
ttgtagctag gtcaggtgcg tagatgtaat acccagtggt aatacctaga ggtcccagtc    83340
tccatgaagg tggctggggg agctctcaat tagatgtgct gaggttttta tcagggagaa    83400
gggtgggagc tacctcagct cctctgccag gccagcagga aaggaatcca cctcccagcc    83460 ttactccctat cccagagttc cagctattca gatcagacag gcatctcttt tcatctgtag    83520
gaacgttgat gttccaagta gggaggaatt gtcactctgc ctcttgtgca agcctgaatc    83580
tggggagtgc tcctcctgtg gggctacaat cattctaaat tgttccagga aggctgtcta    83640
taggttgatg ccctccattt tctcatctga aacaacctgc tcccactagc tcctgcctct    83700
tagatcacgt tgtcctgcat gaaacctctt tatgcagctt tcaaatattg ccaagatgtg    83760
atgggccatg gtagaaataa gcagaatgtg ctaattgcca cattttctcc ttaaaaggag    83820
aaaacaacag catctagcta acattattta ctgaaattgt tttggaccac tgagaaaata    83880
gggccagaga gtttctctat aacaggagat agcaagaggg tctgaagaga gcacaaaatc    83940
tgagcaatgg gagggaaagt ggtaattcca aatatattat tttaagtcat catgaggaaa    84000
tgaagagagt aagatgtgta agaagtggag gttggtttaa tatctttgct ttaataacca    84060
aatcacatag ctagtaaatt gggaagtgaa aatttaaact tggtcttgcc tgatacagca    84120
ttaagaaaaa ggaaaggaca gaaagttttt cttagtagca agataatgat taatatgtag    84180
```

```
aatatccagt gactaggaat attcattggt gatcgttttc tcattttatc aaggaaaatg   84240
ttcacttctt gactattgca agtttcttcc tgaccattaa agtaataata actagctaga   84300
agttattgtg cccttatatg tgtcagtgtc tgagtttaaa caagatctgc tttaacttgg   84360
atgcttttcg acaaagcagt ttttactcaa attgcctgcc acgctattat accactcaag   84420
agtggccaag ggctataggc aaagtagcca tgcctatggc acttctcaga tcaacaggga   84480
ccttctactg tttatgtaca attagaaaaa catttttatt attctctgtt tatacctgtt   84540
catatgaata aaataaatgt ttccttggtt atgggtatca cctacttagt gatatttact   84600
ttcaagtttt atgccgttga attgctgaca tacaatgtgt gttatgatgg aatcaagggt   84660
ttatcctgta ccccttcagc caccatgtca gtagggaaca gcagagcaag cctgggaagg   84720
tcacaggagt tgaaggggct gcaggaggtc cgtgaaatgg gaagtcaata tgtgcccgat   84780
gtctgaggag gaggtgtttg actataatta atgtttggat taggaggatt tggcaggagg   84840
aagaagtttt gactctaacc tttatgctaa tgagcctgct ccctacttcg cggagaagct   84900
gggagctatg gaagagaact tccacaagct cctgcttcca tgtcttccc cttacccata   84960 cctgtgttcc tgtaaccgac cttttctcat gcgactctgc ttccatggtc ctggtgaagg   85020
ccacccctcc tcctgtctgt ccatttcctc aagggcatca ctccagcaat tctctgtcat   85080
gtatcaattt ctacacctcc attagtttgc ttctaccaat ttactagcat tctgtcattt   85140
ttctcattag aaaaataatc catgaaaaag aggacttggt acatagcaag tgctcagaaa   85200
atgcttgttc aatgaataaa tgaatgaatg aataaatgaa tgaaagcact aagggagta    85260 aggcttttgt aataatttag gggtgggctg atttggactt gttggcaatg agaataaaaa   85320
gaaatgggag gtaggatata cactttgaag aaagaattaa aaatccttgg ttagttattc   85380
tatacatatg taatacagga ggggaaataa cctgtaattt taggattgtg tgtttgataa   85440
taagattatt ttgtggtata actgataagg atatagttga tagaagtggt ttgttttcct   85500
ccttcaagta tttttatttc cattttttca tatatctttt tttctaagaa taaaaatctt   85560
atcatcttaa tattagatat gtgcattggc cagggaatgt tttcttttaa gatttataac   85620
taatggtaaa ttattaatgt tgagcctgag acgaatttgc ctctgttcac tatgagttgt   85680
aattactctt tggagtcaac tgagggctag aaagaggtga cccagagtta aaaagcatt    85740 agcccacttt gcccagggca tctgaaagcg ttactgtgac ctctgcagca gccgttaggt   85800
ccactcaaga aatagctagt gcactatgga ctacctagac atggaatata ctttgcaaga   85860
attccctcaa taagtagatt attcccacct tcctctttct ctttcagtct ttctttcttt   85920
cttttctttt tttaaaaact gtggccaggc acggtggctc acgcctgtaa tcctagcact   85980 tgggaggcc gaggcaggca ggtcacaagg tcaggagatc tagaccatcc tggctaacac    86040
ggtgaaaccc tgtctctact aaaaatacaa aaaaagaaa aaaaaaaat agccgggcgt     86100 agtggcgggc gcctgtagtc ctagctactc cggaggctga ggcaggagaa tgatgtgaac   86160
ccaggaggca gagcttgcag tgagccaaga tcatgccact gcactccagc ctgggcaaca   86220
gagcgagact ccgtctcaaa aaaaaaaata ttgtaaccgt attttatttg gtttgggaca   86280
tttcttcaag tagacataca gtgtacattt gtcatatttt ctggctggtc agttaatctt   86340
atgaactcat ttcctatatc tggggggac ttcctacctt atgaatatct tttccttaag    86400
caagtcaaca gaaaaatgtg taatcttagc ctcccttgca gctgaaacac aaccatgtga   86460
cttagactcc atcaatcaga ttcgtcagc aagacttgga tttgcaagtg agaaatggga    86520
gaaagtatgt attggctaga gtccagtttg ggccagggga aagggtggtg ttggaagatg   86580
```

```
gcaggattgg gtctactttc cactgtcagt ggtacaagtt gtgcctgacc caatacaatg    86640
ttggctaaag ctttgtccct ccccgtatgg ccttcaagcc tgactgctgg gtactccagg    86700
gactttgtaa gcttcctaac agcctttaat aagtgttttc ctgtgtaaat gaactttaat    86760
gcttctatag cacaaggtac agtggtaatg gtttttaatg tagcacaata aggattaaag    86820
aaaagagggg acattatgtg cacattctcc agtttcttct tcctgtaaca aagtgggtgt    86880
gatggttaat actgagtgtc aacttgattg gattgaagga tacaaagtat tgatcctggt    86940
tgtgtctgtg aggatgttgc caaaggagat taacatttga gtcagtgggc tgggaaaggt    87000
agacccaccc ttaatcttgg tgggcaccat ctaatcagct gccagcatgg ccagaatata    87060
agcaggcaga aaagtgtgga aagagagact ggcctaacct cccagccttc atctttctcc    87120
catgctggat gcttcctgcc cttgaacact ggactccaag ttctttagtt ttggaactcc    87180
gactgactct ccttgctcct cagcctgcag actgcctatt gtgggacctt gcaattgtgt    87240
aagttaacac ttaataaact cccctttata tacatatcga ttccattatc tctgtccttc    87300
tagagaacct ggactaacac agtgggagaa gaatgcaaaa atagctctgg atcttcatgt    87360
agttataatt aatagtaaca agtgacattt tgtgagcact aactatttca agttactgtg    87420
cttttcagat attgtctaat ataatacttt tggtggtcct atgagaagag ccatcattat    87480
ctctattttt agaagagaaa aaatgatgtt taagcaactt gctatcttag cccgggttcc    87540
atagaaaacg gagcttacat gtgagctttt tattggagag gagaggtagt aatcccaggg    87600
tagtgagagt aaggaaaaaa acaagaaaca aagaagggaa ggaaggacag caaatacaat    87660
gtactgttac tgagcttgtc acagctttat taagaagcag catttacttg gtcatgggag    87720
atgtctctgg acagatctta tgggacttct gtgcattaga agagtcgatt gtgggaggga    87780
aggaagaata attcatttcc tgtctctcat tgatgaaagt ttgcccatag gccttattta    87840
acctccagat tcttttggtt actcaacccc actggaagtg ttgtggggc gggagtatgc    87900 agccagcacc tcttgtagag cagttggcag gggcctgggt acagaagctg ctacagctct    87960
caccagactc ccatgaggga actcatgctg gaagccagcc ctcaccctaa gaagccagac    88020
agctgaaagt gttaagaaat gggactgtcc attgaacagg ctaccaaaag ccggggaggc    88080
agttgggaca ggacagatct gggaagggaa atacttgaca agagacatca ctcttgtctc    88140
tgcctcacct ggcattctct gtgtgtctat gcctgtgtgt ctgttttctc agtacagtag    88200
tcatattgga ttagggccca cccttatgca gtatgacctc atcttaactt gattacctct    88260
gcaaagatcc tctttccaaa caagatcaca ttcacaggta ctgtgagtta ggacttcaac    88320
atatcttttc aggggacaca atccaaccca caaaacttcc tgatgattag agaagacatg    88380
gatagaattt gcagagaaaa ggaagtgatt aatttagttt tgagtatgtt gagtttgaat    88440
tgcttttgag atggtaagac tgttatgtcc aataagcaac ccaaatatgt ttctggagcc    88500
tcaggggagt gtttctggct ggtaaggaga catagggtca tcagcatctg tgtgaaactt    88560
gctgtgaaat agacaagtga tgaataaaac cttgaggagc cacaatgctt aagaggcaaa    88620
cacagagaca ggaaggttgg ggtgacttac aaggagtagg cagacaggaa gttcaaaaga    88680
aaaaaaacta gaagaaagta gtgtcagaca cgatgtgaga aagttcccaa ggaggaacgc    88740
aatgcttttc taagctcagt agtattacag agcagccagg tattgagaat tgttttttata    88800 tggtgatttc atatgcgtcc atgtaaagga tggaagagta tcccttggat gtgcagatgg    88860
acaatggtta tccagagagg tttcagggga gtggtaaggg ctggggtaca gggggatcat    88920
```

```
gacaagcaat ggtaggtaga actgtggcaa cagccaatag aggaaaactg tgctatgatg    88980
aaatatgaga acaggaggtg tggttagaaa tcaggagact tgacgatcct tgtttccaga    89040
caggaaagag ccgttgatgg aggaagagga taaagatgtg agaaagggag caagcaaggg    89100
ctcagaatgc agctcccagc ttcaaacaca gcacctttgt tatggcttct tctacatgtt    89160
gagcttctgc acattattta atatgaagaa agggttctag aaaatcattg gaaactgttg    89220
aattagatgt cctagctcta aaaagttcta ttaattatta attataccts tacactgagt    89280
aatttatagt aatagcttga atgaccacat tcagataatc ctgggctatt taaggtcatg    89340
ttgccaaaaa aaaacttaat aggaataatt attaaagatg taattatttg catttcagtt    89400
cctgactagc tcttacaatt tggacatgtg taaatttcag cttttaaatt ttggtttgtg    89460
tttgaaaaat aaaagcattt ctcagctgaa ctattaaaat atttgtagag ttttttttac    89520
atgaaaatga gattttaata ctggttcaat ttttaagcca tatattacag tttaaccaaa    89580 atatatttt atagctctct gcttaagtaa agttatgggt agtaatacct ctttgtgaaa     89640
cacatgtatt atttattatc attataaaag aaattcatgt tggttggaag agtttgaaaa    89700
aatgtatata catatcaaga aaaaactaaa atcacaatca catataattt caccacctgg    89760
ggctaagaat tatttcgatg ttttcattc ttttgtatta tgaaatattt catatgtgta     89820
acaaataccc atttatgcat actaggtttt actacattat ggctttatta tatattctta    89880
agaaaaggtt tttgttttgt tttgtttgt tttttgaga cggagtctcg ctgtcgccca      89940
ggctggagtg cagtggcatg atctcggctc actgccacct ctgcctctca ggttcaagta    90000
attctcccgt ctcagcctcc agagtagctg ggactacagg caccggccac catgcctggc    90060
taatttttgt attttagta gagacggggt ttcaccatat tggtcaggct ggtcttgaac     90120
tcttgacctc aggtgatcca cctgcccag cctcccaaat tgctgggatt acaggcattt     90180
gccgctgcgc ctggccagga aaagtttttt gaagaaataa tgttacggag tcaattgaag    90240
gctcctcttc atcctacttc cccttcctac ccagaggtaa ccactatctg gaagttttcc    90300
actatctgga aaaagtatgt ttttatactt ttacgatgta tgtaactatt cattcaacat    90360
ggagaagtat cactagtagc tgaaagcact gcctcagcca agccctccct aaggaggtct    90420
caactgggac tcctgaaaag ggcctgaact gaagcctctg aatggaagtg cctgagctag    90480
gaaagcagag aagcctatga gcagggctag tgggggtgga gggaccaggc agtgagttct    90540
tggctgcaaa tccctccaga agctgtaaca tactagctgt gtaccaagtc tgatgtggag    90600
atggcagttt cccccaatga ggtctgccgg gcaaagcctt gtaactgtct agggtcctgc    90660
ctgaaagata atacatagga ttttggcctg cagccatact cctcaatatg gtaattctat    90720
gtttaacttt ttgagaaact gccaaattgt cttccaaagt gactgcacca ttttccattt    90780
ctaccaggaa tatgtgaagg ttccaatctc ctacatgttt gccaatagtt attatttaat    90840
ctgtcttttg gatcatagcc acactagtgg gtatgacatg gtatctcact atggtttttc    90900
attgcatttt tctgtaactc atgaagttta acaactttgt ttttgcccat ttttaaactg    90960
ggttacttgt gttttattta ttgagttata aaagttttta cttattttgg aaagcagata    91020
tgtatcagat atatgatttg taagtgtgtt cttctatgtg ttctcttctc attgtcttga    91080
taatgtcctt tgaggcacaa aagttttcaa ttttgatgaa atccaactta ttgatttggt    91140
tgcttgtgct taagagtcat tctaggaaac cattgtgtaa tccaaaatca caaagactta    91200
cacctatatt ttcttccata agttttatag ttctaattct tatatatagg tctatgactc    91260
atttagcatt aatttttgca tatggtatga ggtaaggttc caacttcatc cttttgcatg    91320
```

```
tgtgtatcca gttgtcccag taccatttgt tgaaataact tcttttccta ttgaattttc    91380
ttgtcattat tgtcaaaaat cagttgacca tatatataag gtttatttct caagggcttc    91440
tcagttttat tttatcaatc tatatgcata tccttatgcc agtctcacac agtgttaatt    91500
actgtagctt tgtagtaagt tttgaaatca agaagtatga gtccttcgtt cttattttc     91560 aaaattatct tggctgttct gtgtcccgtg tgtttctaga taaattttag gatcatcttg    91620
tcaatttctg caagaaaaaa aaaagccaat tgtgttgaat ctgtagatca atttgccaat    91680
tgtgataggc agaaaaatga tccccccacc cccgcaagat gtctacattc tagtataatc    91740
cctagaccct atggatatgt tatgttacat ggtgaagggg aattaaggta gcagatggat    91800
ttgaggctac tggacccagt gtaatgacaa atgtctttaa acatgaaaaa gggaggcaga    91860
agattaagtg ccagagtgac atgctgtgag aaagacttga ctggccattg ctgactttga    91920
agatgaaagt gagccataag ccaaggaatg tgggcagtct ctagaagctg aaaaaggca    91980 aggaaataga ttctctccca gaaccttcag aaagaaatgc agccctacca aaaccttgat    92040
tttagtccag caagaaccaa tttagagcaa ttcaggacta taagatgtgt gttctaaacc    92100
actgaatttg tggtgatttg cacagcaaca agaggaaact aatgcagcca tttaaacaat    92160
ggcaagtctt ctaatttctg aacacaaaat gtctttccat ttatttaggt cttttttaaa    92220
aaactttttt caatgatgtt atgctctttt tagtgtacaa gtcatgtact ttctttgtta    92280
aatttatccc taagttttgg gttttttga agctattgta aataaattgt tttcttaatt    92340
tcatcttgga ttgttcattg ctagagtata gaaatataat ttattttgc atattgattt     92400 tgtgtactat aaacttactg aactcatata ttagctgtaa tttttttgtg aatttcttgc    92460
aattttctac acaaaatatc atagcacctg caaatagaaa ttgtcttact tctttccttc    92520
ccatctggag acctttatt tcctttctg actaagtgac tcaactagaa attccagtgc       92580
aatgttgaat gaagtggtaa gagcagactt ccttgtctta ttcctgatct gaagaagtgt    92640
taggggaata taaattaaaa aacaaaatct cttgccaacc cagacaagct caacccaaaa    92700
gtagaaaaga aaacagtttg gattttgaa taaacatgaa accagatgtc attttcaaca     92760
taggcaatcc actaaagaga tagaaaagac agaagaaat ctcatacagc taagcagatg      92820
taacccttgt catacatgtt ctcaagataa atgataacta gtcttcaagc aagaggactt    92880
gactcaccat ttgtcacaca cagttcatcc taaattcatc tgataattgg ggtaggcatc    92940
tgtgtttact aattgcctta atccaaaaga aaaacaaatc tattatatct ttatgacagg    93000
aggtaggttt gtagtttgga cccaggtgcc tgctgagtta ggctgcaccc tccatggaa     93060 actcccctgg taggtgcatg gtcttcctca ttggcttcat ttcaaagaga tggtggctac    93120
gcctttaagg aaaaggttcc tgggttataa cactgacaag aggcttattt aagttttgga    93180
aagacttaca gagttcattt taaagaggca gagaaagaat gaacaattat aaattttcta    93240
aggcatacgc actaagaaaa ggtggagagt gtggaaaatc tcttaccctt cttgtgttga    93300
gggagaacat aggtggttgt atgtatatgt gtgttttca agattcatgt tatttacccg     93360
tctgagtgga agctgttggt ctttaccgtg aagcacaatg ttacctgaga attgtgcaga    93420
tgtctttcat tgggctgagg atgtttcttt ctgttcctag ctgagtgctt ttatcacgaa    93480
agacagttgg actttgtcaa atgctcttgt ctgcatttac taagatgatc cttttttttt    93540
tttttttttt agacttcatt ctgttaatat gatgttttac ctggattgat ttcgtattt     93600 taagccgtcc ttgcttttct gagacaaatc ccacttggtc atggtataca cagtagtccc    93660
```

```
gtcttttttt tttttttttt ttgagatgga gacttgatac gttgcccagg ctggagtgca    93720
gtggcgtgat ctcggctcac tgcaacctcc gcttcccagg ttcaagggat tctcctgcct    93780
cagcctcctg agcagctggg attaaaggca tgcgccacca agcccggcta attttgtat     93840 ttttagtaga ggcagggttt cactgtgtta gtgaggctag tctcaaactc ctgaccttgt    93900
gatccgcccg ccttggtctc ccaaagtgct gggattacag gcgtgagcca ctgcgcccag    93960
cccacagtag tcccttctta tccatgattt cactttccac agtttcagtc aactgcagtt    94020
tgaaaatagt aaatggaaga tttcagaaat aaacaatttg taagttttaa attgcgtacc    94080
attctgcgca gtgtggtgaa atcttgcact gtcctgctcc ttctcacctg ggatgtgaat    94140
ctgctctttt tccagtgtat ccacactgca tgctctatct acacagtagt cacttagcta    94200
tctcagtgat caggtcaact gtcatggtat ctcagtgctt ctcttcaagt aacccttatt    94260
ttacttagta atagccccaa agcatcaaag tagtgatgct agaatattgt tataattctt    94320
ctattttgtt attagttatt gttaatctct tactgtatct aatttattaa ttaaacttta    94380
tcatagatat gtatatctag ggaaaaaagt ttgtataggg tttggtacta tctttggttt    94440
caggcatcca ctgggggtct tagaacatat ttttccctgga taaggggta ctactgtaat    94500 tctttttata tgttgctggg ttcagtttac tagtatttta ttgaatattt ttgtgtctat    94560
atttataagg gatattggtc tgttttcttt cttgtgattt tacttgcctg ggttttgtag    94620
caggttaata ctgacctcac agaatgagtt gggaagtgac atgatttgga tttgtgtccc    94680
cacccaaatc tcatgttgga ttgtaattcc cagtgtttga ggtggggcct ggtaggaggt    94740
gattgggtca tgggggcgga tgtcccactt tggtggtgct gttttttgtga tagagttctc    94800 acaagatctc attgtttaaa agtgtgtgac acctccctac tctctctctt cctcctgctc    94860
tggccatgcg aagatgcctg ctcccacttt accttctgcc atgagtcaaa gttccctaag    94920
gcctccacag tcatgcctct tctatagcct gtgcgccact taaaactttt ttctttataa    94980 attcccagt ctcagggatt tctttatagc aatgcgagaa tggacgaata caggattttc    95040
ttctttgttt tgtaatgtta tgctagagtt gggttggaaa gtaaatcatg atatgtaggg    95100
ttaaataaaa cccatctgag gccatgactc accagatgcc ttagatagga atttgggcaa    95160
gataaaaaaa tcagaggtta gtcatcattt tcattgtcct tattttctaa gaagcctgtc    95220
agtaaaattt ttttatcttt atcactcata agtaattat aaaatgtttt ttatttcaaa    95280 gttttttggtt ttttctcttt attcaaagct tatattttat ttggctttac tatgtcagaa    95340
tacagcttgt acaattatag tttagaataa attgataaat tgttcatact ctgatgattc    95400
agataatcat tgcatagcat ttatccccaa cttattggtt taatacaata ataataattt    95460
atttgctcaa attctgcagt ttgaacaggg cttattaata acagcttatc tctgctccgt    95520
gaggcattaa ctagggcaac ttaactggaa tgggaggaat ctcttttaag gaggatattg    95580
gtactggctt ttggctggga gcttacctgg ggatattggc tgggttcttg gtttacttcc    95640
atgtgttctc tttaaatggc tagactgggc tttggttttt tcagtatcgt ggttggaatc    95700
tgagagggaa tgttccaaga ggtagagttc tgaaaatata gcctgcatgt acaggcatgc    95760
atcacaattg ctaatgttcc attggctaaa gccagtcaca tggccaaaac cagaaataat    95820
gtatggaggc actacacaag ggcatatata ctagtaaaag tgttttctca atagatcacc    95880
aaagaatttg ccacacctga tatatagaaa agtttatgta agtttatga attccttgaa     95940 gataatgtgt tttgttttta gactgcagta ctcaatatat atttatccaa ctatatttac    96000
tgtattgaat ttgtaatgat actgtctaga attatttgtc ttttctttga ctattaagga    96060
```

```
cccttctctt gggcaggggt tcttttcttt ctgtttcttt tctttctcaa tgacccatt     96120 cacaaagctg gttagtttat acttttcata aatttgagac agtagagaaa aattttaaat    96180
taatgtgtat gtcaatttaa aatcagtgaa acttagtgt tggtacaatc aaggtatact     96240
ttctgatatg gtttggatct ttgtccccac ctaaatttca tgttgaattt taatcccgta    96300
tgttagaggg ggagcctggt gggaggtgat tgtattatgg gggcgaattt ctcccttggt    96360
gctgttctca tgatggtgag ttttcgtgtg atctggttgt ttaaagtgtg cagcacctct    96420
accttcgctc tcctgctcct gctctggcca cataaaacgt gctggctcct cctttgcctt    96480
ctgctatcat tggaagcttc ctgatgcctc ccaagaagca aatgccatca tggttcctgt    96540
acagcctgca gaaccgtgag ccaattaaac ctctcttctt tctaaattac ctagtctcag    96600
gtatttcttt gtagtagtgc aagaacggat tcatacactc tttaaatgtg ataaacaaaa    96660
taaagtacaa tccttatttc agctttgttt acctttgcc tttctctcat ttaaactgcc     96720
aacatccaag gaaagaagag tcaaaactca tctgagtaaa tataaagata ttctatgcct    96780
tatattttaa aaatgtattg catttggcaa ttcttataac acactgaaca ggtcatttttc   96840 atattgtata agaaaggaag ttaaggcaca aagcaaatat cttgttttcc acagtcctac    96900
aattttgaag tgtcatttca ttcagccaca ccaggtccat tgctaaaata gtttattctc    96960
tccatataga gttggcatcc catgggttac ccagatagta gttcattcct aaatggaaca    97020
caataaatct ggaactaaat aaagtgcttt atttccctct gttttgaaaa tctatattgt    97080
gcagaaagag agaagaaagg attatcttta tgtgttcaga gattaagact aattttgatg    97140
gtgttaagag ccgaaactat ggaagttttc aagggtaatg cttttaaaga aaatagctcg    97200
cgagacttgc aggggttgga gcgggaagcc ggccaagagg aaagctggag gcgccggtgg    97260
ggaacaggtc ggagttggag cttggccgga agtgggaccg gtgcctggcg gatgtggtcg    97320
tgaagatagg cactggtttt ggattaggaa ttgtcttctc accttcttta aaagaagaat    97380
gtggccatta gccttccgtt ctggcatggg attaggaatg gcttactcca actgtcacat    97440
gatttccagg ctccatatct tctacacgga aaatatgtca aagagcagga gcagtgactt    97500
cacctgagaa catcccagtg ggaggacaag agaaattatg tttattcctc aggaatactg    97560
aagtgccgtg aagtaagctg ccattcttct gtaacaatgt tatcagtaat gctttaaact    97620
ccagcacctg gttatgtatt cgaaaccaag tctgtttctt gttttgtatt ttctctctgg    97680
aaatggtgag gaggtggtct taaataaatt aaacaaaaat aggaaaaaaa aaaaaaaag    97740 aaagtaagta aaagctgcct gcattgcatt tgagtgactt gaataagtaa agggaagctg    97800
aggtaggcca ttcagcttct tgcttacagg aggagggaaa ctagcgattt agtgcaggta    97860
aaatgggagt aaatatggac tctcactttt taacttttac ctagaaatta ttgataaaaa    97920
aagccaagct ccgtaaaata cttgaagaga tttgttctga gccacatgtg aggaccgtga    97980
cccgtcaaac tgcctcagga ggtcctgata acatatgcct aggggtggtt gggttacagc    98040
ttggttttac atgtttagg gagacctaag acatcaatca acatacgtaa ggtatacatt     98100
gatttggtcc agaaaggtag gacaacttga agcaagtggc gtgggtggga ttcatagatt    98160
ttctgattga tgattagtta aaactgatat tatctaagac ctggaatcag tggaaacaag    98220
tgtctgggtt aagatatggg attgtggaga ccaaggttct tatcatgtag atgaagttgc    98280
ataggtggct gccctagag gcaatagatg gcaaatgctt tctattccta cctttaaaag     98340
gttctagact ctcagttaat ctcttcagga tcagaaaaag acctgaaaag ggaaggagat    98400
```

```
tctctgcaaa atgcatttcc cccacaagag acagctttgc agggccttta aaaatatgtc   98460
aaaggaatat attttggggt aaaatacttt gattttttc  agggcctgct atctgtcgtg   98520
tgatgctaca ccagagtcag gttggaattt ggtatcttat tcctacaaag atcagtcata   98580
agacctgtgt tgtaatgtta atgctgatca gctgtgcctg aattccaaaa agaggagatt   98640
ataatgaggc atgtttgagc acccttacct atcacggcct gaactagttt ttcaggtttc   98700
tttggaattc ccttggccta caggatgggt ccatggattc ggtagagggg cttaaaattt   98760
tagttttggt ttataaaacc taggagtcat atattggaca attgctcatt ttttcaaacc   98820 ttaattttg  gtcacgttag tagaaacgat gaccaattat ggcaaaccag aatgtcaaca   98880
aagcaaaata ccaaggaaaa cggcttgttg tcatgtcaga ggtacagaca gcaaagatca   98940
gttttaataa aatgtgactt aaagttcctc tctctgaaac cccttctttc tttattcccc   99000
ctactctgtc ttttatcttg ttaccagtgg agggagtcca ggttcttggc atcttgaaca   99060
aagaattgga cagaacgcac aaagcaagga aagaatgaag caacaaaaac agagatttat   99120
ttaaaatgaa agtatgcttc acaggtggga gtgggttgag catagggct caagagccct    99180 gttacaggat tttctggggt ttaaataccc tctagaggtt tccattggtt acttggtgta   99240 tccctatgt  aaatgaagag gatgaagtaa agttacagtc atttaaatgg agaggatatt   99300
tcctgtcata gctaaagtgt ttccatttaa tttagttcta ggaagtcagc atgaattggc   99360
cttatgttcc ctgcctccac actctattct cctgcctcca tctcacactc tagtttgagg   99420
gaaattacga taaagttact ccctgtgtgg ccctggcctc agtatcttat caagctatta   99480
tcttttagtc caccaccaac caacagtcac tgtcaaacat actcaagccc tgggttcccc   99540
atgttttcac ccctcttcct cattttctcc ttatctactt cccggaaata actactatat   99600
aacatagaag aataaatcac taattgtgag aactcacaca ttggcctcag agaagatatt   99660
ttgggtaaag gacattcctt ggtcctcaaa tgtcatcaaa tctgtgtttt ctgttgacag   99720
atgtctttgt atctgctcag caaatgggaa tagggagaca gagtgaaatt ggttgtgagg   99780
aagctgtcaa aggccatggc cattggtttt cgcatattca gtgagggaac ttctgcttca   99840
cagatgaaag aggaatacat ttcttttgtt cttcagccac ataagattac agatttagga   99900 tctagttttgt gcagcatttt ttgagcaaat atggtgatga ttcaggttaa gacatctata   99960
attcttaaaa gtcactttga aatatgcgtt agctatctgt taaaataaaa ataccttatt  100020
ttgcttaaaa atcttaaaac acagacttta atactgtacc aaagcaataa tcaaaaatta  100080
tttacatgtt catgaatttg ttttgataga acaaatttta atttggaaaa tattgttgac  100140
tctgtcctca gcgattaaac cacactgaaa aacaaatgta atctttatct taaaactgtg  100200
catatctgtc acaaaggtat ttttagtctt taatcgatgg acatagcatt tggaacagga  100260
atagatatta caaattatct ctctgtctta cagatgtgag gaaattaata tctacccaac  100320
ctcacctcca aagtcaaaca gcctattaag gccacagaac agtttaaaag tcaattcatg  100380
agaaatgtta ttttaaaaaa tagtctgttt tcttcatggc atctaataaa ttttcaatca  100440
atcaatcaat caattaatta gtatattagt tgtctccttt actggaatgt aaacttcatg  100500
aggccaggta ttttgtgtgt gtttgtttgc tcctgtattc tactacgtgc tcctggcaca  100560
tagtattgct tggagatgaa cgagtaaaca tgccagatat gggtttccat gaactagggg  100620
caaagatcag gagggaggct aacatggggtg ggacagggtg agagtaggct gccactcgtg  100680
ttttgagatc atacatgctt ttaccaaact ggacctaatg gaaaggacaa ctgacacccc  100740
tgtcaccact accaacattt ttacctataa tagtaaaggt tcttggtcta tctgactttg  100800
```

```
actttaatag actgagggtc aactatttgg ttgtccactc agaactcctc agaattcagg   100860
aatatgacag tccgttcttc actaccatat ttattctgct gcctgttttt ttctagctca   100920
cttattgtca cagtccctat gaaatgtgac agatctctct atgtaataat aatgccactt   100980
tgcatttgta tagtacttag tattttcat ggcacttgca catttattat ctcatgaaca    101040
gattctacat aaattggaat gtcgcatgaa atgatctgaa atcaattgtg tcattctgtc   101100
aatgtccact gatcctagtg gagaaatgaa aattgagtct gatttgactc atcattttgc   101160
agtaaaaaca agaaactaat taaaggcaga tcaacagcta cactggtaat cacaggtcct   101220
ggtttgcata atgcagtgtc agtctcttct gcttttact gttatgaaat ttatgtatat    101280
tagatataaa atgtttccct aacttgaaga agtattgcat taatctatca aataatggat   101340
tggtttagt tgtagcagtt atctaccact ctttcataaa aaggacattg acaactcttc    101400
caggtggagt gtcttgtcac tctggttcat aaaatgttat ttagaggtct gaatcatgtg   101460
tagggtgaa gataacttcc tccttcctca cccttctgaa ggtttgataa tttgagtcta    101520
taaaacaaat gcataataga cagattgata ggagaaaggt atacaaatta ttacttgcac   101580
atgtgtacat aagaacaata tgaaatatga aaactcagga aaggccagat gactgaagtt   101640
ttataccatc cagaagtcgc agaaggaata ggggcttgga ttgtgcaaga caggttatgg   101700
gagggaggga caagaaaagg cctggctagt gaaggtggtc tcgttataca gagtgctatg   101760
gtttgaaagt ttgttccatc caaaacttag gttgaaactt aattccccat gtggcagtat   101820
taggagatgg gacctttaag agatcgctag atcatgagag aagagcccctt atgatctagt   101880
gcatcatgag gatccattca tggattaagg aattcatgag ttattatgag aatgggacta   101940
gagggagatc caagtgagca ccctcagccc ctttgccgtg tgatgcctca tggtgcctcg   102000
ggactctgca gaaagtccgc accagcaaga gggccctcac cagatgcagc ccctcatcct   102060
tggattttca gcctccagaa ttgtaagaaa caagttcctt ttctttataa attgtctagt   102120
ttcaggtatt ctgttataag gaacagaaac agaaaacaga ctaagacaca tgaaatttca   102180
caggtagcag ttctcagaaa aaatagatgg tggcctgtgg taaaatgtct ctatcagact   102240
ttcaaaggtg tcatactctc cctctcattc atgtgagtta atctttcctg gattcggata   102300
ggagtggggt gggggtgggc tcagagaaac cctagctgtt tatttcatga atgtagattt   102360
tctctacaga tgcaaatatt ctccacaaaa gacagatttt caagaagatt tctgtggttt   102420
gcagttcctt tgaatagcta tatggaaata tgccaaagaa gtgtttttg gggggtgagat   102480
attctggttt tgttcacatg catgtcccta aacacaatcc acaggagcta ggtgacctaa   102540
taagagggt tggcatctag aaaccagtcg tggcccacct ttgctgtggg actaaggagg    102600
ctattctgat ggcttctact ccagtttgtt tattatttaa cttaacattt acagagacat   102660
ttggtaaaaa tgtttataaa aactaggcct gaatttaaca tttcatatct tcaaatgtgt   102720
tttgtacttt aagctgctgc ttatatttta aagagctttt aaatcattga tttcattggt   102780
ggttaaggca tgttaatgca tagcttcatg caacatgaga gaaatagaaa gcatttagag   102840
aagtgtccca aatgcccaat ataaacatcc tgctttgcta ttttgtaaa gtaagtgcag    102900
gaaaccatag atagtgttta aatagctctt tttgtgcctt tctagaataa agatgactta   102960
aacactaaca aagaagggta catgaataat actgcaattt aggattgcca gatgaaatac   103020
agggtggcca atgaaatttg aatttttgaat aaacaccaat gaacatttta gtttatgtcc   103080
cgtttactgt atttttagc atattttca actattgcat ttttaaaagt aattcaaatt    103140
```

```
taactggctg tcctattttt tagtggataa agctgtcaat gctggatgcc gtccaaaagc   103200
aggcaggctc tcaaatttgt gttaaaggtg tgccaatttc ttttagtggc atagtatatt   103260
attccacagc tcttgaatgt gtcatctaat tctcttgtct ctctgtaaga ggtttgtgtt   103320
cagaaaagtt agagctgttt aggtatcaaa tcttttttaac taactgcgta acggcagtag  103380
tcatctgtga gctgagaaca tttccgtgat gccaggctta tagacagcac atgctctgag   103440
gataaggttt tgagagactc ttcacatctg gaatgatgtt gcccattgaa tatccccaat   103500
tgtggatctt gcagacatac atgaattaat atattccaaa ttgatgtcat ttcttcctgc   103560
acatctgctc ccctgtatc tgtgttaatg actcttatac ccatttagtc accagaacca    103620
aatacttggg atcctagaga aggaggggat catctttccc ttctcttttt ctcttcccca   103680
catccaatca attctgaagt cctgtggctt tcatcttctc atttccctga tcaccacatt   103740
agtgggcttg tccaggcttc cagtctcttt tctggctcaa tccctttact cctccatagt   103800
ggagaatgcc ataaggccga tcagggtgct ctttaatttt tatggcsctt gtgggacgag   103860
gttatatttt atcaatgcta ttaagtgctt ataataagta ggacctcata gaagaagatc   103920
aaggcatgga tggatctctc tacattcatg attctgccta gtgtcttctc tgctaagcta   103980
tgcttatctc accatatatc tgaatattat gttgctcact ttttccagaa aatgcaccga   104040
gatttatatc cccatggttt ttccaagttt ccgcaccctc attagttctc attaactcct   104100
atcctaccat agtgatggtt ttttgagcca tttctcggca acggtttacc aaccttcagc   104160
aaccataaat atccatggac atgcacacaa acattcacat acacatacaa acacacagac   104220
atccacaata catgcataca cacaaaaata cacacacaca cattttattc atcctatatt   104280
gctacatgct gtacaatgaa ttataattag agcatcattt gattttcagt ctaaataaat   104340
ggtacttact ggcacacaga cttaattatg tcacctcagg tcagaatttt atcctcatga   104400
gtttagatag agttttgcct ccttgagtgc acaaatagtg gatcttaaac cttcagacag   104460
aaggtttatg ttcttttttc agtaacagtg ataagttagt tctctttctc ctttgtattt   104520
aaggtactcc cgggagatga aggtgtgata gccaatacct gagaactaaa tgtacttttt   104580
aatagactca gaattaacac attgcagtgg gatgcagaaa tcccttttct ctctttacct   104640
agtgaagcaa atattattgg ataaataact tcaataagat agacttacag tagtaagtct   104700 attttttattt atttctaaaa tagacttcgt aatagtcttc aaacaattta gccctcactg   104760
tgtcccaaac tccttgagat tcttttatta atattttcta acacttatta agggaacatt   104820 ttctttttatg acatctctaa atgtcattgt ttccaagatg ctatatcatt atattgtcaa   104880
tgagttactt cttcaatgat agttttttcaa tttctcttaa ggttttaatt tcttcttcaa   104940
tttctcatac ctgtgcccta gtatttcttt cagctcatta gtggtgaaaa taagctagtt   105000
cttataaacc cttagttgtc aaatattatc atcttatctt ttgaggaaag aactagcatt   105060
tagaggataa atttaactgc taatgtggta atgctggaca caccaggaat tagggggcaaa  105120 tctgaagcca gcagatgtcc tggaaacatt agctcttgac atcagaaagg ttccctggga   105180
tgcagagtag tcaccctgga gtcttgcaga ttaagaaaaa gctcccatag cacacacaca   105240
tatttaaaag gattgcttga agtgactagg tttgaagtgc aaatggcagc agaagtggaa   105300
gtagaaaaat aaatagaaat gtttcccagg aagtcatgtg ggggcaaaga cagtcacagg   105360
cccagggctt taagatatct cccagggagc tatcttcctg ttgcagatgc tcaggccttt   105420
gtcctgcagg gttgttttgt acacctcaga aacagtgctt gaaattcaag aaaataaaca   105480
ttgttgactt gggatgagtt ctccactcta atttataaaa taggcaaatt gtttagagtc   105540
```

```
cactgcttta accctatttt cgtcagtgat ttgtaacaga gccttcatct ctgtgcgcac  105600
ttgaggggct tgaagaatgg aaattaggtc tgcgagttac cagcatatgg tttcaatgga  105660
agacttggat gtgaatgaaa ttatccaagg agagagtaaa gtatgaagag aagatgaatg  105720
agtgaatgaa ggaggaagcc actgaagggt cattatatgg tatctgagag ggaggaagga  105780
accattttt  ctaatattgc aacttgccac cttacctcct ctccagacct cctttattct  105840
agtcgagttt atttttcctat agcatttttc acttattaaa atacaacatc atttacttttt 105900
aagttatttt cttgtgtttt atttatatc ttctctgcct cctgtcccctt actagaaagt   105960
gagccccatg agaacagatt ccaagcaggt agaagagtga ctagtacttc tactagtcac  106020
tagtgcttag tcatgtttac tggctgagtg aaaaacatag cagtgtttca agaggaaagt  106080
ctgctacaaa ctgaatgctt gtgtctctct aaaattctta tactgaaatc ctaatctgca  106140
acgtgatggt attagaaaat gtggcctgtg gtaggtgatt aggtcatgag ggctctgccc  106200
tcaccaatgg gattagtgcc cttataaaag agacattgaa aatttatctt ttttttcttgt 106260
aaatttgttt gagttcattg tagattctgg atattagccc tttgtcagat gagtaggttg  106320
cgaaaattt  ctcccatttt gtaggttgcc tgttcactct gatggtagtt tcttttgctg   106380
tgcagaagct ctttagttta attagatccc atttgtcaat tttgtctttt gttgccattg   106440
cttttggtgt tttggacatg aagtccttgc ccatgcctat gtcctgaatg gtaatgccta   106500
ggttttcttc tagggttttt atggttttag gtctaacgtt taaatctttta atccatcttg   106560
aattgatttt tgtataaggt gtaaggaagg gatccagttt cagcttttcta catatggcta   106620
tccagttttc ccagcaccat ttattaaata gggaatcctt tccacattgc ttgttttttct   106680
caggtttgtc aaagatcaga tagttgtagg tatgcggcat tatttgctga gggctctgtt   106740
ctgttccatt gatctatatc tactgttttg gtaccagtac catgctgttt tggttactgt   106800
agccttgtag tatagtttga agtcaggtag tgtgatgcct ccagctattg ttgcttttgg   106860
cttaggattg acttggcgat gcgnnnnnnnn nnnnnnnnnn nnnnnnnnnn nnnnnnnnnn  106920
nnnnnnnnnn nnnnnnnnnn nnnnnnnnnn nnnnnnnnnn nnnnnnnnnn nnnnnnnnnn  106980
nnnnnnnnnn nnnnnnnnnn nnnnnnnnnn nnnnnnnnnn nnnnnnnnnn nnnnnnnnnn  107040
nnnnnnnnnn nnnnnnnnnn nnnnnnnnnn nnnnnnnnnn nnnnnnnnnn nnnnnnnnnn  107100
nnnnnnnnnn nnnnnnnnnn nnnnnnnnnn nnnnnnnnnn nnnnnnnnnn nnnnnnnnnn  107160
nnnnnnnnnn nnnnnnnnnn nnnnnnnnnn nnnnnnnnnn nnnnnnnnnn nnnnnnnnnn  107220
nnnnnnnnnn nnnnnnnnnn nnnnnnnnnn nnnnnnnnnn nnnnnnnnnn nnnnnnnng  107280
ggtgtttatt gggcatcttt tcccaaaaga aaagattggg acccaccca aatgtccacc     107340
aataaaaggg gggattaaaa aattggggcc catacccccc ggggaatttt agcccccaa     107400
aaaaaataag gggttcaggc ccttggaggg gacagggata aattgggaaa tcccctttcc   107460
cggtaaactt tcgcaagaac aaaaacccaa cccgggaatt tttcccttaa aggggggaa    107520
ttgaccaatg agtcccccag ggccccagga ggggaatttt ccccttttgg gaattttgtt   107580
gggggggggg aagggggaag gaaaaccttt gggaaaaaac ccaaatgtta aataagaagt   107640
taggggggtgc ggccccccag ctgggcccag gtaaaaatag gtaattaccc ggcccaaggg  107700
gcccaggccc cctaaacttt aaggtttaat aaaaaaaaaa aaaaaaaacc cccccaaaa    107760
aaaaaaaaaa aaaagaaaaa tttatctttt gaggagaaaa tggaaagctg tcctccaaac   107820
aagtgcaggt gctggctgtg gggagtgaaa gcacaccaaa gataggaaat gcaaaaggga   107880
```

```
tttgagggga tatgggtgga acactcacag cttgtgcttt gtgatctttt ggaaatatga   107940
agcaaatctt ctgagatctc agtagatgag aatatgaaaa atttgtctgt ggggagccaa   108000
agacattttc tgtgttgagc atgttttctt cttgttaaag cattttttt  ttaacatgag   108060
cagttgataa agggatggca gggaatactt tttgtacatt tagaaccgca gagccctgcg   108120
gaagtctcag ccccaattcc cccatttccg tattattgaa ctgaaaaaca ctaaatatga   108180
aaatgcttaa ctgatagacc tagaaatcat acttttcttt gcaaatacat actataaatc   108240
ttaaactagg aattcttctt cctctcaaga acagtaattt gttgattatt tttaagtcaa   108300
tactgatgta tacctgtctt gattgttttg atgccaattt ataaatttct ttataccttg   108360
gccattgtca aagctaacta tattaatctt tactccatta gagtactgag gccagaccca   108420
agtacttatt atggaactga attagcaagc tacttaattt agggtgtgtg tgtgttgagt   108480
acttttagta ctctgttttt tagtgtacat atatgttaga ggaagcttct attagtacaa   108540
aatgttcaag ggaactacac tcgccttcac aaaaattaaa tctaattaaa ttaaaaaata   108600
gattcatgaa ccgttgcaaa ttatttaaat gttgtttaaa ttgtgtggca atttcagaag   108660
cagtgaacat ggtagatatt gtcatttccc gcaacatatt taaatatggt cttccccta   108720
ctttatatgc tagagctgaa tagcaaaggg aaaggctcta tcagtcagtt ttttccaaa    108780
ttaaccctt  atcattagtc accacaaagt ctcagtggca ttcaacttca gaatcacagg    108840
tatgtgagcc tgctaggcta gttctcctgc accctgttgg tatatgggtt gtctggggc    108900
agactggttc tgtgtgtctt atgctgggcc caggctgcaa gggtggaagc tacctgttac   108960
acattcttc  tctggtggtg gaccgaagct cctagaagga taaatggaag ccctcagtac   109020
ctgttcagac tgaggctcta atcaggttat tgtcacttcc acattccatt ggtggtcaaa   109080
ggaagaaaac acagtcaaag ccaaaagcag gaatggatga tgagcactgc ccagaagagg   109140
ctaccacaag gatgggatgt acagaagctc ccagagcagc aaagaactgg ggccagcaac   109200
tccatctacc acagtgggct tgctctttct ggaaataaac acccttggat gcatactagg   109260
tgatacttat atgagttact ggtatttagt gcttaagctg gaattgatat gcttcctggt   109320
tcatctaagg ctgggaaatt tcaaacagac ttttgatat  cctttcctga aatagtgatt   109380
aagttaaaca tttcagatac ttaaaaaata actccaataa agcttgaaaa ttggatcttt   109440
ctgagcggat tctcccttcc ttagcatgta ttaatgtcct tattttactt cagccccgag   109500
gtactgaaga gtgagccgta tggggagaag gctgatgtct gggcagtagg ctgcatcctt   109560
tatcagatgg cgactttgag tccccccttc tacagcacta acatgctgtc cttggctaca   109620
aaagtaagca acgctgggag acagaagggt ctcgtgtagc taaaaatgca attcttttc    109680
ttattaaaca gatcttgtg  atttgtatat aactgcccat taaaagcaag aattgttttt   109740
attaactgca tgatccagtt tattttttcc gctttcttct aaatatatat ctcatgtaat   109800
ggcttatttc cctctataat tgtctttatt tataatacaa aattattttt aaaaagacgt   109860
ttggtcttct attatttatt tatttaattt atttattttt gagacagagt ctcactctgt   109920
cagccaggct ggcgtgcagt gacatgatct tggctcactg caacctccgc ctcctgaggc   109980
tcaagcaatt ctcctgcctc agcctcctga gtagctggga ttacaggtat gtgccaccat   110040
gcccgaattt tttattttt  ttttaggtt  tcaccatgtt ggccaggctg gtcttgaact   110100
cctgacctca ggtaatccac ccaccttggc ctcccaaact gctgggatta tagacgtgag   110160
ccactgcgcc cagctggtct tttatttta  attgcagtct ggactactca caatccagca   110220
ccttatatta tcccatacac cattttatta tgaatctaag gttaattttt aactcagctt   110280
```

```
ggataatata attccagttc aagagctgtt taattgatgc aaatgtttta tttggtcggg   110340
atttctgact aaaatttatg tgtgaagtta tcctgcttaa ttagtaactc tcaggttatg   110400
gtcaagtatt aactattcaa agacatccgt ggccccttta cttccatcac tctagtctgt   110460
ttgttttgca gatagtggag gcggtatatg aaccagtccc agaaggtatc tactctgaaa   110520
aagtaacaga caccatcagc aggtaattag tcttgcggct tcagacatgt agggacaatc   110580
aagaaatacc tcatttctat aataaatcac tatttatgga taaaaggtca tgaagagaaa   110640
gagtccctac ataatccaaa tctagaaaga tgtttgtgca tcatcagtaa cagtgactat   110700
ttggatgcta cttaagtgtc caagaggaag tagagcgttc acttattatg caaccactag   110760
aacgattatt tggaagggtt tgtaacaacc tgtaaaacac attatgatat gtgggtaaga   110820
caaatatgat gtaaagctgt tgtaaccat gacaaacctc ataaaaatat gcaaaaatt    110880
ggaaaaaggc cagacaagaa cacatgaaac aaaaagccat gttagatgat aaagttgcag   110940
gtacttttta atttccattt ttaaactgat aatgtgattt atcataattt ttcatagaga   111000
atcaggagct ccagctatca ctatagcagg agtttaatga aagtcattat ttagttgtac   111060
ttccaaagtt ttggccaatc cctgctggcc tgtcacccat gctccctccc acttcccctt   111120
ctgttttctc tgctccagcc acatggtgct cccactagt cctggcatgc accctccttc    111180
tagacttttg cccttgcttt catggtttcc tagaactctc tttcctcaga tatatgtgtg   111240
acacaggccc tcacttcctc tgggtctctg ctaaaatgtt ccccaccctg atggcccac    111300
tacctcacag tactctctaa cctccttgcc tgctttaaaa agctcacagc actcatcatc   111360
cctgacatat tatacatgtg catacatgag ttttgtttat cgtctgtctc ttccccacca   111420
aaatggaaac tcaagagcag ggacttagtc agttaatttg tagcttttat tgcccaaagc   111480
agtggctggc acagagtaga cccttaataa atattgcttg tatgaataaa tgactcgtgt   111540
atctggctga ttgctatttc tgtaccatct tgggtactta agttgcatct tgagtactta   111600
agttgggtac ttaagttgat gggatttctc catcccatca aactgagtat tttggattgt   111660
agaaattcta gagtcacccc agatagaatc ttttttcatc tgccttctga gtcttttaaa   111720
acttgggttg gtatctatac tagcacttag ccccatctct gatgaaatat aatagatgta   111780
ttattgtggc tgtacccctt tccctttgat ttatccttct agcccattgt ttgtgctaat   111840
attactcctc acctgttttt gtaggatgat atctaaacct ttctttcttt ggcacaatac   111900
taatctacag tcttattttt ttaattgatt ttttttaaaat ttttaagttc agaggtacat   111960
gtgcaggttt gttatacaag gtaaacttgt gtcatggggg tttgttgtat agattgtttc   112020
atcacccagc tattaagcct agtgcccaat agctattttt cctgatgctc tccttcctcc   112080
tgccctccac catccaataa ctcccagtgt ctgctgttcc cctttatgga tccaggtgtt   112140
ctcatcattt agctcccact tacaagtgaa aacatgtagt atttggtttt ctgttcctgc   112200
attagtttgc taaggataat ggcctccagc tccagccatg ttcctacaaa agacatgatg   112260
ttgttgcttt ttatggctac atagtattcc atggtgtgta tataccatat tttcttttatc   112320
cagtctagaa tttatgggca tttatgttga ttccatgtct ttgctattgt gaatagtgct   112380
gcaatgaaca tatgtgtgca tgtgttttta tgatagaatg attcgtattc ctttaggtat   112440
agagccagta atgggattgc tgggttgaat ggtagttctg tttttatgtc tttggggaat   112500
cactacacat tgttttccac aatggtagaa ctaatttaca ctcccaccaa cagtgcataa   112560
gtgttccttt ttcgctgaac cttccagca tctgttattt tttgactttt taataatagc     112620
```

```
cattctgact ggtataagat ggtatctcat tgtgattttg atttgcattt atgtaatgat    112680
cagtaatgtt gagctttatt tcatgcttgt tggctacatg tatgccttct tttgtgaagt    112740
gtctgttcat gttctttgcc cacttttaa tggggttgtt tttctcttgt aaatttgctt    112800
aagttcctta tagaaactgc atattagacc tttgtcaggt gcatagtttg caaaaatttt    112860
cttctgttct gtagattgtc tgtttactct gttgatagta tcctttgctg tgcagaagct    112920
ctttagttta attaaatccc acttgtcaat tttgtctttt tttgtttttt ttttttttga    112980
gatggagtct tgctctgtcg cccaggctgg agtgcagtgg tgtgatctcg gctcactgca    113040
acctccacct cccaggttca gcgattctc ctgcctcagc ctcctgagta gctgggactg    113100
taggcctgtg ccaccacacc tggctaattt cttttgtat ttttagtaga cgggtttc      113160 acggtgttag ccaggatggt ctctatctcc tgacctcatg atctacgcgc ctcggcctcc    113220
caaagtgctg ggattacagt cgtgagtcac cgcacctggc ccccaacttg tcaatttttg    113280
cttttggtat cttttgtcatg aaatctttgc ctgtgcctat gttctgaatg gtattgccta   113340
ggttgtcttc caggtttttt atagtttgg gtttcacatt taagtcttta atctgtcttg    113400
agttgatttt tgtatatggg gttcagttca gatttttgta aaggagttca ttttcagttt    113460
tctgcaactg gctagccagt tatcccagca ccatttgtta cataggggaat cttttccccca   113520 ttgcttgttt ttgtcaggtt tgttgaagat cagatggtgg ttgtacgtgt acagcctat    113580 ttctgggttc tcttttctgt tccattggtc tatgtgtctg tttttgtatc aataccatgc    113640
tgttttggtt actgtagccc tgtagtatag tttgaagtca ggtagcatga tgactcaagc    113700 tttgttttt tttttttttg cttaggattg tcttggctat tcagttgctc ttttggttcc    113760
atgtaaattt aaaatccttt tttagtggt gtgaagaatg tcactggtag tttgataaga    113820
atagcattga atctacaagt tgctttgggc agtattgtca ttttaatggt attgattctt    113880
tctatctgtg agcatgggt atttttccat ttgtttgtgt catctctgat ttcttgagc    113940 agtgttttct agttctctct gtaaagctct tttactggtt agctgtattc ctaggtattt    114000
tattcttttt ttggcaattg taaatgggat tgcatgcctg atctggctct tggcttgacc    114060
cacagccgat gttatactga atgggcaaga gctggaagca tttctcttga aaatcagcac    114120
aagacaatac ttcaacatag tattgacgag ttaatgggtg cagcacacca atatggcaca    114180
tgtatacgta tgtaactaac ctgcacgttg tgcacatgta ccctaaaact tgaagtataa    114240
taaaaaaaaa aaagaaagaa agtactggtc agagcagtca ggcaagggaa agaaagggca    114300
tccatatagg aagagaagaa gtcaaactat ccctgtttgc agatgacatt atcctgtatc    114360 tagaaaccc aatagtattg gctcaaaaac tccttaagct tataaacaac ttcagcgaaa     114420
ttgcaggata caaaaccaat gtgcaaaaat cactagcatt tctatataac aacagtgaag    114480
ccgaaatcta cagtcttaag gcctcaggct ctgaagacag gcctacctgg ggctaagtca    114540
tgtaaacagt tgcaaactct aagaagtgat ttgaggccag gtgcggtggc tcacacctgt    114600
gataccagca ctttgggagg ctgaggcagg cagatcacct gaggtcaggt gtttgagacc    114660
agcctggcca acatggtgaa accccatctc tattaaaaat acaaaaatta gccaggcctg    114720
gtggtgtgcg cctgtaattc cagctactcg ggaggctgag gcaggagaat cacctgaatc    114780
tgggaagtgg aggttgcaat gagctgagat tgagctgttg cactctagcc tgggtgaaaa    114840
gagcaaaact ccatctcaaa aaaatttttt taaataaaaa taaaaaaaaa gagtgatttg    114900
accattattt ctgcgtccct gttttctgat ctagtagaat gagaatcata atagtaccag    114960
tctcattagg ctgatgtgat gattacacaa agtaacatat gcaaatcact taggataggg    115020
```

```
cttgcagaat ggtaaatact tgagcaattt tggcaatcat catggttagt attatgggaa    115080
atgagacgaa cctgtctttta aatcatttga ttccacaaac actggatcat gccttgttgc   115140
taatgaatcc aaatatattt aaactgctca tctctgtgat ttgttcctgt tgtctgttgt    115200
tttttggaaa gtacattaaa aattgacaga gtcgtcagag gtgtcaagac aaaagtacca    115260
tatttgctca tttaatttct cctttttaata ggtatttgag tgccacaaag ggcgagggaa   115320
aggtagcgca ataacaagg ttcagagacg ttgctttgat tttgtgaatc tgggcaaata    115380
gactgtaaat ctcttctgaa actaatagac cctggctatg ctacccagg actcttgggg    115440 ttaacatact agtagggag tcagatagca acattggagt gtaaaggttt agagcgtcac    115500
caagttctgg agtcaactag attctaatgc cccctcttcc actcaattta atttccctga   115560
ggcccaattt tctcatctat gatgtgtggg tagcagtagt aattactttg tagcaggacg   115620
agccacaggc aagaacccct cagatgctga gttgtagaag gaaagggctt tattcagctg    115680
ggagcaccgg cagactcacg tctccaaaaa ctgagctccc tgagtgagca gttcctgtcc   115740
cttttaaggg cttacaactc taaggggtc tgtgtgaaag gatcgtgatc aattgagcag    115800 gcaggggta cttgactggg ggctgcatcc actggtaatc agaacagagc agaacaggac    115860
agggattttc atgatgcttt tccatgcaat gtctgaaatt tatagataac acaagcagtt   115920
aggtcagggg ttgatttta actaacaggt ccagggcaca gtgctgggct atttgcctgt    115980
ggattccatt tctacctttt agttttact tctttctttg gaggcagaaa tcgggcataa    116040
gacaatatga gggtggtctc ctccttaac ttcatgggct tgttttaaag cttaaataag    116100
atagtgcttc tgacccactt aacgcagtac ccagcaagtg gtaggcactc tataaaatta   116160
ggtattatta gtattaataa tgatattgta ttatgtacag aatgaagttt ataaagcaaa    116220
ttgtgataaa tgtgatgaaa aatggtaaag ggggcaatga gagattacag aaggacctgt    116280
cttactctgg gaattggcga aaagtttctc tgaaaaaagg acgtgtaatc tgagacctgg    116340
aacattcatt aactctcaaa tagtaagcag catttcgcag accagtatct gtgaaggctt    116400
tgctgaggga aagagcttct caatttgagg ttgcttttgg ttcaaaatac taagatgcca    116460
caataagtta gaactgacaa ttcaacttta tatctgataa taaattaaga ttgcagggtg    116520
cattctgtaa taaatttatt ttcatttaaa gttaagactc ctcattgtct gggtttacat    116580
tccaaataaa gttttatctt tagaaaattt gacttaaaac tgaaatcaat catgaattat    116640
atgcaattgc atatttaatt tgctttggat tttcagtatt aaaaaattga gttctgaaag    116700
aattagggaa caaactcaaa ttttgtattt tcttaaagca acaatgcaag ggacacataa    116760
aggcaagtat tcttaatgat catttatgac tcagcaaaag atcaggctca cagccaatct    116820
ttagtaattt gatagagcct ttgaaataga agacagctct tgacagaaat gtttattata   116880
atcattccta aaaattatat tgttctaat catatatatc ttctttcctc tattttacta    116940
tcttctcatt attttttcaca tccttgtcaa gtagagctca cacagtttgc atttctaatg    117000
tgcagcatct ttccttttc ctgtttgctc atgtggtata caagcacatt tgttattgaa     117060
acttgtcttt cctagcaggc cttcaaattg ggagaataac ttagcaaccc tgaggagttt    117120
ggggaagaaa ataaatatat ttttttgttc tgctcagtac taggattact atttttacct   117180
actagtgtac tattaagaga atattgtctg tttactttt aaaaggaag aacatttcct     117240 tttatgcata aaatattcta ttaaaatcat tgccttattt ttctttctct gtgcctggtt    117300
gcataagctg cctggtgctt tgcttcagaa gcagtcatga ggactaacaa agttaatact    117360
```

```
ttcagctagc tccaaggaca aatggatctt tatatttttc accccttttca attctttgta    117420
tcttaaaaca tgacatgaat gtaattgaat aaggtatcct tctaattctt tccatctggc    117480
ctttcagagt ggagtgggga caaagtggat gaggtgagaa tatcctcaat ttttttagga    117540
ccagatttta tgcttatttg tttacagaat cattggtaga caatctttag catgtattat    117600
gactctgatt cagttgctgt taagaatttc tctgaggccg ggcgcggtga ctcacccttg    117660
taatcccagc actttgggag gccgaggtgg gtggatcaca aggtcaggag attgagacca    117720
cgatgaaacc ccgtctctac taaaaataca aaaaaattag ccgggcgtgg tggcgggcgc    117780
ctgtagtccc agctgctagg agaggctgag gcaggagaat ggcctgaacc cgggaggcgg    117840
agcttgcagt tagccgagac tgcgccactg cactccagac tgggcgacag agcgagactc    117900
cgtctcaaaa aaaaaaaaa aagaatttc tctgaaatgc ctaagcaggg agtcatttca    117960
gagcaacgag actatcctgg aacttctggt aggaaatgtt cctgggaatc caaaagtcta    118020
tggccaaata ttttgggtta tgggtaggta aacttttag atgttacgct gagtttgttt    118080
gtggatttat tcattgattc attcgttcat ttgctgaata cctatcagga ctcagattcc    118140
attgtatatg ctgggagatc atagtgaaga ggacacatgt ccctcttctc tagaagtttc    118200
cagtctagtg gtgaaacaga ccattatagt aaaataatta caatagtttt aagtacttaa    118260
gtgcaaatgg tgcaaaaaga atgtacaaaa ggggctcagg atatctgtct gaaggcagtc    118320
caaaagtatt cctaatggag cctggaaaaa tagtgggatt ttggcaagta tataagagat    118380
gatggctgag atgatggctg ggaaagataa gataccatgg gcaaaaaaaa aaaaaaaaa    118440
aaaatcaagc atatggaata aaataagcaa agaaatgggg gtataggaga gacaggtgct    118500
atttggggaa gtgcaggtag ccgcattgga tgtgttgctg gaggagggga aagagtggag    118560
gaagttaagg gccagttcaa gagagacctt gtatagcatt ctgggaattt taattttatc    118620
ctattggacc atgagaacta ttgaagaatt ttgagtagag aaataatata gtcagattta    118680
ggaatagtat tctggttagc agtttacagt acagaccaga ggtaggcaag aaatgagtgt    118740
gttatttagg agactctttc agtagtccaa gtaagtgacg ttgtaatagc caaatagctg    118800
tgggattaca ggggaaggat gtggattcaa gaaatattta gaaagtagaa gtcacaggac    118860
ttggtgtttg ttaaatgtag gaagggatgg aggatacata aaagtgtgga ttttcttttc    118920
aatttattga aattttacaa tgcatgtgca cttcacagag attacctcgt tcaaacacca    118980
taccagttta atgaggtagg tactataatt atcccatttt acaggtgggc tatctgagtc    119040
ttagaagcta tgtaacttgc ccaggatctg actaataaat ggtaaatgag gttttaaacc    119100
ccagcaaaat gatccagagc ctgcatgctg agttatgatg ctaaactgca tcttctttgt    119160
ggtgcctttt ccagtgatgg caaatacagg accaggagag taaccttggg caaggagatg    119220
actatatgct aggagaacga aggtcatttc cattcccatg taccataata tgtagctata    119280
taatttataa aactagttta cgttgctttt tttttatttt taaaaagttt cagctgatag    119340
ttcagctgct aatattaccct tgaagcagct taaacatctg cagtctaaga atttagaata    119400
tccacactaa tgaaaggttt agacactggg ctttttttt tttttttcca cctgccagtg    119460
agttggcagt gatttcagaa agcagccaac ccatgcagga gaagatggtc ccatctgccc    119520
atcctgagac ccgaagagca tcttcatgct cagcctggaa cccttacctt ccagcccaag    119580
tgcaaagaga ataacgctga ctccttttcc ttccttagct ttccaaatgc cttttgagaa    119640
gtcttggact caaagctgtg cttgatatcc atcttatccc aggttatctt aggtgaaaat    119700
accatagtgg acacacagtg gagtttaacc ttgacccttt acactctgtg gcctgctccc    119760
```

```
aacattgacc agagtgttat aattatctca tgttatctta ggtgcctcac tcctgatgcg   119820
gaagctcgtc cagatattgt agaagtcagt tcgatgatat cagatgtcat gatgaaatat   119880
ttagacaact tatctacatc ccagttgtcc ttggaaaaga agctagaacg ggaacgaaga   119940
cgcacacaaa ggtattttat ggaagccaac cggaacaccg tcacatgtca ccatgagctg   120000
gctgttctat ctcacgtaag tgcaaatatt tcaatcggtt catgatgcac tctaatgggc   120060
tgtctgaagt tgttcatgct tgttttaagg aacattcatc aaaagttaga aaaatagtta   120120 catgcaaatat tgcagtagta tagttacata tttatatcca tttctgtatc ttatatacaa   120180
attaaaataa atataactga ccttcctaag aatgaatcca taatttattt tattttttgca   120240 aaaatcgagg tatcacaaag ttctcttagc gaagtttaag ttacagactg taaaattagc   120300
agtgaatgct tatatttaat ttcttcagca atctgactgc aacttttggg aatatgtatg   120360
aatatgtgag ttaattcaga gaaggaaata acatttgcct ttaaaatttt tcgtattgta   120420
ctttgcaatc tctttcattg ccatttgtgg tattaataat gttgccatgc ttcaaatcag   120480
aatatgtctt attttttcttg ccaagaacct ttagattgtt ttgatatttta agtatatttc   120540 tgaacattgc ttggaaaaga gatgccaaag ctacaaatat ccacatgtgc aagcaatggt   120600
gccagtgatg ctcttgttgc tgtctcttat tttctttctt ctgtgtctttt gttgcaatca   120660 caatcagtgt tctgttgttt gctcatgctt tgggcctcca cccagtggcg acctggtaag   120720
gggactttca tcctttttttt ttttttcctg ttctgggggt gggcccaagg caattggatc   120780
ataaaactct ttcttagggt acctggtcat taaattcctt cccaggatcc taaggacctg   120840
ctccatctca gctggtaaaa ttatgtatga agttggtctc aaagaggcag ttctgatttc   120900
ttgaataaca gtgtttccag tgaactgctt tctgaaaaga aggaaagtac tactgtttag   120960
tgggtttgtc ttaaggtatt tggaatccag aagttgaaga ctgaatctag ttttcatttg   121020
ggaaggaaac tctttcatct tcattgcctt aaatgctgag cctagatgta atttgcaga   121080 acattccatg atgattattt aagttatatg tttatgtaaa ggagcatata acttggagtt   121140 atagcccctta ctgaacacag ttaaatctca gaaggggagt tagagctcac tttgctttttt   121200 attttactac ctgacttcat aataactagg caacaatgca tcattctatg tatgtcatgt   121260
tgcattctaa atagagtatt cctagtagac taaaatgcaa gagatttagc tatttctata   121320
tatcttaggt atttggggcc ttctattatt aagttctgca ctgcagagtt acttagctta   121380
tttccagttg tatgtgaaag agtcatttca tattagattc atgtggctga tttggggctg   121440
agtggcatta gtttacaatc taacagcaga aagtctgtta tctttagcaa aacaccttga   121500
gaaggaccat tacttatcta tttatttaca cttctcagct taaaaaattc tttattatgg   121560
aaaacttcaa acgtttataa atgcaaagat tacttcctgt acccatccca gcttcaacag   121620
ttagctatta agggctaatc ctgtatcatc tctattccca cctacttcct tccttcccca   121680
gattattttg aagtaaatcc cagataccat ataatttcct ctatcagtat ttccatatgt   121740
gtttggagag tcattttagc tttagaaata tagatttcag gctatcgcca ggtaaaataa   121800
agggaaagct ctgaaaccaa gggagggatt ttaatgttcc agaggttgta tactcatccg   121860
taaattaagg ggtagaggat attatctacc tcagagagta ctaggataaa tgagttaatg   121920
tgtttgaata tattgtatga ctttaaaagt ggcataaatt gtaagatagc atcagttata   121980
taaatgagca tagcttttgt tagaagaata gtttgttgat ggaacttgtt aatctagtgc   122040
tgacttgtcc aagtagtctc tacattaaat ccttatgtca ggcatacagt taatgcatat   122100
```

```
atattagcac ctgctgctag ccagcctcag tgccctcatt gagcattcag gtttttatgg    122160
accatagaga aatgctttac ttcaaagcaa agtttatatt cctgctttaa atagtcatac    122220
agtactttct cctttcgcac tattttaagt ctactgatac attttcattt caaggttaac    122280
caaatgttaa ctaaaaggaa aaaatgcagc tttattaaag aagcaagaag gaagattgca    122340
tttcatcaaa agacagtatg cagttaattg gcattttttct cagtggggac caattattat    122400
ttttaaaaac ttacatctac accattgctg aagaaaaatt ataggtgtaa aattttatga    122460
ctcttttttt cttaagcagt attatgatta tctcatttca gatatactgg aaagttctcc    122520
cagagcagtt attatcaata atgcagttac acaatccagt gataaattat agtcaaggga    122580
aagagaaatt agtgggttca gtagaacttt atgaattccc aatatcaata aggggatcca    122640
ctgtgaatta ctgaaatttt gcaaattagt gggtaagcaa acaattgata agaaacatta    122700
aaggtttcta tttcatgggg aagtattcta tttactttca tattttagtc tattcttaat    122760
tatgcaattt tttatagtgg cctagtaaac gtaagtacta atatatattt tagaagaaca    122820
gagaagtctt cactaaaaag ttcactctat gtactgtggt ttacccacta tgaaagtgaa    122880 ccaaacctttt ccttttgaag aatgttttct gattcttata acttaaaata agagatcata    122940
aggagagcat agagttgaga atgataagaa tcatgtagag taaaaggaaa taaaattttta    123000 acttaaatgt gtaataatta gaatattgtc atgtagaggg tattgtggca tcataatagt    123060
gaaaatcgtt atccatgttt tggcactgtt cacagtgtag tgaacacaga gaatcattac    123120
cctttcgatc ttatatccct ggcagaaaaa tcaattaaag acatttctga agagtctact    123180
gcttatatct tttccaacaa atacaatagt gtgtattaaa gaaattcagc ctgacaaaac    123240
ctggagaatc aatggaaaac ttcaattcca ttagaattat tgggatttta tagagacagc    123300
tttatgctaa catttaaatg ggtgaaaaaa gcatatttct atgtgtacaa atggagcaga    123360
attgagtgtt ccagggagac tgaagagaat taatgagaga agcatgctgt cagtgtgaga    123420
cttgcaggaa tcacaactac ttttccagtg atatttgaca ggaagtttat cttcaccacc    123480
cctatttaaa ggctgaatga tgatttcttt ttactagttt aataagtttg ttcagtttgg    123540
agaactgctt tcacatctat aacagaaaga gagaaagatt gaaaatgcct gtggtatata    123600
attaataatg aaggaacagg gatttgttgg atgtcttctg aatgtaaggc attatgcttg    123660
gtatagtgaa gcttataaaa aattataaac aatgacccca ttcatgaagt aactgataat    123720
ctacttggaa agacaagata gatgtgcata tgcaggagga actttctaat gattccgaac    123780
attttgggta aataaatgag atgagggaaa tgaattaatg aggcctaggg aggatctcag    123840
agccaaacaa agatagggtc ttgataacta aataaggaag tcactcctgg atggaaaaga    123900
ataacgttaa gtgcagaaac tccagctcag ctcacttaat actaagaatc aaacttagaa    123960
atggaattgt tttatgtttt aattgcacaa ggaaagggaa atcaggagaa gttaaaagac    124020
ttgtccaagt tcatccagct agttagggac agccccagga ccaaaaattg ggtctgctga    124080
ttgacaatgc atatttttat atgtgtagtt tgaaaagcct ggggaagtag gctggagcta    124140
gatgatggat gtttgtgaat acctcattaa gctgtttgaa ttaaatcctg tgggtaacgt    124200
ggactaaaac gttgaatttc tccaaaatac ctaacaagca aattgacaaa ctatgaacta    124260
attctttctt ttttttttt ttttgagatg gagtctcact ctgtcgccca ggctggagtg    124320
cagtggcaca atctcagctc actgcaagct ctgcctcact atgggctaat tatttcttat    124380
tgtacatacc cgcttttttaa tgtttttttac tccgcagtgt tttccattac actcctctgt    124440 cctggttttct gtcttctctc tttgaatact cttcctcatt ttctcttcca tccctggcct    124500
```

```
tttaacttta aaggttctgc ctctcttacg cttcccttgg tttccatcta gtcccatggt 124560
atttcatttc atatgaattt gggtaaaaat tggtgtgcaa gatggaaact ttattttcta 124620
taattatata tcattttgtt ttgaacccct gtttgtgctg gtagcagaaa atggtagtag 124680
tagtcaggat caattatgtc ggtctctttt ggtctaaaag tttctttgcc atcccaaggg 124740
ttctcttctc cgtgtcctct tccgaagatg gcaacagagt acaggagaaa gcttaagcat 124800
ccccatgtcg atgagagagg ggcaggggct ctggacttct tctattggcc cctgctgaac 124860
ttagatgaca tgaaccctgt gattttggga tgctgacctc tgtccttatt aaatgtttat 124920
ggcatctgta actcatggcc tcttttatca tcatggctta aacccaaaga attacccatg 124980 atgcccaac tctccccttg gggttactat ttttgatcct ctgagtcttg attgtgactt 125040
tcttggcatt cttagtttaa gcagcctact ctgtggtcct cagtgcagtg atggccaagt 125100
gaactcacct gccagcccca gagctgtctt ctacattggc acaagacaca tgggggcttt 125160
ggattcccat ccacaccaca cacagcccat ggggaactca ctggcactag ggacccctat 125220
ctcagcccca tcagctccag tgccttcttc atccttttct attcttctgt cccaggtgcc 125280
tacaattcaa ttattcattc aacaagtatt tactgagtgc ctaataggtg tcaggcacta 125340
tgtgtacaaa gtataccaca gttagcaaaa tagacaaggc ctctgctctc atgggcctta 125400
tgtatatagt gttatgatga tcatgaagct tcttcaaagc tcccggtctt ttctgtctgt 125460
gccccagttt cccccctcaaa ctctccgtgt atctccatca acagcccaac tctaatccca 125520
aggttcgcat ctgctggagt ggatgtgaga aggaaaaaca aggaggcttg cacttgctct 125580
ttcattttct cttccttctg gcaggctctt attttgagct ccagaagaaa tttccagttc 125640
gcacctttct gccagaagct acccttgcat ctattatatc cttctttttc tccaggtatt 125700
cttttcccct gtcttctcct gggtctataa atctcagcct cataaactgg tcttaacagt 125760
agaagaaaag agctctggag aagtgcacaa aattttctgc gaaggcaaaa tatgttggga 125820
tgtgtttcgc aacataattt ccacacccat ttgctggaga tcaccaaagc tgcctgtctg 125880
atctcagtct ctctgtgtgc cagacctata ttttgaaccg aacattcacc tgcatgtcta 125940
acaggtactt atgctcggca agtccacagt gaatggattc tcctcccttg atcagccatg 126000
ttctgtctcc tcatatcacc ttaattgtaa ccttgacatc ttcaattcac tctctctgaa 126060
atcctgtatt cattttgtta gcaagctcta ctaattctgt ctttgaaatg tctggcaaat 126120
ccatcttatc ctttcagttc tcattctcag tatcttgcat tatatcattg caagatccaa 126180
ctttcttgtc tctagttttt tccttacttc taccaagtga ttcagtcagt atatcacctc 126240
tgcactgtcc actaggggcc attaaggaat gtgtgtactg ggggtggggt ggtataattg 126300
ttgtttatca ctgttagcag ccagggatgc tgatatgtca tatacattga cagtcctgca 126360
caaaatgtga gaaacagaac gagcagtaga tacatattca gatatttatt gcaaggaact 126420
ggcttacatg attgtgggga ctgacgaggc aagtgcaaaa tccatagggra tggttggcag 126480 gaggaacagg ctggaaatct tggtcatggg ctgaagctgt tttccacagg ctgaatctct 126540
tcctcatctc agagatgcct cagctccact ttggagacct gccacctgat taaatcagtt 126600
ccatccagat tatcagggat catctccctc ccttagccat cttccacatt cctacccaaa 126660
ctattttcca aaaaaaatat ctgatcttgg taaattgttt catgcttatg acaataagta 126720
aatgctcatg tagtgagtcc taaaaatttt ctctaagctt ttggtgaatc taaaaaaaga 126780
ttcctatgat aatttgatat tgccagagtc aaaatatggc atacataagt gtcatcttaa 126840
```

```
attccatcta ctttggagga gcaggctggt agagcaatta ttagcaaata ttattttta   126900
aattcacaaa ctgttcataa cttcacttct ttgttataaa attcttattg tagttttcta   126960
atctatgatt tttagcagac attgacagat actgatattt ttcataaatt ctcagatgtc   127020
tttaaagttg agcatataag aattgaacag atatgtaagc atctagattc tcattttttt   127080
aatgcaaatt aaaaaatgtg ctatttattt atctgggttg ctttattttt attataccat   127140
atgtcattta caattgctga gcacaccact aaagtcatgt gtctgcaatc ctctgctagg   127200
agattaaatt aagccatgta gaaaatgatg tatttttaaa ggacaatatt tttgtgaaca   127260
tctttgcttt tattgtctgg ttaattgttg actgaatttc tcccaaggct gtgaaaatgc   127320
tacaagtaat gatgtaggaa gagaaatatc aggaaaaacc atgacttgtt ttggaaatgt   127380
tctatgctca ttatgttata tgaaaataaa gcaatgcctt ataggcttcc tcacaaatac   127440
agacacaatt ctcacatcca cactacaatt ctctcttttt tattgacata taatttacat   127500
gtagtaaaat gtacacatct ttaggtgcct agttcagtgg cttttggcac atgtgtaacc   127560
tccaccccaa acaagagtta gaacatttat ctcacctcag aatgttccct taagcctctt   127620
tctatacaat tctctgcccc aggacgtaga ctggtgattt ctgtcactat aaattacttt   127680
gcctgttgtt tgacttcatt taaatcaaac acatgttctc tttagtggct ggcttttttt   127740
ccatgacaaa atatctatga gattcaccca cgtggtgtgt attagtaatt tgttcatatt   127800
gctaggcagt gttaaattat atgactacac cgtaatttgt ttatctgtcc tgttgatgaa   127860
cacttacgtt ttctccagat ttggaatttc ttaacactgt tgaaaaccta tttcaaaaaa   127920
gacccataca aaaatgttta aactttttt ctcttagata aagacctaga aatagagttt   127980
cagggttata ggtagttgta tgtttaactg ttaaagaaag caccaaatag ttcttcaaaa   128040
ttgtactgtt taacactttc agaagcagta tatgagagtt ctagacgttc cacatccttg   128100
ccactatttg gtattgtcag tcttttccgat tttagccttt gaggtgtaat gatacttctt   128160
tctggttta gtttgcattt tcctgatgat caatgaggtt gagcacattt atgtttgatt   128220
ttagctattt atatatcttt gtgtatgtgt atgtgttaaa tatctgttca aatctttcgc   128280
ctgtgatttt attggattac ttgtctgttt ttgttgattt gtaggagttc tttatatatg   128340
ccagataatg agcctattgt caaacatatg tattgcaaac attttgtata gtctatggct   128400
tgcctgtttt tttaaattaa tgacatttt tggataaaca gaaaattta attttgatga   128460
agacttattc atgtaattgt ttgtggtggt cagtgttttt tgcctctttg taatgaaatt   128520
gttgcctacc ctaaggttgc aaaaataaga ttctttatat ttttgtaaat gttttagacc   128580
tatgatccct tttgatttaa ttttgtgtat agaataatga ggagattgac ttttgttt   128640
ttttttttgg tcatttgggt atccagttt tccagcatca cttcttaaa tgtctagtct   128700
tttcccatgg attttgctaa gcatctttat tgaaaattgc ctgacaatat atatgtagat   128760
ctacttactt ttttctttt tgtttataaa tattttaaa tttaaattt taagttta   128820
attatttga gtacataata attgtacata tttatggtgt acatgtgaaa tttgataca   128880
agaataaaat gtttaatgat caaatcaggg taattgggt atcagccacc tccaacattt   128940
atcatttgtt tgtgttagaa acattccaat tgcattcatt tagttatttt aaatatacaa   129000
taaattattg ttagctatag ccaccctatt ttgctaccaa acactaaatc ttattccttt   129060
tatcttactg tattttgta cccaaccgtt cctttttat cccccctctc ctctcctctt   129120
ccagcctct ggtaaccatt attccactct ttatctccat gaattcgata ctttttagct   129180
cccacgtata agtaggaaca ttttgtattt ctctttctgt gcctggctta tttcacttaa   129240
```

```
cataatgtct tcagttcca cccatgttgt tgaaaatgac aagagttcat tcttttttat 129300
gactgaaaat tttcccattt ctttatcaat tcatcttttg atgggtactt aggttgattc 129360
caaatcttgg ccattgtgaa tagtgctata ataaaaatga gcatgcagat atctcttcaa 129420
catacttatt tctttttcttg tgtataaata cctagcaatg ggattgctgg atcatatggt 129480
atttctattt ttagttttta aaggaaactc catactattc attatagtgg ctgtactaat 129540
ttacattccc accaacagtc tgcaagggtt cccctttctt gcaggtctat ttctgaactc 129600
tattctgttc catggattat atgtctcttc ttagaccaat accacaccgt tttgatttttt 129660 gtagctttta aaaatgtttt taattttaat tggcaaaaaa ttatatatat tgtatacaac 129720
atgatgtttt gaatatatat acattgtgga atggcttaac ggagttaatt aacatatgca 129780
ttaccacaca tatgctttac cacataacat atgcattacc acacaatata attttgtgg 129840 tgagaacact aaaatccaa tctcagtatt tttcaagaat acagtatatt gttattaagt 129900
ataatcatca tgctgtgcaa tagatctctt gaacttatcc tcccatctca ccgaaactct 129960
gtatcttttg atattgtagc tttttaataa gtctcaaaac aagccctgta agtcctccaa 130020
ctttgttgtt ctttgtcaaa tttgatttgg gtgttctagg tctgttgtat ttccttatta 130080
attttagaat aagtttgtct aatttcttca aaaaatcata cctacaattt ttattttttac 130140 cccttgtttt aacatggaga atcttggcaa cattttaaaa aatcagtctt ttatttttact 130200 tattcaacaa aatttattaa gcatttattc tttcctggga cctattctag tattctcctg 130260
atacagtagt gaaccaaaca gccacagact ccctccttca tagtgagaga agacaaataa 130320
tagataaata aaactatatt taagtgctat gaacaaaaat aaaagaaggc aaggtaatag 130380
aaagtgattg tagacacagg gagacaggct attttaaata gggatgtcag tgaagggctt 130440
tataattaca tgacatttgg gcagagacct gaatacagtt gacctttaaa caatgtgggt 130500
ttgaactgca tgaatccact tatacatgaa ttttcttctg cctttgccac tcctgaggca 130560
gcaaaaccaa cccctcctct tcctcttcct cgtcttcagc ctacccaatg tgaagatgac 130620
aaagatgaag acctttatga tgatccactt ccacttaatg aatagtaaat atagtttctc 130680
ttctttgtga ttttcttaat aacaagctag aggaaagaaa atgttattaa gaaaatcaca 130740
aggaagataa actatattta ccatatgaca tatcaagtat gtattaattg tttatgttat 130800
tggtaagctt ctagtaagca gtaggctatt agtagataag ttttagaaa gttaaaagtt 130860 atacatagat ttttgactgc atggagtatt ggtgccctc actccatgt tgttcaaggg 130920 tcaactgtac attaaaggga taacctctgc aaatatctga aggcacaaca ttggtagcag 130980
aaggagtagc atgcccaaag atcctgaggt aggagtgagc ctgccaagct cggggaacag 131040
caaggaggcc tgtgtgtcca gcgtgcggtg aagcagggag agacagttgg acatgcaggt 131100
gccatagtcc ctggcatgca cttgagtaat atgagttctg agcaagccaa ggtggcacca 131160 ctaggctttta aaatgatata ggtggccgct gagtaggaat aaaccactga gagccaagaa 131220
tgaaatcagg gaaattggtt aagaagagat tgcagtgggc caagcaaaag acaatggtga 131280
ctctttttct tgacttttaa ttcttttctct actggcaatt aatcagtttg gaattttgac 131340
aacatgtgca aaatgtgcag tttaacaaga actagacctt tccttatgta actctgtgtt 131400
aaaaatgaaa cagtcaatga ggttctaatt tggtgtttca ttcctgttga taaccactca 131460
tttctaattc catactcttt aattcctttaa gcattggtaa atttcaatga cattgttttt 131520
ttgagaaaca aaaaatttct taaaacttgc ccacttgatt gttctctgta cattgttcct 131580
```

```
tcccttttcct ttcctttccc tccctttccc ctcccctccc ctccccttcc cttccctttgt  131640
cttttctttt tgagatacag tctcactctg tcacccagga tggagtgcag tggtgtgatc  131700
ttggctcact gcaacctcca cctcccatgt tcaagtgatt ctcctgcctt cgcctcctca  131760
atagctgaga ttataggcac gcaccaccat gcctgtctaa ttttatatt tttagtagag  131820
atggggtttc actatttggc caggctggtc tcaaactcct gacctcaaat gatcggtcca  131880
cttttggcct cccaaagtgc tgggattaaa ggcatgagcc accatgcctg cccattgtt  131940
tctttctttt tttctttttt ttcttgagac agagtcttgc tctgttgccc aggctggagt  132000
gcagtagtat gatctcagct cactgcaacc tccgcctccc aggtttaagc aattctcgtg  132060
cttcagcctt gcgagtacct gggattacag gtgcctgcca ccatgtctgg ctaattttg  132120
tattttagt agagaccagg tttcaccttg ttggccagac tggtctcaaa ctcctgacct  132180
caggtgatct gtctgcctca gcctcctgaa gtgctaggat tacaggtgtg aaccaccacg  132240
cccagccccc attgtttctt ttaaatgtta aatagaatta cctgatcctg gcctcatttg  132300
aaatgctttt aaatatattg gtatatacat ttagttctat tggcatgtta gtctgctgtc  132360
ttggaaaaac atggtggtca gtattgttgt gatggaccag atcttctgta ttcttaacaa  132420
atgataattt cagattatga cattgttttc cttctcctct tgttagtat tattccttct  132480
agaaaacctg tatttgagtt aaaagtgata gaaaatccac tcatttctga tacagtacta  132540
ggttagttat gggataacag tgaaacattt ttaaccataa taaatttgat actggagttt  132600
tagattgaat tgtaatgacc aatttattcc ctaatttatt taatttaatc acagctcatt  132660
aatatgtaat agtgctttta agacgttcta attaagatag tataataatg agataataac  132720
tatgtcatga cagtaaaaatt tttagctttg tgtaaatatt taataagttc aaaataaata  132780
agatccaacc taaagagaat atttttcttta ttatataatc catataaatt agttattttt  132840
agggcccaa acaccagtt tttctggttt agatttaact attgctctct taactgtatg  132900
tagagaatgg gagaagggaa attcttcaag attccctgat gaaaatagac gatgttacca  132960
tccaaaccat tttgggaaag ctggacacag tggtgtgcct ctgtatttcc agctactcag  133020
aagaccgagg caggatgatc ccttaaaccc ggaggttcaa gaacagcctg gcaacatag  133080
tgagaaccta tttctaaaaa acaaacaaaa actaactttc aggatcaaag attaaagatt  133140
tccatctacc actgggtagg gggtgggacc aggctccagg cttattccat cagcccacct  133200
ctctgatgtg gcaaagccaa gtcttccata gggaggcctg gagaaaaggt tcctatctca  133260
ccactacagt gagcagttca ctcagctatg gtctagtcca caaggttcct taatcatctg  133320
accacactgg ctgattttta aaaatatacc ttaaaatgta gggactaagt ttatttacaa  133380
tagtatgcag tcaatggcct gtctcctagt ttgaatttc tttgtgcaat catccatgaa  133440
aagcatagaa tgcggtgcca ctgataaaag atcacctcag ctggatgaat ttctagcacc  133500
tggtagcact aaattgagat atttaagggt acagtttatt aacaaaacag atggaagaaa  133560
ctgggtaaaa atatacctaa tagaatatga atatttcaga acacaaagaa atagtgcatt  133620
ttttagagtt ctaaagtaaa gcatctatag gatatagctg ttgttatgct ttatatttat  133680
ttcttgattt tctttctctc ctaaaacttt ctggcaattt taaaaattgc actgattta  133740
ataaaataga tgcccttaat tttcctactg tagcagttaa tttgggtaat gtcagtctgt  133800
tactgttaga attgctattc aactgaaaat gtattatgat ctgctgcaca cataaaaata  133860
ttacattata atgcgcaaaa ccgagctaaa cataattgtg ccaatactag cgtggtgaca  133920
ggaagcatct tctataatgg tgctgatttc catatcagtg ataattttat tgtgtgattt  133980
```

```
gcgttgtatt ctccttgccg ccgtattgat atccggaatg tgtctatcca ttcctaggat   134040
agatgcatgc agatgccaaa aaaactagtt aactccctct cctactcctt gaaaaatctt   134100
agtaattaga aagtgaaaaa gattatagca gccaaattct gtctccaaaa actttgcctt   134160
ttttcttgcc taaatccctt taataggtta atgtacttgc tggatgtgtc ttctgaggac   134220
aacttaatgg ctcaactatt tattgagcct ttgctatgtg taaggcattg tgcaaagcac   134280
taaaggattt aaaatggact aaagtgcccc cagttcttca aggaacaatt ttataaagag   134340
ttggatactc aaatactcac agtgaaaaac tccagaaatc acagtaggga aaatgtgtgg   134400
catatggttt atggcaaggt caaaaattat atcaattttt ttttgaagca aaaactgctg   134460
caagggattg ttatagaaat atatatattt ttttttttg agacaagagt cttgctctgt   134520
cacccaggct ggagtgcagt ggcacaatct cggctcactg caagctccgc ctcctgggat   134580
catgccattc tcctccttca gcctcccgag tagctgggac tacaggcgcc caccaccatg   134640
cccggctaat ttttttgtat ttttagtag agacagggt tcactgtgtt agccaggatg   134700
atcttgatct cctgacctcg tgatccacct gcctcagcct cccaaagtgc tggaattgca   134760
ggagtgagcc accatgcctg gcctagaaat acaaatttta aacccaaact atccatctat   134820
attatcatat ttttatgcat acagagtctg aaaaagcatc tctctcagat tgtaaattcc   134880
cctttatcag aatttatgca aacagtcaat tacccgtgga tgaaattttg gcagttacaa   134940
gtgactattg atttatgacc caattggttc ttgggttttg attgcaagtc cagcgtcctt   135000
aagtctcgaa ttgccttttt cagcggggac tccagcttct cctgactctt catttgttca   135060
aagaaaaatg ttttcctctg atgttttatc catgcctgtt cttaagagac acaaagcctt   135120
tgttaaagtt ttactagttt tagggatatt tgaattccag catcttaatt gcatcgacag   135180
aataaaaagt tttctcaatt caaaaattct ccttcatctt ttttcaacct tggtaatgtt   135240
gacacatctt gggtgtaaag tcctgaaaag gttgcagatg ccagctgtgg tcttcaggat   135300
agggtagaag atgatttact tagaataaaa aaggtcataa gaaggaaaag gccttgaatt   135360 gggttttac ttctgtgtaa atttctaatg acttcagttg aggatagtta gaggaagaag   135420
ggttttgtgg tttgggacga agaaaagagg taggcatgga agaagttgag ttggttttgc   135480
aataaagttt tgagccttag aaagagctcc tggatttggt atcagggggtt gagtgtggca   135540 gagctgaggc tggacttaga agcccgatac tagccttagg cattggaaaa atttctgagt   135600
agcatatatc ttttgccaga gagcggccaa agcatttcct gtctcaggtt gtaagttagc   135660
caaccagggt ggacctcaga agcagaaatt aacaactcag agtcataaaa cagcctttga   135720
acattggatg tactaattat ggaaaatcaa agttaaaata cttcttcacc tgcaaattaa   135780
cttcaacaaa acaaggagct tggtgaaact ttgaagaatc actgaaaaga atctcaggga   135840
aaagaaataa acagcaattg atcagacagt ttgcaatgca caaatgtttt ttgtatttta   135900
aaaatctttt catcttacct atagaacata aatatatgaa agcttttaga ggtttatttc   135960
tgattctagt tatccctaag atcttaggtt ttcttcatct gcaaattcta ttattatgga   136020
gtttttagaa acctgtgcct tggagctgtg tcattttact gtaggaaaaa aataaaaaac   136080
acataaatct gaaataaaata aggctgtctc tgaaatgagc atcattggag ccttttttagt   136140 caagaagtgc taggtaattt gtgactaaat catcttggac acaattcata gagggaattc   136200
tttccccttc aataaaatgca ccttttttctt tcttctcaca ctctctgcct gttatccttt   136260
cctccatcac agcctttctt tgtctttttg tctacctgat ctgtagcttt actttgccag   136320
```

```
cactgtttag ccccacggcc taaaaaggct cttcacgctt gctgcgaata gtcccataca    136380
atgaacatct taggagttgc ttgggtaaag aaacaagtgg tacttttta ctgattcata    136440 gtcattcctt ccgcatggtc tttctcttag aaaaatgaaa acttccagca tcagtggcat    136500
taattaatta atttttattg acccttgaga cataatttt gcagtttcta atactattat    136560
ttagggaaat atggaattac acaaccagat tgatgacttt gtagtgctat cataatggaa    136620
atgcatccat ccgttttgga ggattcagga ggaccctgtg gctagttctg cagagagtgt    136680
tcaagccagg cagtagtgta gagtcccaag tggtttgtaa gttctgttct ctgtagctcc    136740 ttttttgga aaaccttgcc tctcactctc catggcctgg ctttgtctgc tactaatttt    136800
cctggagttt tgaagagaat aagccttact tatttgctgt ggtactgaga ggatttgata    136860
gcaaatgttt ttgaaaaaac ttaagggaga gaaatttctc ctaaattaat atagtctatt    136920
tctagaagta catatttccc cccgctactg ggttatatgg ccttttcta ctgaacactc    136980 ttgccacttc catccttttt gatccaatgt agcttataga cctgcatctt tttgtattta    137040
tggactgaat agattctgta acaggtgtat aggtggaact actgatgcgt cttctgcatc    137100
aaacatttat attgatattt gaagcagtta atatatgttc taacaagatt taggtcctat    137160
agaaggaagg atagagaaag aggctatgaa aaactgaatt tctcttccca ggagaccttt    137220
gagaaggcaa gtttgagtag cagcagcagt ggagcagcca gcctgaaaag tgaactttca    137280
gaaagcgcag acctgccccc tgaaggcttc caggcctcct atggtaaaga cgaagacagg    137340
gcctgtgacg aaatcctgtc agatgataac ttcaacctgg aaaatgctga aaaggtact    137400 gctagtggca gtgtgtcaac gtaggtactg ctagtggcag tgtgtcaaca tgaatgtatt    137460
ctggactcct tcctgtttca agactcattt gctttttat tgtttttatt aatgtgcaga    137520
tacatattca gaggtagatg atgaattgga catttcggat aactccagca gctccagttc    137580
aagccctctg aaagaatcta cattcagtaa gctttctgtt atcaatttgc tgtttgtggg    137640
attccggaag acagtggttt ggaaatcata cttgagtcaa gcaaatatca ccatatacat    137700
aacccagtgg tttgttttc aggtgcagtg ctaattagga cagatgtgtc tgtctctctg    137760
acagagccca aaggttagcc agcacagtgg ttttatattt tctcagctgt caaatgaata    137820
gttttactat ttctaccagc aattgcaggt tctaactaga gagtcaagat atctaacttg    137880
gagacagcca ataaccaca ggagtaatgg acatgacctt ttatgagcct gttggttaga    137940
tgaattcaaa gcctgtagaa gaaattggtc ctggtataga ctaattttg tgcaattta    138000 tttatataaa tctaaaggga tgtgttacat ttaaaacaat aaaataaaag aatttttttt    138060
agagttatta aaaatatgac atataaattc cgtccataat gttaatcttg actcttaatt    138120
taaaacagta agaaaatag tcatactggg atatgggaaa gaaaggaaa aggtatattt    138180 agataaagtt taaagattat aaagagagat agaataaaat acatggaaca aacctgaaac    138240 ttaaagaaa gttaaaatag aaaatgaagg gaaacaattt ttttaaaaaa gagtaagttg    138300
ataaaatatt aaaaaccata gatagaaata ttctgaaata aattaagtga aataattct    138360 ctctcctcag tgactatact atgaaaatct cataaaagaa catttaaaat agcttctcta    138420
aggatcaaag tagaacccta aggatttagc tacattcttt gtcctttcca aacttaattg    138480
gtccatcgaa atgatgatta gatgttccat attttctggg acaacccag ttttcaatat    138540 tctgtcctat tttctccgta gatccctgcc ttctaggtgt attaatttgt gattgggaaa    138600
acatgaagct catatgggaa aaaatattta tgcatataaa catgtataac aaattccaga    138660
agaagtttat tactgactgt tttgagataa gttcagtgtt ctatatacct ggcagcaatg    138720
```

```
gtgggagggt tagtggggag gtaggaaaga gatgcttgac ccttaaattt gcatatggta  138780
acttggcaag gatggttatg acattttatt gcatgacatt ttattgtgtt ttgttagata  138840
ttaataacag ggttgttttt gtttgtttag cacatttgct ttagagaaaa agcccttaaa  138900
caaacctgac aaataaataa caatttgtaa catattttag ttcatgcttt cataatcaaa  138960 gacaatttt acagtatgta caattgctca ggtaaccgaa attcagtatt gttttttgtt  139020
gttgttattg tggtttacca tgaataaagc catgtttgtt tcttgaatgt tgtttgactg  139080
ctttcatgct acaatggcag cagaattcag ctgtgacaga catagtatgg cttgcaaagc  139140
ctagaatatt tcctacctac catttacaga gataagtttg actttagaac aatatgagag  139200
tgtttataga caaagccatt catgaatat atatattctt tattattttg aattttataa  139260
aaaacttatt taaaattttt tctgatatat aatatatttg tacctattta tggatacttg  139320
tgatattttg atatatgcat agaatgtgta gtcattaaat tatacattgt atgggtaatt  139380
cagatattga tcacctcaaa catttatcat ttatttgtgt tggaaacatt tcaaatctcc  139440
ccttctagct attttaaat atttaaacat tttcttatc cattcatctg ctgagggata  139500
cttagtctga tttcatatcc tggtggttgt gagtagtgct gcaataaaca tgagagtaga  139560
gatatctttt tgatatacta acttcccttc ttttggatat ataccagtag tgggattgct  139620
ggatcatata gaagttctat ttttagtttt ttgaagagaa actttattta tttatgtatt  139680
ttaagttttt tttttttttt tttttttttt tgagacgggg tctcgctctg tcaccaggct  139740
ggagtgcagt ggcacgatct tagctcactg caacctccgc ctcctgggtt caagcgattc  139800
tcctgcctta gcctcccgag tagctgggac tacaggcatg ctccaccaca cccagctaat  139860
ttttgtactt tttagtaggg acggggtttc atgttggcca ggaaggtctc gctctcttga  139920
cctcatgatt catctacctc ggcctcacaa agtgctggga ttacaggtgt gagccaccac  139980
acccggccga gaacctttat actgttttcc ataatggcta cactaattta cagtcccacc  140040
aacagtgtat gagttccctt ttctctgcat cttcaccagt attgttgtt cagtattgtt  140100 ttattaaaac ataaaaaata aaagatttgc agaggaaata atgtaaagtt atttctattt  140160
tctcgtctca gacattttaa agagaagttt tagtgcttca ggaggagaaa gacaatccca  140220
aacaaggtag gtgcaaattg aactcctaga aatattttt gattttgcag agctgagtaa  140280
taactcagct gaattgaaac ctgatagcca gaagtttcca tgtgcctgcg gaaataggag  140340
ttagagctta cttgcccaga actgtttata gttcaccaag tagcatactg aaacaggtac  140400
tgatcttgga cctgggtctt agtctagctc tgcctttttc tagctttgtg accttgagca  140460
aatcagttag cctctctgag ctcaagggtg ggccggcggg gtagggcagc tgtgctccat  140520
gaggtcatct ggagccctgg tcttatatct tgttcttcca tatccccagg gtataggttt  140580
catctttttg accaatatga cttatgagac cgcatcctac ctccaagcca gcaagaagaa  140640
gaaaggggaa gtagagacac ccctctttct tttaaggata tgaccgagat gttatgctca  140700
tcacttctgt tcatatacca ttggccagaa cttcctcata tgaccacagc tagttgcaag  140760
ggatggtgaa atatgtttga gagactgtct tttaaaggca aagcaaaatt gttatttgg  140820 gacagctagc tgtgtcagtg acagttgttt cttagagtag ggactgaaac aaaactatta  140880
gattgagcct tctgcaagtt ctcctgacct tcactggcac tgggtgagat tagagggagc  140940
agaaccttga ttcaatgtt ccagaggcag agataggagg catttaagaa gttgagaaat  141000
gagctgggag aatgagctgg tggggaatgt ttgatggaaa aggacctcct agaatcagga  141060
```

```
tgaactcagg gcatttggga cagaggaagg agaagagacc aatggagagg agaaatgaga   141120
gaggaaaaga gataactgac agtatacagt tgcatcatag accagagcca gaggagtggg   141180
cctggaaaag atgagtggca acgccttctt tgtgtctgga gaaagggagg tgaagataaa   141240
attaagctag tgaaataggg aaaggcagat taaggaagaa atatacttta tggtttctgt   141300
atattattat tattattgtt gagatagaat cttgctctgt cacccaggct ggagtgcagt   141360
ggcgtgatca ctgcaacctc tgccttccag gttcaagtga ttctcctgcc tccgcctccc   141420
gagtagctga gattacaggc acctgccacc atacctggct aattttgta ttttaggag    141480 aggttgggtt tcaccatgtt ggccaggctg gtatcgaact cctgacctct ggagatccac   141540
ccaccttagc ctcccaaagt gctgggatta caggcattcg ccactgtgcc cagccagttt   141600
ctatgtatta gttgatattc taggccaata ttctagacag ctgagaggac tgtctagatt   141660
tgtggagtat attcagctag gagcagccaa tgttgagatg agaactgggc agagaatggt   141720
ggaaggactg ccagactgct ctgaggctgg ggcacctgtt gaggttgggc acatataag    141780 tggtgatgcc aggcagggct cttcagagct gtgggatgac ccccactcag gaggtggcag   141840
catctgtgta acaaaaggct aaggctgcga tgtgctatag caggcagggc ttttggata    141900 caagcaaagg agcctgactt tagctaactt atgtgacagg gggttcttta gacgtcattg   141960
tggggcttgt gtaatttaga ctctggagga tcaagcttgg gaaggcatag gagccagttc   142020
agtccctgaa gtctataaag gagacatttt tgggaggctt ataagggcac aggaactctg   142080
ggataaatga actcccagct tgtttattcc attctcatgt cacctttctt aggattcaaa   142140
atcctgagag agagagagcc agattggcct ggctgggatc aggttcctgt ttactgcctt   142200
gaggagagct gagatccttg actagtccat caggggtgct tgctgaaggg agcaggtgtt   142260
agtgctgggc agcctcaatg gaaccacctg gatctacctc tgggtttgag ggtgctggga   142320
atcacataac ataatgaag ttcagaagaa cctgctcagc aaattcctgg gggattcagt    142380
taggtgacaa acgaaggttt ctatagacaa atccttttct tgtttagtca agatgcatc    142440 actgatacat ttatcttcaa atgaagatca ggaggagtta gggtggagcc ttttaatttc   142500
ctaacttttt ttccagtgtt tctgggaata aaaacccaag gaaaacttat caacaggttg   142560
tatgatctat cagaaagata ttcgataaaa ccctgtaaga cctcatgacg ttctttagtg   142620
ggccaaagtg cagaggagtc atggtcagaa gtaatgggga gggcagggga aagaaaagta   142680
ctccaaaatg ccaaagagaa ccacagtggg tgttgtggg gactggagat ctgagttaga    142740
agatattcca aaggatcttt agggcttgct agtacccaac attcctcatt cctcacttac   142800
tgactttcta ttgctaacaa agcaagtatt ttagttcaaa agtaaattat gatatatgat   142860
gtactcccaa ttaagtgagt tttatgttaa aatgacaatt tccaatcaga tgaatgtagg   142920
tatcttggcc ctgtcaaaaa taattctact atttttttaa aggatccatg gaaaattgtc   142980
ttatttgcac aaatccggtt gatgtccacc ccttcaaaac caaacaaaaa ccccatatgg   143040
tctatatctt ttagagcttg agatggcttt taaaaagcta gtcattaact aaatacttta   143100
taacaaattg gataagctag aatcagcaga aaggcaaggt ttaatctgaa gatcattgaa   143160 acagggtat agaacaagct ttaacttggg gttatgacca agtcaacaga tggatatgga    143220
aagtggccca tacattgaag ttgatgtttt ggaaagtatg ttccaaggtg aacaggacct   143280
gacctaaagc aacatttgta aaattgtgcc atgaaatgtg gtaatacagc gtgacatgcc   143340
accagggaac acaggtttgt ttaagacaag ctgtcttcct tcaggagct cacagcaaaa    143400 tgggaagaca agggccgact tcagaagaaa ataaatgata aaagacagcc tttgatttat   143460
```

```
gccaaataag aggagagaaa attaataact tttgactccc tcccaggtaa tccctggggc   143520
ttctctgaat taaaaggaga caatcccaaa atgtatttat aattctttaa agaacgttaa   143580
atagagctaa agttatttgc agtctaattt gtttaggatt ttcctgggtt tctttgttta   143640
ttaatgtgaa atgtgaaccc atcctgcaaa atatttagaa gctaaataag aagtttgaat   143700
ataaaagaag atagcaaagc tacataatag aataaaaata aattgaaaat caagcctgta   143760
gagggttttc ttttttcttt ttttttttcc tattctgtgc catgtataaa atggtataac   143820
aatttcaagg agaccctagg cagctctccc acttggggac ccttactgac tcttttaaaaa  143880 ggcccaatga gagaagtcac agggaagtac atacctgttc tgaccacagc ctccaaaata   143940
tagaagtcag acgtggccct ggctaaatat taatagtacc aagagaaagc ttaagcataa   144000
actcataact ttggtcagat atcagatatc aggagccaga tttaaaccaa ttgcttgcgg   144060
aaaaactaac gtaactccct aataacttag gatatgcttt tgggcaaatg agccagacaa   144120
atggatacaa catgagcaaa tggaactagg agggatagcc cctgcctgct cagaaaagtt   144180
ttgaagtctc aaggctggag aataatatta gaactggaag gcacctcgga atccaagcca   144240
tcatcagttg ataaaacttt ttttaaggaa tatagttaat ggcaagatca agagaggaat   144300
aagccccaat ttcttgaaa tttccaactt taatcatttt caaacttgat atgaaatctt    144360
ttatatctat tactatttgc taggaaggca ttaagaatgg gcttgacttt taccagttttt  144420 tatgcgagtt tcataggctg acctagtata tacacattga ggattctaat ccagcaagtc   144480
atagcatgtt atttcaactt ataaataaaa tactctgtat agtggaactt gataatgctc   144540
actgggcctt cagcctcttt atcacatatt ctcaggtcct agtaaaattt agtcattgtt   144600
ttacgaccat cttaagaacc ttcattcatt tgtttaattg atggatattt attactgtgt   144660
gccaggcctg cgccaaacta tgcctaattc atctttgcat tctccagggc acagtgtatt   144720
gcacataggt accaacctac agatacttgt taattaatag atgaatgact gtgactgtta   144780
tctcagtgta aattctttat ctcattacca aggactgaaa tcttgcctac tgacagcctt   144840
tgccatagcc acagcttaag gcacatttttt tttttttaa aggatcctgt tgctccggca   144900
accagatttc tccacgtctg cttgccttct gtcaccaagg caacagggta tagttggcag   144960
gctggtttga gacactggat gtttgtggta tcagagatgc ctgtggttca caactttttt   145020
gattcatcag tgtatgcata attgtatttg gcagtgtgct cctaagtcta aatctttttt   145080
tttttgagac agaattttgc tctttcaccc aggctggagt gcagtggtgc catctcagct   145140
cactgcaacc tcggcctgct gggttccagc ggttctcctg ccccagcctc cctagtagct   145200
gggattatag gctcctgcca ccacacccag ctaattttttg tatttttagt agagatgggg   145260
tttcaccatg ttgaccaggc tggtctcgaa ctcttgactt caggtgatcc acccgcctgg   145320
gcctcccaaa gtggtaggat tgcaggcata agccaccgtg ccaggccttt ctaagtcttt   145380
atatgtgaag atgattgtgg atgtttgtga caattcagct tcatatttgt gactggaaag   145440
acctcgtgta ttttcaggac ctgtggatct tgcctcttaa aagcggaagt cttgcttatt   145500
tttacttata gctcttctcc ctccatcttt tttataatct gtatctggtt ttactttggt   145560
tgaataaata ctgcatgatt actccttgct agaatcaacc tggcccatct gctaatgtct   145620
cactccaaca gccttaaaac aaacaaacaa acaaacaaac aaaaaacac atagtaagac    145680 cactttgttt cttttctgta atagttctat actttcctgg tttattgctc atttgtttct   145740
agctgttatt ggagtaggag gggatagcca caggaacatt atactacttt gttgtcatga   145800
```

```
taccaactct attaacatta tagataaata ggagaactca aagctacata atgttgctta   145860
ttcacacagg acatatttat gaatgtcact gcctgaaaga gagcttcagc tataaaatgc   145920
tcattagctc acatggtgtg gctgcagtag tttcggaagg cattacctta ctattgtaag   145980
ccaaacctct catttcataa ggtttaatta tttttatcaa tatcaaatag cattgatact   146040
tttcacaatt gaattaaatg atggaataca cttataatgt atttgaaaat gttttctttg   146100
ttcagataca tatttcaagg aattcttatg agagatgata ttctagggct tcatcttctt   146160
cttggccagg actctgctgg caaaattatt atccaaataa ttcaccgtgc tcttgactta   146220
attcagcgaa aagtctattt aaaaaattac gatgctaatt cctagattat tcactttatc   146280
tgttagtgtt ttggggtgga aattgtaggc taacactcat tttcagcact tcagtttctc   146340
ttttgcctta ttaattccag atgaggtcac actaggtctg aagagagctg aagggatgg    146400 cctttagaa ttctttcagc cttctatttt tctgaaattc ttccattggc ctgaagtgct    146460
gttggtcaat gcccatttca aaattttcag agaacacaaa cagtaatatg ttaagcctct   146520
tcaccagaaa ctatttctgg aatgttctct gtgtgaaacc actttggtat attttccagc   146580
ttgtgatacg atgggaacac caccctctgt agccgtaatg ctctattggg cataaacatt   146640
caatgtggtt caatctagag gcagacttcc cccaggctct gcataatttc aaccatttgt   146700
ccatctgtga acccaacaat tgcatagtta aaagctgtca cttctggtga caatgagtct   146760
gttctatttt gaaatttcag atgactatat tttcttgcgg ttagtgatat aatttccaga   146820
gaaattgaca tttattttc tgctatctct atgcaatctt gtaaattcta agactgtgga    146880
aactatttat tttcaccatc ccatctccag tgtctagcat ggtggctaca catcgtgggc   146940
atttaataaa tatttcttga atgaatgaat gaatgtgtaa ttgttctttt tgaagattcc   147000
ctaaagttta ttaaagagga atttaaaatt atataaagga atagcaaaag cggcagcaac   147060
tcagcattgt cagggtgttc tatgtcacat atcccactag cacacattat gcataacatt   147120
tgttaatatg taaaaatgtt tgaaacgtta gattcttcag gacatctgga atagtcatct   147180
tgcaaactca tcatgtgagt gattatcagc ttttcaagaa catgtataac ctgatggata   147240
caagtttgcc acaagttgca ttttttattca ctttttaaga gagtgggatt caggaggtat   147300
tgcaggttta gcagctacat ggcatgaatg taataaatgt atgaagacaa tgaccaacac   147360
ttaaggaagg gcctggacca cattgttaag tatggaggcc actgggcaca tgtgactctt   147420
gagcagctta aatgtggcca gtgcaactga gggactgaat ttttaatttt gtttaatatt   147480
aattaagatg taaaataata agatttcaat ttgtatatgt tgaaataata ttttggatat   147540
ttttgattaa ataaaataga tttatttcac tttattcttt ttactttttg aaaatgtggc   147600
taccagaaaa cttaaaatta tgtttgatgc ttacaatcgg tttccattag acagtactag   147660
cttcatctag aagggtaagg ggcaaagtta ttcggaaagc atttgctggg gtatggcatt   147720
tgtgcaggca tacaaggaac tggaacagat gctctgctcc tcagctcagc cctggggctg   147780
tcctgcctac acatgggcac tgctgtcatc atgcctcttt tcaaactttc tgagggcagg   147840
atcagcttca tttctttttt taaacatgct ccttatctca ggttagggaa agtatataaa   147900
ctgttaaagg ctgcaggtt ccatttactt ttcaaggctc tggaaacttg agctcagaat    147960
ggaacagaat atattatgag atcaagagag tgttagcctg gtgaggatca agagggaatg   148020
gaaaggaaca gggaagaaac tcataggtgg atgcaaagat tttggtatta ttctagtgct   148080
taagttgggt ggtaggtaaa tgagtgccaa ttttgttacg cttaataact taggtaggtg   148140
ttgcatgcat gtatcaaaaa ttctatgatt aaaacgaaaa ggttgggaca agagaattat   148200
```

```
cagccatgtt tacttgtatt tgaattccta tatttattcc tacttaacaa ataacctatc 148260
atgtgcctta tacctagtac atgtatgata tattttgtt ggatttcatt aagtttaaga 148320
atgattctta caacttgtca gggcacagat gtttcttatt tcattccaga aaactattaa 148380
aaacttggtt ctaggccggg cgtggtggct cacacctgta atcccagcac tttaggaggc 148440
tgaggcaggg ggatcatgac gtcaggagat cgagaccatc ctggctaaca tggtgaaaca 148500
ctgtctctac taaaaataca agaaaattag ctgggcgtgg tggcgggcac ctgtagtccc 148560
agctactcgg gaggctgagg caggagaatg gcgtgaacct gggaggtgga ggtttcagtg 148620
agctgagatc gcgtcactgc actccagcct gggtgacaga gctagactcg tctcaaaaaa 148680
aaaaagaaaa attggttcta gggtacagtg gaaaaaacaa ggctgaaggt gatttacaga 148740
tatccctggt ggggtctaag gccacctcca cagagtagaa gacactgaga ccaactcgta 148800
aaatgatcaa ataacctaga attttggggc aaggcaaaca agggatgtta ataacactgg 148860
caactttagg aaagataatt attttcaatg caaaaaacat tttataggag gaggtataag 148920
gttttttttg ttttttttaat agagcaggga caaatcatag aaaatactat atataacatt 148980
ttaaatctta tatcctttta gtgcaaaatc atattttgag tttaagtgta actagaaaat 149040
tattcaggat cctaaaattt aggctcttag tcatacttag agcctaaaaa ctgtggtggg 149100
acgattctgt catttgtcag tagaatgtca attgtactgt ttattgcaat atatttattt 149160
ccctcttaat taaactcttg agagcatctt gagggaaaat aatctctatt aatctttata 149220
atgtagacca tagcaagatg taggctctta gtttgtcaaa tccaagttga acaggtcatt 149280
ctaatggcct gtaattctat tttcagggac ttcactggag gaacaggatc aagaccaaga 149340
ccaggtaact tagtgttggt agcaataaaa tcaaacacaa ctctctaaaa ttcaatgtaa 149400
tttatgttac agtttcatat cttccccct tttatttctt cagctttgct gcctcttgac 149460
ctgcttctga aagtgccacc ccacatgctc agggcccaca ttaaggaaat agaggctgag 149520
ttagtgacag ggtggcagtc ccatagcctt cctgctgtga ttcttcgaaa tctcaaagat 149580
catggtagta cttactagat cacattgatg ttaagcacac aatgggcaaa tgcagaatta 149640
tagttgggcc tgagatgtct gaacgatgct tgggtggtaa ttttaataca aagagcggag 149700
aattctgcct tgtttgttca ccattattag tttggcgatt tgatggtaac aaaatgcctt 149760
ctgtgttcac tgttggttga aatattatgg gctgtttttt ccaaaatttg catttctgcc 149820
gtggcgggaa tgttaaccag ttgacctatt gatgcttcaa gtacatacct acaaacaaaa 149880
aatagtaacc atgttttaca taggtatttc tgtaaactct acacctacat gatacatgta 149940
gaatgaagaa agtaagtcat atttttttct atctcctcta cccttacaca ataaattatc 150000
ttttacttat ttatgtttct tttctttct ttttttttt gagacagaat ctcactttgt 150060
cacccaggct ggagtgcagt ggcacgatct cggctcactg caaccttcac ctcccaggtt 150120
caagtgattc tcctgcctca gcctcctgag tagctgggat tacaggtgcc tgccaccatt 150180
cctggctaat ttttgtattt ttaatttaga tggggtttca ccatggtggc caggctggcc 150240
ttgaactctt gacctcaggt gatccgccca cgattaaaat gacatatcac attgtttccc 150300
taataattga aaaattatag atccttaaac ataaagtttt ctaatagagg tttgggaaga 150360
atgtgttaat gtttctaatt tttgtgaaag aggaccaaag tccatcagta acatttaaat 150420
tattagctaa acctagacaa ttcagaaaaa agtttgatga ttatgctttt atcatatgtg 150480
tgagcataca actcttgagc atagagttct actttactat tggttaattt gggattattg 150540
```

```
tttaatgcta ttttcacttc agcttccttg attcacattc ttttgtagag ctaatgttta   150600
tagtgaatat aggcaaactg actgtaatgt tagcccatgt ctccacattt attaaatttg   150660
ctttggatga gttattgaca gtttgaggcc attacaatgt cagcatagat gccaaaaatg   150720
atggttttat taagatgcct gaaactatca tgttgaccat gctctgctcc tgttattttg   150780
aaaaggtaag ttcaaaatat aattatgaaa ttaagatgat tgttattaat tgatgttcca   150840
acagcaagaa tggaacacac atatatatgt aagcaattga cagttctgtt gtaatccata   150900
ttagaaattc ttttttcctaa acagtatgtt gacttagttc agtgcaagac ttgattttat   150960
gtcggtggca ctgatcagat ctctggacct taaacaaac tatttacatt atggcagagt    151020
ttacatacat ttcttttctta tccctacagt ttgctatatc atctaattct ttaaaatctg   151080
ctgattcata tattgttaaa acttgtatca gaatacacaa aagcatttttt tattttttttg  151140 agacagagtc tccctgtgtt gccaaggctt gagtgcagtg gtatgatctc agctcactga   151200
agcctcctcc tcctgggttc aggcaattct cctgcctcag cctaccgagt agctgggatt   151260
acaggcgtcc actaccatgc ctggctaatt tttgtatttt tagtagagat ggggtttctc   151320
catattggcc aggctggtct ctaactcctg acctcaagtg atctgcccac ctcggcctcc   151380
caaattgctg ggattacaga tgtgagccac cactcctggc cattttgtta tcagtgagtg   151440
ctagattttg tacataaaaa gagtggttag gttttgctaa tattgtacaa cacattaatt   151500
cacagggaac atttgggtta ccacctgaga gttactctac tttcatgtca gaaaatgaga   151560
actttatttt tctcaaccttt catatgaagg tttttttccat taactataaa actcataccet  151620 tttaagtgtt gcaagtcaat ttggatgatt ggttgcttta tcaaattata acagctggt    151680 gccagtgcca ttcacttagg tcaccacatc tgcaaaccat gctgtaatcc agtcattacc   151740
ttggtatctc tgtcttaact aaagtataga gaagtgacat taatctggta gtccaacaat   151800
aaagtagtac gtttggacca aggtgtcatg agacgttgtt ggtcctgtca gtagcgagtt   151860
ataccttaag catttgttat gaaaaatagg taaagcactt aaatttgtga atgatttatt   151920
ttttttaaaa aaataagctg attatattag tgtatttttca tttacttaac atttggtctc   151980
gctttcttgg atagaaagga acatgttgga acttatgcat aaccaacatt tacagccctg   152040
tattgcctaa atgttccgga aaaagcagaa aggggagaat tttgccaaaa tcagggcatt   152100
tccccaggaa tatatctagt atgtgaacat tatttcccat gtattatggc agaatacagg   152160
gttggaacca ttatttttaga gtgccaagtg cctatattgt aatatgatct tgcctgtatg   152220
gtactcctaa aagctgaact tctaggttca tgtcatggta ataacagcag tacctccaaa   152280
ctcttctaga acaaataaca atgaaactat tttacattac ttgtattaaa aatccccttg   152340
ttctatcttt tattactaaa ttgtatcaat aatttatttt ctacaaatta tttcaattaa   152400
ataatagatt gcaattccct gccaatagaa aacttaggaa ttcatatatt atacaaatga   152460
aaatattacc agtaattaat atgaataact gaatgaagaa acattttaac atgttaatta   152520
ttttagctct gttttcccag ctttagtcac tagtgaatta ccatggtaca aatttgccta   152580
tgtctgagaa ctatatgtac tataattttc ctgatatttt tctttacatc gactaactca   152640
atttaaattc attttttagag gaaagttgtt attatttctg taaatgagaa ccagtatagt   152700
atcacttgcc ataagtagat aaccattgta aaagtaaata caaatctaag aaagacaaca   152760
ttaaattcca ggtagatatt gttttctgct tatgctgagg tctgttgtct ttgctgtaaa   152820
ggaacattac ctaatatttg agaaatgatg aaaacatact tgcacgatac tgaaacttaa   152880
tccttgatat aaacaacaga aagaaaactg taaaaggaat acgtttccta ctggactatt   152940
```

```
tcatacctga tatacctact aatgaaatta ggctgtgtag gtgtcccag ttctttaaaa  153000 atagattgat tctgtggtct gtaaagtcaa atcagttaat caaacaactg gatattacca  153060
agtatttgga attggggaaa aaggtctcag gtctgtcttg tataaaaaag aaataatcgt  153120
ttcctttcaa gacaagggaa atgatatata tttgtgaaaa ttaaatcaca caaaaatata  153180
acacaggaaa cgtgttcttt tcaagtacat actataatgt tatggattct attagtgtgg  153240
gtcaaatgta aattttgggg tgtgtaagtc aaacctaaat tttcaagtgc aaatataatg  153300
tcaactaaaa atctggccta atttgactgg attaacactg acattttccc ctcccttgct  153360
caggttttta tttagacagc acctgacacc caggcgctga accgatgtat gggttcttat  153420
gcactgcatt ttgaatagaa attgtcactt tatgatttct gggtccttaa ttatgttttc  153480
ctattggatg actatgaatc tattttatg tttccatttt gttagtaaag gcaaatctaa  153540
atcaaattgt caatgttttt tattttttgc tcaaatattc tagaaagcat agctaacatt  153600
ctagttgtcc ttatacgaac aacttttagt agtttacttt caagttaatt attaacataa  153660
agtacttaaa actcatcttc acaattgcca aagtgatttt aagtacatac cttctttat  153720 tatgttgcat agcattttta atcatataaa aatttgctca caggttttag tcaaaacttc  153780
tatgatacta gtctatacta tataatttgg catataatta tatacattgt tgggatttgt  153840
gaagtattaa ctatgttttc caaccagatt gtaagcacct tcattgcaac tttgatagat  153900
ataggtgtat ctcacagata ttgcaggttc cgtcccggcc aacagcaata aagcaaatat  153960
cacaattaaa catgtcacct gaattttttg gttttccaat gcacataaag gttatgttta  154020
cactatacta agtctattaa gtgcacaata atattatgtc taaaaatata tatactaaa  154080 ttaaaaatgc cttgttgcta aaaagtgcta aagatcatct gagactttta acaagacata  154140 atcatttgc tggtggaggg tcttgcctcc atgtaggtgg ctgcagattg atcaggctgg  154200
tggttgctaa agattggggt ggttgtagca attttgtaaa ataagataac aatgaagttt  154260
gctcaatcaa ttcagtcttt cacaaaagtt tctctgtagc gtgcgatgct gtttgatagc  154320
atcttactca cagtagaact tcttacaaaa actggagtca gtcccctgaa acctactgct  154380
gctttatgaa ctaaatttat agactattct aaattatttg ttgccatttc aacaatgttc  154440
atagcatctt taccaggagt agattccatc acaagaaacc acttttgttg ctcatcccta  154500
agaagcaact gctcatccat tcaagctttt ggatgagact gcagcaattc agtcacatct  154560
tcagtctact tctaattta gttctcttgc tatttctact acatttgcaa ttacttcttc  154620
tactgaagtt ttaaaccctc aaagtcatcc atgagagttg gaaccaactt cttccaaact  154680
cctgttactg ttgatatttt gaccattcat cataattttt taaatttttt aaatttcttt  154740
ccataagtta ttggggtaca attctttagt ggtgatttgt gagattttgg tgcacccatt  154800
acctgagcag tatacactgc accatatttg tagtcttcta ttcctcaccc ctttcccact  154860
cttcccccca agtccccaaa gtccatttta tcattatcat gcctttgcat ccttatagct  154920
tagctcccac atatcagtga gaagatacaa tgtttggttt tccattcctg agttacttca  154980
cttagaataa tagtctccag tctcatccag gtcactgcaa atgctgttaa ttcattcctt  155040
ttttatggct gagtagtatt tcatcatata tatatatata tatatatata tatatatata  155100
tatatatata tatcagtt tctttatgca ctccttgatt gatgggcatt tgggttggtt  155160
ccacaattat gcaattgtga attgtgtggc tacaaacatg catgggcaag tatctttttt  155220
gtattatgat atcttttcct ctgggtagat acccagtagt gggattgctg gcttaaagaa  155280
```

```
cttttagttc tttaaggaat ctccacacta tttccatag tgattgtact agttacattg    155340
ccaccagcag tgaagaagtg ttccctgatc actgcatcca tgccaatatc tactgttttc    155400 tgatttttg attatggtca ttcttgcagg agtaaggtgg tatcgcattt tggttttgat    155460
ttgcatttcc ctgctcatta gtgatgctga acatttttc gtatgttcgt tggtcatttg    155520
agtatcttct tttgagaatt gtctattcat atctttggcc cacttttga taggattgtt    155580 tgttttttac ttactgattt ttttgagttt gttgtagatt ctagatatta gtcctttgtc    155640
acatttatag attgtgaaga ttttcttcca ctctgtgggt tgtctgttta ctctgctgac    155700
tgttcctttt gccatgcaaa agctctatag tttaattagg tccctgctat ttatctttgt    155760
ttttattgca tttgctttta gtttcttggt cattaaatcc ttgcctaagc caatctctag    155820
aaggattttt ctagaattct agaagatcta ggatcttcta gaattttat agttccaggt    155880 cttaggttta agtccttaat ccatcttgag ctgattttg tatggggtga cagatgaggg    155940
tccagtttct tttcctactt gtggctagcc aattatccca gcaccatttg ttgaaaaggg    156000 tgtccttttcc ccactttatg tttttgtttg ctttgttgaa gattggttgg taagtatttg    156060
ggtttacttc tgggttctct attctgttcc attggtctat gtgcctattt ttataccagt    156120
accatgctgt tttggtgact atggccttat agtatagttt gaaatcaggt agtatgatgc    156180
ctccagattt gctcttttg cttagtcttg atttggctat gcagactcct ttttggttgc    156240
atatgaattt tagaattgtt tttctaatt ctgtgagaat gatggtggta ttttgatggg    156300
gattgcattg aatttgtaga ctgttttgg aagtatggtc atttttcacaa tattgattct    156360 actcatccct gagcatggga tgtgtttcca tttgtttgtg tcatctatga tttcttccag    156420
cagtgttttg tagtttcct tgtagaggtc tttcaacttc ttggttaggt atattcctaa    156480
gtattttatt ttatttatt ttattttatt ttattttatt ttattttatt ttatttattt    156540
ttttgagatg gagtctcact ctgttgccag gctggtgtgc agtggcgcaa ttttggctca    156600
ctgcaacctc cgcctcccgg gttcaagtga ttctcttgcc tcagcctccc taatagctgg    156660
gactacaggt gtgtgctacc acacccagct gattttgta tttttagtag agacagggt    156720 tcaccatgtt ggccaggatg gtctcgatct cttgacctcg tgatctgccc accttggcct    156780
cccaaactgc tgggattaca ggtgtgagcc accacgccca gccagtattt gtactttttg    156840
cagctattgt gaaaagaatt gagttcttga ttggattctc cacttggttg ctgttggtgt    156900
atagaagagc tgctgatttg tgtacattaa tcttgtatct agaaaatttg ctgaatgctt    156960
ttatcagttc taggagcttt ctggaggagt ctttaggggt ttcaaggtaa atgatcatat    157020
tgacagcaaa cggtgacagt ttgacttctt ctttactgat ttggatgccc tttatttcct    157080
tctcttgcct gactgctctg gctaggactt ccagtactat gttgaagagt agtggtgaga    157140
gtgggcatcc ttgtcttgtt ccagttctca gagagaatgc tttcaacttt tccccactca    157200
gtattatgtt ttcctatgggt ttatcataga tggctttat tacattgagg tatgtccctt    157260
gtatgccaat tttgctgaga gttttaatca taaagggatg ctggattttg ttgaatgctt    157320
tttctgcata tattgtgatg atcatttgat tttagttttt aattctgttt atgtggtata    157380
tcacatttat tgacttgtgt attttaaacc atccctgtat ccctggtatg aaatccactt    157440
gattatcgtg gactgtcttt ttgatatatt gttggatttt gttagctagt attttgttaa    157500
ggattttacc atctatattc atcaaggatt tcagtctata gttttctttt tgattatgt    157560 cctatcctgg ttttggtatt agggcgatgc tggcgtcata gaatgaatta gggagggttc    157620 cctcttttctc tatcttatgg aatagtgtca gaaggattgg taccaattct ttgaatgtgt    157680
```

```
ggtagaattc tgctgtgaat ccctctggtc ctggaccttt ttttgttggt aattttttaag   157740
ttaccatttc agtctcactg cttgttatag gtctgttcag ggtaactaat tcttcctgat   157800
ttaagctagg aggttgtatt tttctaggaa tttatccatc tcttctaggt tttctagttt   157860
atattcataa aggtgttcat agttacctga atgatgtttt gtatttccat agtgtcagtt   157920
gtaatatctc ctgttttgtt tcttagtgag gttatttgga ttttctctct tttcttgatt   157980
aatcttgata atggtctatc aatttttattt atattttcaa agaattagct ttttgtttca   158040
tgtatctttt gtatatttt tgtttcaatt tcatttaatt ctgctttgat cttggttatt   158100
tcctttcttc tgctgggttt gagtttggtt tgttcttgtt tctatagttc cttgaggtgt   158160
gaccttagaa tgtcagtttg tgctctttca gtcttttcga tgtagttgtt tagggctatg   158220
aacattcctc ttagcaatgc ttttgctgta tcccagacct tttgataggt tgtgtcatta   158280
ttgtcattca attcaaagaa ttttttaaatt tccatcttga ttgtgtttct gacccattgc   158340
tcattcagga gcaggttatt taatttccat gtatttgcat ggttttgaag gttccttttg   158400
cagttgattt ccacttttag tccactgtgg tctaagagag tgcttgatat aatttcaatt   158460
tttaaacatt tattgaggct catttttatgg cctatcatat ggtctatctt ggagaaagtt   158520
ccatgcactg ttgaatagaa tgtatgtttt gcggttgttg gatgaaatgt tctgtatata   158580
tctgttaagt ccatttgttt caaggtattt agttaaatcc attgtttctc tgttgacttt   158640
ctgtcttgat aacctgtcta attgtgtcag tggagtactg aagtccccgc tactgtctgt   158700
ctcatttctt tttttttttt tttttgagat ggagtctcgc tctgtcgccc aggctggagt   158760
gcagtggcac gatcttggct cactgcaagc ttcgcctccc aggttcacgc cattcttctg   158820
cctcagcctc ccgagtagct gagactatag gcgcccgcta ccatgcccgg ctaattttt   158880
gtatttttag tagagatggg gtttcaccat gttagccagg atagtctcga tctcctgacc   158940
tcatgatctg cccacttggc ctcccaaagt gctgggatta caggcatgag ccaccgcgcc   159000
tggccattct catttcttag gtctattagt gttttataaa tttggaagct ccagttttag   159060
gtgcatatat atttaggatt gtgatatttt cctgttggac aaggcctttt accatttat   159120
aatgtccctc tttgtttctt ttaactgctg ttgctttaaa gttttttttg tctgatataa   159180
gaatagctac cttgctcact tttggtgtcc atttgcatga aatgcctttt tccaccccctt   159240
tactttaaac ttttgtgagt ccttatgtgt taggtgaatc tcctgaagac agcagatggt   159300
tggtgagttc tgatccattc tgtggttctg tatgttttaa gcagagcatt taggccatttt   159360
acattcaatg atagtattga aatgtgaggt gctgttgcat tcattgtgct attttgtttcc   159420
tgtgtacttt tgttttttt ttgttttttg gttttgcttt ttaacttgta ttttttgtttt   159480
agagggtttg atatatgctt taagtaggtg ctgttttgat gtgtttccag gatttgtttc   159540
aagatttaga gctcctttta gcagttcctg tagtggtggc ttggtagtgg tgaattctct   159600
tagcatttgt ttgtctgaaa aagattgtat cttttccttca tatatgatgc ttagttttgt   159660
tggatacaaa gttcttggct gataattgtt tagtttgagg aggctgaaga tagggctcca   159720
atcccttcta gcttgtaggg tttctgctga gaaatctgct attaatctga taggttttcc   159780
tttataggtt acctggtgct tctgcctcac agctcttaag attctttcct tcatcttaac   159840
tttggataac agatgacaat gtgcctaggt gatgatcttt ttgcaatgaa tttcccaggt   159900
gttctttgtg cttcttgtat tttcatgtct aggtctctag caaggctagg aattgttcct   159960
caattattcc cccaaatatg ttttccaagc ttttagaatt ctcttcttcc tcaggaatac   160020
```

```
caattattct tggtattggg ttgtttaaca taatcccaga cttcttggag gctttgttca   160080
tattttcttg ttccttttc tttgtctttg ttcgagtggg ttaattcaaa gacctcgtct    160140
ttgagctcta cttgttcaat tctattgctg agactttcca gagcattttg catttctata   160200
agtgtgtcca atgttacctg aatttttat tgtttttact ttaaactatc tatttccctg    160260
aatatttctc ccttcacttc ttgtattgtg ttttggattt ccttgcactg ggcttcacct   160320
ttctctggtt cctccctgat tagctaagta actaacctcc tgaattcttt ttcaggtaaa   160380
tcagggattt cttcttggtt tggctccatt gctggtgaac aagtgtgatt tttgggggt    160440 gttacagagc cttgttttgt catattacca gggctggttt tctggttcct tcttatttgg   160500
gtaggctctg tcagagggaa tatctagggc taaaggctgt tgttgagatt cttttgtccc   160560
atggggtgtt cccttgatgt agtactctta ccctttcct atggatgtgg cctcctgtga    160620
actgaacctc agtgattgtt gtgtctcttc tggatctagc cacccagcaa gtctacccag   160680
ctccaggatg gtactgaggg ttttctgcac agagtcctgt gatgtgaacc atctatgggt   160740
ctctcaaccg tgggtgccag tgcctgttct ggtggaggtg gtggggcggg ggttgcaatg   160800
gactccataa gggttctttg gtggtttaat gctctatttt tgtgctggtt ggcctccttc   160860
cgggaggtgg tgttttccaa agaccatcag ctatggtagc atggagaggg actagcggtg   160920
tgtgaggcct tagaactccc aagattatac gtcctttgtc ttccgctacc agggtgggta   160980
ggaaagaacc atcaggtggg ggcagagcta ggtgtgccag agctcagact ctccttgggc   161040
agatcttgct gcagctggag catttgggt gtctcctagg tcctgcagga gcagtctgct    161100
tccttcagag ggtctgtgaa tcctctcagg attcctagtt tgttcttgga gttgatctgg   161160
agctaaaatg catacatgtt tttaatgaca tctagaatag tgaatccttt ctgggaggtt   161220
ttcaatagac tttgcctaga ttcatcagag gaatcactat ctattgcagc tatagcctta   161280
tgaaacggat ttctgaaata ataagacttg aaagtcaaaa tgactccttg atcattggac   161340
tgcagaatgg atgttatgtt agcatacatg aaaacaacat taatatcctg tacctcctca   161400
tcacagctct taggtgacca agtatttttgt caaagaacat caatattttg ataggaatct   161460
ttatttcagg gcagtagatc tcaagagttg gcttaaaata ttcaataaac agagtgcttt   161520
catccaggct ttgttgttct atttatagag cataggtaga atagatttag tacaattctt   161580
aagggctcta gtatttttgg aatggtcaat aagcattggc ttcaacctaa gattacctgt   161640
tgcgttagct cctaacaaga gagtcagcct gtactttgaa gccaggcttt gatttctcct   161700
ccctagctat gaaagtccta gatggcctct acttgcaata aaaggctgtt ttgtctacct   161760
tgaaaatcta ttgtttagtg tagccatctt catcagttat cttagctgga tcataagaag   161820
atcttacctt gctgcaactt ctatatcagc atttacagct ttgccttgta cttttatgtt   161880
atggaaatgg cttctctcct taaactgcac gaaccaacat ctactacttc tagctttcct   161940
tctgcagctc tctcacctct ctcagacttc atagagttga agagggttgg ggccttcctc   162000
tggattctgc tttggcttaa gggaatgttg tggcaggttt gatctttat cttctaaatc    162060 tttctctata taagcaataa ggctgtcatt gttattattc atgtgttcac tgttgtagca   162120
cttctaattt tccacaaaaa tctttttctct gcattcacag cttggctaac tatttgatgc   162180
aagaggccta gctttctggt atcttggctt ttgacatgcc ttcctcacta agctttatca   162240
tttctgcctt ttgattgaaa gtaagagaca tgtgactctt ttttccactt gaacaattag   162300
aggccattgt aggattatta actggcttaa tctcagtatt gttgtgtctc agggaatagg   162360
aaggcctatg aagaagggaa agatgggga atggctggtt gatggaacag tcagagtaca   162420
```

```
cacaacatcc atccattaag tttactatct tatatgagtg cagtttgtgg tgccccaaaa   162480
caattacaat agtgacatgc aggatccgtc atcacagatc atcacaacag atctaataat   162540
gaaaatgttt gaaatattgc aagaattacc aaaatgtgac acagaggcat gaagtaaatg   162600
catgctacta gaaaaatggt gccagtagcc ttgctcaatg cagaattgac acaaaactta   162660
aatttgtaaa aaaatttaaa aaaagcaaca tctttgaagt gcaatataat aaggtgcaat   162720
gaaatgaggt atacttgtaa ataccttgga gtatttcctc tgagatcagg cccttgaaaa   162780
ctatttattg agtaactgat ttagacccat cactgtataa actcttgttt atctttgcta   162840
ttgtattgag agcaactgca taagtaatca gaagcagtga gggaatcact gatttttttg   162900
tattagactt ttaaaatatt ttattttat taaatttatt ttattatatt aaaatatata     162960
catatatatt ttagatttca gattgagata agaaatttcc tttaccaatg attatttgct   163020
tcctcattct tcatgccaag ggaggtgcca acgactgtg tacagggtcc caggaggatg     163080
cttcttggag atgtagattt ttttcatggt cattttaggg taatgtgttt tcaaatggat   163140
actcatctca caagagttac tggtggttcc aattcaagcc taaatccaaa ttgcatatca   163200
cctgttaaat ggcaactcac actcatgcca tttgggtttc tgcctgggag gaaaggctaa   163260
aggaagtaag ggttgaaagg tatcccactc tctggtagga gtaaagggag gtaggtcagc   163320
atgacttggg tgatgattgt agcatggtgt gtaaaataat tgaattaaca gcgaaaagca   163380
tcaccctcaa attccaaatt gccattatta gtaatttata gtggatttta aaaatatgtt   163440
aaaagtattt acaaatatgc tttgaattag tttgttgcat tgaccaattt gagaattgag   163500
gacagtgaca gaagggccaa ttataagaag aagaaacctg gatatcaaag accttaggtt   163560
catgtggagt ctgttgcaca tgagccatac cattttggac atacatatgg acatctaatc   163620
aaattattcc tgtgtagaaa tgtaagcacc agtagctaag aatctatcca tgtgttggct   163680
cctgtctggg gagtagtttt tttaaggatc tcagagtaca tttaaaccat aagggagtat   163740
taatcattga atcagtcatt aagcttctat taattccctt tcttcaagaa aaatgttgat   163800
acaactaagg ctgtgtccaa accattctat aatggttgct acagcagttc cctctcctga   163860
aagcaagagg cctctttctt ctctctggga tacctgcctg ccctccacta tagctggaac   163920
cttgttcatt cttaattgac tctgctcagt atggattcaa taatttattt gggatgtttc   163980
atatagtgtg tcaattaaaa attttttctgt ttatataact acttattatt ttttatattg   164040
gggtgcaaaa gcacaattct taaagttgtt ctttggcaag tgtctgagtt ttattcaatg   164100
cattgatgat agaaccaggt ggaagacaaa aatgctgatt caagagcatt tgaagaacag   164160
agatttatgt agttaggcaa gaaagaagag ctgacataag attgctaaat taagcgtaag   164220
actggtagaa cttctatagg gcaataaaat gataccattt ttgtgatcaa gttcttgact   164280
gggtgtaaaa tcataccagt atattaattt ctgcaggtta acctctaacg ctacaggcct   164340
gtaaactgtc tgctccttta ttggtgtaga ttgttagtta aatatactgt gacattaccc   164400
attatgggaa tataagacac attacttaaa agaggctcag ccagaattca agagttaagg   164460
acttcaaagc agccttgcct ctggccttta aacagcttat tcctgaagtt tcaaatgaaa   164520
ggaagtttgt tgcctgatca cccagaggtg aaaggagctg atgctttgac tcagcttcct   164580
gccattctgt gagaaactct gccggaggct agggtagcag gggcatctag gcctagactg   164640
ccaagctcct tccaaacact ttttgtctga ttatagaatg gtctactggt ctgtgttggg   164700
aagtttccat tgtccatgca tcatatcctc tgtcacttcc ctctctcttc tgatggaaca   164760
```

```
tcatattctc agtgtctcag tcccaagctt cagcagtcct tggctcctgc tccccatgtg 164820
gaaacagcta cagtgcactg tagattgatt caccccacaa cgtgtatgac ctcagccccc 164880
ttggttctag tcccattttt accattctgc catttcatat gaagaaacta aggcccaaag 164940
aagttgtgac tttctgaaaa ccatattgca atgcaagcca ggcctctgac ttcaactgta 165000
tgatcctctt cccgtgagat cacctttcct gaaatacagt cagccttatt gtttctcacc 165060
atcgtgtatg gtccctggct acctctccag ctgtatacat actgtacttt ttttattgta 165120
ctgcacacca gctaaactga acagtttgct gttcttcagt tgcagccctc acttagctga 165180
cttcactctt tgctggaatt attccttctc ctaagaaccc acactcacat acaacttccc 165240
tcacacccaa tacatttcct gtgctatcga agaccttcta attcttcctg gtcttctcaa 165300
attaacattt gaatttgctc tttagcctac atccatggtt gtctgggtga accttctatg 165360
aaatccttat gagttcaaga ttcttcatct aaccagggac acagggattg attgctgaac 165420
acttacagat ttgaactaca attacgttac tttatttcat tgttatgata gtaaagaggt 165480
gagagtaaat ttgtattgta gtttgacaac actgttggtc caatatagag aagctcatgt 165540
gtgttttggc cccccattca tgaaaacaat atattttttg cttcttcatg gatttccttc 165600
cttaacccct ttttctcca gttgtccaaa agttcctgat ccttagctga gagaattcag 165660
aaaaataatg cattgatacc atattttgat caattgggag agtacagtgt aacccacttt 165720
tttgggttta atttgtagtt attaacagct tcaaagtgta tattgtgaat tatagtttca 165780
atagaatgga catatagtat gtgtcaagtg tcaagtgtca aagcaccagg gatgggcaac 165840
taacttggct attttattat gcaatgatat actaaagcag aatgtagtgc acagcactag 165900
ctgtaaagac ctaatgcttc cagcttatta tgtctcacatg ctttccaaaa ataattaatt 165960
aaatgttgag agagatagat agaacatcgt gttaaaagta gcagtccttt taagaagaga 166020
aataatattt cattatggga aggagatatt gttttgtatt tgcagtaacc agaggcgcct 166080
tctagctgtg tccttgcatg gtagaagggg gtgaccacct ccctctggcc tcttttataa 166140
tggcactgat tccattcatg aggcctccgc cctaggacc taatcacctc ccaagctcac 166200
ttcctccaaa tgccattgcc ttggggatta ggatttcaac ctgtgaattt tggtggttca 166260
gaagcattta gaccacagca ctcagtctcc tcatctgtaa aatgggggta gaatctacac 166320
caataaagga gcagacagtt tacaggcact gggaggtgtt ttatgcattt agtctcctct 166380
gtggattaaa gcagactaaa tgtgtaaaac acctcccagt ttctcaccca agttcttgct 166440
aaaaagaag gactgctctt cttgcaagtc ctctgaccta acactgcaaa ggggaaacaa 166500
aatagctctt tagcgtcatg cttgcaacag agtaagctag caaatataat tatgtaatga 166560
cttttttgacg cttttaagta aattgcctct tataagaaat ttcgtagttt ccttctaagt 166620
tttaaaacac tagccaaatt tactatttta ataaaaacta taaagaata caaagtatcc 166680
caatattta aactttgatt ttatttaaat tttaaggaga ccaaatattg tgtatatatt 166740
ttgcagtagg aaataccaca tagatatgaa tcatgggcat attatgtatg actgacattg 166800
cacatgaact gtgatcagcc tcaccgatgt ctctttaata aaaaattgtt ttaatacaaa 166860
tattctcagt ataaaattga taatataaat atatgctgct ttttttttt tggtgaacag 166920
tcagaaagtg tagcgttttc agtgggctaa tctaaaagat atactgagag agaatgtttt 166980
taaagctaga caaatgttta tggctaacat ttgccaaatg tttggcagtt aataacattt 167040
aaatgaagaa taaaaataca ctttgggagg tcgaggtggg tggatcactt gaggccagga 167100
gttcaagacg agcctgtcca atgtggtgaa accctgtctc tactaaaaat ataaaagtta 167160
```

```
gccaagtgtg gtggtgcatg cctgtggtcc cagctacacg ggaggctgag gcaggaggat  167220
tgcttgagcc caggaggcag aggctgcagt gaactgtgat catgccactg cactccagcc  167280
tgagtgacag agtgagaccc tgtttcaatt ttttaataat gtaataaaag gatgagtatt  167340
cagaatatct aaagagcatt tacaaatcaa taagaacaaa gaactatgga tacaagcaag  167400
aaatttacca agaagtaca gcaacctcac tagcgtttag ataaatacaa aagcaatcag  167460
attggcacag tggaaaagtt tgataatata tattgttgac cgaggtgtag aaaaatggat  167520
tcttttctgg tcagagtgta aattgactca gccacttaaa aatgtatttg ttacaatgta  167580
tccttgggtc cagctatttc acttcactgt gtctacccta aaataactct tgtacttacg  167640
cacaatgagg catgccggtg tatattcact gcagcatcac ttattatcat gagaaattga  167700
aagcaaagga agtgtccact aggacagaag tggctgtgta aactacagtg catccaggac  167760
acatagtagt cttcagcggt tacagagaat gggctagaac tgcatgtgtt gataataaac  167820
catctccatg atagactaag tgaaaaaaat aaattgtaca acagtttatg tgatgtgata  167880
tgtcaccatt tgtttacaaa ggaaggcaag gaaggaggga ggaaagaagg gaggaagagt  167940
gcaagagaga aagagaggaa aggaggaagg gaggacggac agactgctat agattttcca  168000
taatagtagc tttcaaatgc ttggaaatga ctatcaatag aaaacgcatt ttatgtcttg  168060
gctgagtgga ccccttccaat gtactctgaa attttaaaat ctagttccga ttcatttgat  168120 atcattttc aaaatgctga tcataacatt aaaattggct tcaggactca agtatggttt  168180
gaaaaacact gttttgaagt gtacatttat gtatgtaaat ggatagagaa gtgagtggaa  168240
gtcaacacac ccctctgata tcacaggtta tttctgggga ggtggctgtg atgggtggtg  168300
gctcctggga gccttgaatc tcatttgtac aactaacatt tttgtttgtt tgcttgcttg  168360
tttttatagg ggcatgcgta attaaatatt tttaacttta tttttaata actaagtaat  168420 caaaagtatt tccagaagtc aaggatgtgt tgggattgtg agggtagtgg tcaaagggtc  168480
tcaataaaaa taattttga gttaaaaaaa ttgcatagtt gattaattca gaaggaagac  168540
attctagcta actctttgtt tttgtattta gggccacaga tgggcacatt cttgtggcaa  168600
ggtagagtca aacctatgtg atatcccatt caaaatgtca tcacagatct aagaactctt  168660
tgccatgttg tgagatttta actcattaaa atctatgaat ctataaacta tgaatgttgc  168720
atctacaaat cagaaacata gtataaaaat gattttaaaa aatcaagctc tccattttca  168780
gagaatgcaa agttaatttt tctgtagcaa taacaacttg gtcatgttac acactgtcta  168840
gtatttgttt tgggtctaga cgaacagtta cattttaaga attatttctc caagaagcac  168900
tactgtagaa aatatggcat gtgtacactt ggccatctcc acaagatgga gcagacaact  168960
ccagctctct gttttctatt ttagagctac attaactctt tctatttgcc tctttacatt  169020
tttatcccaa gggtatttat taaacctcat attaataatc aaataattca tattaaaagg  169080
agtaaacatt gtgtccatgg gatagagact ctttaaattt caaacattta aacaaggtat  169140
taactgcaga tgagctagaa ctagattatt tcttgtgcta aattctaaac taactcagta  169200
aagatatctg taaagaaagt agtatttctt tgaatgttta tattttattc ttttttgcat  169260
tttatgtctt aaatatacat tttcatgtgc ttataataaa acaagttgac tcttttaaat  169320
gactgcattg aatgttctct ttaaatgtct tgaaaacaaa atatttatgg taaaatatgc  169380
aagctttctc aggaagtgct tataatagaa gcgttttaa agatgtttag ctgttgttaa  169440
agcaataact atattcatgt ttaacttcat agtagctcaa tgttgtgtga agggaagaaa  169500
```

```
agagggtctt tggaactttc atctttttt ttttttaaa aggaaattag caagagaagt  169560
tttattgcgg aaagcacact ctaggttaag gggaggaaag gaaagagaaa gagaaggaag  169620
agaaaggaag gaagataatg cacatcacat atctgaagtc tcttttgtt ttatccagtg  169680
tggttctgtg ggtgaaaaga ggcagaggtg gccttgtagg taatctagag aaaagagtca  169740
ttcctttaaa tagttttata gtcctcaggt taagaacaga ctgtggctat ggcagaggac  169800
gctgggaaag caactaatat gtaatttgac actgaattag tctgaaaact gtgaaggtgg  169860
tgtggctgta tgatgagaat tcaggataaa ttataaatgt gccctactta gacatggaga  169920
gaaatctatg tgaaaattat aatttgtaat aatcaaaggt ttgaaagtta tttaattcta  169980
gctaaaagaa ttttcatttt tttttgctct gtaagaatgt tcagtgatta cattttatag  170040
ttttgataaa attagtctta aaatatgtta tggaaggcat aatgaattta aaagttaaaa  170100
gcatgatagc ctcttaacta tacatgtctg aagcctggct tttcagtggc tactgtatct  170160
aaggcactgc tgactcctga tggcagcctg ctgtaattgc cagcaaaata tccaagtgat  170220
aagcagtctt tcagatgtta ttatagataa tatcattgtg ttacttagaa gtctgagaag  170280
taaagggaag atatttttta ttccatgtca taaaatgttg aagtattaca gggtctctgc  170340
atattgtctc attgataagg tgaagtcttt gctttaaaat ttgtgttaga attttacttc  170400
attttttcac taatgtaact tttgaaagag aacttgacta actacaaaat ttatcaccca  170460
cagcatcagc aggaattgct gtgtcccaga ggaaagtgcg tcagatcagt gatcctattc  170520
agcagatatt aattcagctg cacaaaataa tctatatcac acaggtcagt gttctagctt  170580
tttatttcct tttcatctta aatgcaagtt tggtgctaat attgctgaag aactattttg  170640
gaggacttta gattgaattc ttgttcttat cctccccagc tacatacatg tggggacact  170700
ttagtttagc agcagagctg ggaaggcagt agagtaacaa agcaaatata tgggatttc  170760
cctatgattc ctaacatcct ctcttactgt tagtgcccaa acaaaccaaa cttcaccata  170820
aatggccctc ctgtagggt gcaagtggag acggagttgg gattctttgc tcttaagcag  170880
ctttactcta agaagaaag aggaaaatag tgcccacaca ttaattctga aatgctagg   170940
ttgaaaatag gacctttcag agagtgaaag ccaaaaccac acaaaatcca gaattgttaa  171000
aattttctac ttgtaaatct cagtgattcc tagcactgag aaaataatca gtgctaaaaa  171060
atggctatta attattgaca gaaatatgtc tagaaataac ttgaaggctc tgttatatat  171120
ggttaataaa atcttttttt tagacaaaga agtgcagaag acctttggac atgaaagtca  171180
ctgttatttt gaagtctaaa attgtgtatc ttatgtggtt tattcattca ttcactcact  171240
tgacatataa ttattaggtg cctactatgt gccagatgct attctaggga cttgggatac  171300
atccacgagc aaaacataaa cattgccttg ctctagattc aaagaaccaa tgggggatgc  171360
tgtcagctgc cagttttggc aattccaact aaatattcag atactgaaga gaaataccac  171420
aagttaaatg gaccaactgg gcccattggg ctcatatttc atttaactaa cccccatccc  171480
tacccaaaac atcccaaaac aaaaaatcat taaaaatggt gtaccacagt aacatgataa  171540
gactctagga atcttgatgt cagttttgcaa ccagtgtcta gtatttgctg aaagcctgtg  171600
tatttccttt tccccagtaa acagtcactc tagtaaatgg ctgcggttct ccttggggga  171660
ggtttggagg aaaatgtata gtgtgcactt gtagtaatat ttcaggggcc ttcctcaagg  171720
ggtcccagct ttccacttaa tcaaggggct ttgagtcttt gaattgactt gcatctggaa  171780
actgtgtgag aagctataac tcttcactgt agcaatggca acttagggca ggtttctgtc  171840
taccacacct agataatctt ttctgttaaa ctgatcaagg aatactttaa taggcagacc  171900
```

```
atctatttct tttccaggaa caccctagtc aactaaccac tgccaaagat ctctgttggc  171960
taaggcattc taaataatag tacctccctg ctgcccttta tggaagatgc tctcagtttg  172020
ctattagtgg tcaagtgctg tcagttggcc cctgacaact ggatacattg aaatcatgta  172080
tcgttcggtg tcatacctgg cctccaaagg agagcaacca cagggctttt caaggatgct  172140
ggtgctcccc tttccaatgt atttctcaat gtcttagtga aaggaatggc ttctggatgt  172200
tcttgctgaa tgtggttagg gagtgggtgt gcaagtcaca catggtaaat ctaccccaat  172260
gagcccgtct ctctgagcct ttgaaatcac cccttcacat gccagagaag ctctggcatt  172320
ttaccctcat caaacacaga ccatggttaa gtacaagttt tactcaaaca accagttaaa  172380
ctacttccag ctgcatgaac taacatgtga aatctggagt ctgtagtacg tgcacccata  172440
tcaatgaatt cagcctgatc tagtgctata gttttttaccc ttcttggcct accctttctta  172500 gaatccactc ctgtacatgt tctctgggtt gctgctgaaa tgtaatagca aaatcttgca  172560 attctttttcc tatttcatac tgggtcatgg tgtacatgaa ttcccctgga tcatattgaa  172620
ataggaccct agttatggat ttgacccctca ttgtgttgga tctcatgagg aaatgaacat  172680
cccttttaaa gacatttgtc ctagatgagg ttatcatagg gttttcaagc aaagaaaggt  172740
tcatgttctc agacacagag tggcaagcta tttttaattg ctatgaaggc tcagagtgac  172800
cttggtttta ggattgttag ttttacttgg gtagtctcaa caagatgttc ctattccaag  172860
ttttagaatt ctttttttttt ctaactttca catgagaaat ttgataacat gtgacttcat  172920
ccgaccttgt aatttagtaa gctgctcgat taaatttcga ttatcagcca tatcagcact  172980
gtagcagaag aaagcaatgg attctttttag ggctatcttg ggatctttcc acgtctcaga  173040
ccatgacttc agctgagctg taaaggaccc aagcttgtca ttttctttct gtaagtgctc  173100
caatgcattc aaaagaaccc attctgtgcc atagtccttg tgttcttcat tactgtttac  173160
tagtcaagaa cagcagctat ttgggcttcc aaggcacctg cttcagttgg cacttcatca  173220
ggataacctg attaattgtg atgcaactgc atgccatgga ttactagcat cccatgtcct  173280
attggcaaca agcaaaggaa caaacaaaac tcagcactgg gctcagttcc aagggcacag  173340
tcaaaccagt tcccaaatcc tatctgtatg ggctcttctg ggacattcct aaaacctgta  173400
tctgtatcag tgagggtcta gtcagaaacc ataccatagt ttcaacaggg aaggtttaat  173460
gtaaagaatt attaactatg atgagtatta tctactaggg aggggaagag aaatctaaag  173520
gatgtaggaa gagcacaaaa agaagtcaca acctctaggg ctgaggcaga gcacccaaga  173580
aaggaacaaa tatagaattg ggcactccca cactaggtcg aagtcctgac cttactgaaa  173640
agatcagaaa aattagtaag gtgctatact ggagaaactt gaagcgaagt gtccctctgg  173700
gggacctggg caagccctcc acagtgaggt actgtgccct ggaacttact gggaatcagc  173760
acttgagggt attgtgctgg gtagcaccct ccatgggacc aggggaggcc accctgagtt  173820
aggtgttgct ccatggaatt ctctggggag cgacctgcag agttggtgcc actggatttg  173880
actgggggtt agcaccaacc tctagggtc ccacatgtgc tgtttgctat gagctgccgc  173940
agcaaggcaa cgcaggagca tcactggagc caggaaacaa gatccatcct ccttcagcat  174000
ccctccaggg ctctcttctg atagagctta gcatcctgct agatggcaag ggagaaatgt  174060
tccagtatca caagctggat aatgaaaggg tggacttgga gctgacaggc tgcttactga  174120
cacacttaac ctaggggact agacaaggaa ccgccttctt tggtgtctcc ctacctctga  174180
gttctccttg ctttcccttt agcctgggta gtctttaagc ctggggctga gtagcctggg  174240
```

```
tcttatctat caagttttgt ccaaactctg gtgttcttttt ttctttcccg atggctgcct    174300
tttggagatg caagagtcta aaactgatca cttttctatt ttctgctgtc aagctttctc    174360
ttaggcaacc acagaattgt ctaactaatt acgtaaaaga gggtgaagga gtacagggaa    174420
atattgggggg aagcttgact aatacatcaa aatataatct gccatatcta tattgagtaa    174480
agtggttata ttaatgcatg tccatttaaa tactgatata gaaatatgga aaaagcattc    174540
ttaactttag tgttacggaa atagctttaa atagcttttt agttctctta actattaact    174600
attcaattga gagaaatatc ctttgaaatt taaatatagt tttcatatgc ctgtcttgct    174660
aatttttatg taataaaaaa ctttataatg tataccattt tcttattgga tttcaaagta    174720
gtttaaagca agagtaaaac tattataaat atcttattat tatgctcttg aactgccagt    174780
gtaacaaatg atttcatttt ttttggcaga atggcattcc ttgctacaag ttcaaatata    174840
actatcgtga ttttttaaaat gtatttccag aatactctaa agtttatgac attgcacata    174900
gtcgggaatg attcctcttt gaggaacttt aacttatagt gctaaacaaa gtcaatgact    174960
ttcaaataaa aaagaaaaat acatgtaaat attatactag tgtatttgct ataggttaaa    175020
gaccaagatc agttactttg ctaattgcaa aggaagactg aaagtaagaa tgaattgaaa    175080
aaacaaacaa aaagacaata ttttcacata tttatttact agtcaaactc tctcagactt    175140
aacacttggt agctgcccta aactgagggg ccacatatct cctgacaacc agcagatgaa    175200
cttaacaagg aaaacttctt acttttggtt ggtggtggcc ttttctgtct cgtttccatg    175260
gagacagatc agtgaaaatc atctaaaagc aactatttta gaaggcagga tgttaaaatc    175320
cttaccttgc tttctaactg atttgacctc tgttttttatc aaagctgaaa tggtaatcgt    175380
aagaccagca agctaagtat gaaatcagtg gtttacttct attgctggaa ccccaaatct    175440
accttttggac atataaggtg actaaagtac atatgttacc tttgagtatg agtctttatg    175500
tgttattgct taggtcacac ctgcacagcc cagtgaagca ctggatttaa cttttatactt    175560
acatttagat tgttttgtta aatagatgct ttgaaaatca ggatatatag catctttttaa    175620
aaattaaaca ttggggccgg gcgcggtggc tcacgcctgt aatcccagaa ctttgagagg    175680
ctgagacagg tggatcacaa ggtcaggaga tcgagaccat cctggctaac acagtgaaac    175740
accgtctcta ctaaaaatag aaaaaattag ccgggcgtgg tggtgggcgc ctgtagtccc    175800
agctactcgg gaggctgagg caggatagtg gcgtgaacct gggaggtgga gcttgcagtg    175860
agatgagatg cgccactgc actccagcct gggtgacaga gcaagactct atctcaaaaa    175920
aaaaaaaaaa aaaaaaaaaa aatcgatctc ctagagaaca ggcaagccat ttatttgaag    175980
cgcctttgaa ttgtttgtct tcacaaccac agttattgcc aatggaaaaa aatgtagttc    176040
agaatagcaa tgtgttgtcc tccaatgaaa attatactac tgactgtcat tggtgaaacg    176100
ttctgtgttt tttcagcagt agtgatggat aagactagaa ccatccatac ctgctcatct    176160
ggatctcctg tactaatggc aagggtgacc tagatttaac agaataagat atttaggata    176220
aagttgtatt tcttaaattg actgccattt tcagggtttg taaattctaa gagaagtgtt    176280
atgttttgtg tatttagttt gataacagtc tttgaacatt ctgttttagc atttaggaa    176340
atatcctctt atgcagtaat gtcaaaataa cttttttaaaa aatagaatta ggaactaact    176400
taaatcactt tttatcaaat ggagtcctgt gaacaatgga tagtcttctg atgtattctt    176460
ggagatacta gagaatatag caagttcttt aaaagaatcc atatattctt ccatatgtag    176520
aaatctatat attcttttcc aatattaata ttatgcaagt ttgagaaaac ctagtataaa    176580
acatgcagat cggctttcat tattttgtta ctttgtgtag tatagtaaaa acaagcaaac    176640
```

```
aaaaaccaag cttttaggtg tgtgactttg aggaagtaat tatcttttta agagtcactt   176700
tcttcatttg taagatgggg gagcttatga gactacttgc ctcaaatgaa ataaagtatg   176760
taaaaatgtt tgtttatttg tttctttatt ggagatggat cttgccatgt tgcccaaggc   176820
tggtcttgaa ctctcctggg ctcaagcggt cctcccacct ttgcctccca aagtgctggc   176880
aatacaggca tgaaccaccg tgcctggctg aaaatgtttc taaactataa agtgctatcc   176940
tacagtaatg ctagtcatgg tggcatctgt tctagaataa tggctgtgct agaagacgct   177000
gctcagaaag tattcttgca tgttacataa tgtctttaag ctctgacttc ctcacctata   177060
aaatagtact tgctttataa gtttgtcgtg gagaaaaaag tgagactgcg cataaatgag   177120
tagtcatagt gtctggctca aatgaatcat agacattaat attctattct tagtattata   177180
gtccttacgt ataatatatt attatgttta tatcacctgc aattaaacta tgcatgagtc   177240
atcattttgt gtaaaatttt aaattcttgt atgaaaaaac ttcaaagatg gggtgctgtc   177300
cattgtaata attattccag taagatcaat agctttctaa tatatatgca gcttaagttg   177360
actgaatgtt aacttactca aatgagtttt tgaggcttaa ttcagaccat caggagcagt   177420
aaaaacaatt ctaacttaac tagaggcttc tcaagttaaa taaatcgcaa gaattctcag   177480
agtacctgaa ttaataatct gatactcata gcttccagta gtgggttaag tcccctttga   177540
aggaagctat gagcccactg gtgttccaca cttttcaaaag tttgtcatag cagagaaggc   177600
tcgctgcctt tctgtttgac agccccttgc agtcagctgg gcagcagcta gagggttctg   177660
ggccaacact gccctctggt gtttggtttg gggaagtggc aacttttggt gcattacaaa   177720
agggaattat caaacctgtg ctctgtccag gtactttctg gtcccctcat tactccatcc   177780
catcttcctg ctaggaatat acatgcacat gctcctcacc ttcatgtctg tttctattct   177840
aagttaaatt catttctctt ttgcttttct ctctcacaca catatatcat ttatactcat   177900
tttccttctc atctgtcttt gatttgctcc ttaatgctga gaaatctctc tctctctccc   177960 tgcaccccc ttcctctctt ttctttctct cttccacatt ttttaaatt tcctcctttc   178020 atttcatgtg aaaggacaat aataattatg actatttgct gggagccgag gaagggatcc   178080
catctggatt aaggcaaaag aaactataat attgacctga aaagaggtca gaggagactc   178140
agtgctgcca acctacaaaa catttcagag tacactgaag tgcttcagta tctccagaag   178200
agtcttattt cttcgctaat taacgtattt tgactcaaac actaggataa aagatacatt   178260 tttatttt tgagatggag tttcgctctc attgcccagg ctggagtgca atggcattat   178320
ctcagctcac cacaacctcc acctccgggg ttcaagcaac tgtcctgcct cagcctccca   178380
agtagctggg attacaggca tgcaccacca tgcccggcta attttgtatt tttagtagag   178440
atggggtttc tccatgttgg tcaggctagt cttgaactcc ttacctcagg tgatcctcct   178500
gcctcggcct cccaaagtgc tgggattaaa ggcataagcc actgcaccca gccaaagata   178560
tatttttaaa aacattttc aattgaatta ttttcctgtt ttatataatt acagtacttc   178620
ataatgggcc ctacattcta ctatatttgg gatgatgaaa agttttttatt tggctgtgca   178680 atcagtgttg tgagcccctc cctgtaggcc ctattctttg ctctgccatt atctttata   178740 tgtcctcctg tctgacaaaa cttgagtaaa taagataagg ttaagtcatg ctgaacgaac   178800
agttacaccc tgaaattcct tggcttgaca caatagaggt ttatttctta ctcagttcca   178860
ttcgggctgc tcaggtggcc ctgttccttc ttgtggctgt gcagtcagaa taggatggta   178920
atgccaagct ccttgcagta gggaggacag tggtggagaa aacacactga ctttgaattg   178980
```

```
tcttatcctc agagtgacac acatcatttt tattgaccaa aagtagtcac atggtactaa   179040
ctaagcctgt aaaggagcct agaaaataga gcagggttgg ggtaataatt atttctgata   179100
cattcttctt tcttttgatc tgagctttga attatattct tgtttaatat tgagatctct   179160
tactatcaca ttttcctttc cacttagcca tcttttttct gactggttcc tctttctctc   179220
ccttcaagtt ctttccataa tttaaacaaa accaaatatt atttccactc tgagacccct   179280
ttaatcctga cccaatttct tttctattat ccttcttcta aatgtcactt catctttctg   179340
tgctttccag gacttttgat tttcttgtag agatccaacc tacaaagcat gacaaatcat   179400
tttttaatc cccatttttt ttgttaccat gttttctaag gtcctaccat gactttctac   179460
tactcactta ctaaatgtaa ctcatcctag tctggtctta atatatgcta atctatcctc   179520
tctttcttct ggaatgattg gtacctaaat ctgacctctc tgcagctgaa ttttcaggag   179580
cactccaaga caggcatctg actatatata ctactaaagc agatatgtgt tcctggtcc    179640
aaagtgtcag atcctatagt accaaggcta cagtgtttgg catagttcta ggcatattat   179700
aagcacctaa acatctgata aaagtgcacc attctgtgtc aagactgttc ttcacaaaat   179760
tcagtatatg tgtgcaatta atgaataatt tgttaaatga aaataatat caatcaatga    179820
agaaacaata agataaatgg aagcagccat ttgaaaaaga gcaaataat atattccttc    179880
tgaatcgcag ggtaaaaatt atagcatcta gtcatgctat ttgcagtaaa atttaaattc   179940
ttacatagtc ctattgagtg aatattgtta catgggccct cagcgaatgc ttttgtagt    180000
cagctgtgta gtgttaacaa tttgtttata atgattgttt tcttatttta tgcagcttcc   180060
tccagctttg caccacaatt tgaaaagaag ggttatagag agattcaaga aatccctctt   180120
cagccagcag agtaaccctt gtaatttgaa atctgaaatt aaaaaggtat ggtattctat   180180
atataggaat tcttttgctg acaaaaccac atcataagag gtacatttta tacctccttt   180240
acttcgtact ttaagctcta tcctctatta aagtttctta ttgctgcttt acatactaaa   180300
ttgaggatat gtctttgctt ctgattttct ctatttccgt ggcccttatt tttagataac   180360
aaatggatag cttttttcagt atttttgtat gttttcctaa gaaaaagtaa tatttaattt   180420
gaaatgtgta tattttagcc tcttctagag aattatattc tgatatttta ttagaataat   180480
cttcaataag ctccaaaatt gagatttgtc actctgaaga agtcatttaa ccatctgggg   180540
ccattgattt tttattatct atgaaagctg actgaactat ttctaaggtt cttttccatct  180600
tagatattct acaatcttct agaccttaga tactagcaga catttctgtc catacatata   180660
gcaactaaac tacaaaaata ctaaatcaac tgggcagaaa gaaaattgtt tacctctggt   180720
taacaaaact tgatattgga aaatcccttt gtcctggttg gtagaccttt cgatacagcc   180780
ctggaagtgg ccataagctc ccctgaaagg cccaaggtac aagcaattca ggcccaccta   180840
ggtaaagaca attggtagca ctccaatttc atatttttta aaagtttca tcatattttt    180900
aaatgggtag catagtcatg ctgccagtga acttttcctt taaggtttca cgttccttta   180960
atgcatcaaa gcttcagcat taacttactc attatttaga aaatatgata ggctctttga   181020
taagaaatgc aaacaacatt ctttagcttt gttgtttcac atcactggta tctgcacata   181080
caccaaaaac agatggggga aaaagacaca gctgcaggta acaaaacat aaagcctgct    181140
ccatcagaga ttagagagca aggtttcttt cctgggttgt gttggcaaat agggccaaga   181200
aacaaagctg aaggagatca aagcagtaga agaggcttca gatatttatc ttatgatatt   181260
tatatattgt atcataataa acacattttt aaaagataaa agcttaaatc tcccatgaaa   181320
agataaatatg ttgcttggtt ttttattctt attaaggtca tataactctt attcttattt   181380
```

-continued

```
tatattctta ttaaggtcag aataatctgg tttgagcata gacttatttt aacagaaatc  181440
ctagttttat gagatgaaag catctgctac aaactgtctg agacataaag gtggcttcaa  181500
ctcccactga gtgattttcc atcagtgctt ctctttattt tctcgtttat tacttatgtt  181560
tttggttttg caactcttcc tcactttctt tcctctcctg atagagaaga ttttgtttgt  181620
taaattctcc cacccactcc ttgtcttcct tcctgtgtat tgtggcagca tctctcattg  181680
ggcatttacc ttctgataca cctcgtctgg gaaaataaaa acaggaattg gtagggtggt  181740
aggagatgtt tgggaagcat gggtgagaga accctcagga atagactcat ccttattatt  181800
aacttgttta agaggcagat tatactctcc tataaagact gccatggttc tcttgtctga  181860
tactacaagc ccatggtggt ctttgggaca tcttgtatgg acctttaggt agggaaaggc  181920
cctatatatt gctttagggc tcatgatcaa cagaagtgtg gttccattcc tctacaggca  181980
gcttcaggct tgcgccatct ccccatgaag ttggatgata ccttcatggg ggtgtatcct  182040
cttagtcaga gaggcaggcc tcctgggtgc taaagaaatc ctcagcttgg gatattaaaa  182100
cacttcctat tctttaccac caaactgaaa aaaatagctc tgacaaaaaa aaaaaacctt  182160
tcttaatttt ccctgtccag aattaatctt acctttctct atgggtgaat ccacttttc   182220
acctgtatta ttgtgtttta aatagctttt tatctacctt acattctgtt tcccccaaag  182280
ttggtgggtg tgtcttattt atctttgatt ccccagggcc ttgcacagtg cctggcatgt  182340
ggtaggtact taatgtttaa taattggaga taggatatat aatacattaa tatatattct  182400
gtataatata tagttgttcc attctttatt ggtatactga taaaatatat tcatatatgt  182460
aactttcctg ccttcatcta aacttaaatg agaagagttt gtgacctcca tttttacccc  182520
ttttctggta taatcttttg atagcaacaa cttctgttca taaatggatt tttcattccc  182580
tgtgtaacca tagaggagtg gccaattagc ctttgactga cacagtcacc ccataccagg  182640
gccataggag cagtaagtgg tgacagccca taaatgcact tgatttctac cttctcact   182700
gaaacttcta aaacccacgg gccctgtgtc cctagtttga aggagccatt atgggatgac  182760
tgtgcctact tactaatagc ctaagaccca gaaggataca gaagattcaa aaagtgcaaa  182820
aggccttttc taagacatta agctctttat ttatacctca cctaagttag tcttcaatcc  182880
agtctgctca atcttggcta gaattgcgag gggagtaaag caaccaagta attgtatagg  182940
taccttgggg aactaggatt ttcagcatgg aggaaagggg aaacagaagc aagatagcag  183000
agattcatct aaattggaat tggaagtatc agtgtgaatg aatatgagtt catgataaat  183060
ctcatctatt aaaaaatata cacatttcct aatattttca ttgaaatagt cgagaaacta  183120
atcaagcagc aatgagctcc tccacccatg actccttggg gatataggtg attttggtct  183180
agagcaggaa ctgtacaaga ttagactgga atatttggac atacagatag catagtaagt  183240
atggtgtcaa ggactactga gagtatatca aaagttctca agagccaaat tgaagaggct  183300
cccactggct atttatggga taattggaac atcaataaga ataataaatt gaaagcatta  183360
aataaggttt aaacccaaga gttcataata ccaaaaaaga aaaaaaaaaa tccctcattg  183420
gttacctttg gaagatgcta agtaaccagc ttattatatt gaaaattgtt tacataggaa  183480
agaagaaagc ttttattctg cctttccttt atgaattcta tcgcatgtta acaaaatcat  183540
tgagaggaaa agtttcttat tgtagaagta cttaagctaa taagtgccaa agggataaag  183600
aatattcctg ttttgcagtc cctgttaaa tgatagcacc tagatatgat caccaatggg  183660
cgttaatgtc acaagaagga caatcaggca ttatatgcca cctgatggga gtgtacagca  183720
```

```
ctgtctatga aatattcttg ctaaaagctt gaatctacat ctgattaagg ctgtagatta    183780
gaagtcagca aattacagcc ctcaggccaa tcatttctga tgcctgtgtt tgtaaataaa    183840
gtgttgttgg aacgcaactg cagaggttca cttaatactg tctatggctg cttttgttta    183900
cagacaaagt tgaatagcag ttacagagac catatggcct ggaacgccaa aaatatttac    183960
tatctgatcc tttacgggaa aagtttgtct gtccctgctc tggatctagc tatctacttg    184020
cagcaaataa ggggacaaca gaacatgttt aatgacatca ggggggataat cagcaaaatc    184080 cagccaggaa atccatagga aaagtgacct gttttcttca ataaataaat ttcaggaaga    184140
ggggaggagg agagaagaag ggaagaaaag ggagagaaag agtgtggaga agcggagagg    184200
gattgcctgt aaagattaaa gcattttagg gaaaataacc acttgcaata tatggaatta    184260
tttcttcctg acttaaacat agaaactcta aaagtgtttg aaatatatat ttacaagaaa    184320
gttgggaaaa ttaaaacatt gattatatat ttgttagaga gtcatgcacc acataatgat    184380
gttttggtca gtgatagact ggatatatga cagtggtccc acaagattat aatagcataa    184440
ttttactgta ccttttctgt attcaaatat gtttagatac ataaatacca ttgtgttgcg    184500
gttgcctaca gtatttaata cagtaaaatg ctgcatagtt ttgtagcata ggaacaatag    184560
gctcctattg ctcctattgc cagcatatag cctaggtgtg tagtaggatg tactatctag    184620
ttttgtgtaa atacactcta tgatgtttgc acaatgatga aattgcctaa tgatgtgttt    184680
ctcagaatgg atttctgttg ttaagcagtg catgacagta ttcaggaatc aataacctct    184740
taggtgggat aattatattg tggttttgtt ttttaaaaag aaatccatct cttttaaaga    184800
gccatgctga aatattacgg atagtatgat atgttgtaca ggatttgctt tccaattctt    184860
gagagtgaga caaggtagga agggaagtgg gggagattta aatgaagcaa gattgaacat    184920
gttttaactg ggtgacgggt acgtggaatt cattgaattg ttatctttac ttttgtaaat    184980
gtttgaagtt ttttataata aaatatttta tgggtttttt gtttgtttgt ttgtttgttt    185040
tagtgtattc cgggcttctc ctagatcaat tactgggcat tagcattttg aaaacagctc    185100
tcccatcaaa gctgccagtt agaattggac aggttatttt ctgttcaaga gcacctggat    185160
gaagagactg actggggttg cgtcctccgg aagaagggag tgacttttc taatttgcac    185220 taagacacaa taggggctag ttggctgtct aggagttgga tcaaggtttg ttgttgtttt    185280 tttttttgctc ccaggtgatt ctaatttgca gccaagggtg agaatcagtg gcctggtagg    185340
atcagggttt ctcacatttt attgtttata tcaatcatct ggggatcttg ttaatgtgtg    185400
gattctgatt cagtaggtct ggggaagggt ggagattgtg ctcttccaat catcttccag    185460
gtgatggctg ctgctgctgc tgatccaggg acacactttg agtggcaaac ctataaaata    185520
tagtacctgc ccactgtgaa cttatggtat atccaacagg cttgagactt tttattagaa    185580
agacaggtta tctaataggc caaatattta tccagatgca attgtatcct ggacccaata    185640
ttctgcattt ctgtctagtt cccttatgtt actgatgctg taattctata gatcacgctt    185700
ttgataagaa agcccagaca aaacccagta acatttttccc tgtgttatta cccagattgc    185760
ttcctgtagg catgggcctt tctgacattt ctgtttagtt cctaatctct gtttcaatgc    185820
agatcagcaa ggccaagttt gctttattta gcagctggca cttcctttaa ttcctaactc    185880
caggttttca gctcttctcc aagtaggcag attgcttagg tgctcagact tgaattaacg    185940
gctctttatg catataataa tcatgactta ggtttgcaca acccttatta gggcccatg     186000 gaggcattgt gaatcagcag tgcccagcag caacctgttt tgaacaagta gagaagctcc    186060
tatagcaggg ctctccttcc cagccaggtc aagccaccgt tcactcttcc ttgacatcac    186120
```

-continued

```
cttcagtgtt gagtcaagtt cctgggagga tgagctcctg gttgtaagta gtgtagaaca   186180
gtggtttttc agccttcttt tagtttaggg attttctgtt aggaacacaa tccttgctgg   186240
aaatgtaaac accacagcaa caggaatact tttggcagaa acgggatga gtgtgaggtg    186300
tacatccctg gggcttagaa agtgtggtgg agccagtgat gggccatgca tgtatgggtc   186360
cacatgcata tgtgcatttg tgtgtgtatg tataagaaaa tagtaagtag gaatactgga   186420
catttctgtt aacaaaatgt cccatagaaa gctaataaaa actcatatgg agaagctgta   186480
tgttagaaaa gataaaaaaa ttaggcaata tgttgtatct tataatagtg tagttcagtc   186540
aaagaagata aggaaaatct gagggaagta agaccagaag actggcgagt gcagagtgat   186600
gaaatgtgtt gaaattttc tcacttctgg cacctcattt tatttatgtt tggctcagtt    186660
tccttcagag ttctacctca gttgattaga ttcccaaata ttgtgtgtaa ttgttctaca   186720
gtgaggataa ccctatttta tcatatgaaa aagatgttgt ttgggaaatt taataaatat   186780
tacatgtata gtttctttat tttttctatt taggttttgc ctagaaagta ctatattctc   186840
aattgaccaa ataaatgata aaattgctca atacttgctc aaaaatcagt gttttttggg   186900
gggagaggta gtaacaatga tacagtctgt tctccttaat atatttactt agtttagttc   186960
gaaagtatat tcagtcattt gctctttaga actgtaggtg tctattcaga gcaggagggc   187020
cctattattg tcaactcaga aggaggctct tacacattct ttcaaacaga gtttgaatgc   187080
taaaaggag gtacaactat aagctgaatg ctcatgaggc aaaaaaaagg gttcacacag    187140
cacttgcatt ggactactga accatctcat ggcctcatct agccattggg gcctctgctt   187200
aaagatgttc tgctgtgtcc tccatatttc cacctgctgg gtgaacattt actttgccat   187260
ctggcatgtc gggaattaga ctcaccacct tctcctccct tcctgtgtcc acatcagttt   187320
ccttgaaagc atccgttttc cttcagctaa ttctttaaac ctcacgcttt ttcacctgct   187380
ctgcttcatt tcttttaccc gctaagtcat taatgcctga gtagtctgta gtcactaagg   187440
ttctgacctt tgatgtaaga cagccctagc ttctggccct ggttctgcca cttaatagct   187500
gtttcttgtg taaattactt tccttctcca tttccttgtt tgtaaagggg ggtaatactt   187560
gccttagagg gtagttgtaa gaatcagcta gaatatctac tgtgtctaga atgttgtaag   187620
tattcaatac atgtcaatta gtactactat tgttaaataa gaatattcag tcttccatat   187680
ccattccttc ctttggttgc catctagtct aagctctggg cccttctctc ttgcattagt   187740
gtcacagctc ctttgctgat cttcttgttc tccaatctat cttgtcagac taatagttat   187800
taagcatttt tttattagca tactcaaaaa ccttagtaga ttcctgtttt ctgtctcacc   187860
atctaaactc tgggatccag cttttccaggc ccccttact tgtaggagcc tcttaatagt   187920
ctgtctgcat tcaccctgat gttcccaacc ccacttaaac tgttttgtgt attacatcca   187980
ggatgaacct ttcaaaacag atcatgtcac acttgtacac acacacacac aacacagaaa   188040
atccttcaag gaactcagta taaaatgcca aaatcaggtc taactcctgc ccttctgttc   188100
accctcatct tgtatcactc ttgccccttg ctgtctccac gtcagccacc aggccttttc   188160
taaaatttgt ttatctagca tgctgcttcc ttcgtagtct tgtacatgct ttttcctctg   188220
cctgtaatgt tcttctcgcc ccatctactc attcttactc attctttcag ctcttggcat   188280
aaatgtcact ttttcatgga agcctttgct gactaagtca aatctatctg ctacctccta   188340
aagtcacaaa cctgtctttc aatgcattta gaacagttgc aatttacat gtatctaggt    188400
ggacatttca cagacatatt tctccctaag tagttagcga actccaagag tataattttt   188460
```

```
atccattaat gtgtttttc attgtttgga tctgtgcttg gcacaaaata attgattaaa    188520
aatactaaat taatgaatgg aacttgtttt cctcatttca tcatgaatgc ccatataaca    188580
tggaatcatg tcatatccct ttcatcattt ttccattaat atgcaatgcc caacctttac    188640
ctccaagttc cccctacctg gaatgtccac tttgattgct gtgatttacc taaatttatc    188700
cttcaaagat cagctccagt gtttcttcta cagaacctct aaaaaaacca agctagtctt    188760
catgaaggac ccttcttttt gtaagtttac aaatcactat ttcatttcat ggttcatgat    188820
ttatgatatc accctatttt tgctcattat tatcctgttg tcctagtcag attgcaagtc    188880
tcacagaaac cagattattt ctgcatcctg ctcagatcat aaaccatgct gtccaacata    188940
cactggggc aaaaaatagt ttgctaaaac aatgtgtata tctagaaact gaactgcaaa     189000
aagtagttct gggaagttcc tagaatgaaa gtcagtgtat ctgggattcg tcaaaaaatg    189060
aattttagtc cttgccttca tccgtgtgcc gatctctcta agaatttcca gttcttaagc    189120
tcagtgagac taccagtgtg acataagcac tggaaatgaa aactcctctc ttcagagttt    189180
gagatgaacc ctgaaagatg acttgtcctt gtcatcttaa aatagcaatc ttgacctctc    189240
caagtcacaa ttcatgtaat ttttttgag ctttaaata tctttctgtc tttgaaatct      189300
ttagaattcc aaggtataaa cttaataatt aaattaagta agcttttat aattaggatg     189360
agatttcagg cagccagtta ctcctacgct aaaccatatg aaaaattcca tctgaagtca    189420
tttgaaaggt aataccagga aatcattttc agcatcacaa gacattaaaa agcttatttg    189480
tagccaccta caagctggga tatgagatat acagaatgct cagggctacc tccatgaaac    189540
cctgcagcac agatgagaaa gttttaagt gtgtgactgt cagggcttcc tgtattacag      189600
tatttataat cttacaatct tgtcatatta cagatgggtt atatattagt ccattctcag    189660
gctgcatgaa gaaatgcccg agacttggta atttataaag caaaaggct taattgactc      189720
acagttccac atggctgggg aggcctcagg aaacttacaa tcatggtgga aggcacttct    189780
tcacttcttc actgggcggc aggagagaca atgagtgcaa gcaggggaaa tgccagacac    189840
ttataaaacc atcagatctc gtgagatctc acacactatc atgacaacag catgggggaa    189900
accaccccca tgatccaatt acctcagtta tcagttatca ctgataaaaa tggatataat    189960
catatatttt tttccttaga gggtagtagg tgtttgtcaa catggagact aggaaaccca    190020
caaatgattt gtatttacaa tatccaaagt ccattgatgg aaaaaattaa tttttaattg    190080
ctaatataaa atattttaag gtataaattc atagtgagta caatgaggta catatacagc    190140
ctcatgaagt tttatgaaca cattttcacc catacgacca ccacccacat caatatatag    190200
aatatttcta gctctgcaga agaccccttt gtacggccac attacatctc ctgccacaat    190260
gtaatcatta cctgatttct gttacccttg gttagttttg tctgattgta ttagtctatt    190320
ttcatgctgc tgataaatac gtacccaaga ctgggaaatt tacaaagaa agaggtttaa     190380
ttggacttac atttccacgt ggctggggaa gcctcacaat catggcagaa agcaagaagg    190440
agcaagtcac atcttacacg ggtggcagca ggcaaaaaga gagagagctt gtgcaggcaa    190500
actccagttt tgaggctat cagatcctgc gagacttttt cactatcacg agaacagaca     190560
ggaaagaccc acaccatga ttcaattacc tctcaccagg tcctcccatg acacatggga     190620
attgtgggag ttacaattca agatgagatt tgggtgagga cacagccaaa ccatatcacc    190680
gatgatgaaa atttctaaga atgaagtcat acactatgta ttttgtttct ggcttctttt    190740
ctccaacact gaaccgtgtt gctctgagta tccatagttt gttcttttt attgctttgc     190800
agaattccat tgtatgaaca caccatgata tatatctatc cattcttttc tccacggaca    190860
```

```
attggggttt tctagattt tagttattat gaaaaaaaga tggcatgaat attcttatac    190920
atgtcttttg atgggacata tgcacttatt tctctcatat aaatccttaa gagtcagatt   190980
gctgggtcat agggtaggca tatattatta aaatgtagtg tctattgcaa atagtttct   191040
caagtgattg aacaatgatg tattttaact cataaacaaa gtatatgaat acaagctaac   191100
tactatagca tagtacaaat tatgccattt tttctgactt attattatga atttatattt   191160
taaaagtaat ttaggcacta aaatttggcc agcccaagtg ataattggaa ttaaaggtga   191220
aaggaggtta aaaaacgttt acggtctaaa attctacttt aaaaattcag ctttatagaa   191280
aggcattaaa tgattgaaac tttaataaat accgtcattt ggcaaattac tctttccatc   191340
agagtgctgg gaattaatat ttggagatta aaattaatta atagtaattt cgaaaaatgt   191400
attaagaaac ttatttggcc aggcgcggtg gcttatgcct gtaatcccag cacttcggaa   191460
ggccaaggtg ggtggatcag ctgaggtcag gagttcgaga ccagcctggc caacatggtg   191520
aaaccccatc tctactaaaa aaaaaaaata caaaaattag ctgggcatgg tggtgggtgc   191580
ctataatccc agctactcgg gaggctgagg caggagaatc ccttgagcat ggaggtggaa   191640
gttgcagtga gccgagattg tgccactgca ctgcagcctg ggcgacagag tgagacactg   191700
ttgcagaaaa aaaaaaaaga aaaagaaaa agaaacttac tttccttggt caaacaaaaa    191760
ggaattattc aaagcagata catgaaaaaa aaatagtgat ttgggctaag catattgttc   191820
tgttgaataa ttggagttta ttcctcccat gcctgataaa aataacatct tgacatccca   191880
gcttcatgcc agtatttta tattcatttt tcttttgctc tcataaggcc ataaagtata    191940
tttttcata tgaccagaga attgtccaac ttgctttcac tgtaattttg ctgcatccaa    192000
tttataaatt cttttggaaa gaagattatt tcttatcta tttacaaggg attgaaaacc    192060
acagaacact aaattttctg tgcagagaca tagggaaatg aaaacccca cacagaggtc    192120
tcctgccatt tccttctgag tgtaaactaa gatgtgattt tgcttttct atttcagtta    192180
tctcagggat ctccagaacc gattgagccc aactttttca cagcagatta ccatttatta   192240
catcgttcat ccggtggaaa cagcctgtcc ccaaatgacc ctacaggtaa tagtgatcaa   192300
catgggtaac ctggctttca tgaagaaata tattgtttgg atcaacagct atttctaaaa   192360
gattatctcc aattttttt taaatagagc ttgttttgat tatttatagc aatagttgga   192420
aggcacatat ggtaggaatc tagaaattcc ctgaaattta tcttacccag ttgtggcagc   192480
ttccttgatc atttattaat atcataaaca aacagcagaa tctgtgtggg tgagttgtat   192540
ttcctttat ttcttttgc ttatctgatg atgggaaatc aaattcccta aagcatgtag    192600
ggagataaag agcagaaata aggagtttaa atattcaaaa tagagaaacc cttgaaactc   192660
acctaaagaa tccacattag acacttgaat ttttttctct tttacataaa attcacatag   192720
ggaggcagta tagcataggg attttaaaggc acatattctg gaaacctggg tgcctagatt    192780
caaatcttgg ctaaaccatt tagtagctga ctatggacaa ctatttaacc tctctgaacc   192840
ccagtttcct tgcctgtaaa atggggataa atacttgcat cacaaggtta tagtgaggat   192900
tagagtaaaa ataaaaactg cctgtctatt agtaggggct cagcataatt gaactcttct   192960
tgtcatatct gaattctaag aggaagcttt caagctactc tgaggtttca gtactcctaa   193020
ataatttttg aatctttata aacggtagct atgtcacttg gaggagtgga tagaagtgaa   193080
gattttacag ttaaatgaag acttgccatc tctttagctt ggaaaaaatg ctcacttttg   193140
ttgtgctttt gttgctgact gaacaaatta tttcatgaat taattgacaa actttccttt   193200
```

```
ggtcttctgg gataaagcta aaccctatgt atgcagaatt ttatttaaaa taatctctga    193260
gaaatccaag ataaaaagtt gtttaaagta atttgctttt aaaatcattt ccaagacagg    193320
gaagtttatc tgcaggtcaa acttctccgc atcatagaaa ctctgatgaa atgaagaact    193380
ttgataaaaa tctctcaaaa acctgagggt gagttgacaa actccccca gggcagctgg     193440
atgcccccact ccagagctga ctaggcttgg cccatgtcac agctggctgg gcaaaagcaa   193500
aaacagcaga gcctgccagt actgtggggt atgcctttaa agatgagcca ccagtactca    193560
cattttcaca tctcttcttg accctaaacc cattctctct tctctatttg aattggcaga    193620
gaagtggcct aggcctctac atgtcagtgt tgattggttt gagtgaaagc tggtcaacac    193680
ggctttgggt ggcatcggag tgtgttaagg tgctggtata ccaaattctg atcaaccatc    193740
ataaagtctg tccagcaaga caatcccaag caaaaaggac aaagctggag catcacatt    193800
acctgacttc aaactatact acaaggcttt agtaaccaaa acagcatgga ctggtacaaa    193860
aacagacaca tagaccaatg gaacagaata gagaactcag aaataggacc atacatctgg    193920
aaccatctga tctttgacaa acctgacaaa aacaagcaat ggggaaagga ttccttattt    193980
aataaatggt gctgggagaa ctgactagcc acatgcagaa aattgaaact gggccccttc    194040
cttacacctt atacaaaaat taattcaaga tggattaaag acttaaatgt aaaacccaaa    194100
attataaaaa ccctagaaga aaatctagac aataccattc aggacatagg cctgggcaaa    194160
gatttcatga cgaaaatgcc aaaagcaatt ataacaaaag caaaaattca caatgggat    194220
ctaattaaag agcttctgca cagcaaaaga aactatcatc agagtttaca gacaacctac    194280
agaaagagaa aatttttgca atctatctat ccgacaaagg tgtaatatcc agaatctgca    194340
aggaacttaa acaaatttac aagaaaaaag caaccccatt aaaaagtagg caaaggacat    194400
gaacagatgc tactcaaatg aagacattta tgcggccaac aaacatatga taaaaagctc    194460
aacatcattg atcattagag aaacgcaaat caaaaccaca atgagaaacc atcttgtgcc    194520
agtcagaatg gcaattattt aaatgtcaag aaacaacaga tgttggcaag gctgtggaga    194580
aataggaatg cttttacact gttgctggga atgtaaatta gttcaaccat tgtggaagac    194640
agtgtggcta ttcctcaaag acctagaacc agaaatacca tttgaaccag caatcccatt    194700
actgggtata tacccaaaga aaataaatc attcccttat aaagatacat gcacacatat     194760
gttcattgct atactattca caatagtgaa gacatggaat caacccaaat gcccatcaat    194820
gatagactgg ataaagaaaa tgtggtacac atgcaccatg gaataccatg cagctataaa    194880
gaggaatgag atcatgtcct ttgcaggac atggatggag ctggaagcca ttatcctcag     194940
caaactaaca cgggaacaga aaaccaaaca ccaaatgtcc tcatttataa gtgggagctg    195000
aacaatgaga acacatggac acagagaggg gaacaacaca cactggggcc tgttggggtg    195060
gtggagtggg tgaggggagg gagagcatca ggataaatag ctaatgcatg ctgggcttaa    195120
tacctagcta ctgagttgac aggtgcagca accatcatg gcacacattt acctatatta     195180
caaacctgca catcctgctc atgtatcctg gaacttaaaa ttaaattaaa ttaaaaaaaa    195240
aaatctggcc agccatggtg gcacatgctt ataatgtaca gacgttggaa ggctgtaggc    195300
aagaggatga cttgagctca ggaattcaag accaacctgg gcaacatagt gagaccctat    195360
ctctacaaga tgatgatgat aataataata atagtaataa taaacatttt aaaagtcttc    195420
tggcaataaa tatattttt ccctctaggc agctatatga aagggtcaga tctttggtct     195480
ctttacatct gtatctgcct ccctgtaaga atcaattttc tttctaacgt atatttattc    195540
ttccttagcct gtagattagg gagagtttct taatcagaaa acacccatca ggtaatttgc   195600
```

```
attgggaatc accectcact tgcccttaac acatacacac acacacctct aactttattg   195660
gacactatga gcaatgcccc ttaatcttca tatatcattt tgtgatgccc atgcccaagg   195720
aagtcagtta ttaaagaaag gaaaacaaaa cacttgaata ttcaaagcca aggcagatgc   195780
tttggaattt gcttgttcca tctttatcat taagaaattg acctgtttgc cctgtggttg   195840
aagtcataat tgccagtaaa gaataactaa gaaaatgtga acccaaatgt cagacttttcc  195900
ataatttatc tttttttaggt ttaccaacca gcattgaatt ggaggaagga ataacatatg  195960
aacagatgca ggtgaggttt ttgcagtgtc tctgaatgat tttattttgt tacttctaat   196020
tcaatactaa cctgattttt aaaattttag actgtgattg aagaagtcct tgaggaaagt   196080
ggctattaca atttttacatc taacaggtaa gagctagagt ttgccttcaa ttgtgaaaga  196140
tgaattgagg tcatcagatg ttagatctaa tttctttatc ctttattcca gagggatttt   196200
ttttcagatt ttattttaaa tacttttata aaatatcttg gcttagacta gatacatcta   196260
taagtagaat atatgtgccc atcttttgtg tggacacagt tgctgtattc tcagttgaaa  196320
caaaagggt gattgcttag tagaaattta ttcccataaa aaatcataaa tataagtaaa    196380
tggaaaaagc atttctagat tggtttttta aacatcaaat atttgtttgt ctcattctag   196440
aagagctgaa aactcactcc tatcacttaa atctacccac tatttgcaca gaaggctagg   196500
gacaaagtgc aactgaacaa agaatcattt cttgtgaatt taagatatat ttgtggagaa   196560
gagactttgc tattgtatgt tgccatttgt ttacccctaaa taaaaaacct ccatttactg   196620
gagctgtatg ttatcttcca atatagctat cgttggtgtt ctaagagtat atgctatttt   196680
atcaattgca tcaatttta taattttagt tttggaaata gtgttggcac aacaatttga    196740
gtacaattag tttactatga agttattcaa gaaaggtttt ataatcaagc aaattagcat   196800
tgtaggtgat tgaagcctga tcccactggg gaaatctaag agctgatata gaatatgtac   196860
cagggccatc ccacacaaag agtgagagag ctgaggtatt tatcctccaa tctccatcag   196920
tcattgttta aggcctttcc ctaggaagtg ttaatgccct gttttttttct ggccttttgt   196980
aaatatgaac aaagaagact ccaggggtca gagaaatcct caggaaaaga agtgcaggta   197040
ttccattatt gaatttcttt atatattagc aggtagaaat ctgccagcgt gctttgaagt   197100
ggaatagata ggggtatggg tgtttacaat gtctgctaca caagagttgt ctgttgactt   197160
acctaaggag cctactcata gctgagtcat caaattggtt gcaagtatcc acacacacac   197220
tctatctggg ccacagttgt tttaggaggc atagtccttt ggagtatatt ctctcaaagt   197280
ggtcttttat gcctggaggg actgccttcc ttttcaatta ttgaagctat tttgtgacca   197340
ctatttaaat tattccagaa gtcttcacca aagatgacta gtaacaacgg gaagagaaag   197400
agggctcaag aacatcctgt taaggtcatt atatagaaat tagattcttt tctaaggtta   197460
gttcagtctc cagtgtttct tctccttttt cttctacttc tcccatttca aggagttttt   197520
cttatgagtc acaagtaaaa ttattcaact acttgctctt ttgacttgat aacagtttca   197580
aaatactacc tttataaatt tagatctgtt gtgatttgta actgcagagg aacaatgagt   197640
aattctcatt ttctaaagat ataccgtcaa tagaaattac catctccaca actactctcc   197700
tcccaccatc cctggagaga ttttttgaatt ttcattttct attcaagggc tgagtatatg   197760
cattaggaaa agaaaatggt aacaggaaca gaaagagcag caaggacctc tgaccaagtt   197820
tggatatttc tcatttctgg gcttccggga aaaagggagc taggactgag ttggaaggaa   197880
gaaagctgtg taaagaaagt taaagaaggt cataaaggct tggccagcct cgtagctctt   197940
```

```
cccaaagcag gctctatttt tgatcatttg catggttgta tgataaatta cattttacat   198000
acataagcat actatcatgg atagtatgaa tgtttctgtt tttaactgtg agcctcatta   198060
tttcaagtgc ccttggcttg tactggggaa aagatgactc ttgtcatttt atctgcattt   198120
tctcagagac ttgggatcat gggcaaggaa tgtcttcata tttttttgcag aaaatcattt   198180 aaatatcaag aaaaactaag tgtgcaagga acttaaggaa gctcttacaa gaacttttat   198240
tttcccttta ttaaaaaata tttgtcttat tttggaattt atcattattc ttttttcaatt  198300 ctactttcat taggttttaa accgatctag ttccaaagac atatggcttt attaaaagac   198360
attgcaaatt ttcttattat gataaacaga taataagatg ccttataaca aaggcaaaaa   198420
attattcagt tatatttgta attgtgaatc tattatgaag gtatgatgaa acagtcaagt   198480
ttaagcaata taagttgggt attgcattaa attttcttaa agtgctccaa attaaaatga   198540
atcacattta aaaatccata tatccatggt attcccttt tggcttcttt tttttttttt    198600 tttttttg agatggaatc tcgttatgtt gctcaggcca ggctgaagtg caatggtgcg      198660
atcttggctc actacaaact ccacctcctg ggttcaagcg attctcctgc ctcagcctcc   198720
cgagttgctg ggattatagg cgcccaccac cacacctggc taattttgt attttagta     198780 gaaacggggt ttcttcatgt tggccaggct gatcttgacc tggcctcagg tgatccacct   198840
gccttggcct cccaaagtgc tgggattaca ggcatgatcc accacacccg accccctttt   198900
ggcttctaat agcaatgata gaacatatct tgggagaaaa actctccaga atttgtttgt   198960
aaaaataacc cttgtttgtg cctaaagcca ctctttgttt actagtattc caaaataatt   199020
tccaagaaat aagtcaggct tcaattagaa gcacctacta atccacaaac tgtgaataac   199080
acataactcc aagtacaaat cagattagct ggtactgtca tgcttttttc cacaaaggat   199140
ggagggtgct aaatgtcaca gcatatgtag aggtatttag aatcagtatt tagaattagt   199200
agactgcatt tttccccaat aggtttcata gaatgggcaa tattatcaaa gatgtcaata   199260
gatagtctct gaaaaataaa gtttcatggc cacatatatt tgggaaactc agaatgtaca   199320 atttttata tttggagaat gttgacacct attactatat taaagactct gagatgtact   199380
ataagaaaga aatctgttga ccttgtttgt tgacctcagt gttttcctca ctctttacat   199440
ggaatacaat tgaggaaagc tgttttagct atgtggttgg aaatgaggaa caccgttttc   199500
actccttcac cagggtctac ccagatctct gttgttctca ttgacatggt catcattgtc   199560
atcatcgtca ttgcaaaatt tgttcttaaa tgaattaagc accgtgctga gaaagttaca   199620
tatataattt cggtgttatt caagtttaca atttaagact atcagtttga atagtacaca   199680
catcatctag ccagccagtc actaaaggat taattcaaga taaggtacat ttttggttta   199740
aattataggg tttatattta gttaaggaag agaatagaga ggtgccattt tcagactgaa   199800
agtctcagga taaagccatt atctatctgt tagctatctt tgaggaagat ttctggaact   199860
gtttaaatca tgaggagact gcttggacag ttaggaagaa tgtctcaggc ataaaatgct   199920
gcattaggaa aagaaaatgg taacaggaac agaaagagca gcaaggacct ctgaccaagg   199980 ttgggtatt ctcatttctg ggcttctggg aaaaagggag ctaggactga gttggaagga   200040
agaaagctgt gtaagaaag ttaagaagg tcaaaaaggc ttggccagcc tcatagctct      200100
tcccaaagca ggctctattt tgatcattt gcatggttgt atgataaatt acgtttata     200160 tacataagca tttagcttgc ttaccagaag gatgcaactt aatatgcctt aattttatca   200220
ttgttgtttg tgaggataaa atcatttgag tcatgaataa acagataatg agcatataat   200280
ctttatgaat atacttatgt attacattaa tatttatttt ttaataataa aatgtgttga   200340
```

```
gaaataacag tatacaagat aacaaatcta cattgaatca acttgaattg ttttatttcc    200400
ccaattgact gataagcgtg taaattagtt attttaacct acacaggtat tcaagtatac    200460
aagctatttt gaatgaatat ttgttttctt actacaaagt gttatcagtt cctattgagt    200520
tcataatttg agaaaggcct tgttagcacc agacttcagc caaaggcagc tttttaaaaa    200580
tgtccccatc ctaacaaaaa taatcgtctt tttatttact gtgattttatt tacttatatg   200640 cctgagcccc agtttttgaa attgaatgta tgaactaaaa tatttgtaac tatagagaat    200700
tctttccact tctgaatctt ataggtatca ttcctatcca tggggacca agaatcaccc     200760 aaccaaaaga tgaaaatgct gcattttgag tggacttgat tttctcagtg aagttcaagt    200820
tctggacttc agccgctatt gcaagatgcc caaggattgg gtgctgctag agggtgtgga    200880
aaagaccaag atgccatggg gcctgcagga cttctttctg ggggtcctgt gctggagtat    200940
atgacagctg cggtacttga gggcttcatt gccagaacac attatataca ggatgtcaga    201000
gctaccagtg tgctgctggg agaaaatgct gcaaaattca tcttttggag ggtgggggga    201060
aaacccaaaa acaacaacaa aaaaactctc ttacagaatt ttccttaaca ttaaaaaaaa    201120
cttgtcatat ttttcaaagg cacatttgat actcagaatt gctaaaagta tatttaaaga    201180
catctagcct tccatatgta aaaaatattt tagataaaga cagttacagg actcagaata    201240
atatattggg tgattcactg tatcctccat ttttacattt aaagaaattc aaaatacgtg    201300
attaaatttt tttttttta atggatgggt tggttctcgc ttaaccactt gggtgctagt    201360
ggtcttgaac tgtgatacag tgtagacagt atttgtaacc ttgcacagcc tctgggggta    201420
actgtcaaac tgtcagattt aacttagact aatagaatat attgctgtac agtgtgtgta    201480
tatgtttata tatgagggcg gaaggagaga ggttttgatt agactaatgc tttgctgcta    201540
atcaaactta tagtattttt agagcacttt gaagagttta tagaatctat gaaaaagatg    201600
caatattcct catcctaaat ccctccttat tacaattacc taaattgttt atgaattgtt    201660
taggattttg aaatgaaaat aagttaaatc cctttttac tcattgaggc agctcaatgg    201720
aagtgaaatc agaatgccaa actgtgtatc atcctttatg ccgggagaat tatgatgaaa    201780
atctgctaga ttctcactgg gcttaaactc cttctcttca atcagcttct taaaactctg    201840
gtgtaatgtc aagaaatacc cttattgcga aatctgtcta cacttctagc tacctaaaga    201900
gcaatttatt ctacataatt agtaatctga aagttgaaat tatacttttt atttactttt    201960
catggagttc tgtcatcttt atttacactg aattttttta gtatgattga atcgatttta    202020
gttcaatgta tttacagtgg ttgaaagacc ataaccttct ttctgtatag tatgaaaatc    202080
tacactattt ttaaatgagc atatttaata cttaaattat atccaaattc cctttaatca    202140
tgcactaatg cttttgaaga ttgtcaatgg atctttcttt aagccaaatt aacaattaca    202200
gatacactgt aatgtaagat aatagatgca aatacagtaa tgaaaatttc agtttcagct    202260
ttcaaactaa ttctatccat atgtgaaatt cataaaatca aaatgctatg atattgattt    202320
acccaggcaa aattttattt ctgttccaag ttaatttgaa cctgcactta taattctttt    202380
tatctttcag tgtatgaaag gggcacattt cttcttcatg caggaagcac agacctggag    202440
gggcacaaat tctaattgtg gggtgagagt ttgaaatcaa gttatttccc aaatggtagt    202500
atatagtaaa cagaatttag gaaagaatag tattcaaaag gtgtaccgtg gtaagggaag    202560
ataaatggtt tacttgaaga tgttttaaag tgtatatagt tggccttatt gaccagaaag    202620
tgagcaaaat gtttccatct aactcttttt tttttttttt ttttttaaga cagagtctca    202680
```

```
ctctgttgcc caggcttgag tgcaatggcg agatcttaac ttactgcaac ctccgccacc   202740
caggttcaag caattctcct gcctcagcct cccgagtaac tgggattaca ggcatgtgct   202800
gccatgccca gctaattttt gtgtttttag tagagatggg gttacaccat gttggccagg   202860
ctggtctcaa actcctgacc tcaggtgatc tgcctgcctc ggcctcccaa agtgctggga   202920
ttagaggcgt gagccactgt gcccagccat tgcatgtaac tcttttaggt gataggaatg   202980
ggcatttatt atgctagaag tcagtgaaag ttaagtaagc agaagctgtc cttttttaaca  203040 acagcttcag gcctatcaac tctatgtgga tagatgtatt gttttgctaa aagtatgaat   203100
atgctctatt tgaattctcc ctaaactacc acaatcactg agtctatatt ttcccatgtc   203160
tctaagagaa agtcaggctc tggcaaaagc accattttgt acatagagtc acatcccaac   203220
agagaagtta acttttcaga agcctttcta acacaaatat ggagcacctc ccctcatgac   203280
caagaatgat cattttgttt tgattctcca aactgtctat tagtgcaaag gagttgttac   203340
atgaacttca tagacctctt aatcttttct tgattgcatt tatatatttt ttccctttct   203400
cttgtataat ttttaatgat ttgttgtgca atgaaattcc tatgaatgca cctaatttcc   203460
gtaactgaat atttgcatgg aatagaatat gaatcagtct tttcagatta cttttgaaac   203520
acaaatgctc ccgttaatta tgtttcgacc caccagctct ttctgaatta tgtgtacttg   203580
aaaccttaat ttgcttttta aaagcaaaat gtttcattct cagggaagtg actgcagcag   203640
gaatatttgc ttgcttgtta actttatctt cctccaggca tgtagtcttc aaatggagtc   203700
ttcaagggaa tagtaacgtg gacacttgga cccactgctt gtggatgaat ttcagaaacc   203760
tagagaaatg ctgcttgttt attgtggaca cttgtatggc attaggcagt gtttacagaa   203820
tgtttaggca ttcaaagca gaacacaatt aagaaacact gttaggaaat ttactcaaat   203880
gatataattg attaagagtt aggtcttcct ataagtatca tctatgactc attaaatact   203940
atgaattttg atgtccaaaa acaaatacag gtctgattat gtacaattcc agaaatatca   204000
ttaattaatc accactcatt tttaagatgt gtgaagactg taatattggc tagtgaattt   204060
tatcagtatt aatatgcata gaacccacat tcctcttttt gatttgatgt attatagcat   204120
gtatgtattg ctatttttct cttttttga agtggtgagg aatcatgcac agtcaatatg   204180
ctgggttcct ttagaaatga ctttagctcc tgtctgaagg caggaaaaac ttcttttaa    204240 ggaactttca tcattgcctt ttactttttc tatgatggtt ttcatgagca ctgaaatcac   204300
ttggagaggc aatgcaaaga aatctatctg aaacagcttc ttggcaccct ggagttacag   204360
ctatgaaggg ctccaacgta agggaagctt aatgcttccg aatattgaca ttgactcctt   204420
gggtgaaatt ttgtccaaat ataaaattct tcatgttcaa caactaaatg taataaatga   204480
atttcatata tacttacatg atatctttga gattaaatta attatccttt tgtaggaact   204540
gacagctttg ggtagattat ttttcagtt gaaatgtgtt gctaacaata tgcttacact    204600
tgaacgctgt ttttcatatt gataggaaga cacaaatttc tcagggaaac agctttgtga   204660
taaaggaatt cttatgtgtg tcattacagt aaattgcata ttgtaaatat gactgttgtg   204720
gttgattata gtcctgctgt gatgttgttt tgagatttgc aagagggaca ggaaagattt   204780
tatgagtttc atgggtgtc tgatggatat tgccaattta catattttct gagttcatgg    204840
gcaatagttg ttttttaaaaa tgaagatcac gtaccctaaa atcacagctg catacttgct   204900
atgtgaggta tactagatgc tttattgcat gtatgtaaca attgtctaat aatataaaaa   204960
atttaagata cagttcattg ctttatccta aaagtaaatg aactgtagtc ttaattcaaa   205020
actgaatgtt attcctcaaa acatgagaaa ctgcctttt ctctcctttc cttttgtact    205080
```

```
gtgaagatgt gcactggccc cagctactgt atttagcgat aacagaagta cgtgactgtt   205140
taaatgctgt catttggaaa tagcttacct ttctttctcc taaacaaaga tagaattttg   205200
tctttatgta tggaggatta tggctgactg tcattttgac aatcaacaaa tccagatgga   205260
tacttggaat tgatatggtg agttcacaaa tgaaaaatta gccgaagttt ttgcaaacat   205320
gtgaaaaact ggtcccataa aacatgcaga gagaagtttg tgccagaaat aacaaaccaa   205380
gaggaacaac tgctttaagg ccttggcacc tttaaggcag actgtgaagg tcacttacaa   205440
aatgatattc ttaacccatg atttagctct gcatttcaag tgccatttga gtcaagattc   205500
tgaaatagaa tataaagctt gtaaatggct attaaatttt agctaaaact gttgccctcc   205560
atattctgtg tgtttgcctc atactgcagt gaattttgga ggaaatggag ctggtttagg   205620
gatacttcat gtcatgacaa aacacatgaa gtatttacat gaacctaacc ttactttgag   205680
ggaggttaat aagtataagt actcagaagg gaaaccttga cttgctaaag attaaggata   205740
gatctttcat ggaggtggaa catcttcaaa tagaaattat gttttgagaa gttggagagc   205800
aagaaggcaa gaaattccct agtgcctggg tcgcccagca ggctgcccac tagggggtga   205860
gcaatggcaa agggtagctc gggagccttc cgtgattcct gctgctgggt ttcccagaag   205920
cagctgacca gatgcttccc cagcatgcag ctattgttga acttttagcc aggcaccgtc   205980
accaacaagt tgaccaccca gagcggtagc aaaaggcccc aaagtctctt cataacctgc   206040
tggctggtgg aatccgtagg acaggatccc taggaggcat tccaaagaca ttagactcct   206100
caaagaagca gttttatctg ccattaagtg agtgtgattc tgcccagggg gttatgttcc   206160
ccatctttca tccatgggct caggcccatt ttgtctgaca atgcacattt tacaagaagt   206220
atatgtgaga tgtaaatgga taagtgcagg cagatttgaa tatacttgta ccagttaaat   206280
tagaaaagaa acattgcaag caattttagc tgtttgcaag caaaccagtt gataatcagg   206340
ctgtagaaag attctattat ttcactcttc cacactgaaa aacaaaaatt acttgaaaaa   206400
tttttgggtg catttttgctt actgacattt agtgggtcaa aacaaaaact atagtgcttc   206460
ctgtattcca tcgttcacac tggtgacttt gtgaggataa aaaagaacag agctgtcctc   206520
tgaaaggaag agaaaccccct aatctcatgt tgcccagagc ttttatttttt tggacagccc   206580 aggatccaag acaaaggcct gtgcccacag aagcaaaaat acctgcaatg tgcttttttt   206640
tccctattag cctctaacat agtatctttt tgttgttgtt ctagcacccc tcccatgcgg   206700
gtctctcccc tgacacctct tcccctccca ctattcctac ccaaggaaca aacaaggttt   206760
cctgcacaga gctgtgttat tagagggaat gaatgttcca tagttattta atggtgtgcc   206820
ttgtggaagg cagagggaag tacttctctg tacgtgattt ctatctttct aaaacctccg   206880
caacacttcc ttcatgagca cacctactct agaatgacct caaagtcaga gatcctcaag   206940
agaagaagaa agaaatgatt ctataaaaga tttatataag atatgcaagc agcttttatt   207000
tttgctatga ttaaatatgc cctgtaaaat gctaaaataa tttaaaaagt tattttcaat   207060
tttattggaa aatgatttct cttttattga gaatttacag taaatgatca tctctttttct   207120 ctcaccagct tcccccaattt cttgttttat gctcttaagt cttttgatta aaaaaaaatt   207180
tccagaaagc aatcatatat gtgtgaaagc tcaaatgcat acctcagctt tcattggtgg   207240
gtccctgtag caattatcta ttgctacaca tgttgtataa caaagcacct aaaaactag   207300 tggtttaagg tagcaaccat ttatttttt cttatgagtt catgggtcag ttggaagttc   207360
tgcctatctg agcagagctc cactgatctc tgctagactt tctcctgtgt ctatggttag   207420
```

```
ttggcaggtt ggctgaagtc tagctgattt aggattgacc tagaggggac aaatcagttc   207480
tcttccctgg tctcacacgt gttttcagca acttagccca gatgtgtttt tgtggcagta   207540
gcaagagttg aaaagagaat gcagaaatgc actcctattt tgacaagcca cttcttgtgt   207600
tgttttcttc attctcaatg gtcaaagcag gtcacacggt caaatctatc attagtgtgg   207660
ggagctgtat gaggctttca ctgctgtgca accagttgct ataagtttaa cagtttaaaa   207720
taacacacat ttattagctc acaatttctg tgtgttggaa gtttgagcag gcttacatg    207780 gtcctctgct cagtgtctca caactataat cagtgtcggc taggtctggg gtctcacctg   207840
agcttgggga tcattttcca agatcatgtg attattgaca gggtttattt ccttgtgttt   207900
gtaggactga ggtcctgagc agctagatac catagatgcc acctgtagtc ccctgccatg   207960
tggccctctc cggagacagt tcccatcaag gcagctggct gcttcaaggt ccacaggaga   208020
gtctctttct ctctctctag tctgctaaga tagaatctta taaccaaatc acaggaatga   208080
tatcctgttg ccatattcta gtgggtaaaa gcgagttaca ggtgtactct acactcaaag   208140 gaagggggatt atacaagagc aaggtcattg gggtcacctt ggattgtgtc tgccgcagag   208200
tgcaatacca aagaatgcaa aaaaagtaga cctgaaaaat tggggccatg aagtaccaaa   208260
tgccacaata tcaaattacc acatgataaa aaggctggag aaacgcctag agccctatat   208320
tcgatgggag gtctctggat ggtgtcacac agggtcctga gcagatgcct ccccgctgcc   208380
ttcctttgcc cctgagctca ggtgcatatg gccacctgta ccctggctgc ctaggtgtgt   208440
ggcccccaga accttggcgc tcgcacacat tcgtcccccct catgtgggat catggctctt   208500
ctgcccagag actgcatccg attccttcct ccctcccaaa cagctctgat ggaagactgc   208560
tcgatggtct ggagaagaaa gaattgtgtg gtagtcttat gaaaatgacc tcagagtgca   208620
ggacataaat tccagaatgt ttccagtccc catcccagga ttctgttaga tgtatccagc   208680
aggctatttg aaaatcattt ctaatccacc aagcaaacag acaaacctca gtcagtgaa    208740 tgagaagcag gaatggaaat tattctttct ctagaagcca gaggagcttt cagtagcatc   208800
atagtaaaca tccttcacct ccttaaaact cgttgtgttg caatctgcta ttcttatttt   208860
agtcatttat caaatgggga catattgact gttctcagta attatgttca tatagtagag   208920
aacaggacta cataaatgaa ttatagagta tagcttgata taaatacaaa ctacaatctt   208980
aacagaaaac ccttataagc catgaataaa ggaaaatgtc tcccaagtct cccaaattta   209040
aagattctgt ctctcttctc aagattgagc atcgaatggt atcttcattc tacattcgct   209100
acgatgcggc atcaacaagg cgggtgggag ttcgcatcac accaggtagg ctagttgctc   209160
gtatccatgg ctcctacgcc gacgcggagt agaaatctct tgagccatgc tgtttgtcac   209220
agacattcta accatctttg ggatgtgcca aaaagttgtt tatataactc aggaaaatac   209280
ttgtaatttt cataagtata taggtactta tattgtacat tgttcaagga tcaagaaaca   209340
aatcacttaa aggctagaat ttcctaaatt tatttgcaca taatataata agcaagcatc   209400
attaagaatt taggccctga gcacacatag acttggatct gaatgccagc tccatgatat   209460
tctacttgta taacttctga ccaaggactt aacttttcta atgcttagct ttcacatcta   209520
tatcatgaag aaaatagtag attccacttt aaaagttgt taagcatagg cttgacacaa    209580
gaattaaaca ctataatagt ggcaaggaat tcaagtgcaa tgtcagccta gagcagactt   209640
acccagtact tggtgtactg gcctcctggt acagctcctt tttcaacagc ctgcatctgt   209700
ttgtctttgt ttttgttttt tcttttttttt gagaccgggt cttgctctgt cgcccaggct   209760
ggagtgcagt ggcacaatct cggttcactg cagcctctgc ctcctgggtt caagcaactc   209820
```

```
tcttgcctca gcctcccaag tagatgggat tacaggtgcg tgccaccaca cttggctaat 209880
ttttatattt ttagtagaga cggggtttca ccatgttggc catgctggtc tcaaactcct 209940
gaccccaagt gatccgcccg cctcggcctc ccaaagtgct gggattacag gtgtgagcca 210000
cagagccttg cctgtctttg atgggaactg tcctcaggtt ggtggaacca gcatttcctg 210060
ctggcaatag taacggcctg cagaggctgc ccctatccca tgagaaagag gtgcatggga 210120
accaatcctc cagcaccctc actcctgatt aggacagctc tgagttgtac tcttcgctct 210180
cacagtttcc ctgcagaacc gagccaaagg caccctttgt tggactgaac ctaatgaggc 210240
atccctggct gggcttcctt cctgtcctga tctgacttca cttatcggtt ttcctggcaa 210300
tacttcctga caaatccatc caagggtgca cttctgagga accgcatctg aagcatcttc 210360
agaacatgaa caacctaatc agtattagcc caaaatatct gtgtcaaaga gtgtggattg 210420
gcaacctctt catgatacac atgtgaaagg aaataattca ttgattggtg ctactggggt 210480
gcatcctgca atagcatcac cattaagcag agatgaaagt aggcatagtg gtcaatagca 210540
gtgaccacac ccctgcctcc tcttcctatc ccagtcagca gttaggtgtg gctctcagtg 210600
ggatggcaga gctctgtggc ataattaaag gatagagtca cagtccacaa catctcccca 210660
gcctcctcac atggtttggg ggctcttcct tcctgtcctt agggagtggg gctgcctctc 210720
tctgtgattt cattgttata ctatagatca aggtggggtc agaattccaa aaaaagatgt 210780
cacaggaact ggggagaccc ctaaaacagg tatggtcttg cctggcctcc attcaccaca 210840
aagtcatctc agatttgggg aacctccatg ttgtctgtga tagaagaaaa ggctggctga 210900
cactcatttg gtctctaaga cagatggaat gcttttctct taggtccttc accaattctc 210960
ccgagagtgt tttttttctt ccaaataacc gcaaccaaag taatgagtgt cttggcacct 211020
gctaatttat ttctaaaatg cttttgaatt atgattatta actccactgt gaactttta  211080
gatgatttta tcacctgtct ttccaggaaa ataattctca tgacaaacat ttaacttttta 211140
gtatgaaata tataagaaat gacttaattc tacgcaaatg cttaccatct ttgatcagtc 211200
acacattagg aactattttc attggaaata ttttcatga cagcgaaggt tgtcatatcc 211260
cacgtttgtt gatctcaact gcctggttgg ttcttgtcag tagggccatt aacatttgac 211320
aataggtgct ccagtttggg aagattattc caaagtcacg gttattattc caaatctgct 211380
tgcccctaaa gtgcatgcgt gaggaggaag agctttctca cttggccgtg ttctttgttc 211440
cggatatgag taagtgggag aattgccgct aaaattcttt ggcctcttct acttcctatg 211500
cttgtccttc ctgccccgc ttcctacaca acatacacac acacacacac acacacacac 211560
acacacacac acacacacac agaaacacac gcacgcatac acaccccac cccacacttc 211620
aaggaggaca taatcttcct tgcattggta accatttcct actggttacc attgtcattg 211680
gataactgag gtaaccattt cctactggtt gccattgtca ttggataatt gaggtagcat 211740
gaagatttcat gttggccaca tttccaaatc actactcaag tctttctttc ttttcccct  211800
ttttcttcat tctagaattt ggggtgcatt tcttcatata ttatctctgt ctaactctgt 211860
ttctaatagg aaaaatatct ctctctgtct acataacaca atgacttcaa gagtcaatac 211920
tgtttatatt gtttaatatt acagcttgtc ttcttttcta cattttaat attttaatgt  211980
gtatttcata ctttaagaga tatgaaatgt catggaaact ttgtttctca gttttctcct 212040
gtagatttca tacccagtc tcaggagtat ttatagaaca atcattttaa tttattttcc  212100
ctcagaaaca atacagatga attgctaact ttaaaataaa attctgcttt catctttaac 212160
```

```
tagtatttaa aaagctttat ggagctatat agagttttaa aaacaaacac acaaataaga   212220
gtttgacaaa taacttaata tttaaatcag aagttctgtt cacttagagg ttaattggat   212280
caatttaaag gagtgctaga tttacagggg accatgtgtt catgaggata atttctaaaa   212340
ttctcaccag aaaatcagtc ttcttacctt ccctggaga gggagagatg tgttgaatgg    212400
ttactatgtg gtacgcactg tgcaaggcac cttatttatt cattataaca gccactctga   212460
agggttataa ctaacactat tgtagatatt tttaaaactg aggttcagag gcattaagaa   212520
gacaacagct agttgtaaaa aacaaaaaaa ggcagaatgc aaggaaaaga acctagattt   212580
tacattgctc caatacccat gcttttttc cccatttaca ctaagcaaaa ccctgtttat    212640
atcgtagaga taagattatt aaaattatgg gatttaaaca ttctatatgg gccttattgc   212700
cttgcctctt actcttagtg gccatttgt gcgtgtcatt gatgcgtatg attataaata    212760
gttgtaagga aaaatgctc tattaattct tttcaaaagc agaaatgtag cctacatagg    212820 atttttttt tttttttt tttggagaca gagtttcact cttgttgccc aggctggagt     212880
gcatgcaatc tcggctcact gcaatctcca cctccctggt tcaagtgatt ctcctgcctc   212940
agcctcccga gtagctggga ttacaggcac ccatcaccac acctggctaa ttttatatt    213000 tttagtagag atgggtttca ccatgttggc caggctggtc tcaaactcct aacatcaggt   213060
gatccacccg cctcggcctc ccaaagtgct gggattacag gcttgagcca ccgcacctgg   213120
tgcctacata gcatttaaat aattatttta ctactagagc ctgagcctcc ccagactact   213180
cacaacccag gcttttttat gttttcattt ggacccaact ttccacaaag tgctttggta   213240
actctgctca tgtcaactct tgatatataa tgagagctca agtaatatta ctaattaagt   213300
ggctcaagaa tcagtcaggc attttgactc ttaaactcaa tggactgaaa gaaaaaaagt   213360
caatggactg aagcatttcc tttcagagac aaagtgagag atatactggc cgtttgacct   213420
aaggtgaatg acttaaacca ctctgaacct cagttttcta agatagtagt gctttctatt   213480
gtattatcat atgattaaat gtagtatcat atgattaaat gtaaattaaa ggtggtgact   213540
aacatgagaa atgataagtt caatgtgctg accaaagaaa caaataaata gaaacaatga   213600
gttttattaa gctgtaattt cccaaagatg agggaatgca cttgctgact ttttttgtct   213660
cattttcctc atttaaaaaa tgacccagcc agcattgcct cctctgttgc ggatgtccag   213720
ctctgaagat gtctgtttca gtgcgacagt gtcagaggac tgctgatact ctagcatcct   213780
gttcaattct tagttgcgag agatagaatg ccaactggtt caataagtaa aagggaattt   213840
attggctttt ataattgaaa tgataattgt ccacaaaagg acaagcttga ggcattgcta   213900
aatgcaagaa gatatcaaca ggtctctctc tctctctctt tctactgtcc cctgcctctt   213960
tctgctttca ttttggcct ttgctctcct ccatcatggc cttactctca gtaggttcc     214020 cttcttccca cgatagttcc caggaacact gagatgaaac cctttccagg ccatcagaag   214080
attcccttat cagtttgacg gaagttccag aatcaagtct taataggcca aagtgagtaa   214140
cagactcagt gctttagctg ggagaagatg gtataatggg atatgccaat tgcctgtgtc   214200
atgggccaaa cctgagccaa tcactggcca agggaatgca gtgtccatcc ctggagccca   214260
gatcggagga gccctggaac accatggttt gagagtggga aggaacaaca ctgtgaggat   214320
gctgttgggg gaaatgatga gtctaaggat aatgaggaac taggtttttg gtagatgaaa   214380
agcagatgtt tatgaacttg gcttagtctt acaagaaagc atttgtatct gatcattggc   214440
tgggactcct gaccaattgc tcctgccttc ctcttccatc acctcagtta gcttaaaagt   214500
actgagataa accattgctt aagcaaaaca tatcagcaga gaagcataat caaggcaggc   214560
```

```
taggaagtct gggaaaaaat gaataatatc tgcatagctc ttgtgtttca tttgtcacag 214620
agcccactga gtaagggtgg acagaatagt aacactaaac gagctgcaag aatatgcaaa 214680
tgccctgtgg tcagtttcca gctttgctgc tgtaacacct gttaactccc tgttttttcag 214740 ttttacaaaa ctcagctcaa aagggatgtt gtttctgtgc agggatgcca ttatttctct 214800
tcaccaccct cctccttctg ggtgaaagca tgctccagct tttctctaaa ctcctctcct 214860
cagtctgcac catcgattac taacctacag gctcagtcct tcaaactttg ggcccatctt 214920
aattagggca gccagcagta tattgctggc caactcagag ccacacaaaa cttctcccac 214980
ctcttgcaac tgttaagatc ttgcattact cctgctgggc taagtcaggt atgtcacaca 215040
gatccctgaa catccacata ggtccctgtg ttagcctgtc ctctaaccett ctttcagggg 215100 ttacctgcct gattgtaacc caaatcctgg tctggccttt gactccaacc catttggttg 215160
aatccaaaac aaacttacct tctagaatct aaaacctagc ctgctgtaac tccttgcaaa 215220
tggctcaccc agatcaagcc caagttttca acatgaaatt tgggcagcaa ccctcactct 215280
ttcagttcac aaaggtccca cttttcctgt tcactcacct caattctgta cccatgtgtt 215340
tctgaggtcc cagtgtaaaa tggcaccaag cctgcttaca tgatctatgg cactgggtga 215400
tgttggtgag ttggggtggg aattctcctg tgtaaacaca gcaaaaccgg agtatcctga 215460
tggggagcct ctagtgaact aatggtgttc attcactcat ttattcatac aatgaatatc 215520
aatcacataa tttagtgctt ctgaaacttg agtatgtata caaattcctg tggatcttat 215580
taaaatgcat attctgattc agtagggctg ggattgggcc tgagattctg cattttaaca 215640
cgctcccaga tgatgtgcat gctgatgttt tatgaaccag aatttgggta gcaaggacta 215700
tagaaactca ggaagtattt gttgaacgtt aaatgaatga aaatctgaat aaaagctttg 215760
aataatcgtt tcagtttaga tagaaaagag aagtataatg ttgatggagt tactggtaaa 215820
tgacagttaa tgggtcaaat gctttagcct ttgccaatga gtcttccctg gtgttgtccc 215880
ctcattaccc atcccaatgg actttgaccc atttcccctg cctcttgcta agggaataag 215940
agagccaact tcagactagc attccaattg cctgttaaag cctgttcttt ttgaaccaca 216000
cccatagttt ttcaatgttc tcaacagaag catggctttg tagtcacata cacacacaat 216060
gcccaattac tggcaatttt ggtataacaa ggaatgtaca tccccaaccc tactggtat 216120 caagaccttt tatggcattt catgtctgtg tagattctca acaatgccaa agaaactcaa 216180
aacgtgaaaa gaggaagtac tagaatacca cactagagac aaaacctctt ccccctattt 216240 ttttttttt ctgctgaatg tttctggctt gatttctttg ccaacacaga tttcttactg 216300
gacaaagcaa acactctgtt gtactctcag aaagttccat ttttagctca cagcataatg 216360
tgtggtgtgg tttgttctct aaagaaggaa cacagcaggt aaaaggtaaa ttatttcaca 216420
aaggtcagct gtgagcccgt tctcttttga taataggaat cttgccttgt ggagagctca 216480
ttagaggtcc ccaagaggcc caagaagag gctgggatca ggagatgggg gataaaaatg 216540
cctgctgaaa atgttagggc tgtcattcct accccagaac tctggctctc catttaatga 216600
acaattttcc cttaacaaaa actcactgga aatgatggaa tgctcatgca ttagttatct 216660
ccccgcctct ctgccaaatg cctctctttg ctgctttctt gtctagacca tagactccat 216720
agtcccagac aggaattgta gagacttctt gttcctcaga tatgtcgagt tggagctata 216780
tctttgaaag tcaaatttta tgttaagaga acatcacctt aaacaacttt ggctttgctc 216840
ctaagtccaa ccccataata tattaaattt catttgttct ctctgagtg ggctctcttt 216900
```

```
ccaacttaga tagcaagtga gaaaagtata gttcttgttc agctggcaca ccatttccat 216960
ttaaactgct gtcaacttga gcttagctga ggttatgaat agaaaatgtg cacgtcccat 217020
gaccacaatg gaacaggctt taggaaacaa cccacgacac acaacaactt cctgaatagg 217080
cagcagctga ccacagtttc aacgtcctaa ctgtgataac cattataact ttaataggca 217140
tcctggggca gaaactactc tctgtcaaca gttaaaggtc cctccacaaa gagtcaccaa 217200
attgtgaact tttattgcag aaagggctca gagagaagaa ttctaaggct tcactctgca 217260
gggtcaaaaa cttgtcaaat gtcacaccac ttcggactag tgaaagaatc acagattggg 217320
gggagccctc aggctgaatt tggaaggata aattgaaaaa gtcatacttg aattaaaaaa 217380
tggcttgagt tggacttgtt ccatgaatgc aatttagctt tttactgtgg ctggtgacaa 217440
tgtggtattt tcagcttctg agttgattga cagtggcaaa atactggaag attttattta 217500
ataagagtgc cattgttatc tctacattag acaacttct ttctctggta caatcacttt 217560
ttttttaaag ttaaaactca ttttctcttc tgtattcccc ttccctggg aaggaaaaga 217620
atacatgcac aaagaagaaa aaatgtaaaa cacaaccctg ccatttagga cttttccag 217680
gcttatatgt tgctattatt ctttaaggat actatatgct tcctaatgtg attttttttt 217740
cactaatcaa tataatgtgg gcatctttat atgtcaagga gaannnnnnn nnnnnnnnn 217800
nnnnnnnnnn nnnnnnnnnn nnnnnnnnnn nnnnnnnnnn nnnnnnnnnn nnnnnnnnnn 217860
nnnnnnnnnn nnnnnnnnnn nnnnnnnnnn nnnnnnnnnn nnnnnnnnnn nnnnnnnnnn 217920
nnnnnnnnnn nnnnnnnnnn nnnnnnnnnn nnnnnnnnnn nnnnnnnnnn nnnnnnnnnn 217980
nnnnnnnnnn nnnnnnnnnn nnnnnnnnnn nnnnnnnnnn nnnnnnnnnn nnnnnnnnnn 218040
nnnnnnnnnn nnnnnnnnnn nnnnnnnnnn nnnnnnnnnn nnnnnnnnnn nnnnnnnnnn 218100
nnnnnnnnnn nnnnnnnnnn nnnnnnnnnn nnnnnnnnnn nnnnnnnnnn nnnnnnnnnn 218160
nnnnnnnnnn nnnnnnnnnn nnnnnnnnnn nnnnnnnnnn nnnnnnnnnn nnnnnnnnnn 218220
nnnnnnnnnn nnnnnnnnnn nnnnnnnnnn nnnnnnnnnn nnnnnnnnnn nnnnnnnnnn 218280
nnnnnnnnnn nnnnnnnnnn nnnnnnnnnn nnnnnnnnnn nnnnnnnnnn nnnnnnnnnn 218340
nnnnnnnnnn nnnnnnnnnn nnnnnnnnnn nnnnnnnnnn nnnnnnnnnn nnnnnnnnnn 218400
nnnnnnnnnn nnnnnnnnnn nnnnnnnnnn nnnnnnnnnn nnnnnnnnnn nnnnnnnnnn 218460
nnnnnnnnnn nnnnnnnnnn nnnnnnnnnn nnnnnnnnnn nnnnnnnnnn nnnnnnnnnn 218520
nnnnnnnnnn nnnnnnnnnn nnnnnnnnnn nnnnnnnnnn nnnnnnnnnn nnnnnnnnnn 218580
nnnnnnnnnn nnnnnnnnnn nnnnnnnaat atgcggtgtt tggttttttg ttcttgcgat 218640
agtttactga gaatgatggt ttccaatttc atccatgtcc ctacaaagga tatgaactca 218700
tcatttttta tggctgcata gtattccatg gtgtatatgt gccacatttt cttaatccag 218760
tctatcattg ttggacattt gggttggttc caagtctttg ctattgtgaa tagtgccgca 218820
ataaacatac gtgtgcatgt gtctttatag cagcatgatt tatactcatt tgggtatata 218880
cccagtaatg ggatggctgg gtcaaatggt atttctagtt ctagatccct gaggaatcgc 218940
cacactgact tccacaatgg ttgaactagt ttacagtccc accaacagtg taaaagtgtt 219000
cctatttctc cgcatcctct ccagcacctg ttgtttcctg acttttaat gattgccatt 219060
ctaactggtg tgagatgata tctcatagtg gttttgattt gcattctct gatggccagt 219120
gatgatgatt attattgtga taacagctga tacagagggg ttgcccttc catagtttct 219180
cttgcctatc atctacaaaa ctatactcac agagcccgag acttcaagac cacacagacc 219240
atctaatgga acttgacagt ggggcacact ccattatcga gctccaaatt tgcagcccta 219300
```

-continued

```
gcaattgctg aaaacaagga ctgagagatg aactatcttc caatggtttt gtcctttggc    219360
tcagcgtaca ccacatcctt ataaaaacac cttcattcaa aagtcagcct gtggagccag    219420
cttggagata accagtgtgg tttgactggg gggcttgtgt tatatctttt atgagtttgt    219480
catgacacca agagtaaata atcaaatcca gcctttaata gcccagggtt tggtagctgc    219540
ctcttctcgg gtgatggagg ctgccatgga tggaatgtgg caagttaagt tatttctgtt    219600
tcaggtttct ctttagccag ggcctgaagc agtctgctat gcttctgcta tatagcacta    219660
ggtctaagcc ctaagttcct caggacccccc ttcataacct gatatatgct gggcattttg    219720
tctaaagtag cctccatctc ttttcacaat gcagagagaa aagctaaaat gtaaaacaga    219780
aaagtgtggg ggacatttat ctggtatctt cacttgttaa ccacttctta tggccctaaa    219840
acatatgtgt ttacgtatat ttactcgaag gcaaatataa tctttaatat tattaatatt    219900
aattatatta ggtgtatatg tgttatatac acctaatatt aataatcttt atatatacct    219960
aatattaata atatatgtat gtatacactt aatattaata atatcaaaga ttctgcttga    220020
aaaaacctag ttgattttgt atataagctc ggctttcttt tctctgtgtg ggataacctg    220080
gcactgcact taatcctagt gggacaagtt ctgttggctt ttttctcttc cacgccagtg    220140 gaaaggtga cttcccagcc agtcagagac taagtaagag aatttatata atgaaatgct    220200
atacagcaat ataaatgact gagctactga tgcatgccca ggcaaatctc aaaagcattg    220260
tgctaagtga aagaagccag acacaagagt ccatttacat gaaattctag aaaaggcaaa    220320
actatggtga aagaaaatag attagtggtt attaggggcc ttggatggga tgggattgag    220380
ataatctttt ggaacgatga ccatcttcta tgttttgatt gtggtgtggt aacataaatg    220440
tatacggctg tcaaaattta ctgaagtata aactcttcaa ataggtgcat tctgtaatac    220500
ataaatgata ccttaataaa tttgaagtga tgaaaaagaa gtaaaggaag gaatttgggt    220560
tgatttatga atgtgtggct tgaacattta tatgggtggt ggttccattg gacattagac    220620
aataacaaac aagagcgcaa atataagagg tggtgaggag gatgatgggc acaattttgg    220680
gcctgtcaag ttgagagaca cccaggtgaa gagtccaagt tttggactgg atacgaagat    220740 tttgaattg ctagtgcatt ggtgagagta gactctaaca atgtgcatga aagtggaaag    220800
aaagagaaga ctccagaaat aagggcctat cctgaagaac acccatgcgg aatccactag    220860
```

<210> SEQ ID NO 4
<211> LENGTH: 854
<212> TYPE: PRT
<213> ORGANISM: Homo sapiens

<400> SEQUENCE: 4

```
Met Arg Val Leu Phe Asp Glu Ser Val Leu Pro Pro Thr Val Tyr Phe
  1               5                  10                  15

Lys Asn Cys Ser Ile Leu Phe Leu Ala Ser Leu Cys Ala Phe Gly Val
             20                  25                  30

Leu Thr Gly Leu Leu Val Trp Ser Phe Met Gln Tyr Met Glu Ile Val
         35                  40                  45

Ala Asn Glu Tyr Leu Gly Tyr Gly Glu Glu Gln His Thr Val Asp Lys
     50                  55                  60

Leu Val Asn Met Thr Tyr Ile Phe Gln Lys Leu Ala Ala Val Lys Asp
 65                  70                  75                  80

Gln Arg Glu Trp Val Thr Thr Ser Gly Ala His Lys Thr Leu Val Asn
                 85                  90                  95
```

```
Leu Leu Gly Ala Arg Asp Thr Asn Val Leu Leu Gly Ser Leu Leu Ala
            100                 105                 110

Leu Ala Ser Leu Ala Glu Arg Leu Thr Ala Glu Leu Leu Arg Leu Leu
        115                 120                 125

Cys Ala Glu Pro Gln Val Lys Glu Gln Val Lys Leu Tyr Glu Gly Ile
130                 135                 140

Pro Val Leu Leu Ser Leu Leu His Ser Asp His Leu Lys Leu Leu Trp
145                 150                 155                 160

Ser Ile Val Trp Ile Leu Val Gln Val Cys Glu Asp Pro Glu Thr Ser
                165                 170                 175

Val Glu Ile Arg Ile Trp Gly Gly Ile Lys Gln Leu Leu His Ile Leu
            180                 185                 190

Gln Gly Asp Arg Asn Phe Val Ser Asp His Ser Ser Ile Gly Ser Leu
        195                 200                 205

Ser Ser Ala Asn Ala Ala Gly Arg Ile Gln Gln Leu His Leu Ser Glu
210                 215                 220

Asp Leu Ser Pro Arg Glu Ile Gln Glu Asn Thr Phe Ser Leu Gln Ala
225                 230                 235                 240

Ala Cys Cys Ala Ala Leu Thr Glu Leu Val Leu Asn Asp Thr Asn Ala
                245                 250                 255

His Gln Val Val Gln Glu Asn Gly Val Tyr Thr Ile Ala Lys Leu Ile
            260                 265                 270

Leu Pro Asn Lys Gln Lys Asn Ala Ala Lys Ser Asn Leu Leu Gln Cys
        275                 280                 285

Tyr Ala Phe Arg Ala Leu Arg Phe Leu Phe Ser Met Glu Arg Asn Arg
290                 295                 300

Pro Leu Phe Lys Arg Leu Phe Pro Thr Asp Leu Phe Glu Ile Phe Ile
305                 310                 315                 320

Asp Ile Gly His Tyr Val Arg Asp Ile Ser Ala Tyr Glu Glu Leu Val
                325                 330                 335

Ser Lys Leu Asn Leu Leu Val Glu Asp Glu Leu Lys Gln Ile Ala Glu
            340                 345                 350

Asn Ile Glu Ser Ile Asn Gln Asn Lys Ala Pro Leu Lys Tyr Ile Gly
        355                 360                 365

Asn Tyr Ala Ile Leu Asp His Leu Gly Ser Gly Ala Phe Gly Cys Val
370                 375                 380

Tyr Lys Val Arg Lys His Ser Gly Gln Asn Leu Leu Ala Met Lys Glu
385                 390                 395                 400

Val Asn Leu His Asn Pro Ala Phe Gly Lys Asp Lys Lys Asp Arg Asp
                405                 410                 415

Ser Ser Val Arg Asn Ile Val Ser Glu Leu Thr Ile Ile Lys Glu Gln
            420                 425                 430

Leu Tyr His Pro Asn Ile Val Arg Tyr Tyr Lys Thr Phe Leu Glu Asn
        435                 440                 445

Asp Arg Leu Tyr Ile Val Met Glu Leu Ile Glu Gly Ala Pro Leu Gly
450                 455                 460

Glu His Phe Ser Ser Leu Lys Glu Lys His His Phe Thr Glu Glu
465                 470                 475                 480

Arg Leu Trp Lys Ile Phe Ile Gln Leu Cys Leu Ala Leu Arg Tyr Leu
                485                 490                 495

His Lys Glu Lys Arg Ile Val His Arg Asp Gln Thr Pro Asn Asn Ile
            500                 505                 510

Met Leu Gly Asp Lys Asp Lys Val Thr Val Thr Asp Phe Gly Leu Ala
```

-continued

```
            515                 520                 525
Lys Gln Lys Gln Glu Asn Ser Lys Leu Thr Ser Val Gly Thr Ile
        530                 535                 540
Leu Tyr Ser Cys Pro Glu Val Leu Lys Ser Glu Pro Tyr Gly Lys
545                 550                 555                 560
Ala Asp Val Trp Ala Val Gly Cys Ile Leu Tyr Gln Met Ala Thr Leu
                565                 570                 575
Ser Pro Pro Phe Tyr Ser Thr Asn Met Leu Ser Leu Ala Thr Lys Ile
                580                 585                 590
Val Glu Ala Val Tyr Glu Pro Val Pro Glu Gly Ile Tyr Ser Glu Lys
                595                 600                 605
Val Thr Asp Thr Ile Ser Arg Cys Leu Thr Pro Asp Ala Glu Ala Arg
        610                 615                 620
Pro Asp Ile Val Glu Val Ser Ser Met Ile Ser Asp Val Met Met Lys
625                 630                 635                 640
Tyr Leu Asp Asn Leu Ser Thr Ser Gln Leu Ser Leu Glu Lys Lys Leu
                645                 650                 655
Glu Arg Glu Arg Arg Thr Gln Arg Tyr Phe Met Glu Ala Asn Arg
        660                 665                 670
Asn Thr Val Thr Cys His His Glu Leu Ala Val Leu Ser His Glu Thr
        675                 680                 685
Phe Glu Lys Ala Ser Leu Ser Ser Ser Ser Gly Ala Ala Ser Leu
        690                 695                 700
Lys Ser Glu Leu Ser Glu Ser Ala Asp Leu Pro Pro Glu Gly Phe Gln
705                 710                 715                 720
Ala Ser Tyr Gly Lys Asp Glu Asp Arg Ala Cys Asn Glu Ile Leu Ser
                725                 730                 735
Asp Asp Asn Phe Asn Leu Glu Asn Ala Glu Lys Asp Thr Tyr Ser Glu
                740                 745                 750
Val Asp Asp Glu Leu Asp Ile Ser Asp Asn Ser Ser Ser Ser Ser Ser
                755                 760                 765
Ser Pro Leu Lys Glu Ser Thr Phe Asn Ile Leu Lys Arg Ser Phe Ser
        770                 775                 780
Ala Ser Gly Gly Glu Arg Gln Ser Gln Thr Arg Asp Phe Thr Gly Gly
785                 790                 795                 800
Thr Gly Ser Arg Pro Arg Pro Gly Pro Gln Met Gly Thr Phe Leu Trp
                805                 810                 815
Gln Ala Ser Ala Gly Ile Ala Val Ser Gln Arg Lys Val Arg Gln Ile
                820                 825                 830
Ser Asp Pro Ile Gln Gln Ile Leu Ile Gln Leu His Lys Ile Ile Tyr
        835                 840                 845
Ile Thr Gln Leu Pro Pro
    850

<210> SEQ ID NO 5
<211> LENGTH: 2562
<212> TYPE: DNA
<213> ORGANISM: Homo sapiens

<400> SEQUENCE: 5
atgagagtat tatttgatga atctgttttg ccacctacag tttattttaa gaactgcagc      60
atcttgttcc ttgcttcctt gtgtgctttt ggtgtcctga ctggcttgtt ggtttggtcc     120
ttcatgcagt atatggagat tgtagccaat gagtacctcg ctatggaga agagcagcac     180
```

```
actgtggaca agctggtcaa catgacatat attttttcaaa aacttgctgc agtcaaagat    240
caaagagaat gggtcaccac aagtggagcc cacaagacat tagtaaattt acttggtgcc    300
cgagatacta atgttctatt gggttcccct ctggctctgg ctagtttagc agaaagacta    360
acagcggagt tgctgcgcct actttgtgca gagcccagtg tgaaagagca ggtgaagctc    420
tatgagggga taccggtcct cctcagtctg ctccactctg accacttgaa gctcctctgg    480
agcattgtct ggattctggt acaggtttgt gaggaccctg agaccagcgt ggaaattcgc    540
atttggggag gcatcaaaca gcttcttcat attttacaag agacagaaa ttttgtttct    600 gatcactcct ccattggaag cctgtccagt gcaaatgctg caggccgaat ccagcagctt    660
catttatcag aagacttgag ccctagggaa atacaagaaa atactttctc acttcaagca    720
gcctgctgtg ctgccctcac tgagctggtg ctcaatgaca ccaatgccca ccaggtggtt    780
caggaaaatg gtgtatatac aatagcaaaa ttaattttac caaataagca aaagaatgca    840
gcaaaaagta atctattaca gtgttatgct ttcagagcct tgagatttct cttcagtatg    900
gaaagaaaca gaccactctt taaaagactt ttccccacag acttgtttga gatcttcatt    960
gacatagggc attatgtacg tgatatcagt gcttatgaag aattggtatc caagctgaat   1020
ttattagtgg aggatgaact gaagcaaatt gctgaaaata ttgaaagcat taatcagaac   1080 aaagctccctt tgaaatatat aggcaactat gcaattttgg atcatcttgg aagtggagct   1140
tttggctgtg tttacaaggt tagaaagcat agtggtcaaa atctttagc aatgaaagag   1200 gtcaatttac ataacccagc atttgggaag gataagaaag atcgagacag cagcgtaagg   1260
aatattgttt ctgaattaac aataattaaa gagcagcttt atcatcccaa cattgtacgt   1320
tattacaaaa catttctgga aaatgatagg ttgtacatag ttatggagct gatagaagga   1380
gccccgcttg gagagcattt cagttctttg aaggaaaaac atcaccattt tactgaagaa   1440
agactatgga aaatatttat acagctgtgc ttagctcttc gatacttaca caaggagaag   1500
aggattgtcc atagagatca gacaccaaac aacattatgt tggggataa ggacaaagta   1560 accgttactg actttggcct ggcaaagcaa aaacaagaaa acagtaaaact cacctctgtg   1620 gttggaacaa tcctgtattc ttgtccgag gtactgaaga gtgagccgta tggggagaag   1680
gctgatgtct gggcagtagg ctgcatcctt tatcagatgg cgactttgag tcccccttc   1740 tacagcacta acatgctgtc cttggctaca aaaatagtgg aggcggtata tgaaccagtc   1800
ccagaaggta tctactctga aaaagtaaca gacaccatca gcaggtgcct cactcctgat   1860
gcggaagctc gtccagatat tgtagaagtc agttcgatga tatcagatgt catgatgaaa   1920
tatttagaca acttatctac atcccagttg tccttggaaa agaagctaga acgggaacga   1980
agacgcacac aaaggtattt tatggaagcc aaccggaaca ccgtcacatg tcaccatgag   2040
ctggctgttc tatctcacga gacctttgag aaggcaagtt tgagtagcag cagcagtgga   2100
gcagccagcc tgaaaagtga actttcagaa agcgcagacc tgcccccctga aggcttccag   2160 gcctcctatg gtaaagacga agacagggcc tgtaacgaaa tcctgtcaga tgataacttc   2220
aacctggaaa atgctgagaa agatacatat tcagaggtag atgatgaatt ggacatttcg   2280
gataactcca gcagctccag ttcaagccct ctgaaagaat ctacattcaa cattttaaag   2340 agaagttta gtgcttcagg aggagaaaga caatcccaaa caagggactt cactggggaa   2400
acaggatcaa gaccaagacc agggccacag atgggcacat tcttgtggca agcatcagca   2460
ggaattgctg tgtcccagag gaaagtgcgt cagatcagtg atcctattca gcagatatta   2520
attcagctgc acaaaataat ctatatcaca cagcttcctc ca                      2562
```

<210> SEQ ID NO 6
<211> LENGTH: 2043
<212> TYPE: DNA
<213> ORGANISM: Homo sapiens

<400> SEQUENCE: 6

```
agaaataatg tatggaggga ctatacaagg gcatatatac tagtaaaagt gtttctcaa      60
tagatcacca aagaatttgc cacacctgat atatagaaaa gtttattgtg cagcacctct    120
accttcgctc tcctgctcct gctctggcca cataaaacgt gctggctcct cctttgcctt    180
ctgctatcat tggaagcttc ctgatgcctc caagaagca aatgccatca tggttcctgt    240
acagcctgca gaaccccccg aggtactgaa gagtgagccg tatggggaga aggctgatgt    300
ctgggcagta ggctgcatcc tttatcagat ggcgactttg agtccccct tctacagcac    360
taacatgctg tccttggcta caaaaatagt ggaggcggta tatgaaccag tcccagaagg    420
tatctactct gaaaaagtaa cagacaccat cagcaggtgc ctcactcctg atgcggaagc    480
tcgtccagat attgtagaag tcagttcgat gatatcagat gtcatgatga aatatttaga    540
caacttatct acatcccagt tgtccttgga aagaagcta gaacgggaac gaagacgcac    600
acaaaggtat tttatggaag ccaaccggaa caccgtcaca tgtcaccatg agctggctgt    660
tctatctcac gagacctttg agaaggcaag tttgagtagc agcagcagtg gagcagccag    720
cctgaaaagt gaactttcag aaagcgcaga cctgccccct gaaggcttcc aggcctccta    780
tggtaaagac gaagacaggg cctgtgacga atcctgtca gatgataact tcaacctgga    840
aaatgctgag aaagatacat attcagaggt agatgatgaa ttggacattt cggataactc    900
cagcagctcc agttcaagcc ctctgaaaga atctacattc aacatttta agagaagttt    960
tagtgcttca ggaggagaaa gacaatccca acaagggac ttcactggag aacaggatc   1020
aagaccaaga ccagctttgc tgcctcttga cctgcttctg aaagtgccac cccacatgct   1080
cagggcccac attaaggaaa tagaggctga gttagtgaca gggtggcagt cccatagcct   1140
tcctgctgtg attcttcgaa atctcaaaga tcatgggcca cagatgggca cattcttgtg   1200
gcaagcatca gcaggaattg ctgtgtccca gaggaaagtg cgtcagatca gtgatcctat   1260
tcagcagata ttaattcagc tgcacaaaat aatctatatc acacagcttc ctccagcttt   1320
gcaccacaat ttgaaaagaa gggttataga gagattcaag aaatccctct tcagccagca   1380
gagtaaccct tgtaatttga aatctgaaat taaaaagtta tctcagggat ctccagaacc   1440
gattgagccc aacttttta cagcagatta ccatttatta catcgttcat ccggtggaaa   1500
cagcctgtcc ccaaatgacc ctacaggttt accaaccagc attgaattgg aggaaggaat   1560
aacatatgaa cagatgcaga ctgtgattga agaagtcctt gaggaaagtg gctattacaa   1620
ttttacatct aacaggtatc attcctatcc atggggacc aagaatcacc caaccaaaag   1680
atgaaaatgc tgcattttga gtggacttga ttttctcagt gaagttcaag ttctggactt   1740
cagccgctat tgcaagatgc ccaaggattg ggtgctgcta gagggtgtgg aaaagaccaa   1800
gatgccatgg ggcctgcagg acttctttct gggggtcctg tgctggagta tatgacagct   1860
gcggtacttg agggcttcat tgccagaaca cattatatac aggatgtcag agctaccagt   1920
gtgctgctgg gagaaaatgc tgcaaaattc atcttttgga gggtgggggg aaaacccaaa   1980
aacaacaaca aaaaaactct cttacagaat tttccttaac attaaaaaaa acttgtcata   2040
ttt                                                                 2043
```

<210> SEQ ID NO 7
<211> LENGTH: 2043
<212> TYPE: DNA
<213> ORGANISM: Homo sapiens

<400> SEQUENCE: 7

```
agaaataatg tatggaggga ctacacaagg gcatatatac tagtaaaagt gttttctcaa      60
tagatcacca aagaatttgc cacacctgat atatagaaaa gtttattgtg cagcacctct     120
accttcgctc tcctgctcct gctctggcca cataaaacgt gctggctcct cctttgcctt     180
ctgctatcat tggaagcttc ctgatgcctc ccaagaagca aatgccatca tggttcctgt     240
acagcctgca gaaccccccg aggtactgaa gagtgagccg tatggggaga aggctgatgt     300
ctgggcagta ggctgcatcc tttatcagat ggcgactttg agtccccccct tctacagcac     360
taacatgctg tccttggcta caaaaatagt ggaggcggta tatgaaccag tgccagaagg     420
tatctactct gaaaaagtaa cagacaccat cagcaggtgc ctcactcctg atgcggaagc     480
tcgtccagat attgtagaag tcagttcgat gatatcagat gtcatgatga aatatttaga     540
caacttatct acatcccagt tgtccttgga aaagaagcta gaacgggaac gaagacgcac     600
acaaaggtat tttatggaag ccaaccggaa caccgtcaca tgtcaccatg agctggctgt     660
tctatctcac gagacctttg agaaggcaag tttgagtagc agcagcagtg gagcagccag     720
cctgaaaagt gaactttcag aaagcgcaga cctgcccccct gaaggcttcc aggcctccta     780
tggtaaagac gaagacaggg cctgtgacga aatcctgtca gatgataact tcaacctgga     840
aaatgctgag aaagatacat attcagaggt agatgatgaa ttggacattt cggataactc     900
cagcagctcc agttcaagcc ctctgaaaga atctacattc aacattttaa agagaagttt     960
tagtgcttca ggaggagaaa gacaatccca acaagggac ttcactggag gaacaggatc    1020
aagaccaaga ccagctttgc tgcctcttga cctgcttctg aaagtgccac cccatatgct    1080
cagggcccac attaaggaaa tagaggctga gttagtgaca gggtggcagt cccatagcct    1140
tcctgctgtg attcttcgaa atctcaaaga tcatgggcca cagatgggca cattcttgtg    1200
gcaagcatca gcaggaattg ctgtgtccca gaggaaagtg cgtcagatca gtgatcctat    1260
tcagcagata ttaattcagc tgcacaaaat aatctatatc acacagcttc ctccagcttt    1320
gcaccacaat ttgaaaagaa gggttataga gagattcaag aaatccctct tcagccagca    1380
gagtaaccct tgtaatttga aatctgaaat taaaaagtta tctcagggat ctccagaacc    1440
gattgagccc aacttttttca cagcagatta ccatttatta catcgttcat ccggtggaaa    1500
cagcctgtcc ccaaatgacc ctacaggttt accaaccagc attgaattgg aggaaggaat    1560
aacatatgaa cagatgcaga ctgtgattga agaagtcctt gaggaaagtg gctattacaa    1620
ttttacatct aacaggtatc attcctatcc atggggggacc aagaatcacc caaccaaaag    1680
atgaaaatgc tgcattttga gtggacttga ttttctcagt gaagttcaag ttctggactt    1740
cagccgctat tgcaagatgc ccaaggattg ggtgctgcta gagggtgtgg aaaagaccaa    1800
gatgccatgg ggcctgcagg acttctttct ggggtcctg tgctggagta tatgacagct    1860
gcggtacttg agggcttcat tgccagaaca cattatatac aggatgtcag agctaccagt    1920
gtgctgctgg gagaaaatgc tgcaaaattc atcttttgga gggtgggggg aaaacccaaa    1980
aacaacaaca aaaaaactct cttacagaat tttccttaac attaaaaaaa acttgtcata    2040
ttt                                                                  2043
```

<210> SEQ ID NO 8
<211> LENGTH: 1601
<212> TYPE: DNA
<213> ORGANISM: Homo sapiens

<400> SEQUENCE: 8

```
tttattagtg gaggatgaac tgaagcaaat tgctgaaaat attgaaagca ttaatcagaa      60
caaagctcct ttgaaatata taggcaacta tgcaattttg gatcatcttg gaagtggagc     120
ttttggctgt gtttacaagc tttatcatcc caacattgta cgttattaca aacatttct     180
ggaaaatgat aggttgtaca tagttatgga gctgatagaa ggagcccgc ttggagagca     240
tttcagttct ttgaaggaaa acatcacca tttactgaa gaaagactat ggaaaatatt     300
tatacagctg tgcttagctc ttcgatactt acacaaggag aagaggattg tccatagaga     360
tctgacacca acaacatta tgttggggga taaggacaaa gtaaccgtta ctgactttgg     420
cctggcaaag caaaaacaag aaaacagtaa actcacctct gtggttggaa caatcctgta     480
ttcttgcccc gaggtactga agagtgagcc gtatggggag aaggctgatg tctgggcagt     540
aggctgcatc ctttatcaga tggcgacttt gagtcccccc ttctacagca ctaacatgct     600
gtccttggct acaaaaatag tggaggcggt atatgaacca gtcccagaag gtatctactc     660
tgaaaaagta acagacacca tcagcaggtg cctcactcct gatgcggaag ctcgtccaga     720
tattgtagaa gtcagttcga tgatatcaga tgtcatgatg aaatatttag acaacttatc     780
tacatcccag ttgtccttgg aaaagaagct agaacgggaa cgaagacgca cacaaaggta     840
ttttatggaa gccaaccgga acaccgtcac atgtcaccat gagctggctg ttctatctca     900
cgagaccttt gagaaggcaa gtttgagtag cagcagcagt ggagcagcca gcctgaaaag     960
tgaactttca gaaagcgcag acctgccccc tgaaggcttc caggcctcct atggtaaaga    1020
cgaagacagg gcctgtgacg aaatcctgtc agatgataac ttcaacctgg aaaatgctga    1080
gaaagataca tattcagagg tagatgatga attggacatt tcggataact ccagcagctc    1140
cagttcaagc cccctgaaag aatctacatt caacattta aagagaagtt ttagtgcttc    1200
aggaggagaa agacaatccc aaacaaggga cttcactgga ggaacaggat caagaccaag    1260
accagctttg ctgcctcttg acctgcttct gaaagtgcca ccccacatgc tcagggccca    1320
cattaaggaa atagaggctg agttagtgac agggtggcag tcccatagcc ttcctgctgt    1380
gattcttcga aatctcaaag atcatggtag tacttactag atcacattga tgttaagcac    1440
acaatgggca aatgcagaat tatagttggg cctgagatgt ctgaacgatg cttgggtggt    1500
aatttttaata caaagagcgg agaattctgc cttgtttgtt caccactatt agtttggcga    1560
tttgatggta acaaaatgcc ttctgtgttc actgttggtt g                        1601
```

<210> SEQ ID NO 9
<211> LENGTH: 21
<212> TYPE: DNA
<213> ORGANISM: Homo sapiens

<400> SEQUENCE: 9

```
aatgagtacc tcggctatgg a                                                21
```

<210> SEQ ID NO 10
<211> LENGTH: 21
<212> TYPE: RNA
<213> ORGANISM: Homo sapiens

<400> SEQUENCE: 10

-continued ugaguaccuc ggcuauggau u                                            21

<210> SEQ ID NO 11
<211> LENGTH: 21
<212> TYPE: RNA
<213> ORGANISM: Homo sapiens

<400> SEQUENCE: 11
uuacucaugg agccgauacc u                                            21

<210> SEQ ID NO 12
<211> LENGTH: 21
<212> TYPE: DNA
<213> ORGANISM: Homo sapiens

<400> SEQUENCE: 12
aagactaaca gcggagttgc t                                            21

<210> SEQ ID NO 13
<211> LENGTH: 21
<212> TYPE: RNA
<213> ORGANISM: Homo sapiens

<400> SEQUENCE: 13
gacuaacagc ggaguugcuu u                                            21

<210> SEQ ID NO 14
<211> LENGTH: 21
<212> TYPE: RNA
<213> ORGANISM: Homo sapiens

<400> SEQUENCE: 14
uucugauugu cgccucaacg a                                            21

<210> SEQ ID NO 15
<211> LENGTH: 21
<212> TYPE: DNA
<213> ORGANISM: Homo sapiens

<400> SEQUENCE: 15
aagatcgaga cagcagcgta a                                            21

<210> SEQ ID NO 16
<211> LENGTH: 21
<212> TYPE: RNA
<213> ORGANISM: Homo sapiens

<400> SEQUENCE: 16
gaucgagaca gcagcguaau u                                            21

<210> SEQ ID NO 17
<211> LENGTH: 21
<212> TYPE: RNA
<213> ORGANISM: Homo sapiens

<400> SEQUENCE: 17
uucuagcucu gucgucgcau u                                            21

<210> SEQ ID NO 18
<211> LENGTH: 21
<212> TYPE: DNA
<213> ORGANISM: Homo sapiens

<400> SEQUENCE: 18
aactcacgtc tgtggttgga a                               21

<210> SEQ ID NO 19
<211> LENGTH: 21
<212> TYPE: RNA
<213> ORGANISM: Homo sapiens

<400> SEQUENCE: 19
cucacgucug ugguuggaau u                               21

<210> SEQ ID NO 20
<211> LENGTH: 21
<212> TYPE: RNA
<213> ORGANISM: Homo sapiens

<400> SEQUENCE: 20
uugagugcag acaccaaccu u                               21

<210> SEQ ID NO 21
<211> LENGTH: 21
<212> TYPE: DNA
<213> ORGANISM: Homo sapiens

<400> SEQUENCE: 21
aatagtggag gcggtatatg a                               21

<210> SEQ ID NO 22
<211> LENGTH: 21
<212> TYPE: RNA
<213> ORGANISM: Homo sapiens

<400> SEQUENCE: 22
uaguggaggc gguauaugau u                               21

<210> SEQ ID NO 23
<211> LENGTH: 21
<212> TYPE: RNA
<213> ORGANISM: Homo sapiens

<400> SEQUENCE: 23
uuaucaccuc cgccauauac u                               21

<210> SEQ ID NO 24
<211> LENGTH: 21
<212> TYPE: DNA
<213> ORGANISM: Homo sapiens

<400> SEQUENCE: 24
aagctcgtcc agatattgta g                               21

<210> SEQ ID NO 25
<211> LENGTH: 21
<212> TYPE: RNA
<213> ORGANISM: Homo sapiens

<400> SEQUENCE: 25
gcucguccag auauuguagu u                               21

<210> SEQ ID NO 26
<211> LENGTH: 21
<212> TYPE: RNA
<213> ORGANISM: Homo sapiens

```
<400> SEQUENCE: 26
uucgagcagg ucuauaacau c                                              21

<210> SEQ ID NO 27
<211> LENGTH: 21
<212> TYPE: DNA
<213> ORGANISM: Homo sapiens

<400> SEQUENCE: 27
aacaccgtca catgtcacca t                                              21

<210> SEQ ID NO 28
<211> LENGTH: 21
<212> TYPE: RNA
<213> ORGANISM: Homo sapiens

<400> SEQUENCE: 28
caccgucaca ugucaccauu u                                              21

<210> SEQ ID NO 29
<211> LENGTH: 21
<212> TYPE: RNA
<213> ORGANISM: Homo sapiens

<400> SEQUENCE: 29
uuguggcagu guacaguggu a                                              21

<210> SEQ ID NO 30
<211> LENGTH: 21
<212> TYPE: DNA
<213> ORGANISM: Homo sapiens

<400> SEQUENCE: 30
aatagaggct gagttagtga c                                              21

<210> SEQ ID NO 31
<211> LENGTH: 21
<212> TYPE: RNA
<213> ORGANISM: Homo sapiens

<400> SEQUENCE: 31
uagaggcuga guuagugacu u                                              21

<210> SEQ ID NO 32
<211> LENGTH: 21
<212> TYPE: RNA
<213> ORGANISM: Homo sapiens

<400> SEQUENCE: 32
uuaucuccga cucaaucacu g                                              21

<210> SEQ ID NO 33
<211> LENGTH: 21
<212> TYPE: DNA
<213> ORGANISM: Homo sapiens

<400> SEQUENCE: 33
aattgctagt gcattggtga g                                              21

<210> SEQ ID NO 34
<211> LENGTH: 21
<212> TYPE: RNA
<213> ORGANISM: Homo sapiens
```

```
<400> SEQUENCE: 34
uugcuagugc auuggugagu u                                          21

<210> SEQ ID NO 35
<211> LENGTH: 21
<212> TYPE: RNA
<213> ORGANISM: Homo sapiens

<400> SEQUENCE: 35
uuaacgauca cguaaccacu c                                          21

<210> SEQ ID NO 36
<211> LENGTH: 21
<212> TYPE: DNA
<213> ORGANISM: Homo sapiens

<400> SEQUENCE: 36
caatgagtac ctcggctatg g                                          21

<210> SEQ ID NO 37
<211> LENGTH: 21
<212> TYPE: RNA
<213> ORGANISM: Homo sapiens

<400> SEQUENCE: 37
augaguaccu cggcuauggu u                                          21

<210> SEQ ID NO 38
<211> LENGTH: 21
<212> TYPE: RNA
<213> ORGANISM: Homo sapiens

<400> SEQUENCE: 38
uuuacucaug gagccgauac c                                          21

<210> SEQ ID NO 39
<211> LENGTH: 21
<212> TYPE: DNA
<213> ORGANISM: Homo sapiens

<400> SEQUENCE: 39
cagctgtgct tagctcttcg a                                          21

<210> SEQ ID NO 40
<211> LENGTH: 21
<212> TYPE: RNA
<213> ORGANISM: Homo sapiens

<400> SEQUENCE: 40
gcugugcuua gcucuucgau u                                          21

<210> SEQ ID NO 41
<211> LENGTH: 21
<212> TYPE: RNA
<213> ORGANISM: Homo sapiens

<400> SEQUENCE: 41
uucgacacga aucgagaagc u                                          21

<210> SEQ ID NO 42
<211> LENGTH: 21
<212> TYPE: DNA
```

<213> ORGANISM: Homo sapiens

<400> SEQUENCE: 42
cagcactaac atgctgtcct t                                              21

<210> SEQ ID NO 43
<211> LENGTH: 21
<212> TYPE: RNA
<213> ORGANISM: Homo sapiens

<400> SEQUENCE: 43
gcacuaacau gcuguccuuu u                                              21

<210> SEQ ID NO 44
<211> LENGTH: 21
<212> TYPE: RNA
<213> ORGANISM: Homo sapiens

<400> SEQUENCE: 44
uucgugauug uacgacagga a                                              21

<210> SEQ ID NO 45
<211> LENGTH: 21
<212> TYPE: DNA
<213> ORGANISM: Homo sapiens

<400> SEQUENCE: 45
caagcatcag caggaattgc t                                              21

<210> SEQ ID NO 46
<211> LENGTH: 21
<212> TYPE: RNA
<213> ORGANISM: Homo sapiens

<400> SEQUENCE: 46
agcaucagca ggaauugcuu u                                              21

<210> SEQ ID NO 47
<211> LENGTH: 21
<212> TYPE: RNA
<213> ORGANISM: Homo sapiens

<400> SEQUENCE: 47
uuucguaguc guccuuaacg a                                              21

<210> SEQ ID NO 48
<211> LENGTH: 21
<212> TYPE: DNA
<213> ORGANISM: Homo sapiens

<400> SEQUENCE: 48
caggatgtca gagctaccag t                                              21

<210> SEQ ID NO 49
<211> LENGTH: 22
<212> TYPE: RNA
<213> ORGANISM: Homo sapiens

<400> SEQUENCE: 49
cggaugucag agcuaccagu uu                                             22

<210> SEQ ID NO 50
<211> LENGTH: 21

```
<212> TYPE: RNA
<213> ORGANISM: Homo sapiens

<400> SEQUENCE: 50
uuccuacagu cucgaugguc a                                              21

<210> SEQ ID NO 51
<211> LENGTH: 21
<212> TYPE: DNA
<213> ORGANISM: Homo sapiens

<400> SEQUENCE: 51
gagacagcag cgtaaggaat a                                              21

<210> SEQ ID NO 52
<211> LENGTH: 21
<212> TYPE: RNA
<213> ORGANISM: Homo sapiens

<400> SEQUENCE: 52
gacagcagcg uaaggaauau u                                              21

<210> SEQ ID NO 53
<211> LENGTH: 21
<212> TYPE: RNA
<213> ORGANISM: Homo sapiens

<400> SEQUENCE: 53
uucugucguc gcauuccuua u                                              21

<210> SEQ ID NO 54
<211> LENGTH: 21
<212> TYPE: DNA
<213> ORGANISM: Homo sapiens

<400> SEQUENCE: 54
gaggcggtat atgaaccagt c                                              21

<210> SEQ ID NO 55
<211> LENGTH: 21
<212> TYPE: RNA
<213> ORGANISM: Homo sapiens

<400> SEQUENCE: 55
ggcgguauau gaaccagucu u                                              21

<210> SEQ ID NO 56
<211> LENGTH: 21
<212> TYPE: RNA
<213> ORGANISM: Homo sapiens

<400> SEQUENCE: 56
uuccgccaua uacuugguca g                                              21

<210> SEQ ID NO 57
<211> LENGTH: 21
<212> TYPE: DNA
<213> ORGANISM: Homo sapiens

<400> SEQUENCE: 57
gaacaccgtc acatgtcacc a                                              21

<210> SEQ ID NO 58
```

```
<211> LENGTH: 21
<212> TYPE: RNA
<213> ORGANISM: Homo sapiens

<400> SEQUENCE: 58
acaccgucac augucaccau u                                                    21

<210> SEQ ID NO 59
<211> LENGTH: 21
<212> TYPE: RNA
<213> ORGANISM: Homo sapiens

<400> SEQUENCE: 59
uuuguggcag uguacagugg u                                                    21

<210> SEQ ID NO 60
<211> LENGTH: 21
<212> TYPE: DNA
<213> ORGANISM: Homo sapiens

<400> SEQUENCE: 60
gatctccaga accgattgag c                                                    21

<210> SEQ ID NO 61
<211> LENGTH: 21
<212> TYPE: RNA
<213> ORGANISM: Homo sapiens

<400> SEQUENCE: 61
ucuccagaac cgauugagcu u                                                    21

<210> SEQ ID NO 62
<211> LENGTH: 21
<212> TYPE: RNA
<213> ORGANISM: Homo sapiens

<400> SEQUENCE: 62
uuagaggucu uggcuaacuc g                                                    21

<210> SEQ ID NO 63
<211> LENGTH: 21
<212> TYPE: DNA
<213> ORGANISM: Homo sapiens

<400> SEQUENCE: 63
gacttcagcc gctattgcaa g                                                    21

<210> SEQ ID NO 64
<211> LENGTH: 21
<212> TYPE: RNA
<213> ORGANISM: Homo sapiens

<400> SEQUENCE: 64
cuucagccgc uauugcaagu u                                                    21

<210> SEQ ID NO 65
<211> LENGTH: 21
<212> TYPE: RNA
<213> ORGANISM: Homo sapiens

<400> SEQUENCE: 65
uugaagucgg cgauaacguu c                                                    21
```

```
<210> SEQ ID NO 66
<211> LENGTH: 21
<212> TYPE: DNA
<213> ORGANISM: Homo sapiens

<400> SEQUENCE: 66
gagtatatga cagctgcggt a                                              21

<210> SEQ ID NO 67
<211> LENGTH: 21
<212> TYPE: RNA
<213> ORGANISM: Homo sapiens

<400> SEQUENCE: 67
guauaugaca gcugcgguau u                                              21

<210> SEQ ID NO 68
<211> LENGTH: 21
<212> TYPE: RNA
<213> ORGANISM: Homo sapiens

<400> SEQUENCE: 68
uucauauacu gucgacgcca u                                              21

<210> SEQ ID NO 69
<211> LENGTH: 21
<212> TYPE: DNA
<213> ORGANISM: Homo sapiens

<400> SEQUENCE: 69
gaggattgag catcgaatgg t                                              21

<210> SEQ ID NO 70
<211> LENGTH: 21
<212> TYPE: RNA
<213> ORGANISM: Homo sapiens

<400> SEQUENCE: 70
ggauugagca ucgaaugguu u                                              21

<210> SEQ ID NO 71
<211> LENGTH: 21
<212> TYPE: RNA
<213> ORGANISM: Homo sapiens

<400> SEQUENCE: 71
uuccuaacuc guagcuuacc a                                              21

<210> SEQ ID NO 72
<211> LENGTH: 21
<212> TYPE: DNA
<213> ORGANISM: Homo sapiens

<400> SEQUENCE: 72
gagttcgcat cacaccagat c                                              21

<210> SEQ ID NO 73
<211> LENGTH: 21
<212> TYPE: RNA
<213> ORGANISM: Homo sapiens

<400> SEQUENCE: 73
guucgcauca caccagaucu u                                              21
```

```
<210> SEQ ID NO 74
<211> LENGTH: 21
<212> TYPE: RNA
<213> ORGANISM: Homo sapiens

<400> SEQUENCE: 74
uucaagcgua guguggucua g                                              21

<210> SEQ ID NO 75
<211> LENGTH: 21
<212> TYPE: DNA
<213> ORGANISM: Homo sapiens

<400> SEQUENCE: 75
tagtggaggc ggtatatgaa c                                              21

<210> SEQ ID NO 76
<211> LENGTH: 21
<212> TYPE: RNA
<213> ORGANISM: Homo sapiens

<400> SEQUENCE: 76
guggaggcgg uauaugaacu u                                              21

<210> SEQ ID NO 77
<211> LENGTH: 21
<212> TYPE: RNA
<213> ORGANISM: Homo sapiens

<400> SEQUENCE: 77
uucaccuccg ccauauacuu g                                              21

<210> SEQ ID NO 78
<211> LENGTH: 21
<212> TYPE: DNA
<213> ORGANISM: Homo sapiens

<400> SEQUENCE: 78
tattacatcg ttcatccggt g                                              21

<210> SEQ ID NO 79
<211> LENGTH: 21
<212> TYPE: RNA
<213> ORGANISM: Homo sapiens

<400> SEQUENCE: 79
uuacaucguu cauccggugu u                                              21

<210> SEQ ID NO 80
<211> LENGTH: 21
<212> TYPE: RNA
<213> ORGANISM: Homo sapiens

<400> SEQUENCE: 80
uuaauguagc aaguaggcca c                                              21

<210> SEQ ID NO 81
<211> LENGTH: 21
<212> TYPE: DNA
<213> ORGANISM: Homo sapiens

<400> SEQUENCE: 81
tatatgacag ctgcggtact t                                              21
```

<210> SEQ ID NO 82
<211> LENGTH: 21
<212> TYPE: RNA
<213> ORGANISM: Homo sapiens

<400> SEQUENCE: 82
uaugacagcu gcgguacuuu u                                              21

<210> SEQ ID NO 83
<211> LENGTH: 21
<212> TYPE: RNA
<213> ORGANISM: Homo sapiens

<400> SEQUENCE: 83
uuauacuguc gacgccauga a                                              21

<210> SEQ ID NO 84
<211> LENGTH: 21
<212> TYPE: DNA
<213> ORGANISM: Homo sapiens

<400> SEQUENCE: 84
tatgacagct gcggtacttg a                                              21

<210> SEQ ID NO 85
<211> LENGTH: 21
<212> TYPE: RNA
<213> ORGANISM: Homo sapiens

<400> SEQUENCE: 85
ugacagcugc gguacuugau u                                              21

<210> SEQ ID NO 86
<211> LENGTH: 21
<212> TYPE: RNA
<213> ORGANISM: Homo sapiens

<400> SEQUENCE: 86
uuacugucga cgccaugaac u                                              21

<210> SEQ ID NO 87
<211> LENGTH: 251
<212> TYPE: PRT
<213> ORGANISM: Artificial Sequence
<220> FEATURE:
<223> OTHER INFORMATION: A consensus sequence of the catalytic domain of
      a family of Tyr protein kinases, smart00219.

<400> SEQUENCE: 87

Leu Gly Glu Gly Ala Phe Gly Glu Val Tyr Lys Gly Thr Leu Lys Gly
1               5                   10                  15

Lys Gly Gly Lys Glu Val Glu Val Ala Val Lys Thr Leu Lys Glu Asp
            20                  25                  30

Ala Ser Glu Gln Gln Ile Glu Glu Phe Leu Arg Glu Ala Lys Ile Met
        35                  40                  45

Arg Lys Leu Asp His Pro Asn Ile Val Lys Leu Leu Gly Val Cys Thr
    50                  55                  60

Glu Glu Glu Pro Leu Met Ile Val Met Glu Tyr Met Glu Gly Gly Asp
65                  70                  75                  80

Leu Leu Asp Tyr Leu Arg Lys Asn Arg Pro Lys Glu Leu Ser Leu Ser
                85                  90                  95

```
Asp Leu Leu Ser Phe Ala Leu Gln Ile Ala Arg Gly Met Glu Tyr Leu
            100                 105                 110

Glu Ser Lys Asn Phe Val His Arg Asp Leu Ala Ala Arg Asn Cys Leu
        115                 120                 125

Val Gly Glu Asn Lys Thr Val Lys Ile Ala Asp Phe Gly Leu Ser Arg
    130                 135                 140

Asp Leu Tyr Ser Asp Tyr Tyr Lys Val Lys Gly Gly Lys Leu Pro
145                 150                 155                 160

Ile Arg Trp Met Ala Pro Glu Ser Leu Lys Glu Gly Lys Phe Thr Ser
                165                 170                 175

Lys Ser Asp Val Trp Ser Phe Gly Val Leu Leu Trp Glu Ile Phe Thr
            180                 185                 190

Leu Gly Glu Ser Pro Tyr Pro Gly Met Ser Asn Glu Glu Val Leu Glu
        195                 200                 205

Tyr Leu Lys Lys Gly Tyr Arg Leu Pro Gln Pro Pro Asn Cys Pro Asp
    210                 215                 220

Glu Ile Tyr Asp Leu Met Leu Gln Cys Trp Ala Glu Asp Pro Glu Asp
225                 230                 235                 240

Arg Pro Ser Phe Ser Glu Leu Val Glu Arg Leu
                245                 250

<210> SEQ ID NO 88
<211> LENGTH: 247
<212> TYPE: PRT
<213> ORGANISM: Artificial Sequence
<220> FEATURE:
<223> OTHER INFORMATION: A consensus sequence of the protein kinase
      domain of pkinases, pfam00069.

<400> SEQUENCE: 88

Tyr Glu Leu Gly Glu Lys Leu Gly Ser Gly Ser Phe Gly Lys Val Tyr
1               5                   10                  15

Lys Gly Lys His Lys Asn Thr Gly Glu Ile Val Ala Ile Lys Lys Leu
            20                  25                  30

Lys Lys Glu Ser Ile Lys Glu Lys Lys Arg Phe Leu Arg Glu Ile Arg
        35                  40                  45

Ile Leu Arg Arg Leu Ser His Pro Asn Ile Val Arg Leu Ile Gly Val
    50                  55                  60

Phe Glu Glu Asp Asp His Leu Tyr Leu Val Met Glu Tyr Met Glu Gly
65                  70                  75                  80

Gly Asp Leu Phe Asp Tyr Leu Arg Arg Asn Gly Leu Leu Leu Ser Glu
                85                  90                  95

Lys Glu Ala Lys Lys Ile Ala Leu Gln Ile Leu Arg Gly Leu Glu Tyr
            100                 105                 110

Leu His Ser Arg Gly Ile Val His Arg Asp Leu Lys Pro Glu Asn Ile
        115                 120                 125

Leu Leu Asp Glu Asn Gly Thr Val Lys Ile Ala Asp Phe Gly Leu Ala
    130                 135                 140

Arg Leu Leu Lys Ser Ser Tyr Ser Lys Leu Thr Thr Phe Val Gly Thr
145                 150                 155                 160

Pro Glu Tyr Met Ala Pro Glu Val Leu Glu Gly Arg Gly Tyr Ser Ser
                165                 170                 175

Lys Val Asp Val Trp Ser Leu Gly Val Val Leu Tyr Glu Leu Leu Thr
            180                 185                 190

Gly Lys Pro Pro Phe Ser Gly Ile Asp Pro Leu Glu Glu Leu Phe Arg
```

```
              195                 200                 205
Ile Ile Lys Arg Gly Leu Arg Leu Pro Leu Pro Pro Asn Cys Ser Glu
        210                 215                 220

Glu Leu Lys Asp Leu Ile Lys Lys Cys Leu Asn Lys Asp Pro Glu Lys
225                 230                 235                 240

Arg Pro Thr Ala Lys Glu Ile
                245

<210> SEQ ID NO 89
<211> LENGTH: 250
<212> TYPE: PRT
<213> ORGANISM: Artificial Sequence
<220> FEATURE:
<223> OTHER INFORMATION: A consensus sequence of the catalytic domain of
      a family of serine/threonine kinases, smart00220.

<400> SEQUENCE: 89

Tyr Glu Leu Leu Glu Val Leu Gly Lys Gly Ala Phe Gly Lys Val Tyr
1               5                  10                  15

Leu Ala Arg Asp Lys Lys Thr Gly Lys Leu Val Ala Ile Lys Val Ile
             20                  25                  30

Lys Lys Glu Lys Leu Lys Lys Lys Arg Glu Arg Ile Leu Arg Glu
         35                  40                  45

Ile Lys Ile Leu Lys Lys Leu Asp His Pro Asn Ile Val Lys Leu Tyr
     50                  55                  60

Asp Val Phe Glu Asp Lys Asp Lys Leu Tyr Leu Val Met Glu Tyr Cys
65                  70                  75                  80

Glu Gly Gly Asp Leu Phe Asp Leu Leu Lys Lys Arg Gly Arg Leu Ser
                85                  90                  95

Glu Asp Glu Ala Arg Phe Tyr Ala Arg Gln Ile Leu Ser Ala Leu Glu
            100                 105                 110

Tyr Leu His Ser Asn Gly Ile Ile His Arg Asp Leu Lys Pro Glu Asn
        115                 120                 125

Ile Leu Leu Asp Ser Asp Gly His Val Lys Leu Ala Asp Phe Gly Leu
    130                 135                 140

Ala Lys Gln Leu Asp Ser Gly Gly Thr Leu Leu Thr Thr Phe Val Gly
145                 150                 155                 160

Thr Pro Glu Tyr Met Ala Pro Glu Val Leu Leu Gly Lys Gly Tyr Gly
                165                 170                 175

Lys Ala Val Asp Ile Trp Ser Leu Gly Val Ile Leu Tyr Glu Leu Leu
            180                 185                 190

Thr Gly Lys Pro Pro Phe Pro Gly Asp Asp Gln Leu Asp Ala Leu Phe
        195                 200                 205

Lys Lys Ile Gly Lys Pro Pro Pro Phe Pro Pro Pro Glu Trp Lys
    210                 215                 220

Ile Ser Pro Glu Ala Lys Asp Leu Ile Lys Lys Leu Leu Val Lys Asp
225                 230                 235                 240

Pro Glu Lys Arg Leu Thr Ala Glu Glu Ala
                245                 250

<210> SEQ ID NO 90
<211> LENGTH: 151
<212> TYPE: PRT
<213> ORGANISM: Artificial Sequence
<220> FEATURE:
<223> OTHER INFORMATION: The consensus sequence of RIO-like-kinases,
      smart00090.
```

-continued

```
<400> SEQUENCE: 90

Leu Asp Gly Ser Gly Asn Glu Arg Ala Val Lys Ile Tyr Lys Thr Gly
1               5                   10                  15

Thr Leu Glu Phe Lys Arg Arg Asp Arg Tyr Val Asp Gly Asp Phe Arg
            20                  25                  30

Phe Lys Tyr Arg Lys Ile Asn Pro Arg Lys Leu Val Arg Leu Trp Ala
        35                  40                  45

Glu Lys Glu Phe Arg Asn Leu Gln Arg Leu Tyr Glu Ala Gly Val Pro
    50                  55                  60

Val Pro Lys Pro Ile Ala Trp Arg Arg Asn Val Leu Val Met Glu Phe
65                  70                  75                  80

Ile Gly Gly Asp Gly Leu Pro Ala Pro Arg Leu Lys Asp Val Glu Pro
                85                  90                  95

Glu Glu Glu Glu Glu Asp Glu Leu Tyr Asp Asp Ile Leu Glu Glu Met
            100                 105                 110

Arg Lys Leu Tyr Lys Glu Gly Leu Val His Gly Asp Leu Ser Glu
        115                 120                 125

Tyr Asn Ile Leu Val His Asp Gly Lys Val Val Ile Ile Asp Val Ser
    130                 135                 140

Gln Ser Val Glu Leu Asp His
145             150
```

COMPOSITIONS, ORGANISMS AND METHODOLOGIES EMPLOYING A NOVEL HUMAN KINASE

CROSS-REFERENCE TO RELATED APPLICATIONS

The present application is a division of U.S. patent application Ser. No. 10/684,190 filed Oct. 10, 2003 now U.S. Pat. No. 7,122,361, which claims priority to and the benefit of U.S. Provisional Application No. 60/417,209 filed Oct. 10, 2002, the contents of each of which are hereby incorporated by reference herein in their entireties for all purposes.

REFERENCE TO SEQUENCE LISTING

This application includes as part of the originally filed subject matter two compact discs, labeled "Copy 1" and "Copy 2," each disc containing a Sequence Listing. The machine format of each compact disc is IBM-PC and the operating system of each compact disc is MS-Windows. Each of the compact discs includes a single text file, which is named "Sequence Listing" (325 KB, created Jul. 19, 2006). The contents of the compact discs labeled "Copy 1" and "Copy 2" are hereby incorporated by reference herein in their entireties for all purposes.

FIELD OF THE INVENTION

The present invention relates to compositions, organisms and methodologies employing a novel human protein kinase, HPK3P23, which has sequence homology to the catalytic domain of tyrosine protein kinases and serine/threonine protein kinases. This invention can be used for diagnosing, prognosing, and treating kinase-related diseases and, in particular, diseases associated with aberrant expression of HPK3P23.

BACKGROUND OF THE INVENTION

Protein kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1,000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc.), cell cycle checkpoints, and environmental or nutritional stresses. The phosphorylation process is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups: those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250-300 amino acid catalytic domain. The primary structure of the kinase domains is conserved and can be further subdivided into 11 subdomains. The N-terminal of the kinase domain, which contains subdomains I-IV, generally folds into a lobe-like structure that binds and orients the ATP (or GTP) donor molecule. The C terminal of the kinase domain forms a larger lobe, which contains subdomains VI-XI, binds the protein substrate and carries out the transfer of the gamma phosphate from ATP to the hydroxyl group of a serine, threonine, or tyrosine residue. Subdomain V spans the two lobes. Each of the 11 subdomains contains specific residues and motifs or patterns of amino acids that are characteristic of that subdomain and are highly conserved.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein.

The presence of a phosphate moiety modulates protein function in multiple ways. A common mechanism involves changes in the catalytic properties (Vmax and Km) of an enzyme, leading to its activation or inactivation.

A second widely recognized mechanism involves promoting protein-protein interactions. An example of this is the tyrosine autophosphorylation of the ligand-activated EGF receptor tyrosine kinase. This event triggers the high-affinity binding to the phosphotyrosine residue on the receptor's C-terminal intracellular domain to the SH2 motif of an adaptor molecule Grb2. Grb2, in turn, binds through its SH3 motif to a second adaptor molecule, such as SHC. The formation of this complex activates the signaling events that are responsible for the biological effects of EGF. Serine and threonine phosphorylation events also have been recently recognized to exert their biological function through protein-protein interaction events that are mediated by the high-affinity binding of phosphoserine and phosphothreonine to the WW motifs present in a large variety of proteins.

A third important outcome of protein phosphorylation is changes in the subcellular localization of the substrate. As an example, nuclear import and export events in a large diversity of proteins are regulated by protein phosphorylation.

Many kinases are involved in regulatory cascades wherein their substrates may include other kinases whose activities are regulated by their phosphorylation state. Ultimately the activities of some downstream effectors are modulated by phosphorylation resulting from activation of such a pathway.

SUMMARY OF THE INVENTION

The present invention discloses compositions, organisms and methodologies employing a novel human protein kinase. The new human protein kinase shares sequence homology with the catalytic domain of tyrosine protein kinases and serine/threonine protein kinases. The gene encoding this new protein is localized in or near locus 3p23 of human chromosome 3. This new gene is hereinafter referred to as human protein kinase 3P23 (HPK3P23) gene, and its encoded protein(s) is referred to as HPK3P23 or HPK3P23 kinase.

The kinase domain in HPK3P23 shows 97.7% sequence alignment with the consensus sequences of the catalytic domain of tyrosine kinases, 97.6% sequence alignment with the consensus sequence of the pkinase domain, and 97.7% sequence alignment with the consensus sequences of the catalytic domains of serine/threonine protein kinases. The utilities of various kinase domains are known in the art. The unique peptide sequences, and nucleic acid sequences that encode the peptides, can be used as models for the development of human therapeutic targets, aid in the identification of therapeutic proteins, and serve as targets for the development of human therapeutic agents that modulate kinase activity in cells and tissues that express the kinase.

In one aspect, the invention provides isolated polynucleotides comprising a nucleotide sequence encoding HPK3P23 or a variant of HPK3P23.

In another aspect, the invention provides isolated polypeptides comprising the amino acid sequence of HPK3P23 or a variant of HPK3P23.

In yet another aspect, the invention provides agents that modulate expression level of the HPK3P23 gene or an activity of HPK3P23.

The invention also provides methods for (a) detecting polynucleotides comprising a nucleotide sequence encoding HPK3P23 or a variant of HPK3P23 and (b) detecting polypeptides comprising an amino acid sequence of HPK3P23 or a variant of HPK3P23 in a biological sample.

The invention further provides methods for screening agents that modulate expression level of the HPK3P23 gene or an activity of HPK3P23.

The invention further provides cell lines harboring the HPK3P23 gene, animals transgenic for the HPK3P23 gene, and animals with an interrupted HPK3P23 gene (HPK3P23 knockout animals). These cell lines and animals can be used to study the functions of HPK3P23.

In still another aspect, the invention provides polynucleotides capable of inhibiting HPK3P23 gene expression by RNA interference.

The invention further provides methods of inhibiting HPK3P23 gene expression by introducing siRNAs or other RNAi sequences into target cells.

The preferred embodiments of the inventions are described below in the Detailed Description of the Invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the inventions not be limited only to the specific structure, material or methods that are described in the preferred embodiments, but include any and all structures, materials or methods that perform the claimed function, along with any and all known or later-developed equivalent structures, materials or methods for performing the claimed function.

Further examples exist throughout the disclosure, and it is not applicant's intention to exclude from the scope of his invention the use of structures, materials, or methods that are not expressly identified in the specification, but nonetheless are capable of performing a claimed function.

BRIEF DESCRIPTION OF THE DRAWINGS

The inventions of this application are better understood in conjunction with the following drawings, in which:

FIG. 1 shows the sequence alignment between amino acid residues 369 to 627 of HPK3P23 (SEQ ID NO:2) and the catalytic domain of a family of tyrosine kinases (SEQ ID NO:87).

FIG. 2 shows the sequence alignment between amino acid residues 363 to 623 of HPK3P23 (SEQ ID NO:2) and the protein kinase domain of pkinases (SEQ ID NO:88).

FIG. 3 compares amino acid residues 363 to 623 of HPK3P23 (SEQ ID NO:2) to the catalytic domain of a family of Ser/Thr protein kinases (SEQ ID NO:89).

FIG. 4 illustrates the sequence alignment between amino acid residues 369 to 526 of HPK3P23 (SEQ ID NO:2) and a consensus sequence of RIO-like kinases (SEQ ID NO:90).

DETAILED DESCRIPTION OF THE INVENTION

Figure 5:
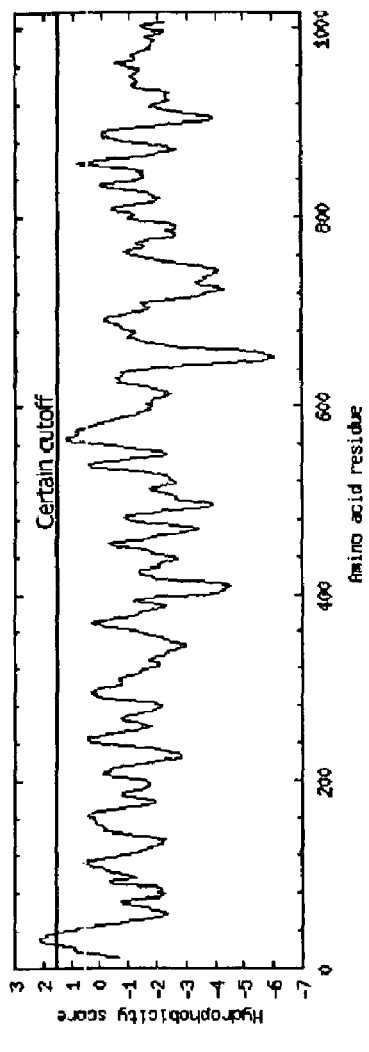
FIG. 5 shows the hydrophobicity profile of HPK3P23.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the spirit and scope of the invention. The present invention is not intended to be limited to the embodiments shown, but is to be accorded the widest possible scope consistent with the principles and features disclosed herein.

The present invention is based on the sequence information obtained from a newly developed genomic prediction pipeline. Briefly, the X-ray crystal structures of the catalytic domains of protein kinases were collected and aligned together according to their structural identity/similarities. The alignment was converted into a "scoring matrix" which carried the structural profile of the kinase catalytic domains. This scoring matrix was then used to search the Celera Human Genome database and pull out sequences that have kinase catalytic domains.

Based on this analysis, the present invention provides the amino acid sequence of a human kinase peptide containing a kinase domain that is highly homologous to the consensus sequences of the catalytic domain of several protein kinases, as well as the cDNA sequences and genomic sequences that encode the kinase peptide. The present invention also provides information about the closest art known protein/peptide/domain that has structural or sequence homology to the kinase of the present invention.

The peptide of the present invention may be used for the development of commercially important products and services. Various aspects of the invention are described in detail in the following subsections. The use of subsections is not meant to limit the invention. Each subsection applies to any aspect of the invention.

Definitions and Terms

To facilitate the understanding of the present invention, a number of terms and phrases are defined below:

As used herein, a polynucleotide or a polypeptide is "isolated" if it is removed from its native environment. For instance, a polynucleotide or a polypeptide is isolated through a purification process such that the polynucleotide or polypeptide is substantially free of cellular material or free of chemical precursors. The polynucleotide/polypeptide of the present invention can be purified to homogeneity or other degrees of purity. The level of purification will be based on the intended use. As appreciated by one of ordinary skill in the art, a polynucleotide/polypeptide can perform its desired function(s) even in the presence of considerable amounts of other components or molecules.

In some uses, a polynucleotide/polypeptide that is "substantially free of cellular material" includes preparations which have less than about 30% (by weight) other polynucleotides/polypeptides including contaminating polynucleotides/polypeptides. For instance, the preparations can have less than about 20%, less than about 10%, or less than about 5% other polynucleotides/polypeptides. If a polynucleotide/polypeptide preparation is recombinantly produced, it can be substantially free of culture medium, i.e., culture medium components representing less than about 20% by weight of the polynucleotide/polypeptide preparation.

The language "substantially free of chemical precursors" includes preparations in which the polynucleotide/polypeptide is separated from chemical precursors or other chemicals that are involved in the synthesis of the polynucleotide/polypeptide. In one embodiment, the language "substantially free of chemical precursors" includes kinase preparations having less than about 30% (by weight), less than about 20% (by weight), less than about 10% (by weight), or less than about 5% (by weight) chemical precursors or other chemicals used in the synthesis.

As used in the present invention, a polynucleotide introduced into a cell is an isolated polynucleotide. Likewise, a polypeptide expressed from an introduced vector in a cell is also an isolated polypeptide.

A "polynucleotide" can include any number of nucleotides. For instance, a polynucleotide can have at least 10, 20, 25, 30, 40, 50, 100 or more nucleotides. A polynucleotide can be DNA or RNA, double-stranded or single-stranded. A polynucleotide encodes a polypeptide if the polypeptide is capable of being transcribed and/or translated from the polynucleotide. Transcriptional and/or translational regulatory sequences, such as promoter and/or enhancer(s), can be added to the polynucleotide before said transcription and/or translation occurs. Moreover, if the polynucleotide is single-stranded, the corresponding double-stranded DNA containing the original polynucleotide and its complementary sequence can be prepared before said transcription and/or translation.

As used herein, "a variant of a polynucleotide" refers to a polynucleotide that differs from the original polynucleotide by one or more substitutions, additions, and/or deletions. For instance, a variant of a polynucleotide can have 1, 2, 5, 10, 15, 20, 25 or more nucleotide substitutions, additions or deletions. Preferably, the modification(s) is in-frame, i.e., the modified polynucleotide can be transcribed and translated to the original or intended stop codon. If the original polynucleotide encodes a polypeptide with a biological activity, the polypeptide encoded by a variant of the original polynucleotide variants substantially retains such activity.

Preferably, the biological activity is reduced/enhanced by less than 50%, or more preferably, less than 20%, relative to the original activity.

A variant of a polynucleotide can be a polynucleotide that is capable of hybridizing to the original polynucleotide, or the complementary sequence thereof, under reduced stringent conditions, preferably stringent conditions, or more preferably, highly stringent conditions. Examples of conditions of different stringency are listed in Table 1. Highly stringent conditions are those that are at least as stringent as conditions A-F; stringent conditions are at least as stringent as conditions G-L; and reduced stringency conditions are at least as stringent as conditions M-R. As used in Table 1, hybridization is carried out under a given hybridization condition for about 2 hours, followed by two 15-minute washes under the corresponding washing condition(s).

TABLE 1

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | >50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | >50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | >50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |

TABLE 1-continued

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| Q | RNA:RNA | >50 | 60° C.; 4xSSC -or- 45° C.; 6xSSC, 50% formamide | 60° C.; 2xSSC |
| R | RNA:RNA | <50 | $T_R^*$; 4xSSC | $T_R^*$; 4xSSC |

[1] The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H] SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) =2(# of A + T bases) + 4(# of G + C bases). For hybrids between 18 and 49 base pairs in length, $T_m$(° C.) = 81.5 + 16.6($\log_{10}Na^+$) + 0.41(% G + C) − (600/N), where N is the number of bases in the hybrid, and $Na^+$ is the concentration of sodium ions in the hybridization buffer ($Na^+$ for 1xSSC = 0.165M).

It will be appreciated by those of ordinary skill in the art that, as a result of the degeneracy of the genetic code, there are many polynucleotide variants that encode the same polypeptide. Some of these polynucleotide variants bear minimal sequence homology to the original polynucleotide. Nonetheless, polynucleotides that vary due to differences in codon usage are specifically contemplated by the present invention.

As used herein, a "polypeptide" can include any number of amino acid residues. For instance, a polypeptide can have 5, 10, 15, 20, 30, 40, 50 or more amino acid residues.

As used herein, a "variant of a polypeptide" is a polypeptide that differs from the original polypeptide by one or more substitutions, deletions, and/or insertions. Preferably, these modifications do not substantially change (e.g., reduce or enhance) the original biological function of the polypeptide. For instance, a variant can reduce or enhance or maintain the biological activities of the original polypeptide. Preferably, the biological activities of the variant is reduced or enhanced by less than 50%, or more preferably, less than 20%, relative to the original polypeptide.

Similarly, the ability of a variant to react with antigen-specific antisera can be enhanced or reduced by less than 50%, preferably less than 20%, relative to the original polypeptide. These variants can be prepared and evaluated by modifying the original polypeptide sequence and then determining the reactivity of the modified polypeptide with the antigen-specific antibodies or antisera.

Preferably, a variant polypeptide contains one or more conservative substitutions. A "conservative substitution" is one in which an amino acid is substituted for another amino acid which has similar properties, such that one skilled in the art would expect that the secondary structure and hydropathic nature of the substituted polypeptide will not be substantially changed. Conservative amino acid substitutions can be made on the basis of similarity in polarity, charge, solubility, hydrophobicity, hydrophilicity and/or the amphipathic nature of the residues. Negatively charged amino acids include aspartic acid and glutamic acid, and positively charged amino acids include lysine and arginine. Amino acids having uncharged polar head groups and similar hydrophilicity values include leucine, isoleucine and valine, or glycine and alanine, or asparagine and glutamine, or serine, threonine, phenylalanine and tyrosine. Other groups of amino acids that can produce conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A polypeptide variant can also contain nonconservative changes.

Polypeptide variants can be prepared by the deletion and/or addition of amino acids that have minimal influence on the biological activity, immunogenicity, secondary structure and/or hydropathic nature of the polypeptide. Variants can be prepared by, for instance, substituting, modifying, deleting or adding one or more amino acids residues in the original sequence. Polypeptide variants preferably exhibit at least about 70%, more preferably at least about 90%, and most preferably at least about 95% sequence homology to the original polypeptide.

Polypeptide variants include polypeptides that are modified from the original polypeptides either by a natural process, such as a post-translational modification, or by a chemical modification. These modifications are well known in the art. Modifications can occur anywhere in the polypeptide, including the backbone, the amino acid side-chains and the amino or carboxyl termini. It will be appreciated that the same type of modification can be present in the same or varying degrees at several sites in a given polypeptide. Also, a given polypeptide can contain many types of modifications. Polypeptides may be branched, for example, as a result of ubiquitination, and they may be cyclic, with or without branching. Cyclic, branched, and branched cyclic polypeptides can result from natural post-translational processes or be made through synthetic methods. Suitable modifications for this invention include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

As used herein, the term "modulation" includes up-regulation, induction, stimulation, potentiation, inhibition, down-regulation or suppression, or relief of inhibition.

A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

As used herein, a "disease-free" human refers to a human who does not have HPK3P23-related diseases. Disease-free cells, tissues or samples refer to cells, tissues or samples obtained from such disease-free human(s).

A polynucleotide is "capable of hybridizing" to a gene if the polynucleotide can hybridize to at least one of the following sequences: (1) the sequence of an RNA transcript of the gene, (2) the complementary sequence of an RNA transcript of the gene, (3) the cDNA sequence of an RNA transcript of the gene, (4) the complementary sequence of the cDNA sequence of an RNA transcript of the gene, (5) a genomic sequence of the gene, and (6) the complementary sequence of a genomic sequence of the gene.

As used herein, sequence "identity" in an alignment can be determined by the standard protein-protein BLAST program (blastp), the standard nucleotide-nucleotide BLAST program (blastn) or the BLAST2 Sequence program. Suitable BLAST programs can be found at the web site maintained by the National Center of Biotechnology Information (NCBI), National Library of Medicine, Washington, D.C., USA.

Human HPK3P23 Gene and HPK3P23 Kinase

The present invention identifies a new human gene (HPK3P23 gene) that encodes a protein containing sequences highly homologous to the consensus sequences of the catalytic domain of tyrosine protein kinases and serine/threonine protein kinases. The nucleotide sequence encoding HPK3P23 and the amino acid sequence of HPK3P23 are depicted in SEQ ID NOS:1 and 2, respectively. HPK3P23 gene is localized in or near locus 3p23 of human chromosome 3. Specifically, the HPK3P23 gene is located between loci LOC131717 and LOC131721, and overlaps with loci LOC152109, LOC152110, and LOC166046.

Human chromosome locus 3p23 and the neighboring regions have been associated with multiple diseases, including but are not limited to, small cell lung cancer, ovarian cancer, esophageal cancer, colorectal cancer, chronic myeloid leukemia, arrhythomegenic right ventricular dysplasia, and polycystic kidney disease. Recurrent deletions 3p23 were found in a number of tumor cells, suggesting the existence of a tumor suppressor gene in the region.

Human HPK3P23 gene has 32 exons. The exons are mapped to the nucleotide sequences of human chromosome 3 in Celera genomic database (SEQ ID NO:3). Exons 1-29, 31 and 32 are also mapped to nucleotides 2719783 to 2940912 of human chromosome 3 in the Entrez Human Genome Sequence Database maintained by NCBI. Table 2 lists the location of these 32 exons in the genomic sequence SEQ ID NO:3. Table 2 also illustration the corresponding location of each exon in the HPK3P23-coding sequence SEQ ID NO:1.

TABLE 2

Exons in Human HPK3P23 Gene

| Exon Numbers | Corresponding Sequence in SEQ ID NO: 3 | Corresponding Sequence in SEQ ID NO: 1 |
|---|---|---|
| 1 | 1-208 | 1-208 |
| 2 | 1291-1358 | 209-276 |
| 3 | 3303-3382 | 277-356 |
| 4 | 7339-7563 | 357-581 |
| 5 | 10475-10614 | 582-721 |
| 6 | 15070-15131 | 722-783 |
| 7 | 16620-16755 | 784-919 |
| 8 | 20738-20826 | 920-1008 |
| 9 | 20920-21048 | 1009-1137 |
| 10 | 21548-21685 | 1138-1275 |
| 11 | 24559-24604 | 1276-1321 |
| 12 | 27341-27462 | 1322-1443 |
| 13 | 27598-27700 | 1444-1546 |
| 14 | 55923-55998 | 1547-1622 |
| 15 | 109494-109623 | 1623-1752 |
| 16 | 110472-110542 | 1753-1823 |
| 17 | 119802-120015 | 1824-2037 |
| 18 | 137212-137395 | 2038-2221 |
| 19 | 137520-137606 | 2222-2308 |
| 20 | 140172-140226 | 2309-2363 |
| 21 | 149307-149344 | 2364-2401 |
| 22 | 149444-149584 | 2402-2542 |
| 23 | 168572-168601 | 2543-2572 |
| 24 | 170464-170564 | 2573-2673 |
| 25 | 180056-180166 | 2674-2784 |
| 26 | 192178-192286 | 2785-2893 |
| 27 | 195919-195971 | 2894-2946 |
| 28 | 196051-196106 | 2947-3002 |
| 29 | 200725-201051 | 3003-3329 |
| 30 | 209064-209145 | 3330-3411 |
| 31 | 210747-210809 | 3412-3474 |
| 32 | 220691-220860 | 3475-3644 |

A conserved domain search using RPS-BLAST program (RPS-BLAST 2.2.3 [Apr. 24, 2002], available at the BLAST web site maintained by NCBI), showed that HPK3P23 contains sequences homologous to the consensus sequences of several protein Kinase domains.

Specifically, the amino acid residues 369 to 627 of HPK3P23 are highly homologous to a catalytic domain of a family of Tyr protein kinases (smart00219). This family includes the tyrosine kinase domain of fibroblast growth factor receptor 1, tyrosine-protein Kinase (KIN15/KIN16 subfamily), and a Drosophila receptor protein-tyrosine Kinase family member (drl-P1). FIG. 1 shows that the amino acid residues 369-627 in HPK3P23's Kinase domain has 97.7% sequence identities to smart00219, with a score of 137 bits and an E value of $2 \times 10^{-33}$. As used in other figures of this invention, "Query" denotes to the sequence of HPK3P23, and "Sbjct" refers to the sequence being compared to the HPK3P23 sequence.

FIG. 2 shows that the amino acid residues 363 to 623 of HPK3P23 also aligned 97.6% with the protein kinase domain of pkinases (pfam00069). The alignment has a score of 222 bits, and an E value of $3 \times 10^{-59}$. This pkinase family includes protein kinase CK2, weel-like protein kinase (WEE1hu), and tyrosine-protein kinase RYK.

FIG. 3 shows the sequence alignment between amino acid residues 369 to 627 of HPK3P23 and the catalytic domain of a family of serine/threonine kinases (smart00220). The amino acid residues 369 to 627 of HPK3P23 are highly homologous to a catalytic domain of a family of serine/threonine protein kinases (smart00220). This kinase family includes C-Jun N-terminal kinase (JNK3), abelson tyrosine kinase, a calmodulin-binding, vesicle-associated, protein kinase-like protein (1G5), serine/threonine protein kinase prp4, Cdc2/Cdc28 subfamily of serine/threonine protein kinases in *C. elegans*, and ribosomal S6 kinase of *C elegans*. The two sequences share 97.7% alignment with a score of 230 bits and an E value of $2 \times 10^{-61}$.

FIG. 4 illustrates the sequence alignment between amino acid residues 369 to 526 of HPK3P23 and the consensus sequence of RIO-like-kinases (smart00090). The two sequences share 64.3% sequence identities with a score of 42.9 bits and an E value of $5 \times 10^{-5}$. The RIO-like-kinase family of protein kinases includes several uncharacterized proteins such as yeast protein RIO1, *C. elegans* hypothetical protein ZK632.3, *Methanococcus jannaschii* hypothetical protein MJ0444; and *Thermoplasma acidophilum* hypothetical protein in rpoA2 3' region. These proteins were found to be evolutionary related. The eukaryotic members of this family are proteins of about 55 to 60 kd, while the archebacterial ones are half that size. The central part of these proteins is highly conserved.

FIG. 5 shows the hydrophobicity profile of HPK3P23. The hydrophobicity analysis indicates that HPK3P23 kinase is not likely a membrane or transmembrane protein.

HPK3P23 shows significant sequence homology to a human protein kinase-like protein SGK237 (Entrez accession number: AX250157, SEQ ID NOS:4 and 5), which was disclosed in PCT Patent Application No. WO01/66594. Analysis using pairwise BLAST algorithm revealed that HPK3P23 and SGK237 share 91% sequence identities at the amino acid level (blastp, matrix: BLOSUM62, gap open: 11, Gap extension: 1, x_dropoff: 50, expect: 10.0, wordsize: 3, filter: unchecked), and 90% sequence identities at nucleotide level (blastn, match: 1, mismatch: −2, gap open: 5, gap extension: 0, x_dropoff: 50, expect: 10.0, wordsize: 11, filter: unchecked).

The existence and expression of the HPK3P23 gene in humans are supported by various EST sequences. For instance, nucleotides 365-861 of SEQ ID NO:1 are supported by the EST sequences disclosed under Incyte accession numbers 5026615H1, 5026615F6, 2509577H1, 6097133H1 and 6097133F6; nucleotides 919-1260 of SEQ ID NO:1 are supported by the EST sequence disclosed under GenBank accession numbers BM976173, AA430250, and AI149647, as well as Incyte accession number 6097133F6; nucleotides 1164-1623 of SEQ ID NO:1 are supported by the EST sequences disclosed under GenBank accession numbers BM976126, BM976173, AI149647, and AW372558; nucleotides 1624-2042 of SEQ ID NO:1 are supported by the EST sequences disclosed under GenBank accession number BG717420; nucleotides 1798-2327 of SEQ ID NO:1 are supported by the EST sequences disclosed under Incyte accession numbers 5546336H1, 5546336F8, 6999077H1, 4123469H1; nucleotides 2783-3329 of SEQ ID NO:1 are supported by the EST sequences disclosed under GenBank accession numbers AI652681, AI962584, AA954906, AA889152, AI611061, and AA843473, as well as Incyte accession numbers 5576248H1, 5547612H1, and 6444587H1.

Utility of the HPK3P23 Gene and HPK3P23 Kinase

Protein kinases are involved in the regulation of many critical biological processes such as signal transduction pathways. Malfunctions of cellular signaling have been associated with many diseases. Regulation of signal transduction by cytokines and association of signal molecules with protooncogenes and tumor suppressor genes have been the subjects of intense research. Many therapeutic strategies can now be developed through the synthesis of compounds which activate or inactivate protein kinases.

The importance of kinases in the etiology of diseases has been well established. Kinase proteins are a major target for drug action and development. A January 2002 survey of ongoing clinical trials in the USA revealed more than 100 clinical trials involving the modulation of kinases. Trials are ongoing in a wide variety of therapeutic indications including asthma, Parkinson's, inflammation, psoriasis, rheumatoid arthritis, spinal cord injuries, muscle conditions, osteoporosis, graft versus host disease, cardiovascular disorders, autoimmune disorders, retinal detachment, stroke, epilepsy, ischemia/reperfusion, breast cancer, ovarian cancer, glioblastoma, non-Hodgkin's lymphoma, colorectal cancer, non-small cell lung cancer, brain cancer, Kaposi's sarcoma, pancreatic cancer, liver cancer, and other tumors. Numerous kinds of modulators of kinase activity are currently in clinical trials including antisense molecules, antibodies, small molecules, and even gene therapy. Accordingly, it is valuable to the field of pharmaceutical development to identify and characterize previously unknown members of the kinase family proteins. The present invention advances the state of the art by providing previously unidentified human kinase proteins.

Many therapeutic strategies are aimed at critical components in signal transduction pathways. Approaches for regulating kinase gene expression include specific antisense oligonucleotides for inhibiting post-transcriptional processing of the messenger RNA, naturally occurring products and their chemical derivatives to inhibit kinase activity and monoclonal antibodies to inhibit receptor linked kinases. In some cases, kinase inhibitors also allow other therapeutic agents additional time to become effective and act synergistically with current treatments.

Among the areas of pharmaceutical research that are currently receiving a great deal of attention are the role of phosphorylation in transcriptional control, apoptosis, protein degradation, nuclear import and export, cytoskeletal regulation, and checkpoint signaling. The accumulating knowledge about signaling networks and the proteins involved will be put to practical use in the development of potent and specific pharmacological modulators of phosphorylation-dependent signaling. The rational structure-based design and development of highly specific kinase modulators is becoming routine and drugs that intercede in signaling pathways are becoming a major class of drug. The functions of some of the kinases are described below.

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease.

Calcium-calmodulin (CaM) dependent protein kinases are also members of the STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR. CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues, such as brain, heart, spleen, and lung, than expected. This distribution suggests that AMPK's functions may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli. MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines, such as tumor necrosis factor (TNF) and interleukin-1 (IL-1).

EGF receptor is found in over half of breast tumors unresponsive to hormone. EGF is found in many tumors, and EGF may be required for tumor cell growth. Antibodies to EGF blocked the growth of tumor xenografts in mice. An antisense oligonucleotide for amphiregulin inhibited growth of a pancreatic cancer cell line.

Tamoxifen, a protein kinase C inhibitor with anti-estrogen activity, is currently a standard treatment for hormone-dependent breast cancer. The use of this compound may increase the risk of developing cancer in other tissues such as the endometrium. Raloxifene, a related compound, has been shown to protect against osteoporosis. The tissue specificity of inhibitors must be considered when identifying therapeutic targets.

Signal transduction to the nucleus in response to extracellular stimulus by a growth factor involves the mitogen activated protein (MAP) kinases. MAP kinases are a family of protein serine/threonine kinases which mediate signal transduction from extracellular receptors or heat shock, or UV radiation. Cell proliferation and differentiation in normal cells are under the regulation and control of multiple MAP kinase cascades. Aberrant and deregulated functioning of MAP kinases can initiate and support carcinogenesis. Insulin and IGF-1 also activate a mitogenic MAP kinase pathway that may be important in acquired insulin resistance occurring in type 2 diabetes.

Many cancers become refractory to chemotherapy by developing a survival strategy involving the constitutive activation of the phosphatidylinositol 3-kinase-protein kinase B/Akt signaling cascade. This survival signaling pathway thus becomes an important target for the development of specific inhibitors that would block its function. PI-3 kinase/Akt signaling is equally important in diabetes. The pathway activated by RTKs subsequently regulates glycogen synthase 3 (GSK3) and glucose uptake. Since AKT has decreased activity in type 2 diabetes, it provides a therapeutic target.

Protein kinase inhibitors provide much of our knowledge about in vivo regulation and coordination of physiological functions of endogenous peptide inhibitors. A pseudosubstrate sequence within PKC acts to inhibit the kinase in the absence of its lipid activator. A PKC inhibitor, such as chelerythrine, acts on the catalytic domain to block substrate interaction, while calphostin acts on the regulatory domain to mimic the pseudosubstrate sequence and block ATPase activity, or to inhibit cofactor binding.

Although some protein kinases have, to date, no known system of physiological regulation, many are activated or inactivated by autophosphorylation or phosphorylation by upstream protein kinases. The regulation of protein kinases also occurs during the transcription, post-transcription, and post-translation processes. The mechanism of post-transcriptional regulation is alternative splicing of precursor mRNA. For example, protein kinase C βI and βII are two isoforms of a single PKCβ gene derived from differences in the splicing of the exon encoding the C-terminal 50-52 amino acids. Splicing can be regulated by a kinase cascade in response to peptide hormones, such as insulin and IGF-1. PKC βI and βII have different specificities for phosphorylating members of the mitogen activated protein (MAP) kinase family, for glycogen synthase 3β, for nuclear transcription factors, such as TLS/Fus, and for other nuclear kinases. By inhibiting the post-transcriptional alternative splicing of PKC βII mRNA, PKC βII-dependent processes are inhibited.

The development of antisense oligonucleotides to inhibit the expression of various protein kinases has been successful. Antisense oligonucleotides are short lengths of synthetically manufactured, chemically modified DNA or RNA designed to specifically interact with mRNA transcripts encoding target proteins. The interaction of the antisense moiety with mRNA inhibits protein translation and, in some cases, post-transcriptional processing (e.g., alternative splicing and stability) of mRNA. Antisense oligonucleotides have been developed to alter alternative splicing of mRNA forms for inhibiting the translation of PKCα.

Protein kinase C isoforms have been implicated in cellular changes observed in the vascular complications of diabetes. Hyperglycemia is associated with increased levels of PKCα and β isoforms in renal glomeruli of diabetic rats. Oral administration of a PKCβ inhibitor prevented the increased mRNA expression of TGF-β1 and extracellular matrix component genes. Administration of the specific PKCβ inhibitor (LY333531) also normalized levels of cytokines, caldesmon, and hemodynamics of retinal and renal blood flow. Overexpression of the PKCβ isoform in the myocardium resulted in cardiac hypertrophy and failure. The use of LY333531 to prevent adverse effects of cardiac PKCβ overexpression in diabetic subjects is under investigation. The compound is also in Phase I/II clinical trials for diabetic retinopathy and diabetic macular edema indicating that it may be pharmacodynamically active.

PRK (proliferation-related kinase) is a serum/cytokine inducible STK that is involved in regulation of the cell cycle and cell proliferation in human megakaroytic cells. PRK is related to the polo (derived from humans polo gene) family of STKs implicated in cell division. PRK is down-regulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

DNA-dependent protein kinase (DNA-PK) is involved in the repair of double-strand breaks in mammalian cells. This enzyme requires ends of double stranded DNA or transitions from single-stranded to double-stranded DNA in order to act as a serine/threonine kinase. Cells with defective or deficient DNA-PK activity are unable to repair radiation induced DNA double-strand breaks and are consequently very sensitive to the lethal effects of ionizing radiation. Inhibition of DNA-PK has the potential to increase the efficacy of anti-tumor treatment with radiation or chemotherapeutic agents.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Cellular inhibitors of CDKs also play a major role in cell cycle progression. Alterations in the expression, function, and structure of cyclin and CDK are encountered in the cancer phenotype. Therefore, CDKs may be important targets for new cancer therapeutic agents.

Chemotherapy resistant cells tend to escape apoptosis. Under certain circumstances, inappropriate CDK activation may even promote apoptosis by encouraging the progression of the cell cycle under unfavorable conditions, i.e., attempting mitosis while DNA damage is largely unrepaired.

Purines and purine analogs act as CDK inhibitors. Flavopiridol is a flavonoid that causes 50% growth inhibition of tumor cells at 60 nM. It also inhibits EGFR and protein kinase A. Flavopiridel induces apoptosis and inhibits lymphoid, myeloid, colon, and prostate cancer cells grown in vivo as tumor xenografts in nude mice.

Staurosporine and its derivative, UCN-01, in addition to inhibiting protein kinase C, inhibit cyclin B/CDK (IC50=3 to 6 nM). Staurosporine is toxic, but its derivative 7-hydroxystaurosporine (UCN-01) has anti-tumor properties and is in clinical trials. UCN-01 affects the phosphorylation of CDKs and alters the cell cycle checkpoint functioning. These compounds illustrate that multiple intracellular targets may be affected as the concentration of an inhibitor is increased within cells.

Protein tyrosine kinases, PTKs, specifically phosphorylate tyrosine residues on their target proteins and may be divided into transmembrane, receptor PTKs and non-transmembrane, non-receptor PTKs. Transmembrane protein tyrosine kinases are receptors for most growth factors. Binding of a growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Since RTKs stimulate tumor cell proliferation, inhibitors of RTKs may inhibit the growth and proliferation of such cancers. Inhibitors of RTKs are also useful in preventing tumor angiogenesis and can eliminate support from the host tissue by targeting RTKs located on vascular cells, such as blood vessel endothelial cells and stromal fibroblasts. For example, VEGF stimulates endothelial cell growth during angiogenesis, and increases the permeability of tumor vasculature so that proteins and other growth factors become accessible to the tumor. Broad-spectrum antitumor efficacy of an oral dosage form of an inhibitor of VEGF signaling has been reported. Thus, inhibition of VEGF receptor signaling presents an important therapeutic target. An extracellular receptor can also be a target for inhibition. For example, the EGF receptor family and its ligands are overexpressed and exist as an autocrine loop in many tumor types.

Increasing knowledge of the structure and activation mechanism of RTKs and the signaling pathways controlled by tyrosine kinases provided the possibility for the development of target specific drugs and new anti-cancer therapies. Approaches towards the prevention or interception of deregulated RTK signaling include the development of selective components that target either the extracellular ligand-binding domain or the intracellular substrate binding region.

The most successful strategy to selectively kill tumor cells is the use of monoclonal antibodies (mAbs) that are directed against the extracellular domain of RTKs, which are critically involved in cancer and are expressed at the surface of tumor cells. In the past years, recombinant antibody technology has made an enormous progress in the design, selection and production of newly engineered antibodies. It is also possible to generate humanized antibodies, human-mouse chimeric or bispecific antibodies for targeted cancer therapy. Mechanistically, anti-RTK mAbs might work by blocking the ligand-receptor interaction and therefore inhibiting ligand-induced RTK signaling and increasing RTK down-regulation and internalization. In addition, binding of mAbs to certain epitopes on the cancer cells may induce immune-mediated responses, such as opsonization and complement-mediated lysis, and trigger antibody-dependent cellular cytotoxicity by macrophages or natural killer cells. In recent years, it became evident that mAbs control tumor growth by altering the intracellular signaling pattern inside the targeted tumor cell, leading to growth inhibition and/or apoptosis. In addition, bispecific antibodies can bridge selected surface molecules on a target cell with receptors on an effector cell, thus triggering cytotoxic responses against the target cell. Despite the toxicity that has been seen in clinical trials of bispecific antibodies, advances in antibody engineering, characterization of tumor antigens and immunology might help to produce rationally designed bispecific antibodies for anti-cancer therapy.

Another promising approach to inhibiting aberrant RTK signaling is to develop small molecule drugs that selectively interfere with the intrinsic tyrosine kinase activity and thereby block receptor autophosphorylation and activation of downstream signal transducers. The tyrphostins, which belong to the quinazolines, are one important group of such inhibitors that compete with ATP for the ATP binding site at the receptor's tyrosine kinase domain and some members of the group have been shown to specifically inhibit the EGFR. Potent and selective inhibitors of receptors involved in neovascularization have been developed and are now undergoing clinical evaluation. New classes of tyrosine kinase inhibitors (TKIs) with increased potency and selectivity, higher in vitro and in vivo efficacy and decreased toxicity have been developed using the advantages of structure-based drug design, crystallographic structure information, combinatorial chemistry and high-throughput screening.

Recombinant immunotoxins provide another possibility of target-selective drug design. Recombinant immunotoxins are composed of a bacterial or plant toxin either fused or chemically conjugated to a specific ligand, such as the variable domains of the heavy and light chains of mAbs or to a growth factor. Immunotoxins may contain bacterial toxins, such as Pseudomouas exotoxin A or diphtheria toxin, or plant toxins, such as ricin A or clavin. These recombinant molecules can selectively kill their target cells when internalized after binding to cell surface receptors of the target cells.

The use of antisense oligonucleotides represents another strategy to inhibit the activation of receptor tyrosine kinase (RTKs). Antisense oligonucleotides are short pieces of synthetic DNA or RNA that are designed to interact with the mRNA to block the transcription and thus the expression of the target proteins. Antisense oligonucleotides interact with the mRNA by Watson-Crick base-pairing and are therefore highly specific to the target protein. Several preclinical and clinical studies suggest that antisense therapy might be therapeutically useful for the treatment of solid tumors.

The potential of RTKs and their relevant signaling as selective anti-cancer targets for therapeutic intervention has been recognized. As a consequence, a variety of successful target specific drugs such as mabs and RTK inhibitors have been developed and are currently being evaluated in clinical trials. Table 3 summarizes the most successful drugs against receptor tyrosine kinase signaling which are currently evaluated in clinical phases or have already been approved by the FDA.

tyrosine kinases, membrane anchors (inhibition of farnesylation) and transcription factors.

Targeting the signaling potential of growth promoting tyrosine kinases such as EGFR, HER2, PDGFR, src, and abl, will block tumor growth while blocking IGF-I and TRK will interfere with tumor cell survival. Inhibition of these kinases will lead to tumor shrinkage and apoptosis. FkII/KDR and src are kinases necessary for neovascularization (angiogenesis) of tumors. Inhibition of these kinases will slow tumor growth and decrease metastases.

Inhibitors of RTKs suppress tumor development by preventing cell migration, invasion and metastases. These drugs are likely to increase the time required for tumor progression, and may inhibit or attenuate the aggressiveness of the disease but may not initially result in measurable tumor regression.

An example of cancer arising from a defective tyrosine kinase is a class of ALK positive lymphomas referred to as "ALKomas" which display inappropriate expression of a neural-specific tyrosine kinase, anaplastic lymphoma kinase (ALK).

Iressa (ZD1839) is an orally active selective EGF-R inhibitor. This compound disrupts signaling involved in cancer cell proliferation. The clinical efficacy of this agent shows that it is well tolerated by patients undergoing Phase I/II clinical trials. The compound has shown promising cytotoxicity towards several cancer cell lines.

Since the majority of protein kinases are expressed in the brain, often in a neuron-specific fashion, protein phosphory-

TABLE 3

RTK Drugs Currently Under Clinical Evaluation

| RTK | Drug | Company | Description | Status |
|---|---|---|---|---|
| EGFR | ZA18539 Iressa | AstraZeneca | TKI that inhibits EGFR signaling | Phase III |
| EGFR | Cetuximab C225 | ImClone Systems | Mab directed against EGFR | Phase III |
| EGFR | EGF fusion protein | Seragen | Recombinant diphtheria toxin-hEGF fusion protein | Phase II |
| HER2 | Trastuzumab Herceptin | Genetech | Mab directed against HER2 | Approved by the FDA in 1998 |
| IGF-IR | INX-4437 | INEX USA | Antisense oligonucleotides targeting IGR-IR | Phase I |
| VEGFR | SU5416 | SUGEN | TKI that inhibits VEGFR2 | Phase II |
| VEGFR/ FGFR/ PDGFR | SU6668 | SUGEN | RTK inhibition of VEGFR, FGFR, and PDGFR | Phase I |

Non-receptor PTKs lack transmembrane regions and, instead, form complexes with the intracellular regions of cell surface receptors. Receptors that function through non-receptor PTKs include those for cytokines, hormones (growth hormone and prolactin) and antigen-specific receptors on T and B lymphocytes.

Many of the PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity.

Many tyrosine kinase inhibitors, such as flavopiridol, genistem, erbstatin, lavendustin A, staurosporine, and UCN-01, are derived from natural products. Inhibitors directed to the ATP binding site are also available. Signals from RTKs can also be inhibited at other target sites such as nuclear lation must play a key role in the development and function of the vertebrate central nervous system. Thus neuron-specific kinases are well established as targets for the development of pharmacologically active modulators.

In summary, kinase proteins are a major target for drug action and development. Accordingly, it is valuable to the field of pharmaceutical development to identify and characterize previously unknown members of kinase proteins. The present invention advances the state of the art by providing a previously unidentified human kinase protein that has sequence and structure similarities to several protein kinases. Specifically, the kinase domain in HPK3P23 shares high sequence identity with the corresponding domains in serine/threonine kinases, tyrosine kinases, and pkinases. This domain, either in the native form or in the mutant form, can be used to affect the function of the corresponding domain in other kinases. The kinase domain in HPK3P23 can be used to phosphorylate suitable substrates. The substrate peptides can be conjugated to antibodies, and the phosphate groups added to the substrate peptides can be radioactively or fluorescently labeled. Antibodies thus labeled can be used in various detection assays, as appreciated by one of ordinary skill in the art.

HPK3P23 gene and the gene product can be used as a molecular marker for diagnosing, prognosing, and monitoring the treatment of disorders related to the aberrant expression of HPK3P23. In addition, the HPK3P23 gene can be used to screen for potential agents or drugs capable of enhancing or inhibiting the HPK3P23 gene expression in human cells. the HPK3P23 gene products (polynucleotide and polypeptide) can be used to screen for potential agents or drugs capable of enhancing or inhibiting HPK3P23 activity. Furthermore, various therapeutic methods for treating disorders related to the aberrant expression of HPK3P23 can be designed based on the HPK3P23 gene, its variants, or the agents/drugs that affect the expression of the HPK3P23 gene or the activity of the HPK3P23 gene products.

The following subsections illustrate examples of the utilities of human HPK3P23 gene and HPK3P23 kinase. Various changes and modifications within the spirit and scope of the present invention will become apparent to those skilled in the art from the present description.

Polynucleotides and Variants Thereof

One aspect of the invention pertains to isolated polynucleotide probes capable of hybridizing to the HPK3P23 gene or its transcripts, such as HPK3P23 mRNAs. These probes can be used to detect the expression level of the HPK3P23 gene in human tissue or cells. The present invention also contemplates polynucleotide fragments for use as PCR primers for the amplification or mutation of the HPK3P23 gene or the HPK3P23 kinase-coding sequences. Another aspect of the invention pertains to isolated polynucleotides that encode HPK3P23, or a fragment or mutant thereof. These polynucleotides can be used for expressing HPK3P23, or a fragment or mutant thereof. The protein products thus expressed can be used to screen for agents/drugs that modulate an activity of HPK3P23. In addition, these polynucleotides can be used to designing gene therapy vectors which target the expression of the HPK3P23 gene or an activity of HPK3P23 in humans.

A polynucleotide comprising SEQ ID NO:1 or SEQ ID NO:3 can be prepared using standard molecular biology techniques as appreciated by one of ordinary skill in the art. For instance, primers derived from the 5' and 3' ends of SEQ ID NO:1 can be used to amplify mRNAs isolated from human tissues. The cDNA thus produced contains SEQ ID NO:1. Likewise, primers for amplifying the human genomic sequence containing SEQ ID NO:3 can be designed and used to prepare the genomic sequence of the HPK3P23 gene. A variant (such as a homolog) or a fragment of SEQ ID NO:1 or SEQ ID NO:3 can be similarly prepared. Alternatively, probes can be designed to screen for cDNA or genomic sequence libraries in order to identify polynucleotide molecules comprising the full-length or fragments of SEQ ID NO:1 or SEQ ID NO:3. The molecules thus identified can be used to create suitable vectors comprising the full-length SEQ ID NO:1 or SEQ ID NO:3.

Polynucleotides capable of hybridizing to the HPK3P23 gene can be prepared by standard synthetic techniques, e.g., using an automated DNA synthesizer. Preferably, the polynucleotide probes can hybridize to the HPK3P23 gene under reduced stringent conditions, stringent conditions, or highly stringent conditions. In one embodiment, the polynucleotides comprise at least 15, 20, 25, 30, 50, 100, 150, 200, 250, 300, 350, 400, 450, 500, 550, 600, 650, 700, 750, 800, 850, 900, 950, 1000 or more consecutive nucleotides of SEQ ID NO:1.

Any fragments of SEQ ID NO:1 and SEQ ID NO:3 may be used as hybridization probes or PCR primers for the HPK3P23 gene or its transcripts. The probes/primers can be substantially purified.

In a preferred embodiment, the hybridization probes for the HPK3P23 gene comprise a label group. The label group can be a radioisotope, a fluorescent compound, an enzyme, or an enzyme co-factor. Probes thus labeled can be used as part of a diagnostic kit for determining the expression level of the HPK3P23 gene in human tissues.

This invention encompasses human HPK3P23 gene homologs in other species. These homologs can be determined by search different sequence databases, such as the Entrez/GenBank sequence databases maintained by the NCBI. The invention also encompasses polynucleotide molecules which are structurally different from the molecules described above, but have the substantially same properties as the molecules described above. Such molecules include allelic variants, which will be described below in greater detail.

DNA sequence polymorphism in human HPK3P23 gene exists among different individuals due to natural allelic variations. An allele is one of a group of genes which occur alternatively at a given genetic locus. DNA polymorphisms that affect the RNA expression level of the HPK3P23 gene can also exist, e.g., through affecting the regulation or degradation of expression of the gene. The present invention contemplates all allelic variants of human HPK3P23 gene. Allelic variants and other homologs of the HPK3P23 gene can be isolated using probes/primers derived from SEQ ID NO:1 or SEQ ID NO:3.

It should, of course, be understood that SEQ ID NO:1 and SEQ ID NO:3 can be modified. The modified polynucleotides can comprise one or more mutations. These mutations can be substitutions, additions or deletions of 1, 2, 3, 5, 10, 15, 20 or more nucleotide residues in SEQ ID NO:1 or SEQ ID NO:3. Standard techniques can be used, such as site-directed mutagenesis or PCR-mediated mutagenesis. Preferably, these mutations create conservative amino acid substitutions. Alternatively, mutations can be introduced randomly along all or part of the HPK3P23 gene or its cDNA, such as by saturation mutagenesis. Following mutagenesis, the encoded proteins can be expressed recombinantly and their activities can be determined.

In one embodiment, nucleotide substitutions leading to amino acid substitutions at "non-essential" amino acid residues can be introduced. A "non-essential" amino acid residue is a residue that can be altered without changing the biological activity of the protein. In contrast, an "essential" amino acid residue is required for the biological activity of the protein. Amino acid residues that are conserved among allelic variants or homologs of the HPK3P23 gene from different species preferably are not changed in the present invention.

Accordingly, another aspect of the invention pertains to HPK3P23 proteins that contain changes in amino acid residues that are not essential for the biological activity of HPK3P23. These proteins differ in amino acid sequence from the original human HPK3P23 kinase, but retain its biological activity. In one embodiment, the modified protein comprises an amino acid sequence at least about 92%, 94%, 96%, 98% or more homologous to SEQ ID NO:2.

In another embodiment, HPK3P23 proteins contain mutations in amino acid residues which result in inhibition of HPK3P23 activity. These mutated HPK3P23 proteins can be used to inhibit HPK3P23 activity in patients with disorders related to the aberrant expression of HPK3P23.

A polynucleotide of this invention can be further modified to increase its stability in vivo. Possible modifications include, but are not limited to, the addition of flanking sequences at the 5' and/or 3' ends; the use of phosphorothioate or 2-o-methyl rather than phosphodiester linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotide molecules which are antisense to the HPK3P23 gene can be prepared. An "antisense" polynucleotide comprises a nucleotide sequence which is complementary to a "sense" polynucleotide which encodes a protein. An antisense polynucleotide can bind via hydrogen bonds to the sense polynucleotide.

Antisense polynucleotides of the invention can be designed according to the rules of Watson and Crick base pairing. The antisense polynucleotide molecule can be complementary to the entire coding region or part of the coding region of the HPK3P23 gene. The antisense polynucleotide molecule can also be complementary to a "noncoding region" in the coding strand of the HPK3P23 gene. Preferably, the antisense polynucleotide is an oligonucleotide which is antisense to only a portion of the HPK3P23 gene. An antisense polynucleotide can be, for example, about 5, 10, 15, 20, 25, 30, 35, 40, 45 or 50 nucleotides in length. An antisense polynucleotide of the invention can be constructed using chemical synthesis and enzymatic ligation reactions as appreciated by one of ordinary skill in the art. For example, an antisense polynucleotide can be chemically synthesized using naturally occurring nucleotides or variously modified nucleotides designed to increase the biological stability of the molecules or to increase the physical stability of the duplex formed between the antisense and sense polynucleotides. Examples of modified nucleotides which can be used to generate the antisense polynucleotide include 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyl adenosine, unacil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3)w, and 2,6-diaminopurine. Phosphorothioate derivatives and acridine substituted nucleotides can also be used. Alternatively, the antisense polynucleotide can be produced biologically using an expression vector into which a polynucleotide has been subcloned in an antisense orientation (i.e., RNA transcribed from the inserted polynucleotide will be of an antisense orientation to the target polynucleotide of interest).

The antisense polynucleotides of the invention can be administered to a subject or applied in situ such that they hybridize or bind to cellular mRNAs and/or genomic DNAs that encode HPK3P23 kinase, thereby inhibiting the expression of HPK3P23 kinase. The hybridization can result in a stable duplex via conventional nucleotide complementarity. An example route for administering antisense polynucleotides includes direct injection at a tissue site. Antisense polynucleotides can also be modified first, and then administered systemically. For example, for systemic administration, antisense molecules can be modified such that they specifically bind to receptors or antigens expressed on a selected cell surface. Suitable modifications include linking the antisense polynucleotides to peptides or antibodies which bind to the cell surface receptors or antigens. In addition, the antisense polynucleotides can be delivered to cells using vectors. To achieve sufficient intracellular concentrations of the antisense molecules, strong pol II or pol III promoters may be used in the vectors.

In one embodiment, the antisense polynucleotides are α-anomeric polynucleotides. An α-anomeric polynucleotide molecule forms specific double-stranded hybrid with a complementary RNA in which, contrary to the usual β-units, the strands run parallel to each other. The antisense polynucleotide molecule can also comprise a 2-o-methylribonucleotide or a chimeric RNA-DNA analogue.

In another embodiment, the antisense polynucleotide is a ribozyme. Ribozymes are catalytic RNA molecules with ribonuclease activity which are capable of cleaving a single-stranded polynucleotide, such as an mRNA, to which they have a complementary region. Thus, ribozymes (e.g., hammerhead ribozymes described in Haselhoif and Gerlach, Nature 334:585-591, 1988) can be used to catalytically cleave mRNA transcripts of HPK3P23 in order to inhibit its expression. A ribozyme having specificity for the HPK3P23 gene or its transcripts can be designed based upon SEQ ID NO:1 or 3. mRNAs transcribed from the HPK3P23 gene can be used to select from a pool of RNA molecules a catalytic RNA having a specific ribonuclease activity.

Alternatively, the expression of the HPK3P23 gene can be inhibited by using nucleotide sequences complementary to the regulatory region (e.g., the promoter and/or enhancers). These nucleotide sequences can form triple helical structures that prevent transcription of the gene in the target cells.

Expression of the HPK3P23 gene can also be inhibited using RNA interference ("RNAi"). RNAi is a phenomenon in which the introduction of double-stranded RNA (dsRNA) into certain organisms or cell types causes degradation of the homologous mRNA. First discovered in the nematode Caenorhabditis elegans, RNAi has since been found to operate in a wide range of organisms. For example, in mammalian cells, introduction of long dsRNA (>30 nt) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knock-out. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

In a preferred embodiment, short interfering RNAs (siRNA) are used. siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 nucleotides with symmetric 2 dinucleotide 3' overhangs. Using synthetic 21 bp siRNA duplexes (19 RNA bases followed by a UU or dTdT 3' overhang), sequence specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins.

Second, siRNAs can be expressed in vivo from vectors. This approach can be used to stably express siRNAs in cells or transgenic animals. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (UU) to hairpin siRNAs—a feature that is helpful for siRNA function. The Pol III expression vectors can also be used to create transgenic mice that express siRNA.

In another embodiment, siRNAs can be expressed in a tissue-specific manner. Under this approach, long double-stranded RNAs (dsRNAs) are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific (pol II) promoters to create tissue-specific knockdown mice.

Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database (human, mouse, rat, etc.). Any target sequences with more than 16-17 contiguous base pairs of homology to other coding sequences may be eliminated from consideration in certain cases.

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., Proc. Natl. Acad. Sci. USA 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., Nature Biotechnology 20:500-505, 2002).

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In a preferred embodiment, the target sequence for RNAi is a 21-mer sequence fragment selected from SEQ ID NO:1. The 5' end of the target sequence has dinucleotide "NA," where "N" can be any base and "A" represents adenine. The remaining 19-mer sequence has a GC content of between 45% and 55%. In addition, the remaining 19-mer sequence does not include (1) any three consecutive identical bases (i.e., GGG, CCC, TTT, or AAA); (2) seven "GC" in a role; and (3) any palindrome sequence with 5 or more bases. Furthermore, the target sequence has low sequence homology to other human genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. Fragments of SEQ ID NO:1 that produce no hit to other human genes under BLASTN search are selected as the preferred candidate sequences for RNAi. During the search, the e-value may be set at a stringent value (such as "1"). Table 4 lists exemplary HPK3P23 gene target sequences for RNAi prepared using the above-described criteria. The siRNA sequences for each target sequence (the sense strand and the antisense strand) are also disclosed. In addition, the 5' end location of each target sequence in SEQ ID NO:1 is identified ("5 End").

TABLE 4

Exemplary RNAi Target Sequences of the HPK3P23 Gene and the Corresponding siRNAs

| Target Sequence (SEQ ID NO) | 5' End | siRNA Sense Strand (SEQ ID NO) | siRNA Antisense Strand (SEQ ID NO) |
|---|---|---|---|
| AATGAGTACCTCGGCTATGGA (SEQ ID NO:9) | 147 | UGAGUACCUCGGCUAUGGAUU (SEQ ID NO:10) | UUACUCAUGGAGCCGAUACCU (SEQ ID NO:11) |
| AAGACTAACAGCGGAGTTGCT (SEQ ID NO:12) | 353 | GACUAACAGCGGAGUUGCUUU (SEQ ID NO:13) | UUCUGAUUGUCGCCUCAACGA (SEQ ID NO:14) |
| AAGATCGAGACAGCAGCGTAA (SEQ ID NO:15) | 1216 | GAUCGAGACAGCAGCGUAAUU (SEQ ID NO:16) | UUCUAGCUCUGUCGUCGCAUU (SEQ ID NO:17) |
| AACTCACGTCTGTGGTTGGAA (SEQ ID NO:18) | 1585 | CUCACGUCUGUGGUUGGAAUU (SEQ ID NO:19) | UUGAGUGCAGACACCAACCUU (SEQ ID NO:20) |
| AATAGTGGAGGCGGTATATGA (SEQ ID NO:21) | 1751 | UAGUGGAGGCGGUAUAUGAUU (SEQ ID NO:22) | UUAUCACCUCCGCCAUAUACU (SEQ ID NO:23) |
| AAGCTCGTCCAGATATTGTAG (SEQ ID NO:24) | 1843 | GCUCGUCCAGAUAUUGUAGUU (SEQ ID NO:25) | UUCGAGCAGGUCUAUAACAUC (SEQ ID NO:26) |
| AACACCGTCACATGTCACCAT (SEQ ID NO:27) | 1995 | CACCGUCACAUGUCACCAUUU (SEQ ID NO:28) | UUGUGGCAGUGUACAGUGGUA (SEQ ID NO:29) |
| AATAGAGGCTGAGTTAGTGAC (SEQ ID NO:30) | 2465 | UAGAGGCUGAGUUAGUGACUU (SEQ ID NO:31) | UUAUCUCCGACUCAAUCACUG (SEQ ID NO:32) |
| AATTGCTAGTGCATTGGTGAG (SEQ ID NO:33) | 3529 | UUGCUAGUGCAUUGGUGAGUU (SEQ ID NO:34) | UUAACGAUCACGUAACCACUC (SEQ ID NO:35) |
| CAATGAGTACCTCGGCTATGG (SEQ ID NO:36) | 146 | AUGAGUACCUCGGCUAUGGUU (SEQ ID NO:37) | UUUACUCAUGGAGCCGAUACC (SEQ ID NO:38) |
| CAGCTGTGCTTAGCTCTTCGA (SEQ ID NO:39) | 1440 | GCUGUGCUUAGCUCUUCGAUU (SEQ ID NO:40) | UUCGACACGAAUCGAGAAGCU (SEQ ID NO:41) |
| CAGCACTAACATGCTGTCCTT (SEQ ID NO:42) | 1721 | GCACUAACAUGCUGUCCUUUU (SEQ ID NO:43) | UUCGUGAUUGUACGACAGGAA (SEQ ID NO:44) |
| CAAGCATCAGCAGGAATTGCT (SEQ ID NO:45) | 2568 | AGCAUCAGCAGGAAUUGCUUU (SEQ ID NO:46) | UUUCGUAGUCGUCCUUAACGA (SEQ ID NO:47) |
| CAGGATGTCAGAGCTACCAG (SEQ ID NO:48) | 3266 | GGAUGUCAGAGCUACCAGUUU (SEQ ID NO:49) | UUCCUACAGUCUCGAUGGUCA (SEQ ID NO:50) |
| GAGACAGCAGCGTAAGGAATA (SEQ ID NO:51) | 1222 | DACAGCAGCGUAAGGAAUAUU (SEQ ID NO:52) | UUCUGUCGUCGCAUUCCUUAU (SEQ ID NO:53) |
| GAGGCGGTATATGAACCAGTC (SEQ ID NO:54) | 1758 | GGCGGUAUAUGAACCAGUCUU (SEQ ID NO:55) | UUCCGCCAUAUACUUGGUCAG (SEQ ID NO:56) |
| GAACACCGTCACATGTCACCA (SEQ ID NO:57) | 1994 | ACACCGUCACAUGUCACCAUU (SEQ ID NO:58) | UUUGUGGCAGUGUACAGUGGU (SEQ ID NO:59) |
| GATCTCCAGAACCGATTGAG (SEQ ID NO:60) | 2794 | UCUCCAGAACCGAUUGAGCUU (SEQ ID NO:61) | UCUCCAGAACCGAUUGAGCUU (SEQ ID NO:62) |
| GACTTCAGCCGCTATTGCAAG (SEQ ID NO:63) | 3102 | CUUCAGCCGCUAUUGCAAGUU (SEQ ID NO:64) | UUGAAGUCGGCGAUAACGUUC (SEQ ID NO:65) |
| GAGTATATGACAGCTGCGGTA (SEQ ID NO:66) | 3212 | GUAUAUGACAGCUGCGGUAUU (SEQ ID NO:67) | UUCAUAUACUGUCGACGCCAU (SEQ ID NO:68) |
| GAGGATTGAGCATCGAATGGT (SEQ ID NO:69) | 3325 | GGAUUGAGCAUCGAAUGGUUU (SEQ ID NO:70) | UUCCUAACUCGUAGCUUACCA (SEQ ID NO:71) |
| GAGTTCGCATCACACCAGATC (SEQ ID NO:72) | 3393 | GUUCGCAUCACACCAGAUCUU (SEQ ID NO:73) | UUCAAGCGUAGUGUGGUCUAG (SEQ ID NO:74) |
| TAGTGGAGGCGGTATATGAAC (SEQ ID NO:75) | 1753 | GUGGAGGCGGUAUAUGAACUU (SEQ ID NO:76) | UUCACCUCCGCCAUAUACUUG (SEQ ID NO:77) |
| TATTACATCGTTCATCCGGTG (SEQ ID NO:78) | 2842 | UUACAUCGUUCAUCCGGUGUU (SEQ ID NO:79) | UUAAUGUAGCAAGUAGGCCAC (SEQ ID NO:80) |

TABLE 4-continued

Exemplary RNAi Target Sequences of the HPK3P23
Gene and the Corresponding siRNAs

| Target Sequence (SEQ ID NO) | 5' End | siRNA Sense Strand (SEQ ID NO) | siRNA Antisense Strand (SEQ ID NO) |
| --- | --- | --- | --- |
| TATATGACAGCTGCGGTACTT (SEQ ID NO:81) | 3215 | UAUGACAGCUGCGGUACUUUU (SEQ ID NO:82) | UUAUACUGUCGACGCCAUGAA (SEQ ID NO:83) |
| TATGACAGCTGCGGTACTTGA (SEQ ID NO:84) | 3217 | UGACAGCUGCGGUACUUGAUU (SEQ ID NO:85) | UUACUGUCGACGCCAUGAACU (SEQ ID NO:86) |

In yet another embodiment, the polynucleotides of the present invention can be modified at the base moiety, sugar moiety or phosphate backbone to improve the stability, hybridization, or solubility of the molecules. For instance, the deoxyribose phosphate backbone of the polynucleotide molecules can be modified to generate peptide polynucleotides (see Hyrup B. et al. Bioorganic & Medicinal Chemistry 4:523, 1996). As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. PNA oligomers can be synthesized using standard solid phase peptide synthesis protocols.

PNAs can be used in therapeutic and diagnostic applications. For example, PNAs can be used as antisense agents for sequence-specific modulation of the HPK3P23 gene expression. PNAs can also be used in the analysis of single base pair mutations in a gene, (e.g., by PNA-directed PCR clamping); as artificial restriction enzymes when used in combination with other enzymes, (e.g., S1 nucleases); or as probes or primers for DNA sequencing or hybridization.

In one embodiment, PNAs can be modified to enhance their stability or cellular uptake by attaching lipophilic or other helper groups to PNA, by the formation of PNA-DNA chimeras, or by the use of liposomes or other drug delivery techniques known in the art. For example, PNA-DNA chimeras of the polynucleotides of the invention can be generated. These chimeras allow DNA recognition enzymes, such as RNase H and DNA polymerases, to interact with the DNA portion while the PNA portion provides high binding affinity and specificity. PNA-DNA chimeras can be linked using linkers of appropriate lengths which are selected based on base stacking, number of bonds between the nucleobases, and orientations. The PNA-DNA chimeras can be synthesized as follows. A DNA chain is synthesized on a solid support using standard phosphoramidite coupling chemistry and modified nucleoside analogs. PNA monomers are then coupled in a stepwise manner to produce a chimeric molecule with a 5' PNA segment and a 3' DNA segment. Alternatively, chimeric molecules can be synthesized with a 5' DNA segment and a 3' PNA segment.

In other embodiments, the polynucleotides of this invention may include other appended groups such as peptides (e.g., for targeting host cell receptors in vivo), or agents facilitating transportation across the cell membrane or the blood-kidney barrier (see, e.g., PCT Publication No. W089/10134). In addition, polynucleotides can be modified using hybridization-triggered cleavage agents or intercalating agents. To this end, the polynucleotides can be conjugated to another molecule (e.g., a peptide, hybridization triggered cross-linking agent, transport agent, or hybridization-triggered cleavage agent). Furthermore, the polynucleotide can be detectably labeled.

Polypeptides and Variants thereof

Several aspects of the invention pertain to isolated HPK3P23 polypeptides and mutated HPK3P23 polypeptides capable of inhibiting normal HPK3P23 activity. The present invention also contemplates immunogenic polypeptide fragments suitable for raising anti-HPK3P23 antibodies.

In one embodiment, native HPK3P23 polypeptides can be isolated from cells or tissue sources by using standard protein purification techniques. Standard purification methods include electrophoresis, molecular, immunological and chromatographic techniques. Specific examples include ion exchange, hydrophobic, affinity or reverse-phase HPLC chromatography, and chromatofocusing. In one embodiment, HPK3P23 polypeptides are purified using a standard affinity column coupled with anti-HPK3P23 antibodies. Ultrafiltration and diafiltration techniques can also be used. The degree of purification depends on the purpose of the use of the HPK3P23 polypeptides. In some instances, purification is not necessary.

In another embodiment, HPK3P23 polypeptides or mutated HPK3P23 polypeptides capable of inhibiting normal HPK3P23 activity are produced by recombinant DNA techniques. Alternative to recombinant expression, HPK3P23 polypeptides or mutated HPK3P23 polypeptides can be synthesized chemically using standard peptide synthesis techniques.

The invention provides HPK3P23 polypeptides encoded by the human HPK3P23 gene, or homologs thereof. The polypeptides of this invention can be substantially homologous to human HPK3P23 kinase (SEQ ID NO:2). Preferably, these polypeptides retain the biological activity of the native HPK3P23 kinase. In one embodiment, the polypeptides comprise an amino acid sequence which is at least about 92%, 94%, 96%, 98% or more homologous to SEQ ID NO:2.

Comparison of sequences and determination of percent identity between two sequences can be accomplished using a mathematical algorithm. The percent identity between two amino acid sequences can be determined using the Needleman and Wunsch (J. Mol. Biol. 48:444-453, 1970) algorithm, or the GAP program in the GCG software package which uses either a Blossom 62 matrix or a PAM250 matrix, and a gap weight of 16, 14, 12, 10, 8, 6, or 4 and a length weight of 1, 2, 3, 4, 5, or 6. The percent identity between two nucleotide sequences can be determined using the GAP program in the GCG software package, which uses a NWSgapdna.CMP matrix and a gap weight of 40, 50, 60, 70, or 80 and a length weight of 1, 2, 3, 4, 5, or 6. The percent identity between two amino acid or nucleotide sequences can also be determined using the algorithm of E. Meyers and W. Miller (CABIOS, 4:11-17, 1989) which has been incorporated into the ALIGN program (version 2.0), or the pairwise BLAST program available at NCBI's BLAST web site.

The polypeptide and polynucleotide sequences of the present invention can be used as query sequences for searching public databases in order to identify similar sequences. The search can be conducted using BLAST programs, such as the protein BLAST, nucleotide BLAST, pairwise BLAST, and genomic BLAST, that are available at the BLAST web site maintained by the NCBI. When using BLAST programs, the default parameters of the respective programs can also be used.

The invention further provides chimeric or fusion HPK3P23 polypeptides. A fusion HPK3P23 polypeptide contains an HPK3P23-related polypeptide and a non-HPK3P23 polypeptide. The HPK3P23-related polypeptides include all or a portion of SEQ ID NO:2 or its variant. A peptide linker sequence can be employed to separate the HPK3P23-related polypeptide from the non-HPK3P23 polypeptide components by a distance sufficient to ensure that each polypeptide folds into its native secondary and tertiary structures. Such a peptide linker sequence is incorporated into the fusion protein using standard techniques well known in the art. Suitable peptide linker sequences can be chosen based on the following factors: (1) their ability to adopt a flexible extended conformation; (2) their inability to adopt a secondary structure that could interact with functional epitopes on the HPK3P23-related polypeptide and non-HPK3P23 polypeptide; and (3) the lack of hydrophobic or charged residues that might react with the polypeptide functional epitopes. Preferred peptide linker sequences contain Gly, Asn and Ser residues. Other near neutral amino acids, such as Thr and Ala can also be used in the linker sequence. Amino acid sequences suitable as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequences may be from 1 to about 50 amino acids in length. Linker sequences are not required when the HPK3P23-related polypeptide or the non-HPK3P23 polypeptide has non-essential N-terminal amino acid regions that can be used to separate the respective functional domains and thereby prevent steric interference.

In one embodiment, the fusion protein is a GST-HPK3P23 fusion protein in which an HPK3P23-related sequence, such as SEQ ID NO:2, is fused to the C-terminus of the GST sequence. This fusion protein can facilitate the purification of the recombinant HPK3P23.

The HPK3P23-fusion proteins of the invention can be incorporated into pharmaceutical compositions and administered to a subject. The HPK3P23-fusion proteins can be used to affect the bioavailability of an HPK3P23 substrate. The HPK3P23-fusion proteins can also be used for the treatment or prevention of damages caused by (i) aberrant modification or mutation of HPK3P23, or (ii) aberrant post-translational modification of HPK3P23. It is also conceivable that a fusion protein containing a normal or mutated HPK3P23 polypeptide, or a fragment thereof, can be used to inhibit HPK3P23 activity in a human subject.

Moreover, the HPK3P23-fusion proteins can be used as immunogens to produce anti-HPK3P23 antibodies. They can also be used to purify HPK3P23 ligands and to screen for molecules capable of inhibiting the interaction between HPK3P23 and its substrates.

Preferably, the HPK3P23-chimeric or fusion proteins of the invention are produced using standard recombinant DNA techniques. Commercially available expression vectors which encode a fusion moiety (e.g., a GST polypeptide) can be used.

A signal sequence can be used to facilitate secretion and isolation of the secreted protein or other proteins of interest. Signal sequences are typically characterized by a core of hydrophobic amino acids which are generally cleaved from the mature protein. Such signal peptides contain processing sites that allow cleavage of the signal sequence from the mature proteins as they pass through the secretory pathway. The present invention encompasses HPK3P23 polypeptides having a signal sequence, or the polynucleotide sequences encoding the same.

The present invention also pertains to HPK3P23 mutants which function as antagonists to HPK3P23. In one embodiment, antagonists of HPK3P23 are used as therapeutic agents. For example, a mutant of HPK3P23 that forms a non-functional dimer with a wide-type HPK3P23 (the so-called dominant negative mutant) can decrease the activity of HPK3P23 and may ameliorate diseases in a subject wherein HPK3P23 are abnormally increased in level or activity. Dominant negative HPK3P23 mutants can be generated by mutagenesis, as appreciated by one skilled in the art.

HPK3P23 mutants which function as either HPK3P23 agonists or antagonists can be identified by screening combinatorial libraries of mutants. A variegated library of HPK3P23 mutants can be produced by, for example, enzymatically ligating a mixture of synthetic oligonucleotides into gene sequences such that a degenerate set of potential HPK3P23 sequences is expressible as individual polypeptides, or alternatively, as a set of larger fusion proteins containing the set of HPK3P23 sequences therein. There are a variety of methods which can be used to produce libraries of potential HPK3P23 mutants from a degenerate oligonucleotide sequence. A degenerate gene sequence can be chemically synthesized using an automatic DNA synthesizer. The synthetic gene can then be ligated into an appropriate expression vector.

In one embodiment, a library of coding sequences can be generated using nucleases. For instance, double stranded PCR fragments of the HPK3P23 coding sequence can be treated by a nuclease which produces about one nick per molecule. The double-stranded DNAs then are subject to a cycle of denaturing and re-naturing. The newly reformed DNAs, which may include sense/antisense pairs from different nicked products, are treated with S1 nuclease to remove single stranded portions. Using this method, an expression library which encodes N-terminal, C-terminal or internal fragments of HPK3P23 can be derived.

In addition, recursive ensemble mutagenesis (REM), a technique which enhances the frequency of functional mutants in the libraries, can be used to prepare HPK3P23 mutants (Delgrave et al., Protein Engineering 6:327-331, 1993).

HPK3P23 fragments, or variants thereof, can also be generated using synthetic means, such as solid-phase synthesis methods. Preferably, the synthesized fragment has less than about 100 amino acids, or preferably, less than about 50 amino acids.

Antibodies

In accordance with another aspect of the present invention, antibodies specific to HPK3P23 or its variants are prepared. An antibody is considered to bind "specifically" to an antigen if the binding affinity between the antibody and the antigen is equal to, or greater than $10^5$ M$^{-1}$. The antibodies can be monoclonal or polyclonal. Preferably, the antibodies are monoclonal. More preferably, the antibodies are humanized antibodies.

Polyclonal anti-HPK3P23 antibodies can be prepared by immunizing a suitable subject with HPK3P23 or fragments thereof. The anti-HPK3P23 antibody titer in the immunized subject can be monitored over the time using standard techniques, such as ELISA. The anti-HPK3P23 antibody can be isolated from the immunized subject using well known techniques.

In one embodiment, hybridomas capable of producing anti-HPK3P23 antibodies are prepared. Purified HPK3P23 or its variants, or fragments thereof, are used to immunize a vertebrate, such as a mammal. Suitable mammals include mice, rabbits and sheep. Preferably, the fragment used for immunization comprises at least 8 amino acid residues, more preferably at least 12 amino acid residues, highly preferably at least 16 amino acid residues, and most preferably at least 20 amino acid residues.

Immunogenic fragments (epitopes) of HPK3P23 can be identified using well known techniques. In general, any fragment of SEQ ID NO:2 can be used to raise antibodies specific to HPK3P23. Preferred epitopes are regions that are located on the surface of HPK3P23. These regions are usually hydrophilic.

Splenocytes are isolated from the immunized vertebrate and fused with an immortalized cell line (such as a myeloma) to form hybridomas. Preferably, the immortal cell line is derived from the same mammalian species as the lymphocytes. For example, murine hybridomas can be made by fusing an immortalized mouse cell line with lymphocytes isolated from a mouse that is immunized with an immunogenic preparation of the present invention. Preferred immortalized cell lines include mouse myeloma cell lines that are sensitive to culture medium containing hypoxanthine, aminopterin and thymidine ("HAT medium"). Suitable myeloma cell lines include, but are not limited to, the P3-NS1/I-Ag4-1, P3-x63-Ag8.653 or Sp210-Ag14 myeloma lines, all of which are available from ATCC. In one embodiment, HAT-sensitive mouse myeloma cells are fused to mouse splenocytes using polyethylene glycol ("PEG"). Hybridoma cells thus produced are selected against HAT medium, which kills unfused or unproductively fused myeloma cells. Hybridoma cells which produce monoclonal anti-HPK3P23 antibodies are then detected by screening the hybridoma culture supernatants.

A monoclonal anti-HPK3P23 antibody can also be prepared by screening a recombinant combinatorial immunoglobulin library (e.g., an antibody phage display library). Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

The anti-HPK3P23 antibodies of the present invention also include "single-chain Fv" or "scFv." The scFv fragments comprise the VH and VL domains of an antibody. Generally, the scFv polypeptide further comprises a polypeptide linker between the VH and VL domains. The polypeptide linker enables the scFv to form the desired structure for antigen binding. Additionally, recombinant anti-HPK3P23 antibodies, such as chimeric and humanized monoclonal antibodies, can be prepared, as appreciated by one of ordinary skill in the art.

Humanized antibodies are particularly desirable for therapeutic treatment of human subjects. Humanized forms of non-human (e.g., murine) antibodies are chimeric immunoglobulins, immunoglobulin chains, or fragments thereof (such as Fv, Fab, Fab', F(ab')2 or other antigen-binding subsequences of antibodies) which contain minimal sequence derived from non-human immunoglobulin. Humanized antibodies are derived from human immunoglobulins in which the residues forming the complementary determining regions (CDRs) are replaced by the residues from CDRs of a non-human antibody, such as a mouse, rat or rabbit antibody having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. The humanized antibody can comprise at least one or two variable domains, in which all or substantially all of the CDR regions correspond to those of a non-human immunoglobulin and all or substantially all of the constant regions are those of a human immunoglobulin consensus sequence. The humanized antibody preferably comprises at least a portion of an immunoglobulin constant region (Fc) of a human immunoglobulin.

Humanized antibodies can be produced using transgenic mice which are incapable of expressing endogenous immunoglobulin heavy and light chains but can express human heavy and light chains. The transgenic mice are immunized in the normal fashion with a selected antigen. Monoclonal antibodies directed against the antigen can be obtained using conventional hybridoma technology. The human immunoglobulin transgenes harbored in the transgenic mice rearrange during B cell differentiation, and subsequently undergo class switching and somatic mutation. Using this technique, therapeutically useful IgG, IgA and IgE antibodies can be prepared.

In addition, humanized antibodies which recognize a selected epitope can be generated using a technique referred to as "guided selection." In this approach a selected non-human monoclonal antibody, e.g., a murine antibody, is used to guide the selection of a humanized antibody recognizing the same epitope.

In a preferred embodiment, the antibodies to HPK3P23 are capable of reducing or eliminating the biological function of HPK3P23. Preferably, the antibodies reduce at least 25% of HPK3P23 activity. More preferably, the antibodies reduce at least about 50% of the activity. Highly preferably, the antibodies reduce about 95-100% of HPK3P23 activity.

Anti-HPK3P23 antibodies can be used to isolate HPK3P23. Suitable methods include affinity chromatography and immunoprecipitation. Moreover, anti-HPK3P23 antibodies can be used to evaluate the expression level of HPK3P23. Anti-HPK3P23 antibodies can also be used to monitor HPK3P23 level as part of a clinical testing procedure, or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include 125I, 131I, 35S or 3H.

Anti-HPK3P23 antibodies are also useful for targeting a therapeutic agent/drug to a particular cell or tissue. The therapeutic agent/drug may be coupled to an antibody, either covalently or non-covalently. For instance, a therapeutic agent can be coupled to an antibody via a linker group. A linker group can function as a spacer to separate the antibody from the agent so as to avoid interference with antibody's binding capabilities. The linker group can also serve to increase the chemical reactivity of a substituent on the agent or the antibody, and thus increase the coupling efficiency. A variety of bifunctional or polyfunctional reagents, either homo- or hetero-functional (such as those described in the catalog of the Pierce Chemical Co., Rockford, Ill.), can be employed as the linker group. Coupling may be effected, for example, through amino groups, carboxyl groups, sulfhydryl groups or oxidized carbohydrate residues. There are numerous references describing this methodology. See e.g., U.S. Pat. No. 4,671,958.

Where a therapeutic agent is more potent when free from the antibody, it may be desirable to use a linker group which is cleavable during or upon internalization into the target cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), or by acid-catalyzed hydrolysis (e.g., U.S. Pat. No. 4,569,789).

It may also be desirable to couple more than one agent to an antibody. In one embodiment, multiple agents are coupled to one antibody molecule. In another embodiment, at least two different types of agents are coupled to one antibody. Regardless of the particular embodiment, immunoconjugates coupled with more than one agent can be prepared in a variety of ways, as appreciated by one of ordinary skill in the art.

Vectors, Expression Vectors and Gene Delivery Vectors

Another aspect of the invention pertains to vectors containing a polynucleotide encoding HPK3P23 or a portion thereof. One type of vector is a "plasmid," which includes a circular double stranded DNA into which additional DNA segments can be introduced. Vectors also include expression vectors and gene delivery vectors.

The expression vectors of the present invention comprise a polynucleotide encoding HPK3P23 or a portion thereof. The expression vectors also include one or more regulatory sequences operably linked to the polynucleotide being expressed. These regulatory sequences are selected based on the type of host cells. It will be appreciated by those skilled in the art that the design of the expression vector depends on such factors as the choice of the host cells and the desired expression levels. HPK3P23 can be expressed in bacterial cells such as E. coli, insect cells (using baculovirus expression vectors), yeast cells or mammalian cells. The expression vector can also be transcribed and translated in vitro, for example, by using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Suitable cleavage enzymes include Factor Xa, thrombin and enterokinase. Examples of fusion expression vectors include pGEX (Pharmacia Piscataway, N.J.), pMAL (New England Biolabs, Beverly, Mass.) and pRITS (Pharmacia, Piscataway, N.J.). Purified fusion proteins can be utilized in HPK3P23 activity assays, or to generate antibodies specific for HPK3P23.

Examples of suitable inducible non-fusion E. coli expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HSLE174 (DE3) from a resident prophage harboring a T7 gn1 gene under the transcriptional control of the lacUV 5 promoter.

One strategy to maximize recombinant protein expression in E. coli is to express the protein in host bacteria that have an impaired capacity to proteolytically cleave the recombinant protein. Another strategy is to alter the polynucleotide sequence encoding the protein so that the individual codons for each amino acid are those preferentially utilized in E. coli.

In another embodiment, the HPK3P23 expression vector is a yeast expression vector. Examples of yeast expression vectors include pYepSec1, pMFa, pJRY88, pYES2 (Invitrogen Corporation, San Diego, Calif.), and picZ (Invitrogen Corp, San Diego, Calif.).

Alternatively, HPK3P23 or its variant can be expressed in insect cells using baculovirus expression vectors. Suitable baculovirus vectors include the pAc series and the pVL series.

In yet another embodiment, HPK3P23 or its variant is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus and Simian Virus 40.

In another embodiment, the mammalian expression vector contains tissue-specific regulatory elements. Examples of suitable tissue-specific promoters include the liver-specific albumin promoter, lymphoid-specific promoters, promoters of T cell receptors and immunoglobulins, neuron-specific promoters (e.g., the neurofilament promoter), pancreas-specific promoters, and mammary gland-specific promoters (e.g., milk whey promoter). Developmentally-regulated promoters are also contemplated, which include, for example, the α-fetoprotein promoter.

The present invention also provides a recombinant expression vector comprising a polynucleotide which encodes HPK3P23 but is cloned into the expression vector in an antisense orientation. Regulatory sequences that are operatively linked to the antisense-oriented polynucleotide can be chosen to direct continuous expression of the antisense RNA molecule in a variety of cell types. Suitable regulatory sequences include viral promoters and/or enhancers. Regulatory sequences can also be chosen to direct constitutive, tissue specific or cell type specific expression of the antisense RNA. The antisense expression vector can be in the form of a recombinant plasmid, phagemid, or attenuated virus in which antisense polynucleotides are produced under the control of a highly efficient regulatory region.

The present invention further provides gene delivery vehicles for delivering polynucleotides to mammals. A polynucleotide sequence of the invention can be administered either locally or systemically via a gene delivery vehicle. Expression of the polynucleotide can be induced using endogenous mammalian or heterologous promoters. Expression of the polynucleotide in vivo can be either constituted or regulated. The gene delivery vehicles preferably are viral vectors, including retroviral, lentiviral, adenoviral, adeno-associated viral (AAV), herpes viral, or alphavirus vectors. The viral vectors can also be astrovirus, coronavirus, orthomyxovirus, papovavirus, paramyxovirus, parvovirus, picornavirus, poxvirus, or togavirus vectors.

Delivery of gene therapy constructs is not limited to the above mentioned viral vectors. Other delivery methods can also be employed. These methods include nucleic acid expression vectors, polycationic condensed DNA linked or unlinked to killed adenovirus, ligand linked DNA, liposome-DNA conjugates, gene guns, ionizing radiation, nucleic charge neutralization, or fusion with cell membranes. Naked DNA can also be employed. Uptake efficiency of the naked DNA may be improved using biodegradable latex beads. This method can be further improved by treating the beads to increase their hydrophobicity.

Regulatable Expression Systems

Another aspect of the present invention pertains to the use of regulatable expression systems to express desirable polynucleotides or polypeptides in cells. Systems suitable for this invention are briefly described below:

Tet-on/off system. The Tet-system is based on two regulatory elements derived from the tetracycline-resistance operon of the *E. coli* Tn10 transposon: the tet repressor protein (TetR) and the Tet operator DNA sequence (tetO) to which TetR binds (Gossen et al., Science 268: 1766-1769, 1995). The system consists of two components, a "regulator" and a "reporter" plasmid. The "regulator" plasmid encodes a hybrid protein containing a mutated Tet repressor (rtetR) fused to the VP16 activation domain of herpes simplex virus. The "reporter" plasmid contains a tet-responsive element (TRE), which controls the "reporter" gene of choice. The rtetR-VP16 fusion protein can only bind to the TRE, therefore activating the transcription of the "reporter" gene in the presence of tetracycline. The system has been incorporated into a number of viral vectors including retrovirus, adenovirus and AAV.

Ecdysone system. The Ecdysone system is based on the molting induction system found in *Drosophila*, but modified for inducible expression in mammalian cells. The system uses an analog of the *Drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., Proc. Natl. Acad. Sci. USA 93: 3346-3351, 1996).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., Nat. Biotech 15: 239-243, 1997).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons (Ye et al., Science 283: 88-91, 1999).

Detection Methods

In patients with disorders related to the aberrant expression of HPK3P23. The expression level of HPK3P23 can be used as an indicator for detecting the presence of HPK3P23-related diseases in humans. Detection and measurement of the relative amount of the HPK3P23 gene product can be carried out using various methods known in the art.

Typical methodologies for detecting the transcription level of a gene include extracting RNA from a cell or tissue sample, hybridizing a labeled probe to the extracted RNA or derivative thereof (such as cDNA or cRNA), and detecting the probe. Suitable methods include Northern Blot and quantitative RCR or RT-PCR. In situ hybridization can also be used to detect the transcription level of the HPK3P23 gene in human tissues.

Typical methodologies for detecting a polypeptide include extracting proteins from a cell or tissue sample, binding an antibody to the target polypeptide and detecting the antibody. Suitable methods include enzyme linked immunosorbent assays (ELISAs), Western blots, immunoprecipitations, and immunofluorescence. The antibody can be polyclonal, or preferably, monoclonal. The antibody can be an intact antibody, or a fragment thereof (e.g. Fab or F(ab')2). The antibody can be labeled with a radioisotope, a fluorescent compound, an enzyme, an enzyme co-factor, or a detectable ligand. The term "labeled," with regard to a probe or antibody, is intended to encompass direct labeling such as through covalent coupling, as well as indirect labeling such as being mediated by another reagent which is directly labeled. Examples of indirect labeling include labeling a primary antibody using a fluorescently labeled secondary antibody, or attaching a DNA probe with a biotin which can be detected, for example, by a fluorescence-labeled streptavidin.

Preferably, the binding affinity of the antibody to HPK3P23 is at least 105 M−1. More preferably, the binding affinity is at least 106 M−1. Other methods such as electrophoresis, chromatography or direct sequencing can also be used to detect the amount of a polypeptide in a biological sample. Anti-HPK3P23 antibodies can also be directly introduced into a subject. The antibody can be labeled with a radioactive marker whose presence and location in the subject can be detected using standard imaging techniques.

In one embodiment, the genomic copies of the HPK3P23 gene in the genome of a human subject may indicate the presence or predisposition of a disease. Detection of the presence or number of copies of the HPK3P23 gene in the genome can be performed using methods known in the art. For instance, it can be assessed using Southern Blot. The probes for Southern Blot can be labeled with a radioisotope, a fluorescent compound, an enzyme, or an enzyme co-factor.

In the field of diagnostic assays, the above-described detection methods can be used to determine the severity of HPK3P23-related diseases. A biological sample is isolated from a test subject, and the presence, quantity and/or activity of HPK3P23 in the sample relative to a disease-free or control sample is evaluated. The expression level of HPK3P23 in the biological sample can indicate the presence or severity of HPK3P23-related diseases in the test subject. The term "biological sample" is intended to include tissues, cells or biological fluids isolated from the subject. A preferred biological sample is a serum sample isolated from the subject using conventional means.

Screening Methods

The present invention also provides methods for identifying HPK3P23 modulators. Suitable modulators include compounds or agents comprising therapeutic moieties, such as peptides, peptidomimetics, peptoids, polynucleotides, small molecules or other drugs. These moieties can either bind to HPK3P23, or have a modulatory (e.g., stimulatory or inhibitory) effect on the activity of HPK3P23. In one embodiment, the moieties have a modulatory effect on the interactions of HPK3P23 with one or more of its natural substrates. These moieties can also exert a modulatory effect on the expression of HPK3P23. The screen assays of the present invention comprise detecting the interactions between HPK3P23 and test components.

The test compounds of the present invention can be either small molecules or bioactive agents. In a preferred embodiment, the test compound is a small organic or inorganic molecule. In another preferred embodiment, the test compounds are polypeptides, oligopeptides, polysaccharides, nucleotides or polynucleotides.

In accordance with one aspect of this invention, methods for screening for compounds that inhibit the biological activities of HPK3P23 are provided. Pharmaceutical compositions comprising these compounds can subsequently be prepared. The screening method comprises (1) contacting a sample with a compound, and (2) comparing expression profile or biological activity of HPK3P23 in the sample to determine whether the compound substantially decreases the expression level or activities of HPK3P23. The screening method can be carried out either in vivo or in vitro.

The present invention further includes a method for screening for compounds capable of modulating the binding between HPK3P23 and a binding partner. As used herein, the term "binding partner" refers to a bioactive agent which serves as either a substrate for HPK3P23, or a ligand having a binding affinity to HPK3P23. The bioactive agent may be selected from a variety of naturally-occurring or synthetic compounds, proteins, peptides, polysaccharides, nucleotides or polynucleotides.

Inhibitors of the expression, activity or binding ability of HPK3P23 may be used as therapeutic compositions. These inhibitors can be formulated in suitable pharmaceutical compositions, as described herein below.

The present invention also provides methods for conducting high-throughput screening for compounds capable of inhibiting activity or expression of HPK3P23. In one embodiment, the high-throughput screening method involves contacting test compounds with HPK3P23, and then detecting the effect of the test compounds on HPK3P23. Functional assays, such as cytosensor microphysiometer-based assays, calcium flux assays (e.g., FLIPR®, Molecular Devices Corp, Sunnyvale, Calif.), or the TUNEL assay, can be employed to measure HPK3P23 cellular activity. Fluorescence-based techniques can be used for high-throughput and ultra high-throughput screening. They include, but are not limited to, BRET® and FRET® (both by Packard Instrument Co., Meriden, Conn.).

In a preferred embodiment, the high-throughput screening assay uses label-free plasmon resonance technology as provided by BIACORE® systems (Biacore International AB, Uppsala, Sweden). Plasmon free resonance occurs when surface plasmon waves are excited at a metal/liquid interface. By reflecting directed light from the surface as a result of contact with a sample, the surface plasmon resonance causes a change in the refractive index at the surface layer. The refractive index change for a given change of mass concentration at the surface layer is similar for many bioactive agents (including proteins, peptides, lipids and polynucleotides), and since the BIACORE® sensor surface can be functionalized to bind a variety of these bioactive agents, detection of a wide selection of test compounds can thus be accomplished.

Monitoring Efficacy of a Drug During Clinical Trials

Using the HPK3P23 detection methods of this invention, the efficacy of a therapeutic agent for HPK3P23-related diseases can be monitored during clinical trials. The therapeutic agent may be a drug, small molecule, agonist, antagonist, peptidomimetic, protein, peptide, or polynucleotide. The changes in the expression or activity of the HPK3P23 gene in response to the treatment of the agent can be used to evaluate the therapeutic effect of the agent on patients with HPK3P23-related diseases. In addition, the expression or activity of HPK3P23 in response to the agent can be measured at various points during the clinical trial.

In a preferred embodiment, the method for monitoring the effectiveness of the therapeutic agent includes the steps of (i) obtaining a pre-administration sample from a subject; (ii) detecting the level of expression or activity of HPK3P23 in the pre-administration sample; (iii) obtaining one or more post-administration samples from the subject; (iv) detecting the level of expression or activity of HPK3P23 in the post-administration samples; (v) comparing the level of expression or activity of HPK3P23 in the pre-administration sample to the level of expression or activity of HPK3P23 in the post administration samples. The dose or frequency of the administration of the agent may be adjusted based on the effectiveness of the agent in a particular patient. Therefore, HPK3P23 expression or activity can be used as an indicator of the effectiveness of a therapeutic agent for HPK3P23-related diseases, even if the agent does not produce an observable phenotypic response.

Prognostic Assays

The detection methods described herein can be used to identify subjects having or at risk of developing HPK3P23-related diseases. In addition, the detection methods can be used to determine whether an agent (e.g., an agonist, antagonist, peptidomimetic, protein, peptide, polynucleotide, small molecule, or other drug candidate) can be administered to a subject for effectively treating or preventing HPK3P23-related diseases.

HPK3P23 expression profiles at different progression stages of HPK3P23-related diseases can be established. In addition, HPK3P23 expression profiles in different patients who have different responses to a drug treatment are determined. A pattern may emerge such that a particular expression profile may be correlated to an increased likelihood of a poor prognosis. Therefore, the prognostic assay of the present invention may be used to determine whether a subject undergoing a treatment for a HPK3P23-related disease has a poor outlook for long term survival or disease progression. Preferably, prognosis is performed shortly after diagnosis, such as within a few days after diagnosis. The result of prognosis can then be used to devise individualized treatment program, thereby enhancing the effectiveness of the treatment as well as the likelihood of long-term survival and well being.

The method of the invention can also be used to detect genetic alterations in the HPK3P23 gene, thereby determining if a subject with the altered gene is at risk for damages characterized by aberrant regulation in HPK3P23 activity or expression. In a preferred embodiment, the method includes detecting the presence or absence of a genetic alteration that affects the integrity of the HPK3P23 gene, or detecting the aberrant expression of the HPK3P23 gene. The genetic alteration can be detected by ascertaining the existence of at least one of the following: 1) deletion of one or more nucleotides from the HPK3P23 gene; 2) addition of one or more nucleotides to the HPK3P23 gene; 3) substitution of one or more nucleotides of the HPK3P23 gene, 4) a chromosomal rearrangement in the HPK3P23 gene; 5) alteration in the level of a messenger RNA transcript of the HPK3P23 gene, 6) aberrant modification of the HPK3P23 gene, 7) the presence of a non-wild type splicing pattern of a messenger RNA transcript of the HPK3P23 gene, 8) non-wild type level HPK3P23, 9) allelic loss of an HPK3P23 gene, and 10) inappropriate post-translational modification of HPK3P23.

In one embodiment, detection of the alteration involves the use of a probe/primer in a polymerase chain reaction (such as anchor PCR or RACE PCR) or alternatively, in a ligation chain reaction (LCR). LCR can be particularly useful for detecting point mutations in the HPK3P23 gene. This method includes the steps of collecting a sample from a subject, isolating polynucleotides (e.g., genomic DNA, mRNA, or both) from the sample, contacting the polynucleotide with one or more primers which specifically hybridize to the HPK3P23 gene or gene product, and detecting the presence or absence of an amplification product, or detecting the size of the amplification product and comparing its length to a control. It is understood that PCR and/or LCR can be used as a preliminary amplification step in conjunction with any other techniques described herein.

Alternative amplification methods include: self sustained sequence replication (Guatelli et al., Proc. Natl. Acad. Sci. USA 87:1874-1878, 1990), transcriptional amplification system (Kwoh et al., Proc. Natl. Acad. Sci. USA 86:1173-1177, 1989), and Q-Beta Replicase (Lizardi et al. Bio-Technology 6:1197, 1988).

In another embodiment, mutations in the HPK3P23 gene can be identified using restriction enzymes. Differences in restriction enzyme digestion patterns indicate mutation(s) in the HPK3P23 gene or its transcripts. Moreover, sequence specific ribozymes can be used to detect the presence of specific mutations. See, for example, U.S. Pat. No. 5,498,531.

In yet another embodiment, genetic mutations in the HPK3P23 gene can be identified using high density arrays which contain a large number of oligonucleotides probes. For example, genetic mutations in the HPK3P23 gene can be identified in two dimensional arrays. In this example, a first hybridization array of probes is used to scan through long stretches of DNA in a sample and a control in order to identify base changes between the two sequences. This step allows the identification of point mutations. This step is followed by a second hybridization array that allows the characterization of specific mutations by using smaller and specialized probe arrays which are complementary to all variants or mutations detected. Each mutation array is composed of parallel probe sets, one complementary to the wild-type gene and the other complementary to the mutant gene.

In still another embodiment, any sequencing reactions known in the art can be used to directly sequence the HPK3P23 gene in order to detect mutations. It is contemplated that any automated sequencing procedures can be utilized, including sequencing by mass spectrometry.

In one embodiment, protection from cleavage agents is used to detect mismatched bases in RNA/RNA or RNA/DNA heteroduplexes. In general, the "mismatch cleavage" technique involves forming heteroduplexes by hybridizing an RNA or DNA (labeled) containing the wild-type HPK3P23 gene sequence to a potentially mutant RNA or DNA obtained from a tissue sample. The double-stranded duplexes are treated with an agent which cleaves single-stranded regions of the duplex. The agent may be RNase (for RNA/DNA duplexes), or S1 nuclease (for DNA/DNA hybrids). In one case, either DNA/DNA or RNA/DNA duplexes are treated with piperidine and hydroxylamine, or piperidine and osmium tetroxide, in order to digest mismatched regions. After the digestion, the resulting material is separated by size on a denaturing polyacrylamide gel from which the site(s) of mutation may be determined.

In a preferred embodiment, the mismatch cleavage reaction employs one or more proteins that recognize mismatched base pairs in double-stranded DNA. Examples of these proteins include "DNA mismatch repair" enzymes. For instance, the mutY enzyme of *E. coli* cleaves A at G/A mismatches, and the thymidine DNA glycosylase from HeLa cells cleaves T at G/T mismatches. In one case, cDNAs are prepared from mRNAs isolated from test cells. The cDNAs are then hybridized to a probe derived from the HPK3P23 gene. The duplex thus formed is treated with a DNA mismatch repair enzyme, and the cleavage products, if any, can be detected from electrophoresis protocols or the like. See, for example, U.S. Pat. No. 5,459,039.

In another embodiment, alterations in electrophoretic mobility are used to identify mutations in the HPK3P23 gene. Differences in electrophoretic mobility between mutant and wild type polynucleotides can be detected using single strand conformation polymorphism (SSCP). The resulting alteration in electrophoretic mobility enables the detection of a single base change. The DNA fragments can be labeled or detected with probes. In one case, the sensitivity of the assay is enhanced by using RNA, in which the secondary structure is more sensitive to a change in sequence. In a preferred embodiment, the assay utilizes heteroduplex analysis to separate double stranded heteroduplex molecules on the basis of changes in electrophoretic mobility (Keen et al., Trends Genet 7:5, 1991).

In yet another embodiment, the movement of mutant or wild-type fragments is evaluated using denaturing gradient gel electrophoresis (DGGE). For this purpose, DNA fragments can be modified to insure that they do not completely denature. For instance, a GC clamp of approximately 40 GC-rich base pairs can be added to the DNA fragment using PCR. In a further embodiment, a temperature gradient is used in place of a denaturing gradient (Rosenbaum and Reissner, Biophys Chem 265:12753, 1987).

Examples of other techniques for detecting point mutations include, but are not limited to, selective oligonucleotide hybridization, selective amplification, or selective primer extension. In one embodiment, oligonucleotide primers for specific amplification carry the mutation of interest in the center of the molecule (so that amplification depends on differential hybridization) or at the extreme 3' end of one primer where, under appropriate conditions, mismatch can prevent or reduce polymerase extension. See, for example, Saiki et al., Proc. Natl. Acad. Sci USA 86:6230, 1989. In addition, it may be desirable to introduce a novel restriction site in the region of the mutation to create cleavage-based detection.

The methods described herein can be performed using prepackaged diagnostic kits which comprise at least one polynucleotide probe or one antibody of the present invention. These kits can be used in clinical settings to diagnose subjects exhibiting symptoms or family history of a HPK3P23-related disease. Any cell type or tissue in which HPK3P23 is expressed can be used for prognostic or diagnostic purposes.

Prophylactic Methods

This invention also provides methods for preventing diseases associated with aberrant HPK3P23 expression or activity. The methods comprise administering to a target subject an agent which modulates HPK3P23 expression or activity.

Subjects at risk of diseases which are caused by or attributed to aberrant HPK3P23 expression or activity can be identified using the diagnostic or prognostic assays described herein. A prophylactic agent can be administered prior to the manifestation of HPK3P23-related disease symptoms in order to prevent or delay HPK3P23-related diseases. Suitable prophylactic agents include mutant HPK3P23 proteins, HPK3P23 antagonist agents, or HPK3P23 antisense polynucleotides.

The prophylactic methods of this invention can be specifically tailored or modified based on knowledge obtained from the study of pharmacogenomics. Pharmacogenomics includes the application of genomics technologies, such as gene sequencing, statistical genetics, and gene expression analysis, to drugs which are either in clinical development or on the market. Pharmacogenomics can be used to determine a subject's response to a drug (e.g., a subject's "drug response phenotype" or "drug response genotype"). Thus, another aspect of this invention is to provide methods for tailoring an individual's prophylactic or therapeutic treatment using HPK3P23 modulators according to the individual's drug response genotype. Pharmacogenomics allows a clinician or physician to target prophylactic or therapeutic treatments to subjects who will most benefit from the treatment and to avoid treatment of subjects who will experience toxic drug-related side effects.

One pharmacogenomics approach to identify genes that predict drug response, known as "a genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial in order to identify genes associated with a particular observed drug response or side effect. Alternatively, such a high resolution map can be generated from a combination of some ten-million known single nucleotide polymorphisms (SNPs) in the human genome. A "SNP" is a common alteration that occurs in a single nucleotide base in a stretch of DNA. For example, a SNP may occur once per every 1000 bases of DNA. A SNP may be involved in a disease process. However, the vast majority of SNPs may be not related to diseases. Given a genetic map based on the occurrence of SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the HPK3P23 gene to SNP maps of patients with HPK3P23-related diseases may facilitate the identification of drug-response-prediction genes.

Alternatively, the "candidate gene approach" can be utilized to identify genes that predict drug response. According to this method, if a gene that encodes a drug target is known, all common variants of that gene can be easily identified in the population. It then can be determined if a particular drug response is associated with one version of the gene versus another.

The activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response. The other extreme are the so called ultra-rapid metabolizers who do not respond to standard doses. Recently, the molecular basis of ultra-rapid metabolism has been identified to be due to CYP2D6 gene amplification.

In one embodiment, the "gene expression profiling" method can be utilized to identify genes that predict drug response. In this regard, the gene expression profile of an animal dosed with a drug can give an indication of whether the gene pathways related to toxicity have been turned on.

Information generated from the above pharmacogenomics approaches can be used to determine the appropriate dosage or treatment regimen suitable for a particular individual. This knowledge can avoid adverse reactions or therapeutic failure, and therefore enhance therapeutic or prophylactic efficiency when treating a subject with an HPK3P23 modulator.

Therapeutic Methods

As described above, the present invention includes therapeutic methods for treating a subject at risk for, susceptible to, or diagnosed with HPK3P23-related diseases. The therapeutic methods can be individually tailored based on the subject's drug response genotype. Typically, the therapeutic methods comprise modulating the expression or activity of HPK3P23 in the subject. In one embodiment, the method comprises contacting a plurality of cells in the subject with an agent that inhibits the expression or activity of HPK3P23. Suitable agents include polynucleotides (e.g., an antisense oligonucleotides of HPK3P23), polypeptides (e.g., a dominant negative mutant of HPK3P23), or polysaccharides, naturally-occurring target molecules of HPK3P23 protein (e.g., an HPK3P23 protein substrate or receptor), anti-HPK3P23 antibodies, HPK3P23 antagonists, or other small organic and inorganic molecule. They may also include vectors comprising polynucleotides encoding HPK3P23 inhibitors or antisense sequences. Moreover, the agents can be anti-HPK3P23 antibodies conjugated with therapeutic moieties. Suitable agents can be identified using the screening assays of the present invention.

Pharmaceutical Compositions

The present invention is further directed to pharmaceutical compositions comprising an HPK3P23 modulator and a pharmaceutically acceptable carrier. As used herein, a "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active modulator (e.g., an anti-HPK3P23 antibody, an HPK3P23 activity inhibitor, or a gene therapy vector expressing antisense nucleotide to HPK3P23) in the required amount in an appropriate solvent, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Kits

The invention also encompasses kits for detecting the presence of an HPK3P23 gene product in a biological sample. An example kit comprises reagents for assessing expression of HPK3P23 at MRNA or protein level. Preferably, the reagents include an antibody or fragment thereof, wherein the antibody or fragment specifically binds to HPK3P23. Optionally, the kits may comprise a polynucleotide probe capable of specifically binding to a transcript of the HPK3P23 gene. The kit may also contain means for determining the amount of HPK3P23 protein or mRNA in the test sample, and/or means for comparing the amount of HPK3P23 protein or mRNA in the test sample to a control or standard. The compound or agent can be packaged in a suitable container.

The invention further provides kits for assessing the suitability of each of a plurality of compounds for inhibiting HPK3P23-related diseases in cells or human subjects. Such kits include a plurality of compounds to be tested, and a reagent (such as an antibody specific to HPK3P23 proteins, or a polynucleotide probe or primer capable of hybridizing to the HPK3P23 gene) for assessing expression of HPK3P23.

It should be understood that the above-described embodiments are given by way of illustration, not limitation. Various changes and modifications within the scope of the present invention will become apparent to those skilled in the art from the present description.

Host Cells

Another aspect of the invention pertains to host cells into which a polynucleotide molecule of the invention is introduced, e.g., an HPK3P23 gene or homolog thereof, within an expression vector, a gene delivery vector, or a polynucleotide molecule of the invention containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an HPK3P23 gene can be expressed in bacterial cells such as E. coli, insect cells, yeast or mammalian cells (such as Chinese hamster ovary cells (CHO), COS cells, Fischer 344 rat cells, HLA-B27 rat cells, HeLa cells, A549 cells, or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DAKD-dextran-mediated transfection, lipofection, or electoporation.

For stable transfection of mammalian cells, it is known that, depending upon the expression vector and transfection technique used, only a small fraction of cells may integrate the foreign DNA into their genome. In order to identify and select these integrants, a gene that encodes a selectable flag (e.g., resistance to antibiotics) is generally introduced into the host cells along with the gene of interest. Preferred selectable flags include those which confer resistance to drugs, such as G418, hygromycin and methotrexate. A polynucleotide encoding a selectable flag can be introduced into a host cell by the same vector as that encoding HPK3P23 or can be introduced by a separate vector. Cells stably transfected with the introduced polynucleotide can be identified by drug selection (e.g., cells that have incorporated the selectable flag gene will survive, while the other cells die).

A host cell of the invention, such as a prokaryotic or eukaryotic host cell in culture, can be used to produce (i.e., express) HPK3P23. Accordingly, the invention further provides methods for producing HPK3P23 using the host cells of the invention. In one embodiment, the method comprises culturing the host cell of invention (into which a recombinant expression vector containing an HPK3P23 gene has been introduced) in a suitable medium such that HPK3P23 is produced. In another embodiment, the method further comprises isolating HPK3P23 from the medium or the host cell.

Transgenic and Knockout Animals

The host cells of the invention can also be used to produce non-human transgenic animals. For example, in one embodiment, a host cell of the invention is a fertilized oocyte or an embryonic stem cell into which HPK3P23-coding sequences have been introduced. Such host cells can then be used to create non-human transgenic animals in which exogenous sequences encoding HPK3P23 have been introduced into their genome or homologous recombinant animals in which endogenous sequences encoding HPK3P23 have been altered. Such animals are useful for studying the function and/or activity of HPK3P23 and for identifying and/or evaluating modulators of HPK3P23 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" or "knockout animal" is a non-human animal, preferably a mammal, more preferably a mouse, in which an endogenous HPK3P23 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an HPK3P23-encoding polynucleotide into the mate pronuclei of a fertilized oocyte, e.g., by microinjection or retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a transgene to direct expression of HPK3P23 to particular cells. Methods for generating transgenic animals via embryo manipulation and microinjection, particularly animals such as mice, have become conventional in the art. Similar methods are used for production of other transgenic animals. A transgenic founder animal can be identified based upon the presence of a transgene of the invention in its genome and/or expression of mRNA corresponding to a gene of the invention in tissues or cells of the animals. A transgenic founder animal can then be used to breed additional animals carrying the transgene. Moreover, transgenic animals carrying a transgene encoding HPK3P23 can further be bred to other transgenic animals carrying other transgenes.

To create a homologous recombinant animal (knockout animal), a vector is prepared which contains at least a portion of a gene of the invention into which a deletion, addition or substitution has been introduced to thereby alter, e.g., functionally disrupt, the gene. The gene can be a human gene, but more preferably, is a non-human homolog of a human gene of the invention (e.g., a homolog of the HPK3P23 gene). For example, a mouse gene can be used to construct a homologous recombination polynucleotide molecule, e.g., a vector, suitable for altering an endogenous gene of the invention in the mouse genome. In a preferred embodiment, the homologous recombination polynucleotide molecule is designed such that, upon homologous recombination, the endogenous gene of the invention is functionally disrupted (i.e., no longer encodes a functional protein; also referred to as a "knockout" vector). Alternatively, the homologous recombination polynucleotide molecule can be designed such that, upon homologous recombination, the endogenous gene is mutated or otherwise altered but still encodes functional protein (e.g., the upstream regulatory region can be altered to thereby alter the expression of the endogenous HPK3P23 gene). In the homologous recombination polynucleotide molecule, the altered portion of the gene of the invention is flanked at its 5' and 3' ends by additional polynucleotide sequence of the gene of the invention to allow for homologous recombination to occur between the exogenous gene carried by the homologous recombination polynucleotide molecule and an endogenous gene in a cell, e.g., an embryonic stem cell. The additional flanking polynucleotide sequence is of sufficient length for successful homologous recombination with the endogenous gene.

Typically, several kilobases of flanking DNA (both at the 5' and 3' ends) are included in the homologous recombination polynucleotide molecule. The homologous recombination polynucleotide molecule is introduced into embryonic stem cells by electroporation. The cells in which the introduced gene has homologously recombined with the endogenous gene are selected. The selected cells can then be injected into a blastocyst of an animal (e.g., a mouse) to form aggregation chimeras. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the homologously recombined DNA. Methods for constructing homologous recombination polynucleotide molecules, e.g., vectors, or homologous recombinant animals are well known in the art.

In another embodiment, transgenic non-human animals can be produced which contain selected systems which allow for regulated expression of the transgene. One example of such a system is the cre/loxP recombinase system of bacteriophage P1. Another example of a recombinase system is the FLP recombinase system of Saccharomyces cerevisiae (see e.g., O'Gorman et al., Science 251:1351-1355, 1991). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al., Nature 385:810-813, 1997, and PCT International Publication Nos. WO97/07668 and WO97/07669. In brief, a cell, e.g., a somatic cell, from the transgenic animal can be isolated and induced to exit the growth cycle and enter G0 phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

EXAMPLES

Example 1

Identification of the HPK3P23 Sequence in Human Genome Database

The nucleic acid sequence of HPK3P23 is obtained from a newly developed genomic prediction pipeline. Briefly, the X-ray crystal structures of the catalytic domains of protein kinases were collected and aligned together according to their structural identity/similarities. The alignment was converted into a "scoring matrix" which carried the structural profile of the kinase catalytic domains. This scoring matrix was then used to search the Celera Human Genome database for sequences that have kinase catalytic domains.

Example 2

BLAST and Hydrophobicity Analysis

Sequence alignments between HPK3P23 and other sequences in GenBank database were performed using the standard protein-protein BLAST(blastp), standard nucleotide-nucleotide BLAST(blastn), BLAST2 Sequences, and human genome BLAST programs. The programs are available at NCBI's BLAST website.

A standard protein-protein BLAST search in the "nr" database (available at NCBI's BLAST website) with "Filter" setting unchecked, "Expect" setting at 10.0, "Word Size" setting at 3, "Matrix" setting at BLOSUM62, "Gap costs" setting at Existence: 11 and Extension: 1, identified partial amino acid sequence similarities between HPK3P23 and a number of proteins. These proteins include, but are not limited to, a human protein similar to putative ser/thr protein kinase D1044.3 in chromosome 3 (Entrez accession numbers: XM_087381, 100% alignment to amino acid residues 542-1016 of HPK3P23), a mouse protein similar to putative ser/thr protein kinase D1044.3 in chromosome 3 (Entrez accession number: XM_138903, 76% alignment to amino acid residues 45-516 of HPK3P23), and an unnamed human protein (Entrez accession number: BAC05427.1, 100% sequence alignment to amino acid residues 448-848 of HPK3P23).

A conserved domain search was performed within the standard protein-protein BLAST search with the RPS-BLAST 2.2.3 [Apr. 24, 2002] program. The amino acid residues 363-627 of HPK3P23 share high homologies to the consensus sequences of the catalytic domain of tyrosine kinase, the kinase domain of pkinase, and the catalytic domain of serine/threonine protein kinase.

A standard nucleotide-nucleotide BLAST search in database nr (available at NCBI's BLAST website) with "Filter" setting unchecked, "Expect" setting at 10.0, "Word Size" setting at 3, identified several nucleotide sequences that showed significant homology to HPK3P23. These sequences include, but are not limited to, a human cDNA coding a protein similar to putative ser/thr protein kinase D1044.3 in chromosome 3 (LOC152110) (Entrez accession numbers: XM_087381.4, SEQ ID NO:6, 100% alignment to nucleotides 1623-3329 of HPK3P23), human cDNA FLJ32685 fis, clone TESTI2000154 (Entrez accession numbers: AK057247.1, SEQ ID NO:7, 99% alignment to nucleotides 1623-3329 of HPK3P23), and human cDNA FLJ25966 fis, clone TEST05207 (Entrez accession numbers: AK098832.1, SEQ ID NO:8, 99% alignment to nucleotides 1274-2543 of HPK3P23).

A standard nucleotide-nucleotide BLAST search in the "pat" database (available at NCBI's BLAST website) with "Filter" setting unchecked, "Expect" setting at 10.0, "Word Size" setting at 3, identified significant nucleotide sequence similarities between HPK3P23 with a human protein kinase-like protein SGK237 (Entrez accession number: AX250157, SEQ ID NOS:4 and 5), which was disclosed in PCT patent application WO 01/66594. Further analysis using pairwise BLAST algorithm revealed that HPK3P23 and SGK237 share 91% sequence identities at the amino acid level (blastp, matrix: BLOSUM62, gap open: 11, Gap extension: 1, x_dropoff: 50, expect: 10.0, wordsize:3, filter: unchecked), and 90% sequence identities at nucleotide level (blastn, match: 1, mismatch: -2, gap open: 5, gap extension: 0, $x_{13}$ dropoff: 50, expect: 10.0, wordsize: 11, filter: unchecked).

A human genome search was carried out using blastn program with Expect setting at 0.01, Filter setting at default, Descriptions setting at 100, and Alignment settings at 100. The HPK3P23 gene was mapped to or near loci 3p23 of human chromosome 3. Specifically, the HPK3P23 gene is located between loci LOC131717 and LOC131721, and overlaps with loci LOC152109, LOC152110, and LOC166046. Thirty-one of the thirty-two exons of the HPK3P23 gene were mapped to nucleotides 2719783 to 2940912 in human chromosome 3 of the Entrez Human Genome Sequence Database maintained by NCBI. All thirty-two exons were mapped to Celera genomic database (SEQ ID NO:3). The exons/introns in the HPK3P23 gene were determined using the program "sim4" described by Florea et al. in "A computer program for aligning a cDNA sequence with a genomic DNA sequence." Genome Res. 8:967-974, 1998.

Example 3

Hydrophobicity Analysis

The hydrophobicity profile of HPK3P23 sequence (FIG. 5) was generated using the GES (Goldman, Engelman and Steitz) hydrophobicity scale (Engelman, D. M. et al., *Ann. Rev. Biophys. Biophys. Chem.* 15:321-353, 1986). Briefly, the GES scale is used to identify nonpolar transbilayer helices. The curve is the average of a residue-specific hydrophobicity scale over a window of 20 residues. When the line is in the upper half of the frame (positive), it indicates a hydrophobic region and when it is in the lower half (negative), a hydrophilic region.

In FIG. 5, the X-axis represents the length of the protein in amino acids (aa), while the Y-axis represents the GES score. The curve line shows the GES pattern of the entire protein, while the strait line represent certain cutoff for potential membrane spanning domains. The hydrophobicity profile indicates that HPK3P23 is probably not a membrane protein.

Having described the preferred embodiments of compositions, organisms and methodologies employing a novel human gene HPK3P23 (which are intended to be illustrative and not limiting), it is noted that modifications and variations can be made by persons skilled in the art in light of the above teachings. Therefore, it is understood that changes may be made in the particular embodiments disclosed which are within the scope of what is described as defined by the appended claims.

What is claimed is:

1. An isolated polynucleotide comprising a nucleic acid sequence which encodes the amino acid sequence depicted in SEQ ID NO:2.

2. The polynucleotide according to claim 1, wherein the nucleic acid sequence is selected from the group consisting of:

(a) the nucleic acid sequence as shown in SEQ ID NO: 1;
(b) the full complement of (a); and
(c) a nucleic acid sequence that differs from (a) or (b) due to the degeneracy of the genetic code.

3. An isolated host cell containing the polynucleotide of claim 1 or claim 2.

4. An isolated polynucleotide comprising a nucleic acid sequence, wherein said nucleic acid sequence is 95% identical to the sequence of SEQ ID NO: 1 and encodes a protein kinase.

* * * * *